US009857361B2

United States Patent
Wanders et al.

(10) Patent No.: US 9,857,361 B2
(45) Date of Patent: Jan. 2, 2018

(54) FLOWCELL, SHEATH FLUID, AND AUTOFOCUS SYSTEMS AND METHODS FOR PARTICLE ANALYSIS IN URINE SAMPLES

(71) Applicant: IRIS International, Inc., Chatsworth, CA (US)

(72) Inventors: Bart J. Wanders, Trabuco Canyon, CA (US); Eric Chapoulaud, Pasadena, CA (US); Brett Jordan, Los Angeles, CA (US)

(73) Assignee: IRIS International, Inc., Chatsworth, CA (US)

(*) Notice: Subject to any disclaimer, the term of this patent is extended or adjusted under 35 U.S.C. 154(b) by 611 days.

(21) Appl. No.: 14/217,228

(22) Filed: Mar. 17, 2014

(65) Prior Publication Data

US 2014/0329265 A1 Nov. 6, 2014

Related U.S. Application Data

(60) Provisional application No. 61/799,014, filed on Mar. 15, 2013.

(51) Int. Cl.
  *G01N 21/00* (2006.01)
  *G01N 33/50* (2006.01)
  (Continued)

(52) U.S. Cl.
  CPC ..... *G01N 33/5091* (2013.01); *G01N 15/1404* (2013.01); *G01N 15/147* (2013.01);
  (Continued)

(58) Field of Classification Search
  CPC ......... G01N 15/1404; G01N 2015/149; G01N 2015/1413
  (Continued)

(56) References Cited

U.S. PATENT DOCUMENTS 3,822,095 A 7/1974 Hirschfeld
4,338,024 A 7/1982 Bolz et al.
(Continued)

FOREIGN PATENT DOCUMENTS

CA 2349995 A1 12/2001
EP 0468100 A1 1/1992
(Continued)

OTHER PUBLICATIONS

Form PCT/ISA 206 from PCT/US2014/030940, mailed on Jul. 21, 2014, 6 pages.
(Continued)

*Primary Examiner* — Natalia Levkovich
(74) *Attorney, Agent, or Firm* — Kilpatrick Townsend & Stockton LLP

(57) ABSTRACT

The present disclosure relates to apparatus, systems, compositions, and methods for analyzing a sample containing particles. A particle imaging system or analyzer can include a flowcell through which a urine sample containing particles is caused to flow, and a high optical resolution imaging device which captures images for image analysis. A contrast pattern for autofocusing is provided on the flowcell. The image processor assesses focus accuracy from pixel data contrast. A positioning motor moves the microscope and/or flowcell along the optical axis for autofocusing on the contrast pattern target. The processor then displaces microscope and flowcell by a known distance between the contrast pattern and the sample stream, thus focusing on the sample stream. Cell or particle images are collected from that position until autofocus is reinitiated, periodically, by input signal, or when detecting temperature changes or focus inaccuracy in the image data.

15 Claims, 37 Drawing Sheets

(51) Int. Cl.
*G01N 15/14* (2006.01)
*G01N 15/00* (2006.01)
*G01N 21/85* (2006.01)

(52) U.S. Cl.
CPC . *G01N 15/1468* (2013.01); *G01N 2015/0065* (2013.01); *G01N 2015/1452* (2013.01); *G01N 2021/8557* (2013.01)

(58) Field of Classification Search
USPC .......................................... 422/82.09, 82.05
See application file for complete search history.

(56) References Cited

U.S. PATENT DOCUMENTS

| | | | |
|---|---|---|---|
| 4,393,466 | A | 7/1983 | Deindorfer et al. |
| 5,457,526 | A | 10/1995 | Kosaka |
| 5,619,032 | A | 4/1997 | Kasdan |
| 5,633,503 | A | 5/1997 | Kosaka |
| 5,822,447 | A | 10/1998 | Kasdan |
| 6,184,978 | B1 | 2/2001 | Kasdan et al. |
| 6,424,415 | B1 | 7/2002 | Kasdan et al. |
| 6,441,894 | B1 | 8/2002 | Manian et al. |
| 6,590,646 | B2 | 7/2003 | Kasdan et al. |
| 6,825,926 | B2 | 11/2004 | Turner et al. |
| 6,947,586 | B2 | 9/2005 | Kasdan et al. |
| 7,041,952 | B2 | 5/2006 | Iffland et al. |
| 7,071,451 | B2 | 7/2006 | Ishikawa et al. |
| 7,236,623 | B2 | 6/2007 | Chapoulaud et al. |
| 7,319,907 | B2 | 1/2008 | Kasdan et al. |
| 7,324,694 | B2 | 1/2008 | Chapoulaud et al. |
| 7,486,329 | B2 | 2/2009 | Endo |
| 7,825,360 | B2 | 11/2010 | Karasawa et al. |
| 7,855,831 | B2 | 12/2010 | Wolleschensky et al. |
| 8,174,686 | B2 | 5/2012 | Namba et al. |
| 8,362,409 | B2 | 1/2013 | Cooper et al. |
| 2005/0042760 | A1* | 2/2005 | Yount ................ G01N 15/1459 436/63 |
| 2006/0148026 | A1 | 7/2006 | Noda et al. |
| 2008/0283722 | A1 | 11/2008 | Uchiyama et al. |
| 2011/0070606 | A1 | 3/2011 | Winkelman et al. |
| 2013/0070249 | A1 | 3/2013 | Choi et al. |

FOREIGN PATENT DOCUMENTS

| | | |
|---|---|---|
| EP | 0486747 A2 | 5/1992 |
| EP | 0708334 A2 | 4/1996 |
| EP | 0949498 A2 | 10/1999 |
| EP | 1264205 A2 | 12/2002 |
| EP | 1761817 A1 | 3/2007 |
| EP | 2028264 A1 | 2/2009 |
| EP | 2030062 A1 | 3/2009 |
| GB | 2121976 A | 1/1984 |
| GB | 2167880 A | 6/1986 |
| JP | 2003/005088 A | 1/2003 |
| WO | 01/48455 A2 | 7/2001 |
| WO | 2004/045488 A2 | 6/2004 |

OTHER PUBLICATIONS

International Search Report and Written Opinion from PCT/US2014/030940 dated Oct. 23, 2014, 25 pages.

\* cited by examiner

CONCENTRATED URINE CONTROL IN PIOAL VS. NON-PIOAL SHEATH
NON-PIOAL SHEATH (A)                    PIOAL (B)
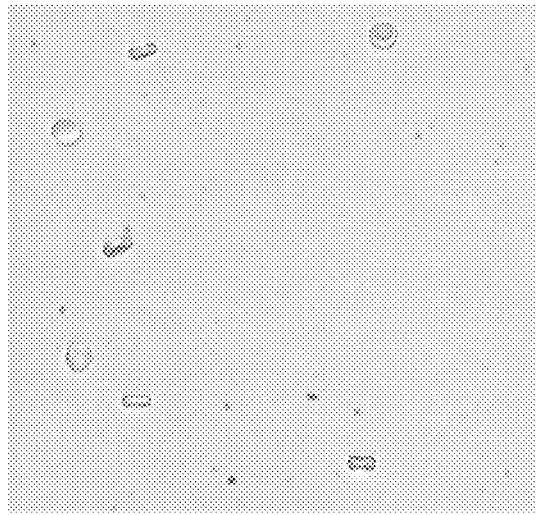 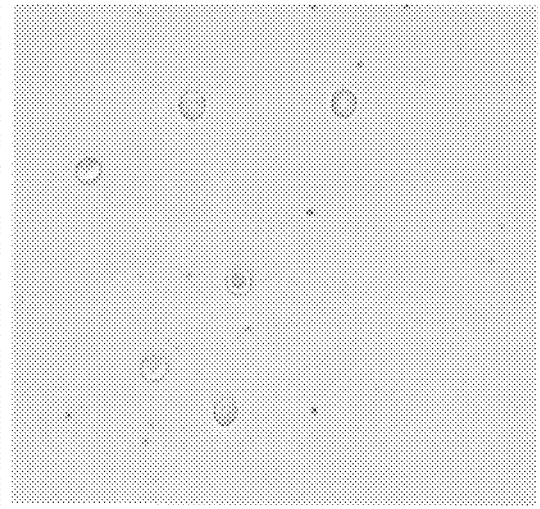
FIG.4O                    FIG.4P

FLOWCELL, SHEATH FLUID, AND AUTOFOCUS SYSTEMS AND METHODS FOR PARTICLE ANALYSIS IN URINE SAMPLES

CROSS-REFERENCES TO RELATED APPLICATIONS

This application is a non-provisional of, and claims the benefit of priority to, U.S. Provisional Patent Application No. 61/799,014 filed Mar. 15, 2013, the content of which is incorporated herein by reference. This application is also related to U.S. patent application Ser. No. 14/216,562 and International Patent Application No. PCT/US14/30856, both filed Mar. 17, 2014. The content of each of these filings is incorporated herein by reference.

BACKGROUND OF THE INVENTION

This disclosure relates to the field of systems, analyzers, compositions, and methods for analysis of particles, including imaging of particles in fluid samples, such as urine samples, using wholly or partly automated devices to discriminate and quantify particles in the sample. The present disclosure also relates to a particle and/or intracellular organelle alignment liquid (PIOAL) useful for analyzing particles in a urine sample from a subject, methods for producing the liquid, and methods for using the liquid to detect and analyze particles in urine. Compositions and methods useful for conducting image-based urine sample analysis are also disclosed. The compositions and methods of the present disclosure are also useful for detecting, counting and characterizing particles in urine, such particles can comprise for example, cells, casts, crystals, or fat bodies for image and morphologically-based particle counting, categorization, subcategorization, characterization and/or analysis.

Urine sediment analysis is one of the most commonly performed diagnostic tests for providing an overview of a patient's health status. A urine sample can be obtained from a patient's body and stored in a test tube for later processing and analysis. The appearance of certain characteristic sediments also called formed elements in a urine sample may be clinically significant and/or be indicative of pathological conditions in a subject.

Generally, abnormal urine may contain a variety of formed elements, such as blood cells, epithelial cells, crystals, casts, or microorganisms. For example, urine samples may contain cells of hematological origin. Erythrocytes or red blood cells (RBCs) may be present in the urine as a result of bleeding (hematuria) at any point in the urogenital system from the glomerulus to the urethra. The presence of leukocytes or WBCs, neutrophils, eosinophils may have clinical significance. Glitter cells are a type of neutrophil seen in hypotonic urine of specific gravity 1.010 or less. The presence of lymphocytes has been used as an early indicator of renal rejection after transplant. Eosinophils are associated with drug-induced interstitial nephritis, Mucus threads originating from the kidney or the lower urinary tract can be present.

Urine samples may also contain cells of epithelial origin. A few renal epithelial cells also called renal tubular cells, may be found in the urine of healthy persons because of normal exfoliation. However, the presence of excessive renal tubular cells is indicative of active renal disease or tubular injury. Of the various types of epithelial cells found in urine (renal, transitional or urothelial, and squamous), renal epithelial cells are the most significant clinically. They are associated with acute tubular necrosis, viral infections (such as cytomegalovirus), and renal transplant rejection. Their presence is also increased with fever, chemical toxins, drugs (especially aspirin), heavy metals, inflammation, infection, and neoplasms. Moreover, the presence of inclusion bodies may be seen in viral infections, such as *rubella* and herpes, and especially with cytomegalovirus.

Urine can also contain transitional epithelial cells or urothelial cells. Transitional epithelial cells are the multilayer of epithelial cells that line the urinary tract from the renal pelvis to the distal part of the male urethra and to the base of the bladder (trigone) in females. They may be difficult to distinguish from renal epithelial cells, but they are generally larger and more spherical. A few transitional cells are present in the urine of healthy persons. Increased numbers are associated with infection. Large clumps or sheets of these cells may be seen with transitional cell carcinoma.

Urine can also contain squamous epithelial cells. Squamous epithelial cells line the urethra in females and the distal portion of the male urethra. The presence of large numbers of squamous cells in females generally indicates vaginal contamination.

Urine can also contain clue cells. Clue cells are another type of squamous cell of vaginal origin, may be seen contaminating the urine sediment. This squamous epithelial cell is covered or encrusted with a bacterium, *Gardnerella vaginalis*, whose presence is indicative of a bacterial vaginitis.

Urine can also contain oval fat bodies, renal tubular fat, or renal tubular fat bodies. These bodies are renal epithelial cells (or macrophages) that have filled with fat or lipid droplets. The fat may be either neutral fat (triglyceride) or cholesterol; they have the same significance clinically. Presence of oval fat bodies in urine is indicative of disease abnormality and should not be overlooked. They are often seen with fatty casts and fat droplets in the urine sediment and are associated with massive proteinuria as seen in nephrotic syndrome.

Urine can also contain microorganisms such as bacteria and yeast. Normally, urine is sterile, or free of bacteria. However, certain bacteria are typically seen in urine of an alkaline pH. Associated sediment findings may include the presence of WBCs (neutrophils) and casts (WBC, cellular, granular, or bacterial). Although infections are most often due to gram-negative rods of enteric origin, infectious organisms may also be gram-positive cocci.

In addition, yeast may be seen in urine, especially as the result of vaginal contamination such as contamination from female patients with yeast infections. It is also associated with diabetes mellitus owing to the presence of urinary glucose. Yeast is a common contaminant, from skin and the environment, and infections are a problem in debilitated and immunosuppressed or immunocompromised patients.

Traditionally, analysis of sediments in urine has been performed by visual inspection using a microscope in a general laboratory. With these approaches, a urine sample is first subjected to centrifugal separation and enriched. Sediments thus obtained are in some cases stained and then loaded on a microscope slide, and are subjected to manual determination and counting under the microscope.

Sample preparation steps can include concentration of the urine sediments by centrifugation and sometimes application of a microscopy stain to enhance contrast, e.g., between sediment types such as RBCs, WBCs, and epithelial cells. In a manual count, the technician views the wet mount slide, distinguishing among types of visible cells or by their appearance using professional judgment, and manually counts the number of observed urine sediment of different types within a predetermined area.

The use of systems for urine analysis is generally described in U.S. Pat. No. 4,473,530 to Villa-Real, entitled "Compact Sanitary Urinalysis Unit"; U.S. Pat. No. 3,894, 845, entitled "Urine Collection and Analysis Device" and U.S. Pat. No. 3,988,209, entitled "Microorganism Analysis Device", both to McDonald; U.S. Pat. No. 4,973,450 to Schluter, entitled "Device for Urinalysis"; U.S. Pat. No. 4,622,298 to Mansour, et al., entitled "Detection and Quantitation of Microorganisms, Leukocytes and Squamous Epithelial Cells in Urine"; and U.S. Pat. No. 5,132,232 to Parker, entitled "Method and Apparatus for Preparation of Liquids for Examination." U.S. Pat. No. 4,612,614 to Deindoerfer, et al., entitled "Method of Analyzing Particles in a Fluid Sample", reports a method for analyzing urinary sediments by distributing a sample over an extended area, such as a microscope slide or a flow cell. Deindoerfer, et al. reports the use of a plurality of optical still images of the sample that are converted into electronic images which are displayed in an array ordered by classes of visually discernible characteristics. However, many of these earlier developed urine analysis systems generally lacked the throughput, the accuracy, and/or the general applicability required for adaptation across all targets/subjects for all intended purposes.

For automation of urinary sediment determination, an automated flow microscope may be used (e.g., flow-type automatic microscope—iQ® 200, Iris Diagnostics). With these types of devices, a urine sample is introduced to a flat type flow cell without pre-concentration and images are taken and stored while the sample is flowing through the flow cell. However, urinary sediments are diversified in their morphology and many sediments are being damaged, and therefore, determination of images taken with good accuracy are difficult to achieve. It is particularly difficult to determine small-sized sediments, such as erythrocytes (especially dysmorphic erythrocytes), bacteria and crystals with good accuracy without external user validation.

Although currently known particle analysis systems and methods, along with related medical diagnostic techniques, can provide real benefits to doctors, clinicians, and patients, still further improvements are desirable. Embodiments of the present invention provide solutions for at least some of these outstanding needs.

BRIEF SUMMARY OF THE INVENTION

The present disclosure relates to analyzer, systems, compositions, and methods for analyzing a prepared sample containing particles, such as a urine sample. In some aspects the system includes an analyzer which may be an visual analyzer. In some aspects, the analyzer contains a visual (e.g., imaging) analyzer and a processor. In one aspect, this disclosure relates to an automated particle imaging system in which a urine sample containing particles of interest is caused to flow through a flowcell having a viewport through which a high optical resolution imaging device captures an image. In some aspects the high optical resolution imaging device comprises a camera such as a digital camera. In one aspect the high optical resolution imaging device comprises an objective lens.

The flowcell is coupled to a source of sample fluid, such as a prepared sample, and to a source of particle and/or intracellular organelle alignment liquid (PIOAL). The system permits capture of focused images of particles in a sample in flow. In some embodiments the images can be used in automated, high throughput processes for categorizing and subcategorizing particles.

In one embodiment, the analyzer is configured to detect particles in the sample having one or more visual distinctions and determine accurate particle count or concentration of different categories or subcategories of particles in the sample.

The samples can be obtained by any conventional method, e.g., a urine sample collection. The sample can be from a subject considered to be healthy, for example, a sample collected as part of a routine physical examination or control group. The sample can also be from a subject who has, who is at risk for, or who is suspected of having, a disorder. The disorder can be the result of a disease, a genetic abnormality, an infection, an injury or unknown causes. Alternatively or in addition, the methods can be useful for monitoring a subject during the course of treatment for a disorder. Where there are signs of non-responsiveness to treatment, a clinician can choose an alternative or adjunctive treatment. Depending upon the condition of the subject and the particular disorder, if any, samples can be collected once (or twice, three times, etc.) daily, weekly, monthly, or yearly. The sample may be prepared by contact with a particle contrast agent composition as described herein.

The particles can vary depending upon the sample. The particles can be biological cells, for example, epithelial cells or blood cells. In some embodiments the particles can be an infectious agent, for example, a bacterium, protist, protozoa, fungus or parasite.

In one aspect, embodiments of the present invention encompass methods for imaging particles using a particle analysis system. In some cases, the system is configured for geometric hydrofocusing. The particles can be included within a body fluid sample. Exemplary methods include injecting a sheath fluid along a flowpath of a flowcell of the particle analyzer, injecting the body fluid sample from a sample fluid injection tube at a flow rate into the flowing sheath fluid within the flowcell so as to provide a sample flowstream having a first thickness adjacent the injection tube, the flowpath of the flowcell having a decrease in flowpath size such that thickness of the sample flowstream decreases from the initial thickness to a second thickness adjacent an image capture site, focusing an image capture device by imaging an imaging target having a position fixed relative to the flowcell, the imaging target and sample flowstream defining a predetermined displacement distance along the imaging axis, and acquiring a focused image of a first plurality of the particles from the first sample along the imaging axis at the image capture site of the flowcell, suitable for particle characterization and counting, within the flowstream with the image capture device, wherein the image capture device is focused on the sample flowstream using the focusing step and the predetermined displacement distance. The decrease in flowpath size can be defined by a proximal flowpath portion having a proximal thickness, and distal flowpath portion having a distal thickness less than the proximal thickness. A downstream end of the sample fluid injection tube can be positioned distal to the proximal flowpath portion. A velocity difference between the sheath and blood fluid samples, in combination with the decrease in flowpath size and the flow rate of the sample, can be effective to deliver cells in the sample from the sample fluid injection tube to the image capture site in four seconds or less. In some cases, the body fluid sample is a urine fluid sample. In some cases, the image capture site has a field of view of about 800 μm×800 μm. In some cases, the sample fluid has a volume of about 900 μL. In some cases, the sample fluid travels from an exit port of the sample fluid injection tube to the imaging axis at the image capture site in about 1.5 seconds. In some cases, the decrease in flowpath size is defined by opposed walls of the flowpath angling radially inwardly along the flowpath generally symmetric about a transverse plane that bisects the sample fluid stream first and second thicknesses. In some cases, the flowcell is configured to receive the sheath fluid from a sheath fluid source into the flowpath in a first flow direction that is perpendicular to second flow direction of the sheath fluid along the flowpath at the imaging site. In some cases, the flowcell includes an autofocus target for the image capture device. In some cases, the autofocus target can be at a fixed position relative to the flowcell. In some cases, the body fluid sample has a sample viscosity, and the sheath fluid has a sheath fluid viscosity that is different from the sample viscosity.

In another aspect, embodiments of the present invention encompass a particle analysis system that performs geometric hydrofocusing for imaging particles in a body fluid sample. Exemplary systems can include a flowcell having a flowpath configured for transmitting a flow of sheath fluid, a sample fluid injection system in fluid communication with the flowpath and configured for injecting the sample into the flowing sheath fluid within the flowcell so as to provide a sample fluid stream having a first thickness adjacent the injection tube, the flowpath of the flowcell having a decrease in flowpath size such that thickness of the sample fluid stream decreases from the initial thickness to a second thickness adjacent an image capture site. Systems can also include an image capture device aligned with the image capture site so as to image a plurality of the particles from the sample fluid at the image capture site of the flowcell, a focusing mechanism configured to set a focal state of the image capture device relative to the flowcell, an imaging target having a position fixed relative to the flowcell. The imaging target and sample flowstream can define a displacement distance along the imaging axis. Systems may also include a processor, a focusing module having a tangible medium embodying machine-readable code executed on the processor for operating the focusing mechanism to set the focal state of the image capture device, suitable for particle characterization and counting, using the displacement distance. In some cases, the sample fluid injection system is configured to deliver the sample fluid such that the sample fluid has a transit time through the flowcell within a range from about 2 to 4 seconds. In some cases, the body fluid sample is a urine fluid sample. In some cases, the image capture site has a field of view of about 800 μm×800 μm. In some cases, the sample fluid has a volume of about 900 μL. In some cases, the decrease in flowpath size is defined by opposed walls of the flowpath angling radially inwardly along the flowpath generally symmetric about a transverse plane that bisects the sample fluid stream first and second thicknesses. In some cases, the flowcell is configured to receive the sheath fluid from a sheath fluid source into the flowpath in a first flow direction that is perpendicular to second flow direction of the sheath fluid along the flowpath at the imaging site. In some cases, the flowcell includes an autofocus target for the image capture device. In some cases, the autofocus target has a fixed position relative to the flowcell. In some cases, the body fluid sample has a sample viscosity, and the sheath fluid has a sheath fluid viscosity that is different from the sample viscosity.

In another aspect, embodiments of the present invention encompass methods for imaging particles in a body fluid sample using a particle analysis system configured for geometric hydrofocusing. The particles can be included in the fluid sample, the fluid sample having a sample fluid viscosity. Exemplary methods include injecting the fluid sample into a flowcell so that the fluid sample fluid flows in a sample flowstream with a flowstream width greater than a flowstream thickness, the sample flowstream flowing through a decrease in flowpath size and traversing an imaging axis, focusing an image capture device by imaging an imaging target having a position fixed relative to the flowcell, and acquiring a focused image of the particles, suitable for particle characterization and counting, within the flowstream with the image capture device, wherein the image capture device is focused on the sample flowstream using a displacement distance. In some cases, the body fluid sample is a urine sample.

In another aspect, embodiments of the present invention encompass particle analysis systems that perform geometric hydrofocusing for imaging particles in a body fluid sample. Exemplary systems can include a flowcell having a flowpath with an injection tube and an imaging window with an imaging axis therethrough, the flowpath of the flowcell having a decrease in flowpath size, a fluid input in fluid communication with the infection tube, the fluid input configured for injecting the fluid sample into a flowcell so that the fluid sample flows in a sample flowstream with a flowstream width greater than a flowstream thickness, an image capture device, a focusing mechanism configured to set a focal state of the image capture device relative to the flowcell, an imaging target having a position fixed relative to the flowcell, the imaging target and sample flowstream defining a displacement distance along the imaging axis, a processor, and a focusing module having a tangible medium embodying machine-readable code executed on the processor for operating the focusing mechanism to set the focal state of the image capture device, suitable for particle characterization and counting, using the displacement distance. In some embodiments, the body fluid sample is a urine sample.

In another aspect, embodiments of the present invention encompass methods for imaging a plurality of particles using a particle analysis system configured for combined viscosity and geometric hydrofocusing. The particles can be included in a body fluid sample having a sample fluid viscosity. Exemplary methods include flowing a sheath fluid along a flowpath of a flowcell, the sheath fluid having a sheath fluid viscosity that differs from the sample fluid viscosity by a viscosity difference in a predetermined viscosity difference range, and injecting the body fluid sample into the flowing sheath fluid within the flowcell so as to provide a sample fluid stream enveloped by the sheath fluid. Methods can also include flowing the sample fluid stream and the sheath fluid through a reduction in flowpath size toward an imaging site, such that a viscosity hydrofocusing effect induced by an interaction between the sheath fluid and the sample fluid stream associated with the viscosity difference, in combination with a geometric hydrofocusing effect induced by an interaction between the sheath fluid and the sample fluid stream associated with the reduction in flowpath size, is effective to provide a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid. Further, methods can include imaging the plurality of particles at the imaging site. In some embodiments, the body fluid sample is a urine sample.

In yet another aspect, embodiments of the present invention encompass systems for imaging a plurality of particles in a body fluid sample having a sample fluid viscosity. Systems can be configured for use with a sheath fluid having a sheath fluid viscosity that differs from the sample fluid viscosity by a viscosity difference in a predetermined viscosity difference range. Exemplary systems can include a flowcell having a flowpath and a sample fluid injection tube, the flowpath having a reduction in flowpath size, a sheath fluid input in fluid communication with the flowpath of the flowcell so as to transmit a flow of the sheath fluid along the flowpath of the flowcell, and a body fluid sample input in fluid communication with the injection tube of the flowcell so as to inject a flow of the body fluid sample into the flowing sheath fluid within the flowcell, such that as the sheath fluid and the sample fluid flow through the reduction in flowpath size and toward an imaging site, a viscosity hydrofocusing effect induced by an interaction between the sheath fluid and the sample fluid associated with the viscosity difference, in combination with a geometric hydrofocusing effect induced by an interaction between the sheath fluid and the sample fluid associated with the reduction in flowpath size, provides a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid. Systems may further include an imaging device that images the plurality of particles at the imaging site. In some embodiments, the body fluid sample is a urine sample.

The above described and many other features and attendant advantages of embodiments of the present invention will become apparent and further understood by reference to the following detailed description when considered in conjunction with the accompanying drawings.

BRIEF DESCRIPTION OF THE DRAWINGS

FIGS. 4A, 4B-1, and 4B-2 depict aspects of flowcells according to embodiments of the present invention.

FIGS. 4A-1 and 4A-2 depict cross-section views of sheath fluid (e.g. PIOAL) envelope and sample fluidstream dimensions within a flowcell at a cannula exit port and an image capture site, respectively, according to embodiments of the present invention.

FIGS. 4C-4G, 4C-1, and 4D-1 depict aspects of cannula configurations according to embodiments of the present invention.

FIGS. 4K-1, and 4K-2 show a target imaging site according to embodiments of the present invention.

FIG. 4K-3 depicts aspect of particle alignment in a sample flowstream, according to embodiments of the present invention.

FIG. 4L-1 depicts aspects of fluid flowstream velocity profiles within a flowpath of a flowcell, according to embodiments of the present invention.

FIGS. 4O and 4P show images demonstrating the comparison between images obtained using a PIOAL versus a conventional sheath fluid according to embodiments of the present invention.

DETAILED DESCRIPTION OF THE INVENTION

Figure 1:
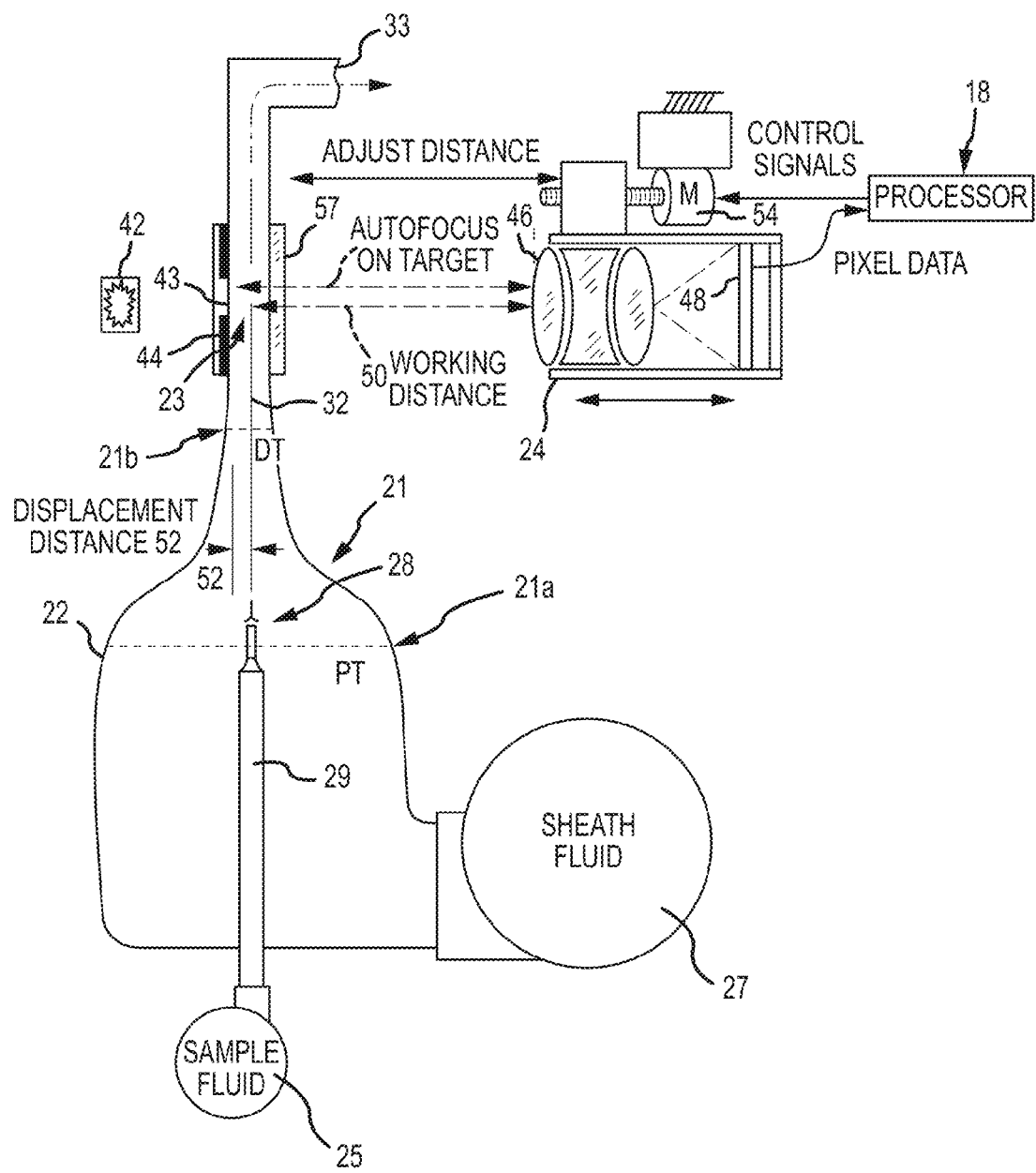
FIG. 1 is a schematic illustration, partly in section and not to scale, showing operational aspects of an exemplary flowcell, and autofocus system and high optical resolution imaging device for sample image analysis using digital image processing.

The present disclosure relates to analyzer, systems, compositions, and methods for analyzing a urine sample containing particles. In one embodiment, the invention relates to an automated particle imaging system which may comprise an visual analyzer. In some embodiments, the visual analyzer may further comprise a processor to facilitate automated analysis of the images. Exemplary urine particles can include urine sediment particles. Exemplary urine sediment particles can include erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments. Exemplary cells can include red blood cells, white blood cells, and epithelials. Exemplary casts can include acellular pigment casts, unclassified cast (e.g. granular casts). Exemplary acellular casts can include, for example, waxy casts, broad casts, fatty casts, and crystal casts. Exemplary cellular casts can include, for example, RBC casts, WBC casts, and cellular casts. Exemplary crystals can include, for example, calcium oxalate, triple phosphate, calcium phosphate, uric acid, calcium carbonate, leucine, cystine, tyrosine, and amorphous crystals. Exemplary non-squamous epithelial cells can include, for example, renal epithelials and transitional epithelials. Exemplary yeast can include, for example, budding yeast and yeast with pseudohyphae. Exemplary urinary sediment particle can also include RBC clumps, fat, oval fat bodies, and trichomonas.

According to this disclosure, a system comprising an analyzer is provided for obtaining images of a sample comprising particles suspended in a liquid. The system may be useful, for example, in characterizing particles in biological fluids, such as detecting and quantifying erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments, categorization and subcategorization, counting and analysis. Other similar uses such as characterizing cells and particles from other fluids are also contemplated.

The discrimination of urine sediment particles in a urine sample is an exemplary application for which the subject matter is particularly well suited. The sample is prepared by automated techniques and presented to a high optical resolution imaging device as a thin, ribbon-shaped sample stream to be imaged periodically while the ribbon-shaped sample stream flows across a field of view. The images of the particles (such as in urine) can be distinguished from one another, categorized, subcategorized, and counted, using pixel image data programmed processing techniques, either exclusively automatically or with limited human assistance, to identify and count cells and/or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cell counts of each distinguished category and/or subcategory in the sample as a whole. The sample used for image-based (e.g., visual) discrimination can be diluted, but the ratios of cell counts in each category and/or subcategory are proportionally represented in the diluted sample, particularly after a number of images have been processed.

Urinalysis—Particle Analysis System

Turning now to the drawings, FIG. 1 schematically shows an exemplary flowcell 22 for conveying a sample fluid through a viewing zone 23 of a high optical resolution imaging device 24 in a configuration for imaging microscopic particles in a sample flow stream 32 using digital image processing. Flowcell 22 is coupled to a source 25 of sample fluid which may have been subjected to processing, such as contact with a particle contrast agent composition and heating. Flowcell 22 is also coupled to one or more sources 27 of sheath fluid or a particle and/or intracellular organelle alignment liquid (PIOAL), such as a clear glycerol solution having a viscosity that is greater than the viscosity of the sample fluid.

The sample fluid is injected through a flattened opening at a distal end 28 of a sample feed tube 29, and into the interior of the flowcell 22 at a point where the PIOAL flow has been substantially established resulting in a stable and symmetric laminar flow of the PIOAL above and below (or on opposing sides of) the ribbon-shaped sample stream. The sample and PIOAL streams may be supplied by precision metering pumps that move the PIOAL with the injected sample fluid along a flowpath that narrows substantially. The PIOAL envelopes and compresses the sample fluid in the zone 21 where the flowpath narrows. Hence, the decrease in flowpath thickness at zone 21 can contribute to a geometric focusing of the sample stream 32. The sample fluid ribbon 32 is enveloped and carried along with the PIOAL downstream of the narrowing zone 21, passing in front of, or otherwise through the viewing zone 23 of, the high optical resolution imaging device 24 where images are collected, for example, using a CCD 48. Processor 18 can receive, as input, pixel data from CCD 48. The sample fluid ribbon flows together with the PIOAL to a discharge 33.

As shown here, the narrowing zone 21 can have a proximal flowpath portion 21a having a proximal thickness PT and a distal flowpath portion 21b having a distal thickness DT, such that distal thickness DT is less than proximal thickness PT. The sample fluid can therefore be injected through the distal end 28 of sample tube 29 at a location that is distal to the proximal portion 21a and proximal to the distal portion 21b. Hence, the sample fluid can enter the PIOAL envelope as the PIOAL stream is compressed by the zone 21.

The digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

The present disclosure provides a technique for automatically achieving a correct working position of the high optical resolution imaging device 24 for focusing on the ribbon-shaped sample stream 32. The flowcell structure 22 can be configured such that the ribbon-shaped sample stream 32 has a fixed and dependable location within the flowcell defining the flow path of sample fluid, in a thin ribbon between layers of PIOAL, passing through a viewing zone 23 in the flowcell 22. In certain flowcell embodiments, the cross section of the flowpath for the PIOAL narrows symmetrically at the point at which the sample is inserted through a flattened orifice such as a tube 29 with a rectangular lumen at the orifice, or cannula. The narrowing flowpath (for example geometrically narrowing in cross sectional area by a ratio of 20:1, or by a ratio between 20:1 to 70:1) along with a differential viscosity between the PIOAL and sample fluids, and optionally, a difference in linear speed of the PIOAL compared to the flow of the sample, cooperate to compress the sample cross section by a ratio of about 20:1 to 70:1. In some embodiments the cross section thickness ratio may be 40:1.

In one aspect, the symmetrical nature of the flowcell 22 and the manner of injection of the sample fluid and PIOAL provide a repeatable position within the flowcell 22 for the ribbon-shaped sample stream 32 between the two layers of the PIOAL. As a result, process variations such as the specific linear velocities of the sample and the PIOAL; do not tend to displace the ribbon-shaped sample stream from its location in the flow. Relative to the structure of the flowcell 22, the ribbon-shaped sample stream 32 location is stable and repeatable.

However, the relative positions of the flowcell 22 and the high optical resolution imaging device 24 of the optical system may be subject to change and may benefit from occasional position adjustments to maintain an optimal or desired distance between the high optical resolution imaging device 24 and the ribbon-shaped sample stream 32, thus providing a quality focus image of the enveloped particles in the ribbon-shaped sample stream 32. According to some embodiments, there can be an optimal or desired distance between the high optical resolution imaging device 24 and the ribbon-shaped sample stream 32 for obtaining focused images of the enveloped particles. The optics can first be positioned accurately relative to the flowcell 22 by autofocus or other techniques to locate the high optical resolution imaging device 24 at the optimal or desired distance from an autofocus target 44 with a fixed position relative to the flowcell 22. The displacement distance between the autofocus target 44 and the ribbon-shaped sample stream 32 is known precisely, for example as a result of initial calibration steps. After autofocusing on the autofocus target 44, the flowcell 22 and/or high optical resolution imaging device 24 is then displaced over the known displacement distance between the autofocus target 44 and the ribbon-shaped sample stream 32. As a result, the objective lens of the high optical resolution imaging device 44 is focused precisely on the ribbon-shaped sample stream 32 containing the enveloped particles.

Exemplary embodiments of the present invention involve autofocusing on the focus or imaging target 44, which is a high contrast figure defining a known location along the optical axis of the high optical resolution imaging device or the digital image capture device 24. The target 44 can have a known displacement distance relative to the location of the ribbon-shaped sample stream 32. A contrast measurement algorithm can be employed specifically on the target features. In one example, the position of the high optical resolution imaging device 24 can be varied along a line parallel to the optical axis of the high optical resolution imaging device or the digital image capture device, to find the depth or distance at which one or more maximum differential amplitudes are found among the pixel luminance values occurring along a line of pixels in the image that is known to cross over an edge of the contrast figure. In some cases, the autofocus pattern has no variation along the line parallel to the optical axis, which is also the line along which a motorized control operates to adjust the position of the high optical resolution imaging device 24 to provide the recorded displacement distance.

In this way, it may not be necessary to autofocus or rely upon an image content aspect that is variable between different images, that is less highly defined as to contrast, or that might be located somewhere in a range of positions, as the basis for determining a distance location for reference. Having found the location of optimal or desired focus on the autofocus target 44, the relative positions of the high optical resolution imaging device objective 24 and the flowcell 22 can be displaced by the recorded displacement distance to provide the optimal or desired focus position for particles in the ribbon-shaped sample stream 32.

According to some embodiments, the high optical resolution imaging device 24 can resolve an image of the ribbon-shaped sample stream 32 as backlighted by a light source 42 applied through an illumination opening (window) 43. In the embodiments shown in FIG. 1, the perimeter of the illumination opening 43 forms an autofocusing target 44. However the object is to collect a precisely focused image of the ribbon-shaped sample stream 32 through high optical resolution imaging device optics 46 on an array of photosensitive elements, such as an integrated charge coupled device.

The high optical resolution imaging device 24 and its optics 46 are configured to resolve an image of the particles in the ribbon-shaped sample stream 32 that is in focus at distance 50, which distance can be a result of the dimensions of the optical system, the shape of the lenses, and the refractive indices of their materials. In some cases, the optimal or desired distance between the high optical resolution imaging device 24 and the ribbon-shaped sample stream 32 does not change, but the distance between the flowcell 22 and the high optical resolution imaging device and its optics 46 can be changed. Moving the high optical resolution imaging device 24 and/or flowcell 22 closer or further apart, relative to one another (e.g. by adjusting distance 51 between the imaging device 24 and the flowcell 22), moves the location of the focusing point at the end of distance 50 relative to the flowcell.

According to embodiments of the present invention, a focus target 44 can be located at a distance from the ribbon-shaped sample stream 32, in this case fixed directly to the flowcell 22 at the edges of the opening 43 for light from illumination source 42. The focus target 44 is at a constant displacement distance 52 from the ribbon-shaped sample stream 32. Often, the displacement distance 52 is constant because the location of the ribbon-shaped sample stream 32 in the flowcell can remain constant.

An exemplary autofocus procedure involves adjusting the relative positions of the high optical resolution imaging device 24 and flowcell 22 using a motor 54 to cause the high optical resolution imaging device 24 to focus on the autofocus target 44. In this example, the autofocus target 44 is behind the ribbon-shaped sample stream 32 in the flowcell. Then the high optical resolution imaging device 24 and/or flowcell 22 are moved toward one another until autofocus procedures establish that the image resolved on photosensor is an accurately focused image of autofocus target 44. Then motor 54 is operated to displace the relative positions of high optical resolution imaging device 24 and flowcell 22 to cause the high optical resolution imaging device to focus on the ribbon-shaped sample stream 32, namely by moving the high optical resolution imaging device 24 and/or flowcell 22 away from one another, precisely by the span of the displacement distance 52.

These directions of movement would of course be reversed if the focus target 44 was located on the front viewport window as opposed to the rear illumination window 43. In that case, the displacement distance would be the span between the ribbon-shaped sample stream 32 and a target 44 at the front viewport (not shown).

The displacement distance 52, which is equal to the distance between ribbon-shaped sample stream 32 and autofocus target 44 along the optical axis of the high optical resolution imaging device 24, can be established in a factory calibration step. Typically, once established, the displacement distance 52 does not change. Thermal expansion variations and vibrations may cause the precise position of the high optical resolution imaging device 24 and flowcell 22 to vary relative to one another, thus necessitating re-initiation of the autofocus process. But autofocusing on the target 44 provides a position reference that is fixed relative to the flowcell 22 and thus fixed relative to the ribbon-shaped sample stream 32. Likewise, the displacement distance is constant. Therefore, by autofocusing on the target 44 and displacing the high optical resolution imaging device 24 and flowcell 22 by the span of the displacement distance, the result is the high optical resolution imaging device being focused on the ribbon-shaped sample stream 32.

According to some embodiments, the focusing target is provided as a high contrast circle printed or applied around the illumination opening 43. Alternative focusing target configurations are discussed elsewhere herein. When a square or rectangular image is collected in focus on the target 44, a high contrast border appears around the center of illumination. Seeking the position at which the highest contrast is obtained in the image at the inner edges of the opening automatically focuses the high optical resolution imaging device at the working location of the target 44. According to some embodiments, the term "working distance" can refer to the distance between the objective and its focal plane and the term "working location" can refer to the focal plane of the imaging device. The highest contrast measure of an image is where the brightest white and darkest black measured pixels are adjacent to one another along a line through an inner edge. The highest contrast measure can be used to evaluate whether the focal plane of the imaging device is in the desired position relative to the target 44. Other autofocus techniques can be used as well, such as integrating the differences in amplitude between adjacent pixels and seeking the highest sum of differences. In one technique, the sum of differences is calculated at three distances that encompass working positions on either side of the target 44 and matching the resulting values to a characteristic curve, wherein the optimal distance is at the peak value on the curve. Relatedly, exemplary autofocus techniques can involve collecting images of the flow cell target at different positions and analyzes the images to find the best focus position using a metric that is largest when the image of the target is sharpest. During a first step (coarse) the autofocus technique can operate to find a preliminary best position from a set of images collected at 2.5 µm intervals. From that position the autofocus technique can then involve collecting a second set of images (fine) at 0.5 µm intervals, and calculating the final best focus position on the target.

In some cases, the focus target (autofocus pattern) can reside on the periphery of the area of view in which the sample is to appear. It is also possible that the focus target could be defined by contrasting shapes that reside in the field of view, such as that depicted in FIG. 15. Typically, the autofocus target is mounted on the flowcell or attached rigidly in fixed position relative to the flowcell. Under power of a positioning motor controlled by a detector responsive to maximizing the contrast of the image of the autofocusing target, the apparatus autofocuses on the target as opposed to the ribbon-shaped sample stream. Then by displacing the flowcell and/or the high optical resolution imaging device relative to one another, by the displacement distance known to be the distance between the autofocus target and the ribbon-shaped sample stream, the working position of the high optical resolution imaging device is displaced from the autofocus target to the ribbon-shaped sample stream. As a result, the ribbon-shaped sample stream appears in focus in the collected digital image.

In order to distinguish particle types by data processing techniques, such as categories and/or subcategories of red and white blood cells, it is advantageous to record microscopic pixel images that have sufficient resolution and clarity to reveal the aspects that distinguish one category or subcategory from the others. It is an object of the invention to facilitate autofocus techniques as described.

Figure 1A:
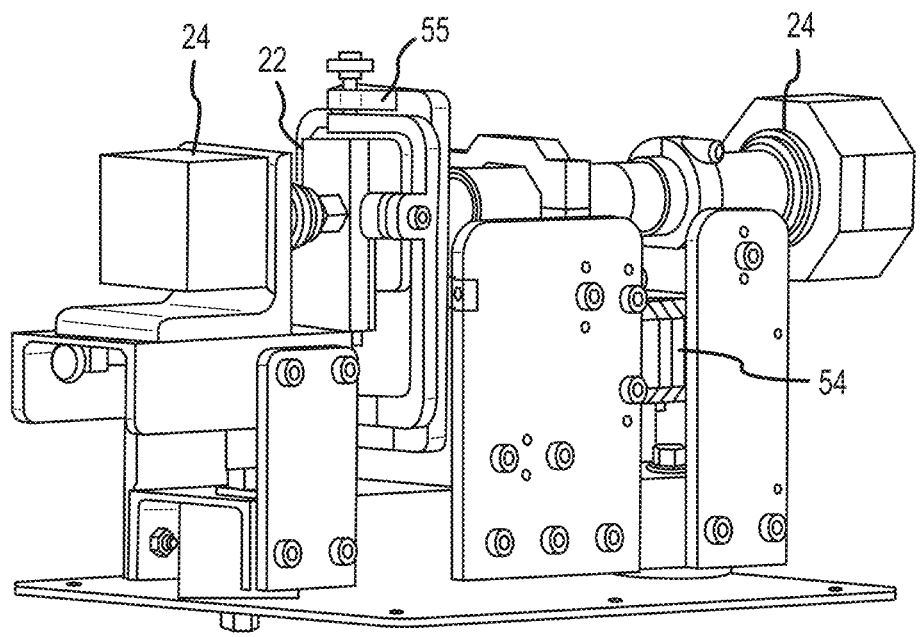
FIGS. 1A and 1B show an optical bench arrangement according to embodiments of the present invention.
Figure 1B:
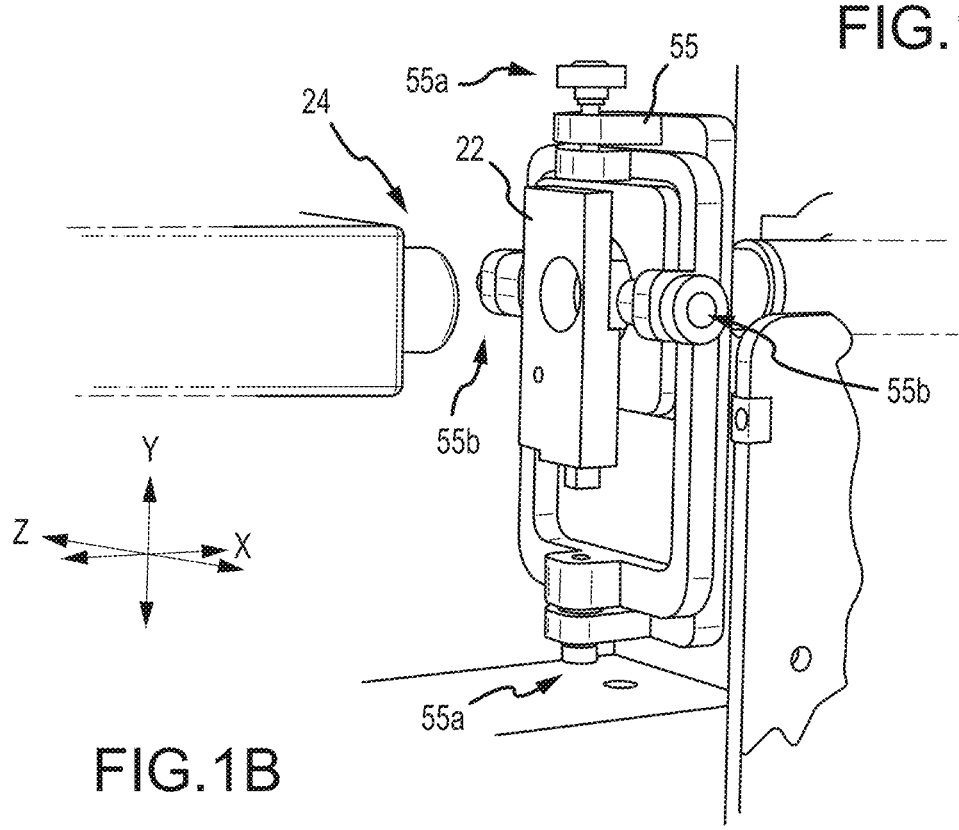

In a practical embodiment, the apparatus can be based on an optical bench arrangement such as shown in FIG. 1A and as enlarged in FIG. 1B, having a source of illumination 42 directed onto a flowcell 22 mounted in a gimbaled carrier 55, backlighting the contents of the flowcell 22 in an image obtained by a high optical resolution imaging device 24. The flow cell carrier 55 is mounted on a motor drive so as to be precisely movable toward and away from the high optical resolution imaging device 24. The gimbaled carrier 55 also allows a precise alignment of the flowcell relative to the optical viewing axis of the high optical resolution imaging device or the digital image capture device, so that the ribbon-shaped sample stream flows in a plane normal to the viewing axis in the zone where the ribbon-shaped sample stream is imaged, namely between the illumination opening 43 and viewing port 57 as depicted in FIG. 1. The focus target 44 can assist in adjustment of the gimbaled carrier 55, for example to establish the plane of the ribbon-shaped sample stream normal to the optical axis of the high optical resolution imaging device or the digital image capture device.

Hence, the carrier or flowcell holder 55 provides for very precise linear and angular adjustment of the position and orientation of flowcell 22, for example relative to the image capture device 24 or the image capture device objective. As shown here, the carrier 55 includes two pivot points 55a, 55b to facilitate angular adjustment of the carrier and flowcell relative to the image capture device. Angular adjustment pivot points 55a, 55b are located in the same plane and centered to the flow cell channel (e.g. at the image capture site). This allows for adjustment of the angles without causing any linear translation of the flow cell position. The carrier 55 can be rotated about an axis of pivot point 55a or about an axis of pivot point 55b, or about both axes. Such rotation can be controlled by a processor and a flowcell movement control mechanism, such as processor 440 and flowcell control mechanism 442 depicted in FIG. 4.

With returning reference to FIG. 1B, it can be seen that either or both of the image capture device 24 and the carrier 55 (along with flowcell 22) can be rotated or translated along various axes (e.g. X, Y, Z) in three dimensions. Hence, an exemplary technique for adjusting focus of the image capture device can include implementing axial rotation of the image capture device 24 about the imaging axis, for example by rotating device 24 about axis X. Focus adjustment can also be achieved by axial rotation of the flowcell 22 and/or carrier carrier 55 about an axis extending along the imaging axis, for example about axis X, and within the field of view of the imaging device. In some cases, focus adjustment may include tip rotation (e.g. rotation about axis Y) of the image capture device. In some cases, focus adjustment may include tip rotation (e.g. rotation about axis Y, or about pivot point 55a) of the flowcell. As depicted here, pivot point 55a corresponds to a Y axis that extends along and within the flowpath of the flowcell. In some cases, focus adjustment can include tilt rotation (e.g. rotation about axis Z) of the image capture device. In some cases, focus adjustment may include tilt rotation (e.g. rotation about axis Z, or about pivot point 55b) of the flowcell. As depicted here, pivot point 55b corresponds to a Z axis that traverses the flowpath and the imaging axis. In some cases, the image capture device can be focused on the sample flowstream by implementing a rotation of the flowcell (e.g. about axis X), such that the rotation is centered in the field of view of the image capture device. The three dimensional rotational adjustments described herein can be implemented so as to account for positional drift in one or more components of the analyzer system. In some cases, the three dimensional rotational adjustments can be implemented so as to account for temperature fluctuations in one or more components of the analyzer system. In some cases, adjustment of an analyzer system may include translating imaging device 24 along axis X. In some cases, adjustment of analyzer system may include translating carrier 55 or flowcell 22 along axis X.

According to some embodiments, a visual analyzer for obtaining images of a sample containing particles suspended in a liquid includes flowcell 22, coupled to a source 25 of the sample and to a source 27 of sheath fluid or PIOAL material as depicted in FIG. 1. As seen in the section view of FIG. 3, the flowcell 22 defines an internal flowpath that narrows symmetrically in the flow direction (right to left in FIG. 3 or bottom to top in FIG. 1). The flowcell 22 is configured to direct a flow 32 of the sample enveloped with the PIOAL through a viewing zone in the flowcell, namely behind viewing port 57.

Referring again to FIG. 1, the digital high optical resolution imaging device 24 with objective lens 46 is directed along an optical axis that intersects the ribbon-shaped sample stream 32. The relative distance between the objective 46 and the flowcell 33 is variable by operation of a motor drive 54, for resolving and collecting a focused digitized image on a photosensor array.

The autofocus pattern 44, having a position that is fixed relative to the flowcell 22, is located at a displacement distance 52 from the plane of the ribbon-shaped sample stream 32. In the embodiment shown, the autofocus pattern (target 44) is applied directly to the flowcell 22 at a location that is visible in the image collected by the high optical resolution imaging device 24. In another embodiment, the target can be carried on a part that is rigidly fixed in position relative to the flowcell 22 and the ribbon-shaped sample stream 32 therein, if not applied directly to the body of the flowcell in an integral manner.

The light source 42, which can be a steady source or can be a strobe that is flashed in time with operation of the high optical resolution imaging device photosensor, is configured to illuminate the ribbon-shaped sample stream 32 and also to contribute to the contrast of the target 44. In the depicted embodiment, the illumination is from back-lighting.

Figure 1C:
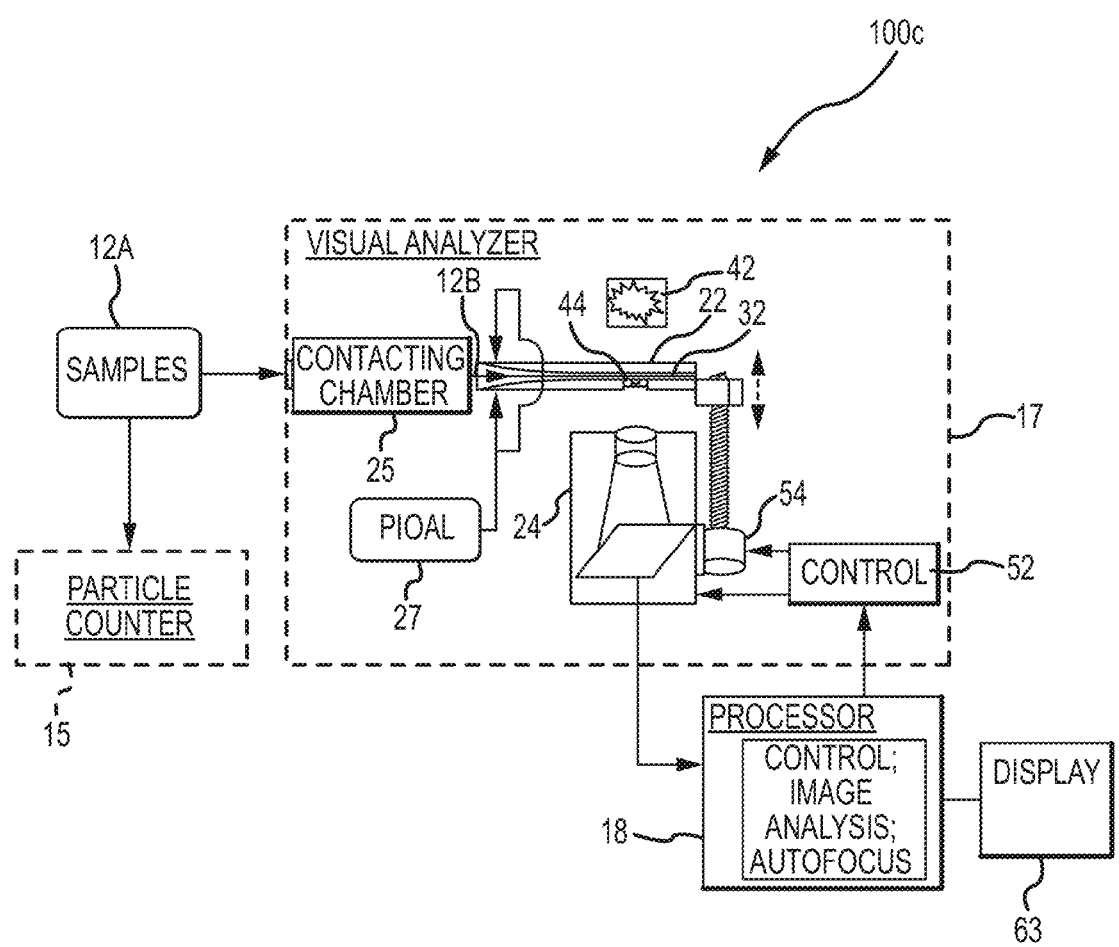
FIG. 1C is a block diagram of a urinalysis analyzer according to embodiments of the present invention.

FIG. 1C provides a block diagram showing additional aspects of an exemplary urinalysis analyzer. As shown here, the analyzer 100c includes at least one digital processor 18 coupled to operate the motor drive 54 and to analyze the digitized image from the photosensor array as collected at different focus positions relative to the target autofocus pattern 44. The processor 18 is configured to determine a focus position of the autofocus pattern 44, i.e., to autofocus on the target autofocus pattern 44 and thus establish an optimal distance between the high optical resolution imaging device 24 and the autofocus pattern 44. This can be accomplished by image processing steps such as applying an algorithm to assess the level of contrast in the image at a first distance, which can apply to the entire image or at least at an edge of the autofocus pattern 44. The processor moves the motor 54 to another position and assesses the contrast at that position or edge, and after two or more iterations determines an optimal distance that maximizes the accuracy of focus on the autofocus pattern 44 (or would optimize the accuracy of focus if moved to that position). The processor relies on the fixed spacing between the autofocus target autofocus pattern 44 and the ribbon-shaped sample stream, the processor 18 then controls the motor 54 to move the high optical resolution imaging device 24 to the correct distance to focus on the ribbon-shaped sample stream 32. More particularly, the processor operates the motor to displace the distance between the high optical resolution imaging device and the ribbon-shaped sample stream 32 by the displacement distance 52 (for example as depicted in FIG. 1) by which the ribbon-shaped sample stream is displaced from the target autofocus pattern 44. In this way, the high optical resolution imaging device is focused on the ribbon-shaped sample stream.

The motor 54 can comprise a geared stepping motor with precision somewhat smaller than the distinguishing features imaged by the high optical resolution imaging device or the digital image capture device, especially aspects of blood cells. Provided that the location of the high optical resolution imaging device 24 is adjusted to locate the position of the optical objective within the width of the ribbon-shaped sample stream, the view of the cell/particle in the ribbon-shaped sample stream is in focus. An autofocus pattern 44 can be located at an edge of a field of view of the high optical resolution imaging device or the digital image capture device, and does not interfere with viewing for that reason.

Figure 15:
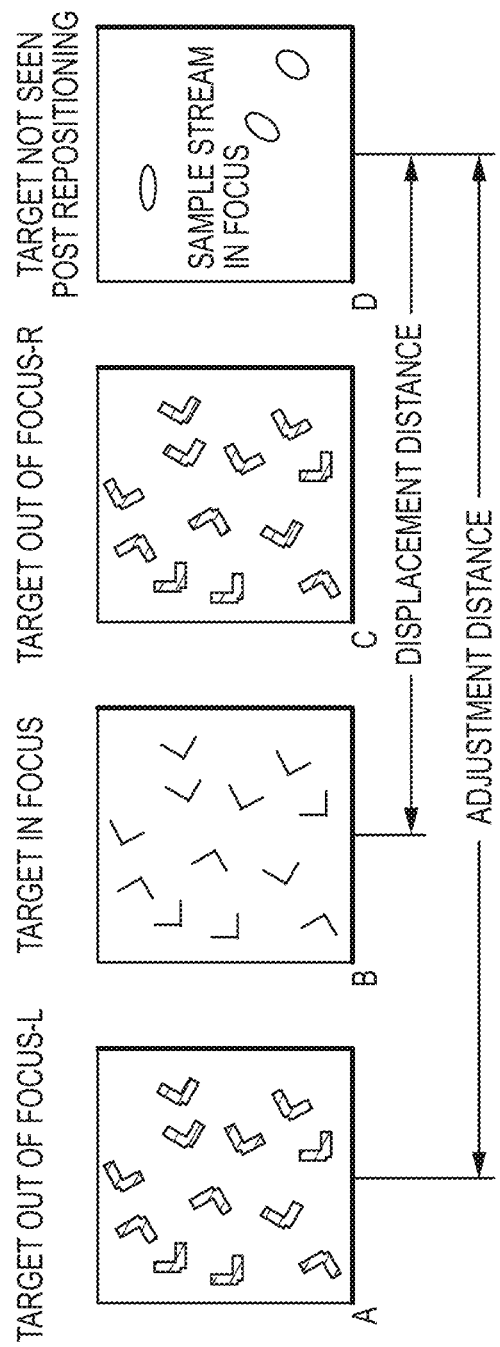
FIG. 15 depicts aspects of autofocus pattern and focusing techniques, according to embodiments of the present invention.

Furthermore, when the high optical resolution imaging device is moved over the displacement distance and the autofocus pattern goes out of focus, the features that appear in focus are the blood cells as opposed to the autofocus pattern. In the embodiment of FIG. 15, for example, the autofocus pattern is defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 μm in a flowcell dimensioned for urinalysis imaging applications. In some embodiments, the autofocus feature maintains the high optical resolution imaging device within 1 μm of the optimal focus distance.

The flowcell internal contour and the PIOAL and sample flow rates can be adjusted such that the sample is formed into a ribbon shaped stream. The stream can be approximately as thin as or even thinner than the particles that are enveloped in the ribbon-shaped sample stream. White blood cells may have a diameter around 10 µm, for example. By providing a ribbon-shaped sample stream with a thickness less than 10 µm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second. Another embodiment of the sheath fluid may be LAMINA™ (IRIS International, Inc.) solution. LAMINA™ may have a pH around 7.0 and a specific gravity of 1.007 at 20° C. In a related embodiment, a sheath fluid can be provides as a saline solution. In some embodiments, the sheath fluid is an aqueous salt composition. In some embodiments, the viscosity of the sheath fluid is the same as or similar to the viscosity of the sample fluid.

The ribbon-shaped sample stream thickness can be affected by the relative viscosities and flow rates of the sample fluid and the PIOAL. With returning reference to FIG. 1, the source 25 of the sample and/or the source 27 of the sheath fluid or PIOAL, for example comprising precision displacement pumps, can be configured to provide the sample and/or the PIOAL at controllable flow rates for optimizing the dimensions of the ribbon-shaped sample stream 32, namely as a thin ribbon at least as wide as the field of view of the high optical resolution imaging device 24.

In one embodiment, the source 27 of the sheath fluid or PIOAL is configured to provide the PIOAL at a predetermined viscosity. That viscosity may be different than the viscosity of the sample, and can be higher than the viscosity of the sample. The viscosity and density of the PIOAL, the viscosity of the sample material, the flow rate of the PIOAL and the flow rate of the sample material are coordinated to maintain the ribbon-shaped sample stream at the displacement distance from the autofocus pattern, and with predetermined dimensional characteristics, such as an advantageous ribbon-shaped sample stream thickness.

In a practical embodiment, the PIOAL has a higher linear velocity than the sample and a higher viscosity than the sample, thereby stretching the sample into the flat ribbon. In some cases the PIOAL viscosity can be up to 10 centipoise.

In the embodiment shown in FIG. 1C, the same digital processor 18 that is used to analyze the pixel digital image obtained from photosensor array is also used to control the autofocusing motor 54. However typically the high optical resolution imaging device 24 is not autofocused for every image captured. The autofocus process can be accomplished periodically (at the beginning of the day or at the beginning of a shift) or for example when temperature or other process changes are detected by appropriate sensors, or when image analysis detects a potential need for refocusing. In some cases, an automated autofocusing process may be performed within a time duration of about 10 seconds. In some cases, an autofocus procedure can be performed prior to processing a rack of samples (e.g. 10 samples per rack). It is also possible in other embodiments to have the urine sample image analysis accomplished by one processor and to have a separate processor, optionally associated with its own photosensor array, arranged to handle the steps of autofocusing to a fixed target 44.

The digital processor 18 can be configured to autofocus at programmed times or in programmed conditions or on user demand, and also is configured to perform image based categorization and subcategorization of the particles. Exemplary particles include cells, white blood cells, red blood cells and the like.

In one embodiment, the digital processor 18 of FIG. 1 or FIG. 1C is configured to detect an autofocus re-initiation signal. The autofocus re-initiation signal can be triggered by a detected change in temperature, a decrease in focus quality as discerned by parameters of the pixel image date, passage of time, or user-input. Advantageously, it is not necessary to recalibrate in the sense of measuring the displacement distance 52 depicted in FIG. 1 to recalibrate. Optionally, the autofocus can be programmed to re-calibrate at certain frequencies/intervals between runs for quality control and or to maintain focus.

The displacement distance 52 varies slightly from one flowcell to another, but remains constant for a given flowcell. As a setup process when fitting out an image analyzer with a flowcell, the displacement distance is first estimated and then during calibration steps wherein the autofocus and imaging aspects are exercised, the exact displacement distance for the flowcell is determined and entered as a constant into the programming of processor 18.

Figure 1D:
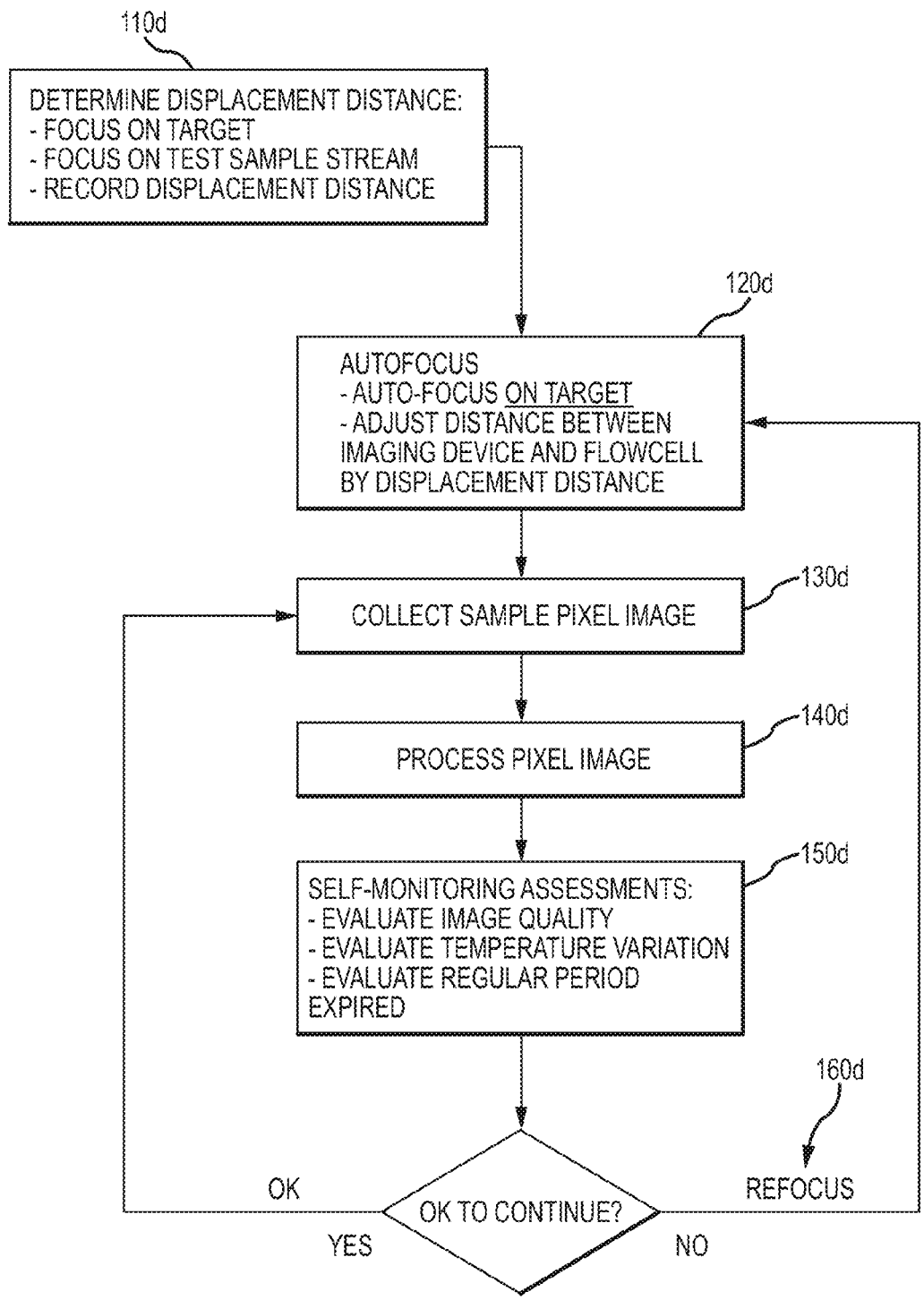
FIG. 1D shows a flowchart of a process according to embodiments of the present invention.

Accordingly, as shown in flowchart form in FIG. 1D, and with reference to urinalysis analyzer of FIG. 1 and/or FIG. 1C, the process undertaken according to the disclosed methods and apparatus may involve calibrating once or rarely. Calibration can include focusing on the contrast target 44, focusing on the ribbon-shaped sample stream 32, and noting the displacement along the optical axis between these two locations, as indicated in step 110*d*. That displacement can be noted as a constant. Thereafter by controlling motor 54 and analyzing image data from photosensor array, the processor 18 autofocuses on target 44 and displaces the high optical resolution imaging device 24 and/or flowcell 22 relative to one another by the noted displacement distance, as indicated in step 120*d*. The ribbon-shaped sample stream 32 is then in focus and its image can be collected (as indicated in step 130*d*) and processed (as indicated in step 140*d*) at regular intervals, especially at intervals sufficient to collect substantially non-overlapping adjacent views of portions of the ribbon-shaped sample stream passing through the viewing zone at viewing port 57. When self-monitoring (as indicated in step 150*d*) reveals a data anomaly or a temperature change that might have altered relative positions of the high optical resolution imaging device 24 and flowcell 22 due to differences in thermal expansion, then autofocus (at indicated in step 160*d*) is initiated, after which regular operation resumes. Hence, an autofocusing process may include detecting an autofocus re-initiation signal, and repeating autofocusing and image acquisition steps in response to the auto-focus re-initiation signal. In some embodiments the autofocus re-initiation signal can include or be based on change in temperature, a decrease in focus quality, a lapsed time interval, or a user-input.

The linear velocity of the ribbon-shaped sample stream can be limited sufficiently to prevent motion blurring of the digitized image at the image exposure time of the photosensor array. The light source can optionally be a strobe light that is flashed to apply high incident amplitude for a brief time. Inasmuch as the autofocus pattern 44 and the image are in the same field of view, the light source is configured to illuminate the ribbon-shaped sample stream and the autofocus pattern simultaneously. However in other embodiments, the field of view for imaging and for autofocus can be different, e.g., illuminated and/or imaged separately.

The subject developments have method as well as apparatus aspects. A method of focusing a visual analyzer comprises focusing a high optical resolution imaging device 24, which may be a digital high optical resolution imaging device or the digital image capture device, on an autofocus pattern 44 fixed relative to a flowcell 22, wherein the autofocus pattern 44 is located at a displacement distance 52 from a ribbon-shaped sample stream 32. The digital high optical resolution imaging device 24 has an objective with an optical axis that intersects the ribbon-shaped sample stream 32. A relative distance between the objective and the flowcell 22 is varied by operation of a motor drive 54, whereas the distance along the optical axis between the high optical resolution imaging device and the point of optimal focus is known. The digital high optical resolution imaging device is configured to resolve and collect a digitized image on a photosensor array. The motor drive is operated to focus on the autofocus pattern in an autofocus process. The motor drive then is operated over the displacement distance, thereby focusing the high optical resolution imaging device on the ribbon-shaped sample stream.

It is possible to use autofocusing on the target and displacement by the displacement distance to obtain a distance appropriate for focusing on the ribbon-shaped sample stream. Advantageously, however, autofocusing is not needed or repeated for each image capture. However autofocusing is commenced on certain conditions. An autofocus re-initiation signal can be detected or generated, leading to steps of refocusing on the autofocus pattern, operating the motor drive over the displacement distance, and refocusing the high optical resolution imaging device on the ribbon-shaped sample stream. The autofocus re-initiation signal can be cause by detection of a change for example in temperature, a decrease in focus quality, the passage of time, other process parameters or user-input.

Figure 1E:
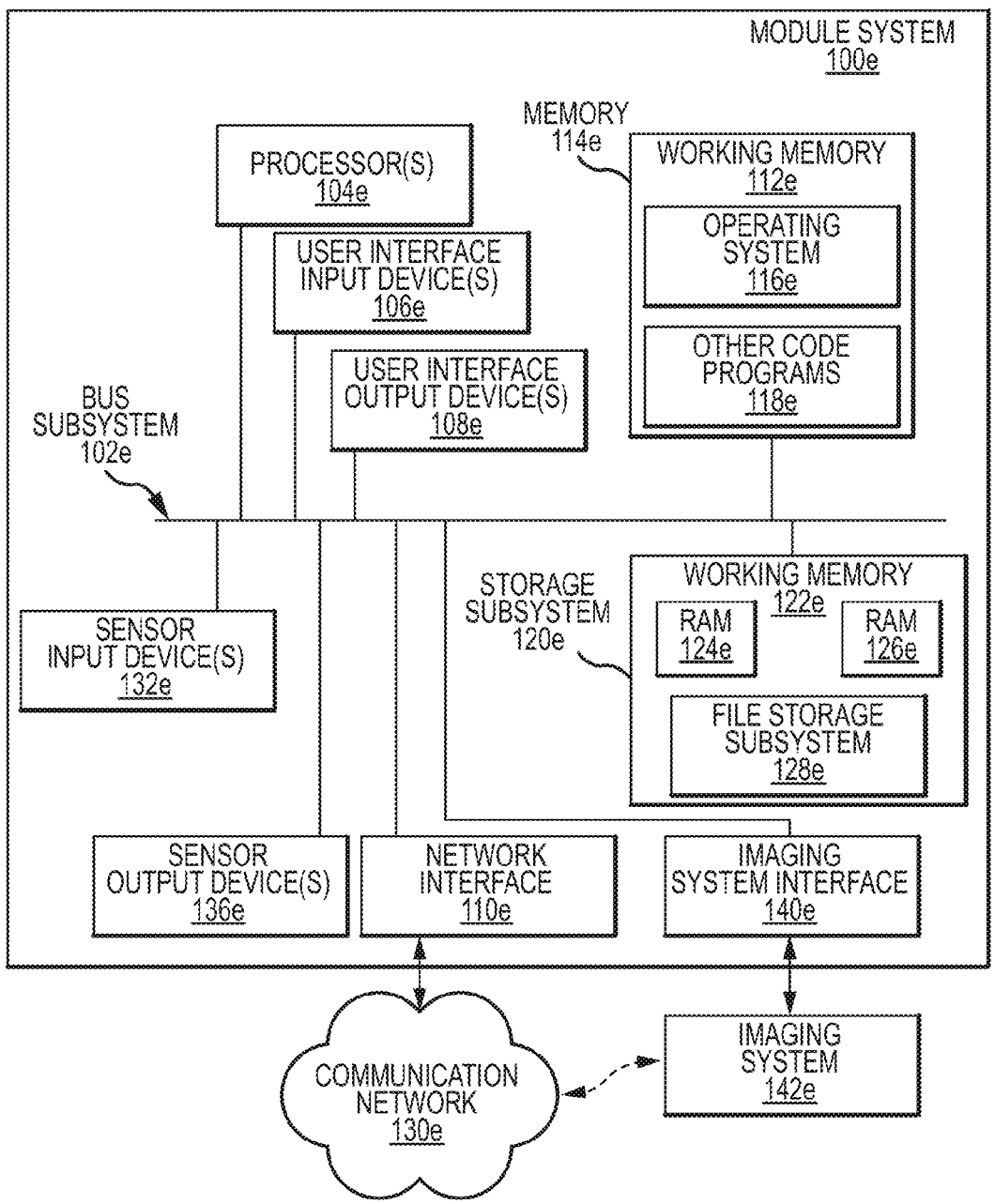
FIG. 1E depicts aspects of a module system according to embodiments of the present invention.

FIG. 1E is a simplified block diagram of an exemplary module system that broadly illustrates how individual system elements for a module system 100e may be implemented in a separated or more integrated manner. Module system 100e may be part of or in connectivity with a particle analysis system for imaging particles in a body fluid sample, such as a urine sample, according to embodiments of the present invention. Module system 100e is well suited for producing data or instructions related to focusing and imaging techniques, receiving input related to focusing and imaging techniques, and/or processing information or data related to focusing and imaging techniques, as described elsewhere herein. In some instances, module system 100e includes hardware elements that are electrically coupled via a bus subsystem 102e, including one or more processors 104e, one or more input devices 106e such as user interface input devices, and/or one or more output devices 108e such as user interface output devices. In some instances, system 100e includes a network interface 110e, and/or an imaging system interface 140e that can receive signals from and/or transmit signals to an imaging system 142e. In some instances, system 100e includes software elements, for example shown here as being currently located within a working memory 112e of a memory 114e, an operating system 116e, and/or other code 118e, such as a program configured to implement one or more aspects of the techniques disclosed herein.

In some embodiments, module system 100e may include a storage subsystem 120e that can store the basic programming and data constructs that provide the functionality of the various techniques disclosed herein. For example, software modules implementing the functionality of method aspects, as described herein, may be stored in storage subsystem 120e. These software modules may be executed by the one or more processors 104e. In a distributed environment, the software modules may be stored on a plurality of computer systems and executed by processors of the plurality of computer systems. Storage subsystem 120e can include memory subsystem 122e and file storage subsystem 128e. Memory subsystem 122e may include a number of memories including a main random access memory (RAM) 126e for storage of instructions and data during program execution and a read only memory (ROM) 124e in which fixed instructions are stored. File storage subsystem 128e can provide persistent (non-volatile) storage for program and data files, and may include tangible storage media which may optionally embody sample, patient, treatment, assessment, or other data. File storage subsystem 128e may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 100e. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 128e. In some embodiments, the software or code will provide protocol to allow the module system 100e to communicate with communication network 130e. Optionally, such communications may include dial-up or internet connection communications.

It is appreciated that system 100e can be configured to carry out various aspects of methods of the present invention. For example, processor component or module 104e can be a microprocessor control module configured to receive temperature parameter signals and/or flowcell operational parameters from a sensor input device or module 132e, from a user interface input device or module 106e, and/or from an imaging system 142e, optionally via an image system interface 140e and/or a network interface 110e and a communication network 130e. In some instances, sensor input device(s) may include or be part of a particle analysis system that is equipped to obtain images of body fluid samples such as urine samples. In some instances, user interface input device(s) 106e and/or network interface 110e may be configured to receive image parameter signals generated by a particle analysis system that is equipped to obtain image parameters. In some instances, imaging system 142e may include or be part of a particle analysis system that is equipped to obtain image parameters related to body fluid samples, such as urine samples.

Processor component or module 104e can also be configured to transmit particle analysis parameter signals or image parameter signals, optionally processed according to any of the techniques disclosed herein, to sensor output device or module 136e, to user interface output device or module 108e, to network interface device or module 110e, to imaging system interface 140e, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, MacIntosh, and Unix, along with any of a variety of commonly used programming languages, may be used to implement embodiments of the present invention.

User interface input devices 106e may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 106e may also download a computer executable code from a tangible storage media or from communication network 130e, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 100e.

User interface output devices 106e may include, for example, a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from module system 100e to a user.

Bus subsystem 102e provides a mechanism for letting the various components and subsystems of module system 100e communicate with each other as intended or desired. The various subsystems and components of module system 100e need not be at the same physical location but may be distributed at various locations within a distributed network. Although bus subsystem 102e is shown schematically as a single bus, alternate embodiments of the bus subsystem may utilize multiple busses.

Network interface 110e can provide an interface to an outside network 130e or other devices. Outside communication network 130e can be configured to effect communications as needed or desired with other parties. It can thus receive an electronic packet from module system 100e and transmit any information as needed or desired back to module system 100e. As depicted here, communication network 130e and/or imaging system interface 142e may transmit information to or receive information from an imaging system 142e that is equipped to obtain images or image parameters corresponding to body fluid samples, such as urine samples.

In addition to providing such infrastructure communications links internal to the system, the communications network system 130e may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 100e itself can be of varying types including a computer terminal, a personal computer, a portable computer, a workstation, a network computer, or any other data processing system. Due to the ever-changing nature of computers and networks, the description of module system 100e depicted in FIG. 1E is intended only as a specific example for purposes of illustrating one or more embodiments of the present invention. Many other configurations of module system 100e are possible having more or less components than the module system depicted in FIG. 1E. Any of the modules or components of module system 100e, or any combinations of such modules or components, can be coupled with, or integrated into, or otherwise configured to be in connectivity with, any of the particle analysis and/or imaging system embodiments disclosed herein. Relatedly, any of the hardware and software components discussed above can be integrated with or configured to interface with other medical assessment or treatment systems used at other locations.

In some embodiments, the module system 100e can be configured to receive one or more image parameters of a body fluid sample, such as a urine sample, at an input module. Image parameter data can be transmitted to an assessment module where diagnostic or other results can be predicted or determined based on analysis of the image data. Image or diagnostic data can be output to a system user via an output module. In some cases, the module system 100e can determine diagnostic results for a body fluid sample, such as a urine sample, for example by using a diagnostic module. The diagnostic information can be output to a system user via an output module. Optionally, certain aspects of the diagnosis can be determined by an output device, and transmitted to a diagnosis system or a sub-device of a diagnosis system. Any of a variety of data related to the body fluid samples, such as urine samples, or patients from whom samples are obtained can be input into the module system, including age, weight, sex, treatment history, medical history, and the like. Parameters of treatment regimens or diagnostic evaluations can be determined based on such data.

Relatedly, in some instances a system includes a processor configured to receive the image data as input. Optionally, a processor, storage medium, or both, may be incorporated within a urinalysis or particle analysis machine. In some instances, the urinalysis machine may generate image data or other information for input into the processor. In some instances, a processor, a storage medium, or both, can be incorporated within a computer, and the computer can be in communication with a urinalysis machine. In some instances, a processor, a storage medium, or both, can be incorporated within a computer, and the computer can be in remote communication with a urinalysis machine via a network.

Flowcell

Figure 2:
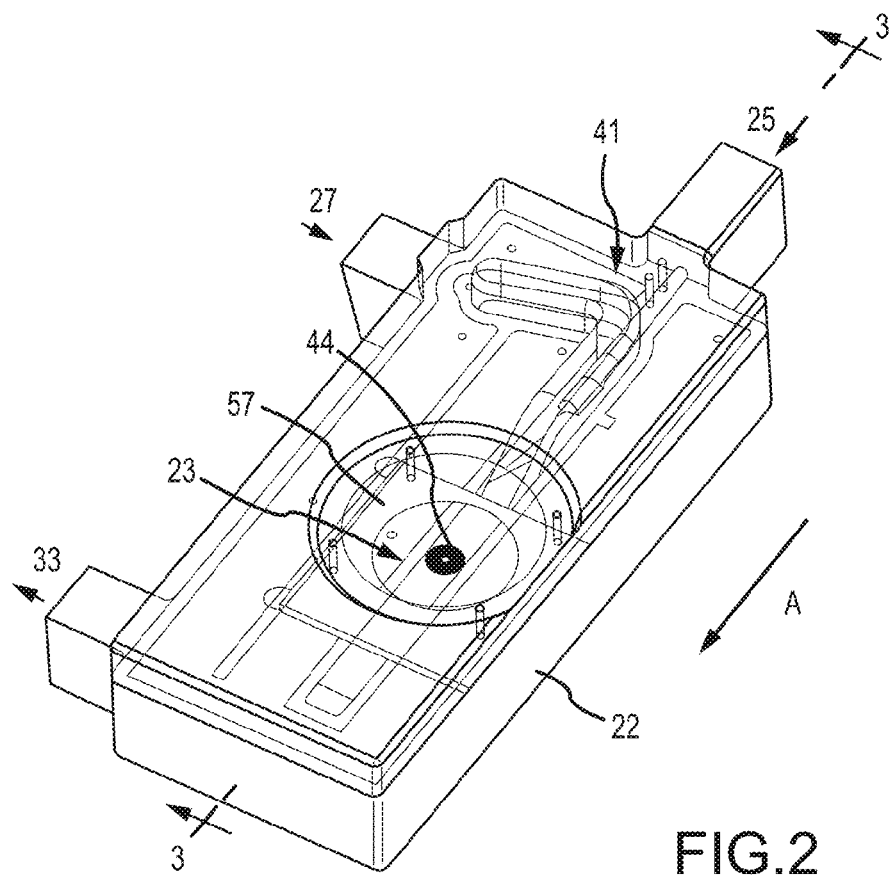
FIG. 2 is a perspective illustration of a flowcell according to an exemplary embodiment.
Figure 3:
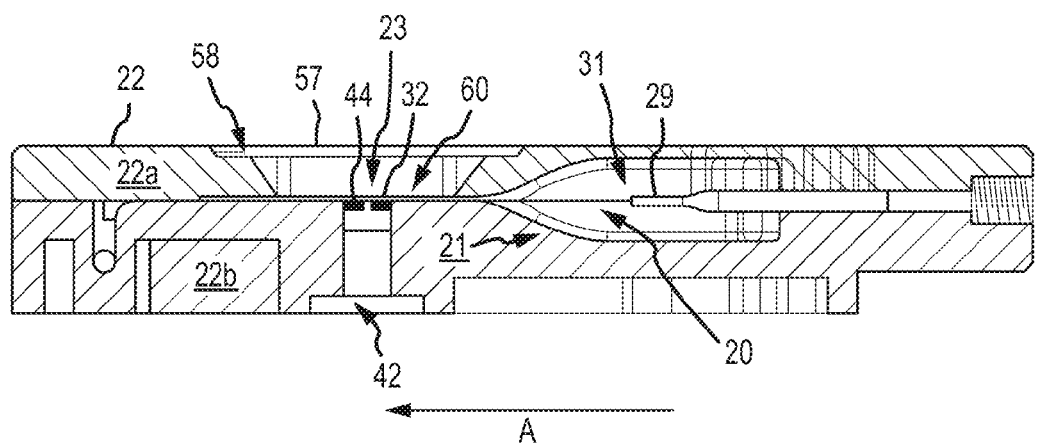
FIG. 3 is a longitudinal median section view along lines 3-3 of the flowcell shown in FIG. 2.

A practical embodiment of flowcell 22 is further depicted in FIGS. 2 and 3. As shown here, flowcell 22 can be coupled with a sample source 25 and also to a source 27 of sheath fluid or PIOAL material. The sample fluid is injected into the flowcell 22 via the cannula 29, for example through a distal exit port 31 of the cannula 29. Typically, the PIOAL sheath fluid is not in a laminar flow state as it travels through a curved channel section 41 in the flowcell from the source 27 toward the viewing zone 23. However, the flowcell 22 can be configured so that the PIOAL sheath fluid is or becomes laminar, or presents a flat velocity profile, as it flows past the distal exit port 31 where sample fluid is introduced into the flowing sheath fluid. The sample fluid and the PIOAL can flow along the flowcell 22 in a direction generally indicated by arrow A, and then out of the flowcell 22 via discharge 33. The flowcell 22 defines an internal flowpath 20 that narrows symmetrically (e.g. at transition zone 21) in the flow direction A. The symmetry of the flowpath contributes to a robust and centered flow of the sample stream. The flowcell 22 is configured to direct a flow 32 of the sample enveloped with the PIOAL through a viewing zone 23 in the flowcell, namely behind viewing port 57. Associated with the viewport 57 is an autofocus pattern 44. Flowcell 22 also has a rounded or recessed seat 58 which is configured to accept or receive a microscope objective (not shown).

According to some embodiments, the autofocus pattern 44 can have a position that is fixed relative to the flowcell 22, and that is located at a displacement distance from the plane of the ribbon-shaped sample stream 32. In the embodiment shown here, the autofocus pattern (target 44) is applied directly to the flowcell 22 at a location that is visible in an image collected through viewport 57 by a high optical resolution imaging device (not shown). Flowcell 22 can be constructed of a first or upper section or layer 22a and a second or lower section or layer 22b. As shown here, a glass or transparent window pane 60 is attached to or integral with the first section 22a. The pane 60 can define at least a portion of the sample flowpath within the flowcell. Light from light source 42 can travel through an aperture or passage of the autofocus pattern 44 so as to illuminate sample particles flowing within the flow stream 32.

In some cases, the thickness of pane 60 can have a value within a range from about 150 µm to about 170 µm. As noted above, the pane 60 can define or form part of the flowpath or sheath (e.g. PIOAL) channel. By using a thin pane 60, it is possible to place the microscope objective very close to the sample fluid ribbon, and hence obtain highly magnified images of particles flowing along the flowpath.

Figure 3A:
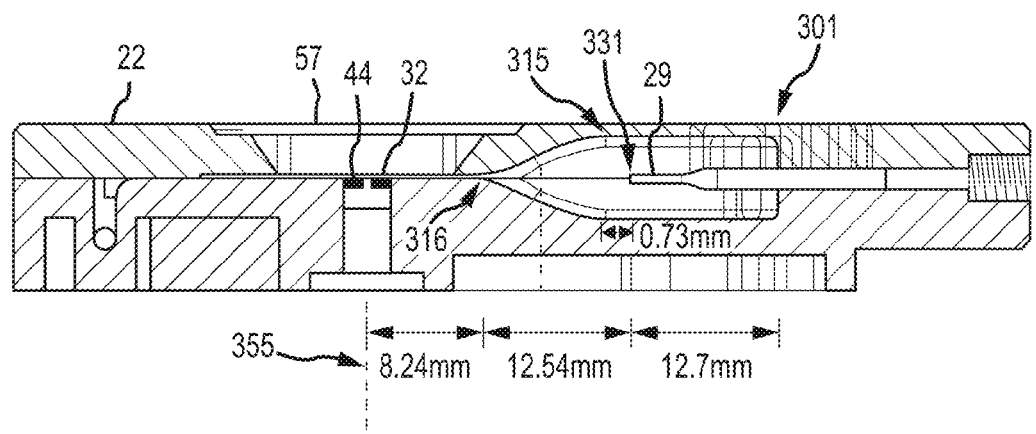
FIGS. 3A and 3B provide additional section views of flowcells according to embodiments of the present invention.
Figure 3B:
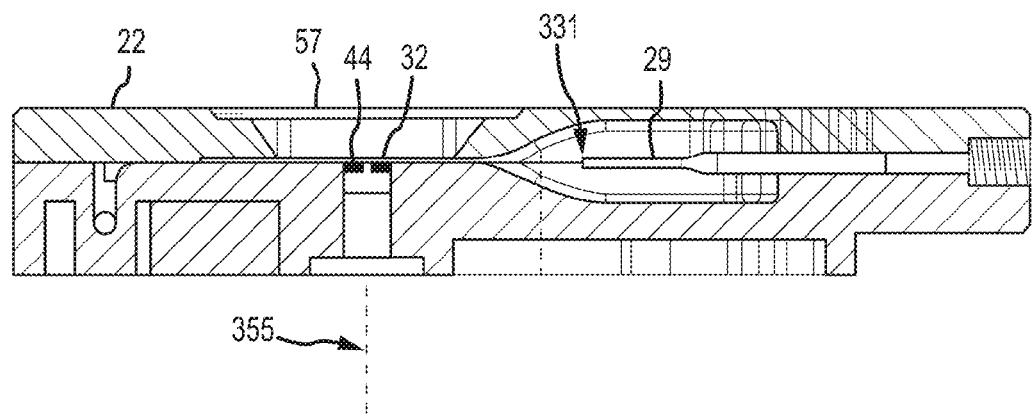

FIG. 3A depicts aspects of a flowcell embodiment, where a distance between the imaging axis 355 and the distal transition zone portion 316 is about 8.24 mm. A distance between the distal transition zone portion 316 and the cannula exit port 331 is about 12.54 mm. A distance between the cannula exit port 331 and the sheath fluid entrance 301 is about 12.7 mm. A distance between the cannula exit port 331 and a proximal transition zone portion 318 is about 0.73 mm. FIG. 3B depicts aspects of a flowcell embodiment where the cannula exit port has been moved to a more distal location relative transition zone, as compared to the FIG. 3A embodiment. As shown here, the cannula distal end is advanced into the narrowing transition zone of the flowcell, and a distance between the imaging axis 355 and the distal transition zone portion 316 is within a range from about 16 mm to about 26 mm. In some case, the distance between the imaging axis 355 and the distal transition zone portion 316 is about 21 mm.

With returning reference to FIG. 1, the flowcell internal contour (e.g. at transition zone 21) and the PIOAL and sample flow rates can be adjusted such that the sample is formed into a ribbon shaped stream 32. The stream can be approximately as thin as or even thinner than the particles that are enveloped in the ribbon-shaped sample stream. White blood cells may have a diameter around 10 µm, for example. By providing a ribbon-shaped sample stream with a thickness less than 10 µm, the cells may be oriented when the ribbon-shaped sample stream is stretched by the sheath fluid, or PIOAL. Surprisingly stretching of the ribbon-shaped sample stream along a narrowing flowpath within PIOAL layers of different viscosity than the ribbon-shaped sample stream, such as higher viscosity, advantageously tends to align non-spherical particles in a plane substantially parallel to the flow direction, and apply forces on the cells, improving the in-focus contents of intracellular structures of cells. The optical axis of the high optical resolution imaging device 24 is substantially normal (perpendicular) to the plane of the ribbon-shaped sample stream. The linear velocity of the ribbon-shaped sample stream at the point of imaging may be, for example, 20-200 mm/second. In some embodiments, the linear velocity of the ribbon-shaped sample stream may be, for example, 50-150 mm/second.

Referring also to FIGS. 2 and 3, the internal flowpath of the flowcell narrows downstream of the point of injection of the ribbon-shaped sample stream into the PIOAL, to produce a ribbon-shaped sample stream thickness, for example, up to 7 µm, and/or the internal flowpath produces a ribbon-shaped sample stream width of 500-3,000 µm. In exemplary embodiments, as depicted in FIG. 1, the internal flowpath of the flowcell begins a narrowing transition zone upstream of the point of injection of the sample stream into the PIOAL.

In another embodiment the internal flowpath narrows to produce a ribbon-shaped sample stream thickness of 2-4 µm in thickness, and/or the internal flowpath results in the ribbon-shaped sample stream of 2000 µm in width. In some cases, the sample stream has a width of about 2190 µm. The thickness of the stream in this case is less than the diameter of some particles, such as red blood cells in their relaxed state. Accordingly, those particles can become reoriented to face their wider a dimension to the imaging axis, which is helpful in revealing distinguishing characteristics.

The method further can further include forming the ribbon-shaped sample stream into a ribbon-shape. The ribbon shape is presented such that the optical axis of the high optical resolution imaging device is substantially perpendicular to the ribbon-shaped sample stream, namely normal to the plane of the ribbon-shaped stream.

Figure 4:
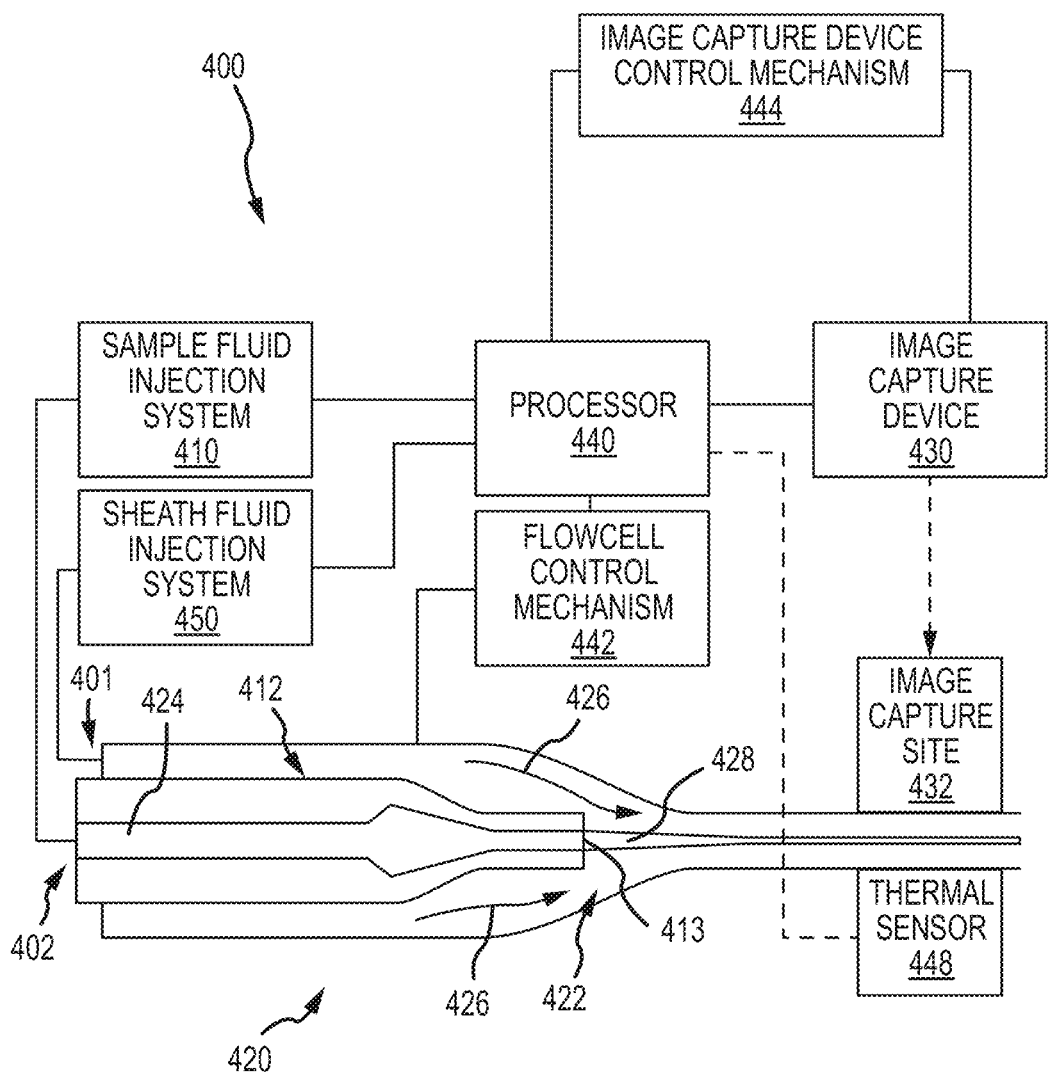
FIG. 4 illustrates aspects of an imaging system according to embodiments of the present invention.

FIG. 4 depicts aspects of a system 400 for imaging particles in a urine sample. As shown here, system 400 includes a sample fluid injection system 410, a flowcell 420, and image capture device 430, and a processor 440. The flowcell 420 provides a flowpath 422 that transmits a flow of the sheath fluid, optionally in combination with the sample fluid. According to some embodiments, the sample fluid injection system 410 can include or be coupled with a cannula or tube 412. The sample fluid injection system 410 can be in fluid communication with the flowpath 422, and can operate to inject sample fluid 424 through a distal exit port 413 of the cannula 412 and into a flowing sheath fluid 426 within the flowcell 420 so as to provide a sample fluid stream 428. For example, the processor 440 may include or be in operative association with a storage medium having a computer application that, when executed by the processor, is configured to cause the sample fluid injection system 410 to inject sample fluid 424 into the flowing sheath fluid 426. As shown here, sheath fluid 426 can be introduced into the flowcell 420 by a sheath fluid injection system 450. For example, the processor 440 may include or be in operative association with a storage medium having a computer application that, when executed by the processor, is configured to cause the sheath fluid injection system 450 to inject sheath fluid 426 into the flowcell 420.

The sample fluid stream 428 has a first thickness T1 (see, e.g., FIG. 4A) adjacent the injection tube 412. The flowpath 422 of the flowcell having a decrease in flowpath size such that the thickness of the sample fluid stream 428 decreases from the initial thickness T1 to a second thickness T2 adjacent an image capture site 432. The image capture device 430 is aligned with the image capture site 432 so as to image a first plurality of the particles from the first sample fluid at the image capture site 432 of the flowcell 420.

The processor 440 is coupled with the sample fluid injector system 410, the image capture device 430, and optionally the sheath fluid injection system 450. The processor 440 is configured to terminate injection of the first sample fluid into the flowing sheath fluid 426 and begin injection of the second sample fluid into the flowing sheath fluid 426 such that sample fluid transients are initiated. For example, the processor 440 may include or be in operative association with a storage medium having a computer application that, when executed by the processor, is configured to cause the sample fluid injection system 410 to inject the second sample fluid into the flowing sheath fluid 426 such that sample fluid transients are initiated.

Further, the processor 440 is configured to initiate capture of an image a second plurality of the particles from the second sample fluid at the image capture site 432 of the flowcell 420 after the sample fluid transients and within 4 seconds of the imaging of the first plurality the particles. For example, the processor 440 may include or be in operative association with a storage medium having a computer application that, when executed by the processor, is configured to cause the image capture device 430 to initiate capture of an image a second plurality of the particles from the second sample fluid at the image capture site 432 of the flowcell 420 after the sample fluid transients and within four seconds of the imaging of the first plurality the particles.

In some embodiments, processor 440 may include or be in operative association with a storage medium having a computer application that, when executed by the processor, is configured to cause a flowcell movement control mechanism 442 to adjust the position of the flowcell 420, for example relative to the image capture device 430. In some embodiments, processor 440 may include or be in operative association with a storage medium having a computer application that, when executed by the processor, is configured to cause an image capture device movement control mechanism 444 to adjust the position of the image capture device 430, for example relative to the flowcell 420. The movement control mechanisms 442, 444 may include motors, gimbals, and other mechanical features that facilitate and produce movement in the flowcell and image capture device, respectively. In some cases, flowcell control mechanism 442 and/or image capture device control mechanism 444 may include a high precision stepper motor control that provides motorized and automated focusing of image capture device relative to the flowcell. As depicted in FIG. 1, a processor can control movement of the image capture device 24. Similarly, as depicted in FIG. 1B, a processor can control movement of a flowcell carrier 55.

Hence, embodiments of the present invention encompass particle analysis systems that perform combined viscosity and geometric hydrofocusing for imaging particles in a urine sample. Exemplary systems can include a flowcell having a flowpath with an injection tube and an imaging window with an imaging axis therethrough. The flowpath of the flowcell can have a decrease in flowpath size. Further, analyzer systems can include a sheath fluid input in fluid communication with the flowpath, and a urine input in fluid communication with the injection tube. The urine input can be configured for injecting the urine sample into the flowing sheath fluid within the flowcell so that the urine sample flows in a sample flowstream with a flowstream width greater than a flowstream thickness. The sheath fluid can have a viscosity that is greater than a viscosity of the urine sample. What is more, the analyzer system can include an image capture device, and a focusing mechanism that sets a focal state of the image capture device relative to the flowcell. Further, the system can include an imaging target having a position fixed relative to the flowcell, where the imaging target and sample flowstream defining a displacement distance along the imaging axis. The system can also include a processor, and a focusing module having a tangible medium embodying machine-readable code executed on the processor for operating the focusing mechanism to set the focal state of the image capture device, suitable for particle characterization and counting, using the displacement distance. The viscosity difference between the sheath fluid and urine sample, in combination with the decrease in flowpath size, can be effective to hydrofocus the first and second sample fluids at the imaging axis while retaining viability of cells in the urine sample. In some cases, the focusing mechanism can include a drive motor configured to adjust a distance between the image capture device and the flowcell.

In some cases, an analyzer system 400 may include a temperature or thermal sensor 448 that is thermally coupled with the flowcell 420, as depicted in FIG. 4. A focusing module, which may operationally associated with the processor, can include a tangible medium embodying machine-readable code that is executed on the processor for operating a focusing mechanism (e.g. flowcell control mechanism 442 or image capture device control mechanism 444) so as to set the focal state or focal plane of the image capture device, suitable for particle characterization and counting, in response to a change in temperature sensed by the temperature sensor and a known relationship between temperature and a desired focus.

Accordingly, embodiments of the present invention encompass a system 400 for imaging a plurality of particles in a urine sample 424 having a sample fluid viscosity The system 400 can be used with a sheath fluid 426 having a sheath fluid viscosity that differs from the sample fluid viscosity by a viscosity difference in a predetermined viscosity difference range. The system 400 can include a flowcell 420 having a flowpath 422 and a sample fluid injection tube 412. The flowpath 422 can have a reduction in flowpath size or narrowing transition zone. Further, the system 400 can include a sheath fluid input 401 in fluid communication with the flowpath 422 of the flowcell 420 so as to transmit a flow of the sheath fluid along the flowpath 422 of the flowcell 420. The system 400 can also include a urine sample input 402 in fluid communication with the injection tube 412 of the flowcell 420 so as to inject a flow or stream 428 of the urine sample into the flowing sheath fluid 428 within the flowcell 420. For example, the sample fluid 424 can exit the distal exit port 423 of the cannula 412 and into an envelope of the flowing sheath fluid 426 to form a sample ribbon 428 therein.

As the sheath fluid 426, along with the sample fluid ribbon 428 formed from the sample fluid 424, flow through a reduction 419 in flowpath size and toward an imaging site 432, a viscosity hydrofocusing effect induced by an interaction between the sheath fluid 426 and the sample fluid 424 associated with the viscosity difference, in combination with a geometric hydrofocusing effect induced by an interaction between the sheath fluid 426 and the sample fluid 424 associated with the reduction in flowpath size, provides a target imaging state in at least some of the plurality of particles at the imaging site 432. As shown here, the system

400 also includes an imaging device 430 that images the plurality of particles at the imaging site 432.

Figure 4A:
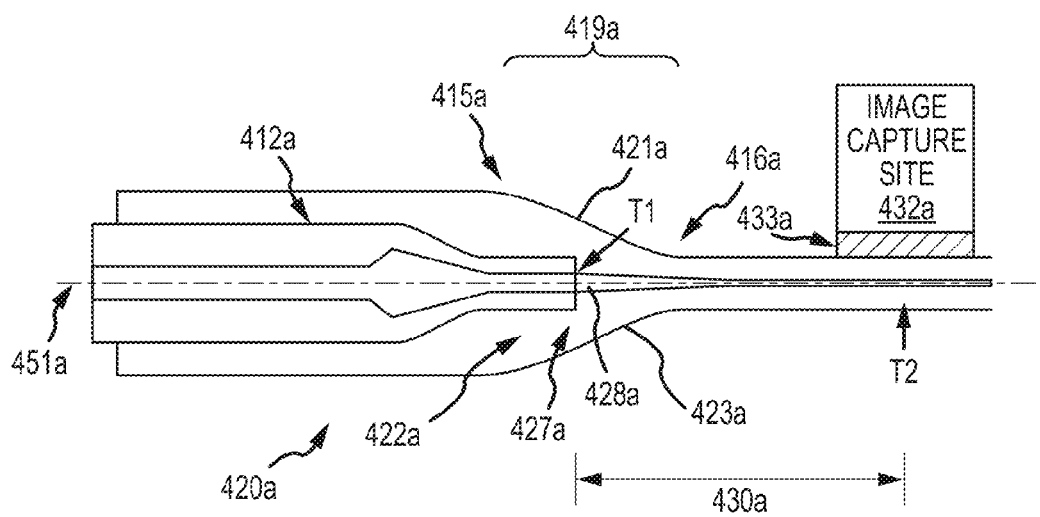

As shown in the flowcell embodiment depicted in FIG. 4A, a decrease in flowpath size (e.g. at transition zone 419*a*) can be defined by opposed walls 421*a*, 423*a* of the flowpath 422*a*. The opposed walls 421*a*, 423*a* can angle radially inward along the flowpath 422*a*, generally symmetric about a transverse plane 451*a* that bisects the sample fluid stream 428*a*. The plane 451*a* can bisect the sample stream 428*a* where the sample stream has a first thickness T1, at a location where the sample stream 428*a* exits a distal portion 427*a* of the cannula or sample injection tube 412*a*. Similarly, the plane 451*a* can bisect the sample stream 428*a* where the sample stream has a second thickness T2, at a location where the sample stream 428*a* passes the image capture site 432*a*. According to some embodiments, the first thickness T1 has a value of about 150 μm and the second thickness T2 has a value of about 2 μm. In such cases, the compression ratio of the sample ribbon stream is 75:1. According to some embodiments, the first thickness T1 has a value within a range from about 50 μm to about 250 μm and the second thickness T2 has a value within a range from about 2 μm to about 10 μm. As the sample stream fluid flows through the flowcell, the ribbon thins out as it accelerates and is stretched. Two features of the flowcell can contribute to thinning of the sample fluid ribbon. First, a velocity difference between the sheath fluid envelope and the sample fluid ribbon can operate to reduce the thickness of the ribbon. Second, the tapered geometry of the transition zone can operate to reduce the thickness of the ribbon. As depicted in FIG. 4A, the distal exit port 413*a* of cannula 412*a* can be positioned at a central location along the length of the narrowing transition zone 419*a*. In some cases, the distal exit port can be positioned more closely to the beginning (proximal portion 415*a*) of the transition zone 419*a*. In some cases, the distal exit port can be positioned more closely to the end (distal portion 416*a*) of the transition zone 419*a*. In some cases, the distal exit port 413*a* can be positioned entirely outside of the transition zone 419*a*, for example as depicted in FIG. 3A (where distal exit port 331 is disposed proximal to the narrowing transition zone).

As depicted in FIG. 4A (as well as in FIGS. 4 and 4B-1), the transition zone 419*a* can be defined by an angular transitions at the proximal (415*a*) and distal (416*a*) portions. It is also understood that the transition zone 419*a* can instead present smooth or curved transitions at the proximal (415*a*) and distal (416*a*) portions, similar to the smooth or curved transitions as depicted in FIGS. 1, 3, 3A, 3B, and 4B-2).

Typically, the first thickness T1 is much larger than the size of the sample particles, and hence the particles are contained entirely within the sample ribbon stream. However, the second thickness T2 may be smaller than the size of certain sample particles, and hence those particles may extend out of the sample fluid and into surrounding sheath fluid. As shown in FIG. 4A, the sample ribbon stream can flow generally along the same plane as it exits the cannula and travels toward the image capture site.

The flowcell can also provide a separation distance 430*a* between the distal cannula portion 427*a* and the image capture site 432*a*. According to some embodiments, the distal portion 427*a* of the sample fluid injection tube 412*a* can be positioned at an axial separation distance 430*a* from the image capture site 432*a*, where the axial separation distance 432*a* has a value of about 21 mm. According to some embodiments, the axial separation distance 430*a* has a value within a range from about 16 mm to about 26 mm.

The axial separation distance 430*a* between the cannula exit port and image capture site can impact the transition time for the sample fluid as the fluid travels from the exit port to the image capture site. For instance, a relatively shorter axial separation distance 430*a* can contribute to a shorter transition time, and a relatively longer axial separation distance 430*a* can contribute to a longer transition time.

The position of the exit port at the cannula distal portion 427*a* relative to the flowpath transition zone 419*a*, or relative to the proximal portion 415*a* of the flowpath transition zone 419*a*, can also inference the transition time for the sample fluid as the fluid travels from the exit port to the image capture site. For example, the sheath fluid may have a relatively slower speed at the proximal portion 415*a*, and a relatively faster speed at a location between the proximal portion 415*a* and the distal portion 416*a*. Hence, if the cannula exit port at distal portion 427*a* is positioned at the proximal portion 415*a*, it will take a longer amount of time for the sample fluid to reach the image capture site, not only because the travel distance is longer, but also because the initial speed of the sample fluid after it exits the cannula distal port is slower (due to the slower sheath fluid speed). Put another way, the longer the sample fluid is present in the thicker portion (e.g. near proximal portion 415*a*) of the flowcell, the longer it takes the sample to reach the image capture site. Conversely, if the cannula exit port at distal portion 427*a* is positioned distal to the proximal portion 415*a* (e.g. at a central location between proximal portion 415*a* and distal portion 416*a*, as depicted in FIG. 4A), it will take a shorter amount of time for the sample fluid to reach the image capture site, not only because the travel distance is shorter, but also because the initial speed of the sample fluid after it exits the cannula distal port is faster (due to the faster sheath fluid speed). As discussed elsewhere herein, the sheath fluid is accelerated as it flows through the transition zone 419*a*, due to the narrowing cross-sectional area of the zone 419*a*.

According to some embodiments, with a shorter transition time, more time is available for image collection at the image capture site. For example, as the duration of the transition time from the cannula distal tip to the imaging area decreases, it is possible to process more samples in a specific amount of time, and relatedly it is possible to obtain more images in a specific amount of time (e.g. images per minute).

Although there are advantages associated with positioning the exit port of the cannula distal portion 427*a* more closely to the image capture site 432*a*, it is also desirable to maintain a certain distance between the port and the capture site. For example, as depicted in FIG. 3, an optical objective or front lens of an imaging device can be positioned in the seat 58 of the flowcell 22. If the exit port 31 of the cannula is too close to the seat 58, then the sample fluid may not be sufficient stabilized after it is injected into the sheath fluid so as to provide desired imaging properties at the image capture site. Similarly, it may be desirable to maintain the tapered transition region 21 at a distance from the viewing zone 23, so that the tapered region does not interfere with the positioning of the seat 58 which receives the image capture device objective.

With continuing reference to FIG. 4A, the downstream end 427*a* of the sample fluid injection tube 412*a* can be positioned distal to a proximal portion 415*a* of the flowpath transition zone 419*a*. Relatedly, the downstream end 427*a* of the sample fluid injection tube 412*a* can be positioned proximal to a distal portion 416*a* of the flowpath transition zone 419*a*. Hence, according to some embodiments, the sample fluid can be injected from the injection cannula 412a and into the flowcell at a location within the transition zone 419a.

According to some embodiments, symmetry in the decrease in flowpath size (e.g. at flowpath transition zone 419a) operates to limit particle misalignment in the urine sample. For example, such symmetry can be effective to limit red blood cells imaging orientation misalignment in the urine sample to less than about 20%.

According to some embodiments, methods disclosed herein are operable to the flagging rate during blood count analysis to below 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6% or 5% of samples.

According to some embodiments, the image capture site 432a has a field of view 433a of between about 800 μm×800 μm. In some cases, the image capture site 432a has a field of view 433a of about 275 μm×275 μm. In some cases, the field of view can be defined in terms of length times width. If expressed as surface area, a 275 μm×275 μm field of view has an area of 75,625 μm$^2$. According to some embodiments, the field of view can be determined by the imaging device objective and its magnification. In some cases, the field of view can correspond to the extent of the field (area) that is imaged by the collection optics (e.g. objective, tube lens, and camera). In some cases, the field of view is much smaller than the viewing port of transparent area at the image capture site.

Figures 1, 2, 4B:
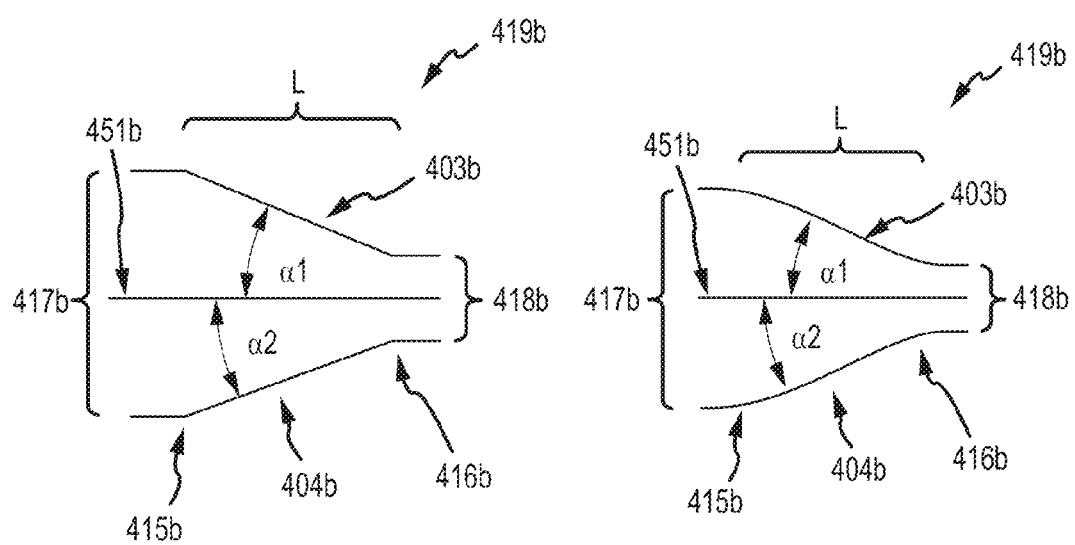
Figures 1, 4A:
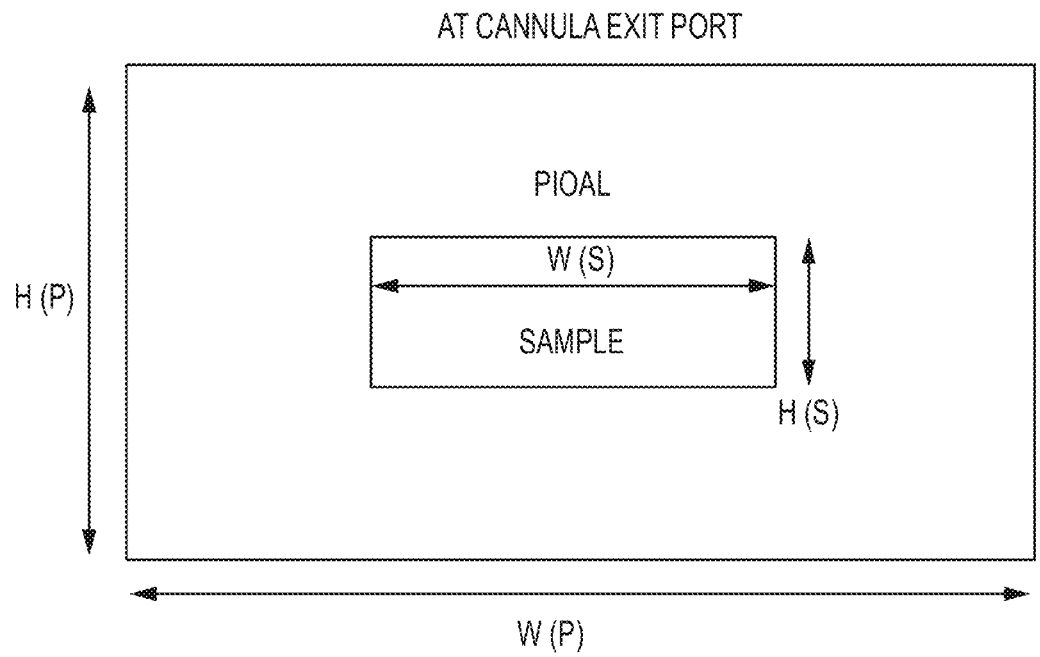
Figures 2, 4A:
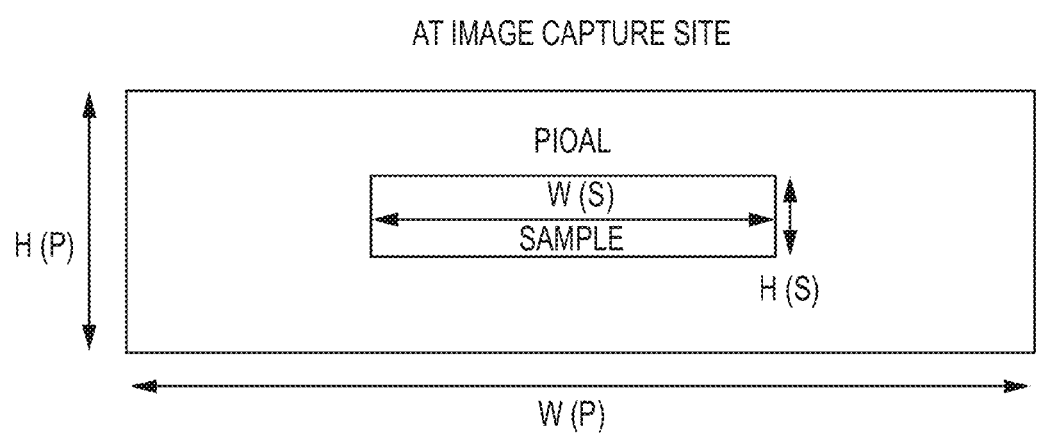

FIGS. 4A-1 and 4A-2 illustrate the effects of hydrofocusing on the sample stream as it travels from the cannula exit port to the image capture site. As shown in FIG. 4A-1, the sample stream can have a height H(S) of about 150 μm and a width W(S) of about 1350 μm. In some cases, width W(S) is about 1600 um. In some cases, width W(S) is about 2000 μm in width. In some cases, the sample stream has a width of about 2190 μm. In some cases, width W(S) has a value within a range from about 1350 μm to about 2200 μm. The sample stream dimensions depicted here can correspond to the cannula exit port dimensions, for example as depicted in FIG. 4E. Further, the PIOAL sheath stream can have a height H(P) of about 6000 μm and a width W(P) of about 4000 μm. Subsequent to the hydrofocusing, as shown in FIG. 4A-2, the sample stream can have a height H(S) of about 2 μm and a width W(S) of about 1350 μm. In some cases, width W(S) is about 1600 um. In some cases, width W(S) is about 2000 μm in width. In some cases, the sample stream has a width of about 2190 μm. In some cases, width W(S) has a value within a range from about 1350 μm to about 2200 μm. Further, the PIOAL sheath stream can have a height H(P) of about 150 μm and a width W(P) of about 4000 μm. In one embodiment, the cross sectional area of the PIOAL sheath stream at the cannula exit is 40 times larger than the cross sectional area near the image capture site.

According to some embodiments, it can be useful to determine the cross-section of the flowcell channel at the image capture site. This can correspond to the PIOAL sheath stream height H(P) of about 150 μm and a width W(P) of about 4000 μm as depicted in FIG. 4A-2. It can also be useful to determine the volumetric flow rate of the combined sample and sheath fluid streaming through the flowcell at the image capture site. When the cross-section area and the flow rate are known, it is possible to determine the velocity of the combined sample and sheath fluid at the image capture site.

According to some embodiments, the flow of the sample and sheath fluids through the flowcell can be approximated with a parallel plate profile model. Relatedly, the flow rate in the center of the sample fluid stream (e.g. as depicted in FIG. 4A-2), can be about 1.5 times the average flow rate of the combined sample and sheath fluid stream.

According to some embodiments, the cross-sectional area of the sample flow at the cannula exit (e.g. W(S)×H(S) in FIG. 4A-1) is 40 times larger than the cross-sectional area of the sample flow at the imaging site (e.g. W(S)×H(S) in FIG. 4A-2). The volumetric flow rate of sheath fluid at the imaging area can be about 45 μL/second. The volumetric flow rate of sample fluid at the imaging area can be about 0.232 μL/second. In some cases, the cross-sectional area of the combined sheath and sample streams at the imaging site is 600,000 μm$^2$. In some cases, the average flowstream velocity at the imaging site is 75 mm/second.

The flow rate or velocity can be determined as the rate that results in clear and focused cellular images. Exemplary flow rates and velocities were discovered based on flow rates of the two samples that were observed to achieve certain sample flowstream ribbon shapes or characteristics at the imaging site. For example, at flow rate of about 75 mm/sec (or within a range from 20-200 mm/sec), the cells do not flow too slow such that there are overlaps of cells in consecutive images, and the cells do not flow too fast such that ghosting effects are created (blurred image). Relatedly, by avoiding excessively high flow rates, it is possible to conserve more reagent and sample. According to some embodiments, an optimal or desired linear velocity can be achieved by either changing the volumetric flow (pump rate) or the shape of cannula.

The flow velocity of the sample stream through the image capture zone can also be related to the performance of the image capture device relative to the flowcell function. For example, if the sample stream if flowing too quickly, it may be difficult to obtain clear images of particles contained in the sample (e.g. the shutter speed of the image capture device may be too low, thus producing a blurred image). Similarly, if the sample stream is flowing too slowly, the image capture device may obtain consecutive images of the same particle (e.g. the same particle remains in the capture frame during two image captures). In some embodiments, the velocity of the sample ribbon can be modulated (e.g. by adjusting any of a variety of the flowcell operational parameters) relative to the image capture rate, so that there is minimal flow between frame captures, and hence a high percentage of the sample is imaged.

According to some embodiments, the particle analysis system and associated components can be configured so that as the sheath fluid and fluid sample flow through the flowcell, the sheath fluid can flow at a sheath fluid volumetric rate of 45 μL/s and the fluid sample can flow at a fluid sample volumetric flow rate of 0.232 μL/s (or within a range from 0.2 to 0.35 μL/s). In some cases, a flow rate of the sample fluid can have a value within a range from 0.2 μL/s to 1 μL/s. In some cases, the sheath fluid can have a flow rate of about 40 μL/s. In some cases, the sample fluid can have a flow rate of about 0.56 μL/s. In some case, for an imaging duration of about 19 seconds, a volume of sample fluid that is flowed through the flowcell can have a value within a range from about 8 μL to about 12 μL. In some cases, the ratio of the sheath fluid flow rate to the sample fluid flow rate is about 200. In some cases, the ratio of the sheath fluid flow rate to the sample fluid flow rate has a value within a range from about 70 to 200. In some cases, the ratio of the sheath fluid flow rate to the sample fluid flow rate is about 193. In some cases, the ratio of the sheath fluid flow rate to the sample fluid flow rate is about 70. In some instances, a ratio of sheath fluid volume to fluid sample volume flowing within the flowcell can be within a range from 25:1 to 250:1.

According to some embodiments, the system and associated components can be configured so that as sheath fluid and fluid sample flow through the flowcell 420, the sheath fluid can flow at a sheath fluid velocity of 75 mm/sec before the imaging area and the fluid sample can flow at a fluid sample velocity of 130 mm/sec before the imaging area. In some instances, a ratio of sheath fluid volume to fluid sample volume flowing within the flowcell can be within a range from 100:1 to 200:1.

In some instances, a flowcell can have a minimum compression ratio of about 50:1 and a maximum compression ratio of about 125:1. In some cases, the minimum compression ratio can be about 30:1 or 20:1. This compression ratio refers to the ratio of flow stream thicknesses H(S):H(S) when comparing FIG. 4A-1 to FIG. 4A-2. This compression ratio can be influenced by a combination of geometric compression (e.g. the ratio of the sheath fluid thicknesses H(P):H(P) when comparing FIG. 4A-1 to FIG. 4A-2, which can also correspond generally to the dimensions of the flowcell narrowing tapered transition zone 419a shown in FIG. 4A) and a hydrodynamic compression (e.g. also corresponding to a difference in velocity). According to some embodiments, the geometric compression ratio is about 40:1.

The decrease in flowpath size, corresponding to the transition zone, can be defined by a proximal flowpath portion having a proximal thickness or height, and a distal flowpath portion having a distal thickness or height that is less than the proximal thickness or height. For example, as shown in the partial views of FIGS. 4B-1 and 4B-2, the transition zone 419b of the flowpath can have a length L between a proximal portion 415b and a distal portion 416b, where the proximal portion 415b has a proximal height 417b, and the distal portion 416b has a distal height 418b. As depicted in FIG. 4B-2, and as noted elsewhere herein, the shape or contour of the transition zone can be curved or smooth, and for example can be provided in the shape of an S-curve, a sigmoidal curve, or a tangent curve. According to some embodiments, the proximal height 417b has a value of about 6000 μm. In some cases, the proximal height 417b has a value within a range from about 3000 μm to about 8000 μm. According to some embodiments, the distal height 418b has a value of about 150 μm. In some cases, the distal height 418b has a value within a range from about 50 μm to about 400 μm.

The geometry of the transition zone 419a can provide a first angle α1 between the first flowpath boundary 403b and the bisecting transverse plane 451b, and a second angle α2 between the second flowpath boundary 404b and the bisecting transverse plane 451b. In some cases, angle α1 is about 45 degrees and angle α2 is about 45 degrees. In some cases, angle α1 has a value within a range from about 10 degrees to about 60 degrees. In some cases, angle α2 has a value within a range from about 10 degrees to about 60 degrees. According to some embodiments, angles α1 and α2 have the same value. The angles α1 and α2 can be selected so as to maintain laminar flow or minimize turbulence of the sample fluid as it travels from proximal portion 415b to distal portion 416b, which in turn can enhance alignment of particles within the sample along the transverse plane 451b. As noted above with reference to FIG. 4A, the distal and proximal boundaries or portions of the transition zone may be curved or smooth, instead of angled.

Figure 4C:
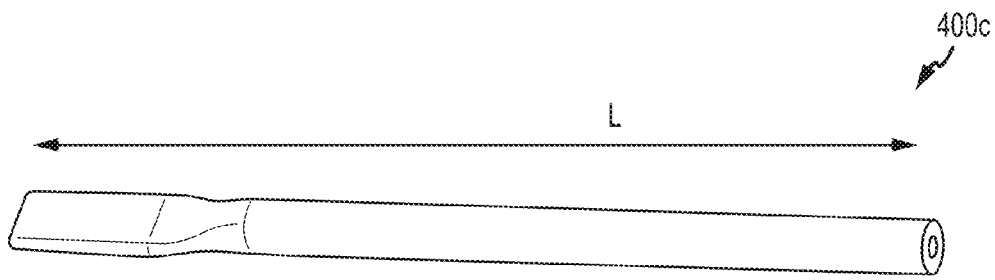
Figure 4D:
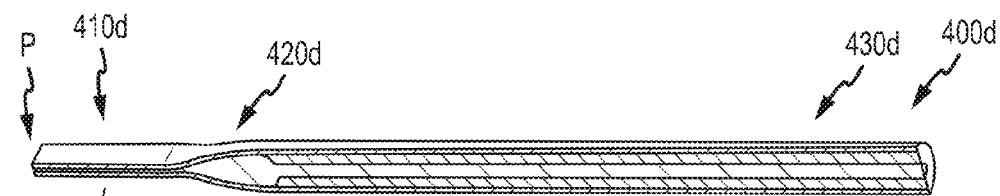
Figure 4E:
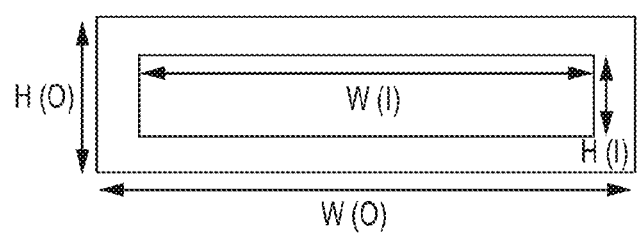

FIG. 4C depicts features of an exemplary cannula or sample feed tube 400c according to embodiments of the present invention, where the cannula has a length L. FIG. 4D depicts a longitudinal cross-section of cannula 400d. As shown here, the cannula 400d includes a distal flattened section 410d, a central tapered section 420d, and a proximal tubular portion 430d. As depicted in FIG. 4C-1, an exemplary cannula or sample feed tube 400c-1 can have a distal portion 410c-1 and a proximal portion 430c-1. In some cases, the distal portion 410c-1 has a length of about 1.359 mm and a width of about 1.43 mm. In some cases, the exit port of the distal end has an exit width W(E) of about 1.359 mm. According to some embodiments, a cannula may have an internal flowpath geometry that is different from what is depicted in FIGS. 4C and 4D. For example, as illustrated in FIG. 4D-1, the cannula 400d-1 does not include a tapered central section having an expanded flow area cross-section. As depicted in FIG. 4D-1, cannula 400d-1 has a distal section 410d-1, a central tapered section 420d-1 having a tapering inner diameter, and a proximal section 430d-1. Corresponding to the tapering inner diameter of central section 420d-1, the cross-sectional inner area of 410d-1 is smaller than the cross-sectional inner area of 430d-1.

A urinalysis system according to embodiments of the present invention can process a urine sample having a volume of about 900 μL. The cannula or injection tube 400d shown in FIG. 4D has an internal volume of about 13 uL. According to some embodiments, the cannula or injection tube has an internal volume of less than about 30 uL.

FIG. 4E illustrates a transverse cross-section of a distal flattened section 410e. As shown here, the distal section 410e has an inner width W(I) and an inner height H(I), through which a sample stream flows. Further, the distal section 410e has an outer width W(O) and an outer height H(O). As depicted in FIGS. 4D and 4E taken in combination, the distal portion 410e of the sample fluid injection tube has an outlet port P having a height H(I) and a width W(I), where the height H(I) is less than the width W(I). According to some embodiments, the height H(I) of the outlet port P of distal portion 410e (or the inner height of the distal portion 410d) can have a value of about 150 μm. In some cases, the height H(I) can be within a range from about 50 μm to about 250 μm. According to some embodiments, the width W(I) of the outlet port P of distal portion 410e (or the inner width of the distal portion 410d) can have a value of about 1350 μm. In some cases, the width is about 1194 μm. In some cases, the width W(I) can have a value within a range from about 500 μm to about 3000 μm. In some cases, height H(I) can be about 150 μm and width W(I) can be about 1350 μm. In some cases, width W(I) is about 1600 um. In some cases, width W(I) is about 2000 μm in width. In some cases, width W(I) is about 2190 μm. In some cases, width W(I) has a value within a range from about 1350 μm to about 2200 μm. As discussed elsewhere herein the value for width W(I) can determine the width of the sample stream at the imaging site. In some cases, distal flattened section 410d can be manufactured by applying a clamping force to a tube or conduit. In some cases, the cannula can have a length of about 1.23 in and an inner diameter of about 0.055 in. In some cases, the cannula can have an inner volume of about 48 μL.

Figure 4F:
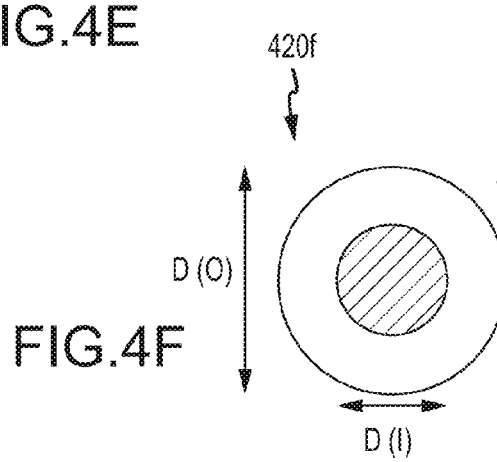
Figure 4G:
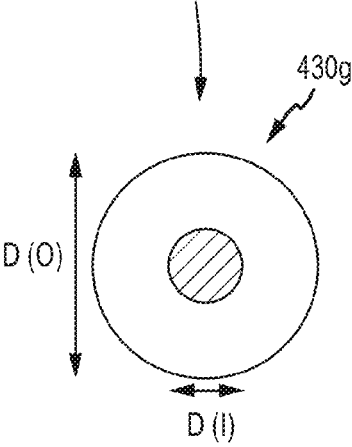
Figures 1, 4C:
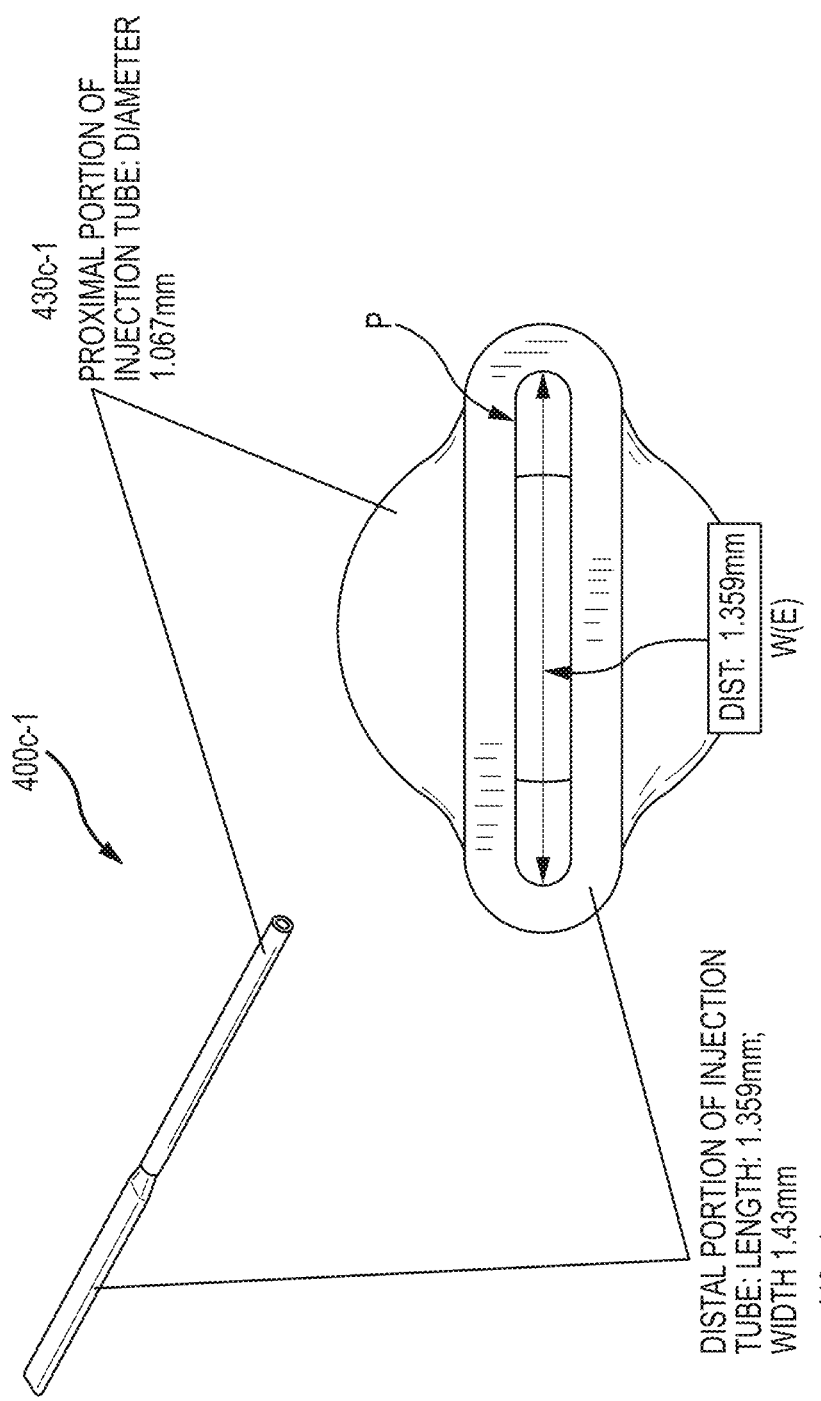
Figures 1, 4D:
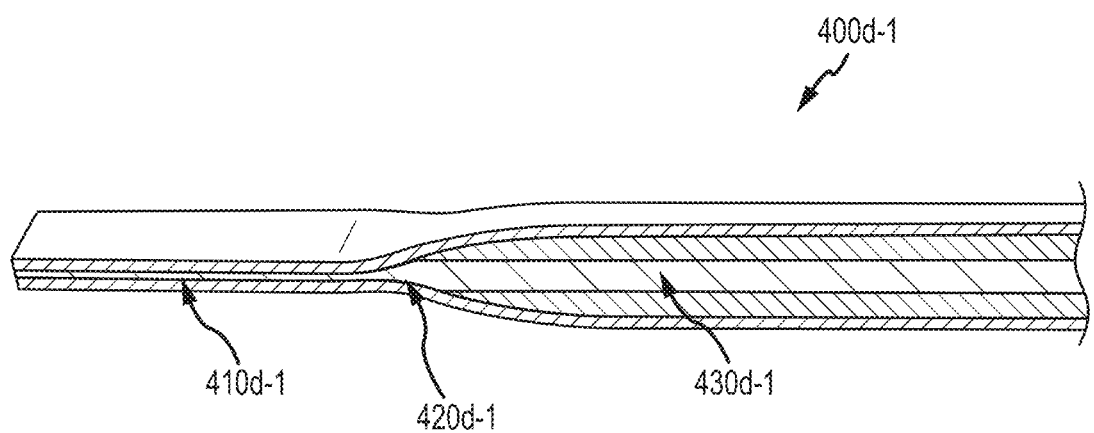

FIG. 4F illustrates a transverse cross-section of a central tapered section 420f. As shown here, the central tapered section 420f has an inner diameter D(I) through which a sample stream flows. Further, the central tapered section 420f has an outer diameter D(O). FIG. 4G illustrates a transverse cross-section of a proximal section 430g. As shown here, the proximal section 430g has an inner diameter D(I) through which a sample stream flows. Further, the distal section 430g has an outer diameter D(O).

As depicted in FIG. 4D, the injection tube or cannula 400d can have a proximal portion 430d having a first flow cross-section area (e.g. $\pi*(D/2)^2$ shown in FIG. 4G), a distal portion 410d having a second flow cross-section area (e.g. W(I)*H(I) shown in FIG. 4E) that is less than the first flow cross-section area, and a third portion 420d disposed between the proximal portion 430d and the distal portion 410d. The third portion 420d can have a third flow cross-section (e.g. $\pi*(D/2)^2$ shown in FIG. 4F) that is larger than the first and second flow cross-sections. In some instance, the outer diameter D(O) of proximal portion 430g is about 1067 μm and the inner diameter D(I) of proximal portion 430g is about 813 μm.

Figure 4H:
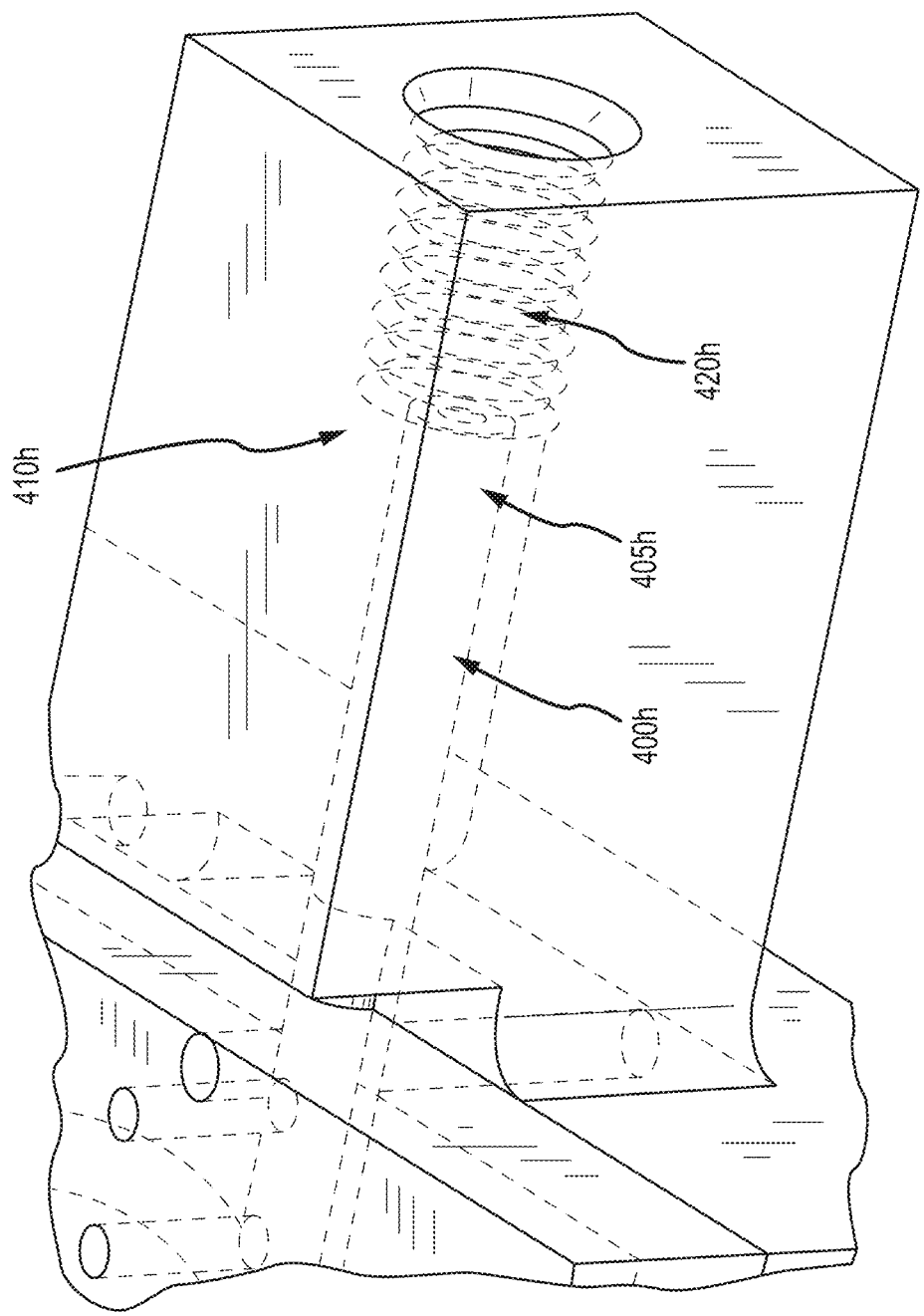
FIG. 4H shows a portion of a cannula according to embodiments of the present invention.

According to some embodiments, a proximal portion of an injection tube can be coupled with a sample port of a sample inlet fitting. For example, as shown in FIG. 4H, a proximal portion 405h of a cannula 400h can be coupled directly to a sample port 410h at an exit of a sample inlet fitting 420h.

Figure 4I:
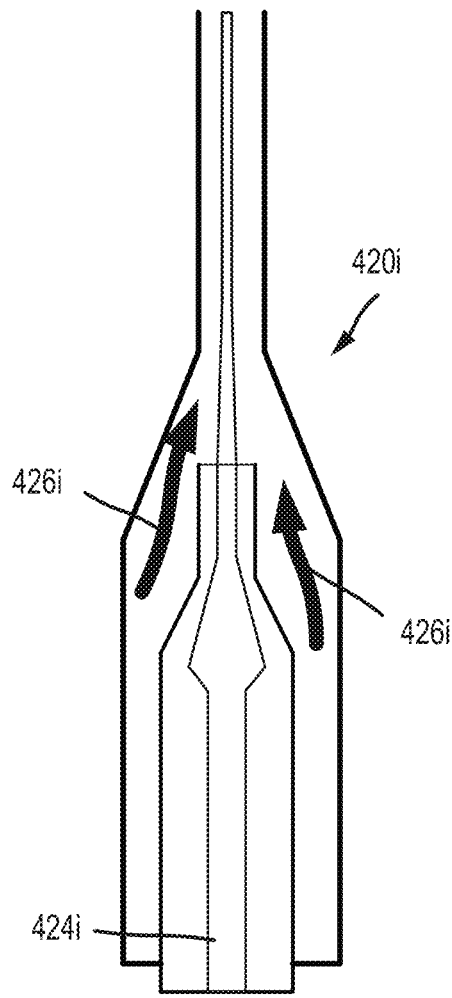
FIGS. 4I and 4J depict flowcells according to embodiments of the present invention.
Figure 4J:
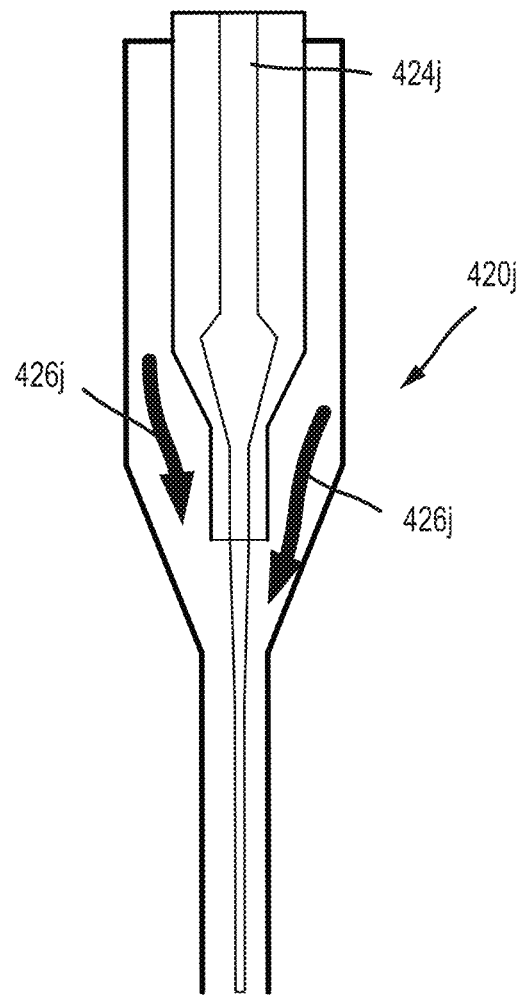

A flowcell of a system for imaging particles in a urine sample can be oriented at any desired angle or direction relative to the direction of the force of gravity. For example, a flowcell can be oriented in an upward direction, so that fluid flowing within the flowcell (e.g. sheath fluid, optionally in combination with sample fluid) can travel in an upward direction, against the force of gravity. Likewise, a flowcell can be oriented in an downward direction, so that fluid flowing within the flowcell (e.g. sheath fluid, optionally in combination with sample fluid) can travel in a downward direction, with the force of gravity. FIG. 4I depicts a flowcell 420i oriented in an upward direction, so that sample fluid 424i and sheath fluid 426i flowing within the flowcell 420i flow against gravity G. FIG. 4J depicts a flowcell 420j oriented in a downward direction, so that sample fluid 424j and sheath fluid 426j flowing within the flowcell 420j do not flow against gravity G, but rather flow with gravity G.

Figure 4K:
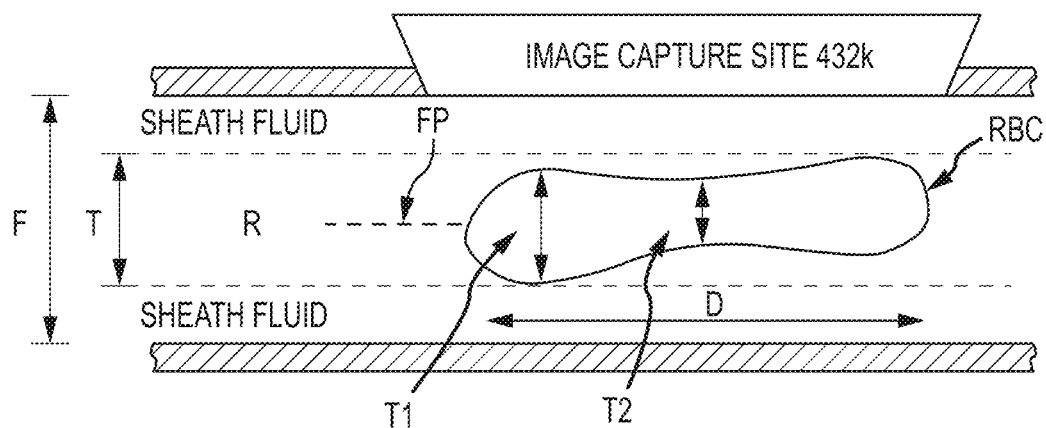
FIGS. 4K and 4L show a sample stream flowing through an image capture site of a flowcell according to embodiments of the present invention.

As shown in FIG. 4K, a sample stream ribbon R flowing through an image capture site 432k of a flowcell 420k can have a thickness T of about 2 μm. In some cases, thickness T of the sample stream ribbon can be up to about 3 μm. Typically, cells or particles that are smaller than the sample stream thickness will be contained within the ribbon. An exemplary red blood cell (RBC) can be present as a biconcave disk and can have a diameter D of between about 6.2 μm and about 8.2 μm. Further, an exemplary red blood cell can have a maximum thickness T1 of between about 2 μm and about 2.5 μm and a minimum thickness T2 of between about 0.8 μm and about 1 μm. In some cases, red blood cells can have a thickness of up to about 3 μm. Exemplary human platelets can vary in size, and can also have a thickness or diameter of about 2 μm. Although not shown to scale here, the flowcell can define a flow path thickness H having a value of about 150 μm, at the image capture site. In some cases, the flowpath thickness F has a value between 50 μm and 400 μm. This flowpath thickness F can also correspond to the distal height 418b of distal portion 461b depicted in FIGS. 4B-1 and 4B-2.

As shown in FIG. 4K, the ratio of the thickness T of the sample fluid stream to the thickness of the particle (red blood cell) is about 1:1. According so some embodiments, a ratio of the thickness T of the sample fluid stream at the image capture site to a size of one of the particles is within a range from 0.25 to 25. In some cases, the thickness T can have a value within a range from 0.5 μm to 5 μm.

As discussed elsewhere herein, as well as in co-pending U.S. patent application Ser. No. 14/215,834, filed Mar. 17, 2014, viscosity differences between fluid of the sample ribbon R and the sheath fluid can operate to align or orient particles in the sample stream, for example red blood cells, along the direction of the flow. When so aligned, as shown in FIG. 4K, the imaging device or camera can obtain images of the red blood cells such they appear round, because the major surface of the blood cell is facing toward the camera. In this way, the red blood cell assumes an alignment that presents a low resistance relative to the flow. Hence, the relative viscosity characteristics of the sheath fluid and the sample fluid can contribute to a high percentage or number of red blood cells facing toward the camera, thus enhancing the evaluation capability of the particle analysis system.

According to some embodiments, the viscosity characteristics of the sheath fluid operate to limit particle misalignment in the urine sample. For example, viscosity differentials can be effective to limit red blood cells imaging orientation misalignment in the urine fluid sample to less than about 10%. That is, 90 or more red blood cells out of 100 red blood cells in a sample can be aligned so that their major surfaces face toward the imaging device. A symmetrical narrowing transition zone can provide a value of 20%. An image of a processed urine sample using a flowcell without a viscous sheath fluid is depicted in FIG. 4O, and in comparison an image of a processed urine sample using a flowcell with a viscous sheath fluid is depicted in FIG. 4P. As shown here, the use of a viscous sheath fluid can limit misalignment in particles within the sample fluidstream. According to some embodiments, the sheath fluid has an index of refraction similar to that of water (i.e. n=1.3330). In some cases, the sheath fluid has a water content of about 89%. In addition to alignment effects observed as a result of the viscosity differential, alignment effects are also observed as a result of a bilateral tapered transition zone. In some cases, it is observed that a bilateral (i.e. symmetrical) tapered transition zone is twice as effective at aligning particles as compared to an asymmetric tapered transition zone design.

Efficient alignment of the red blood cells can contribute to improved diagnosis. In some cases, the shape of the imaged red blood cells can be used to determine whether a patient from whom the sample is obtained has a particular physiological condition or disease. For example, patients with sickle cell disease present with blood cells having an abnormal shape (i.e. in the shape of a sickle). Hence, by obtaining high quality images of aligned red blood cells, it is possible to ensure an accurate diagnosis. Other shape variations in red blood cells, for example red blood cells having thin peripheral area and a large flat central area, whereby the red blood cell appears to have the profile of a bicycle tire, can effectively be imaged using the instant alignment techniques. Similarly, red blood cells having a small central portion, and a thick peripheral area, whereby the red blood cell appears to have the profile of a truck tire, can be imaged for diagnostic purposes. The improved imaging techniques disclosed herein are also useful for evaluating other red blood cell characteristics, such as hemoglobin content, iron content, and the like.

Without being bound by any particular theory, it is believed that a viscosity differential between the viscosity of the sheath fluid and the viscosity of the sample fluid produces a modified parabolic profile, wherein the profile is generally parabolic and has a central bump corresponding to a center area of the flow where the acceleration is increased, and the central bump contributes to alignment of sample particles or intraparticle organelles. According to some embodiments, the velocity difference between the sheath and sample ribbon and the viscosity difference generate shear forces to increase alignment of the organelles or intracellular particles. Exemplary aspects of the sheath fluid parabolic profile are discussed in co-pending U.S. patent application Ser. No. 14/216,533, filed Mar. 17, 2014, the content of which is incorporated herein by reference.

Figure 4L:
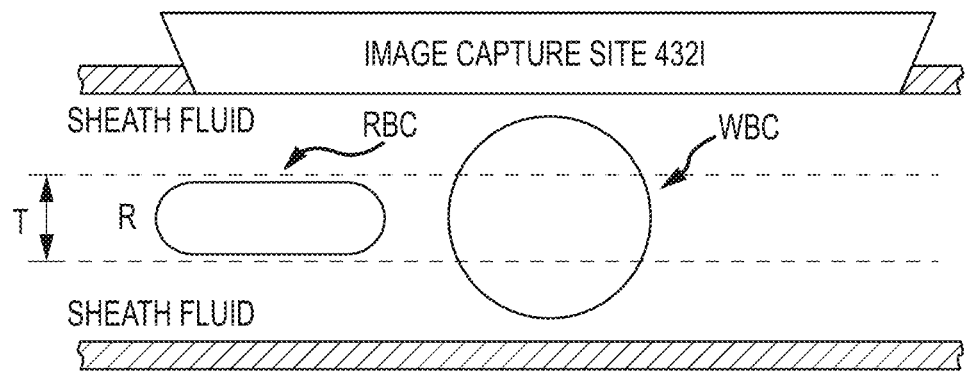
Figures 1, 4K:
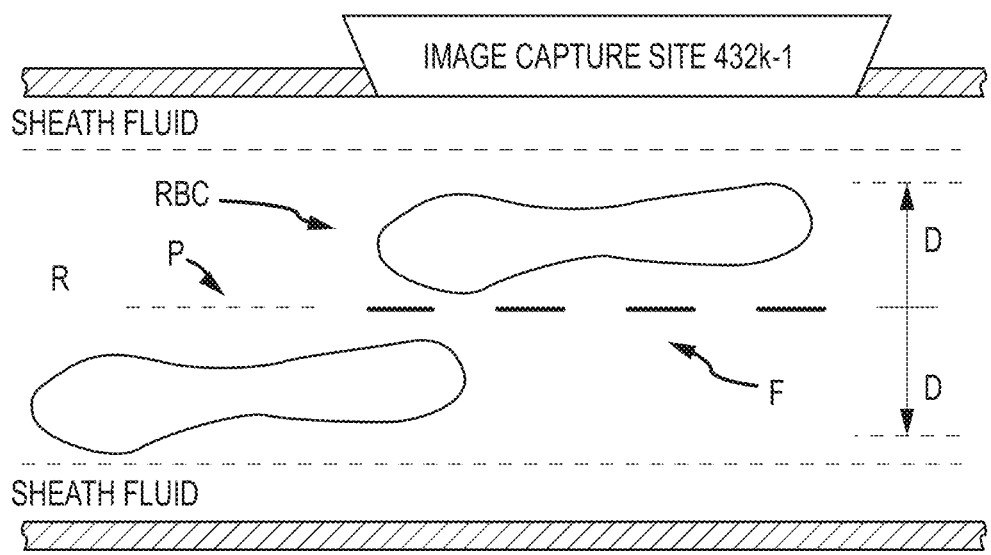
Figures 2, 4K:
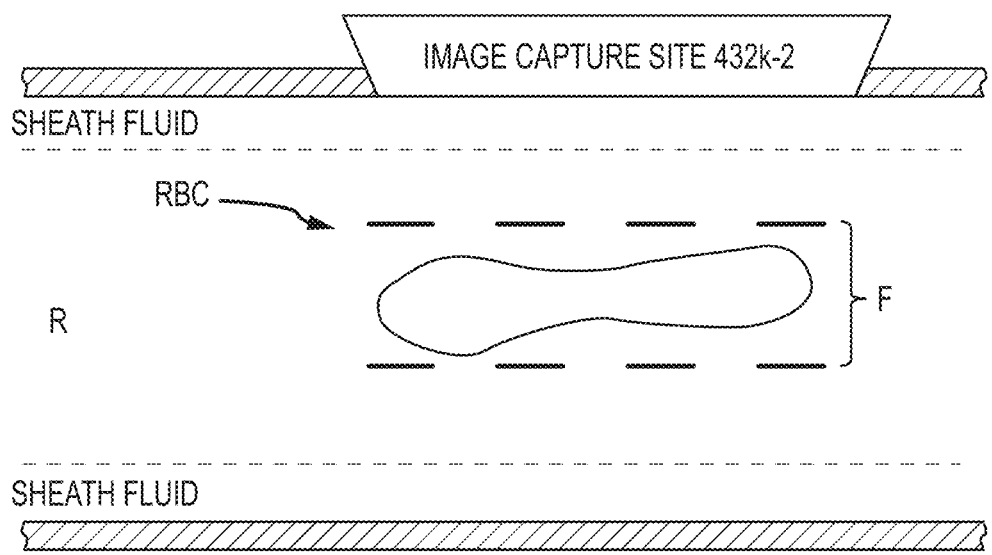
Figures 3, 4K:
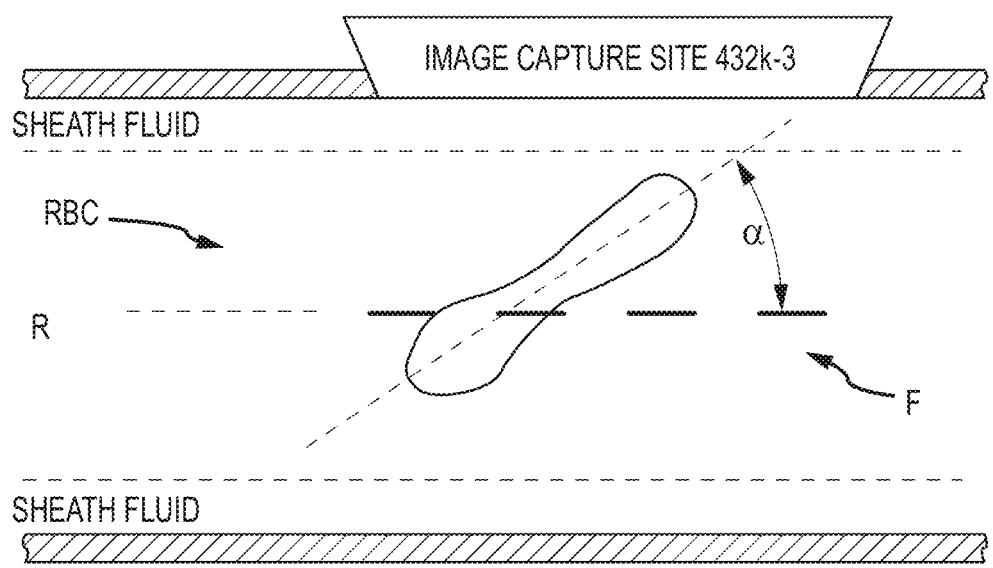
Figures 1, 4L:
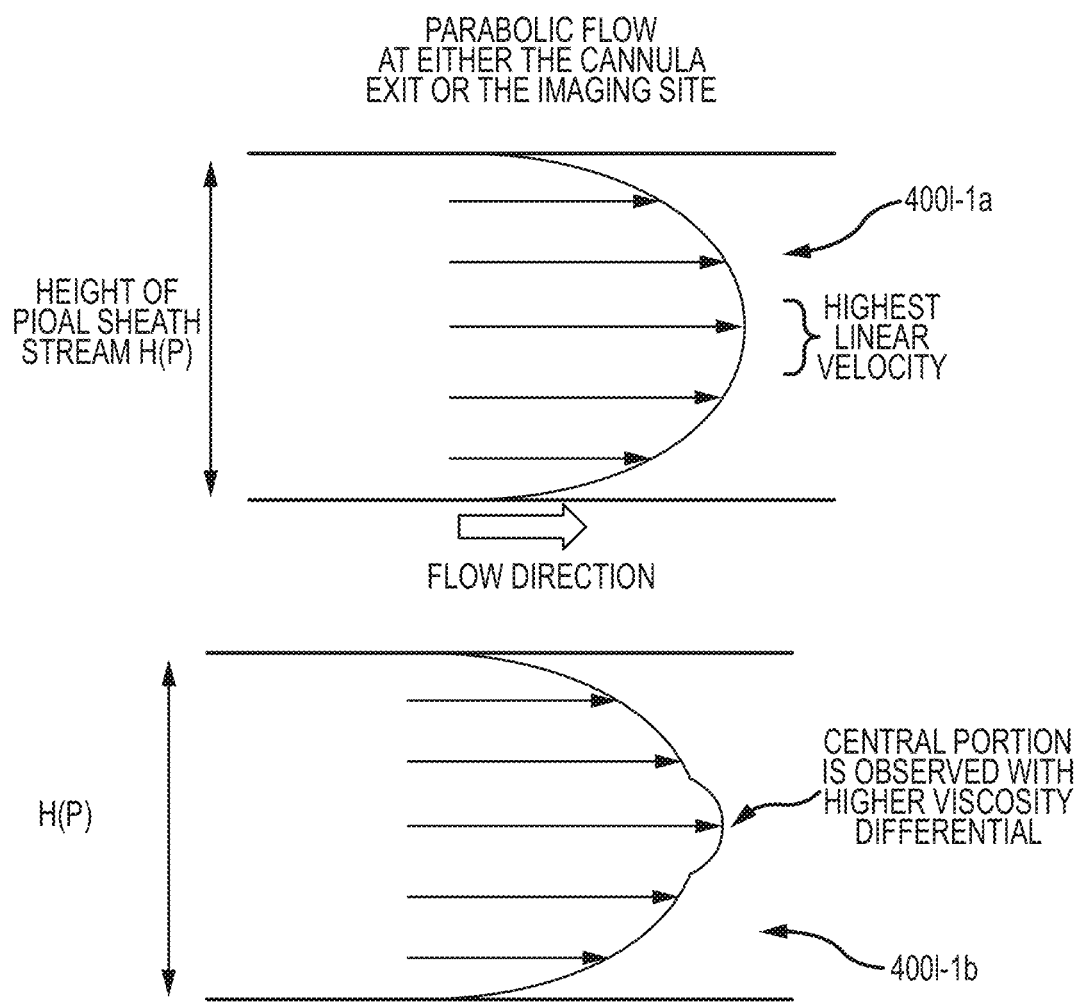

White blood cells are typically larger than red blood cells and platelets. For example, exemplary neutrophils and eosinophils can have a diameter of between about 10 μm and about 12 μm. Exemplary basophils can have a diameter of between about 12 μm and about 15 μm. Exemplary lymphocytes (small) can have a diameter of between about 7 μm and about 8 μm, and exemplary lymphocytes (large) can have a diameter of between about 12 μm and about 15 μm. Exemplary monocytes can have a diameter of between about 12 μm and about 20 μm. The configuration of the particle analysis system, including interaction between the sheath fluid and the fluid sample ribbon as they pass through the flowcell, can operate to compress white blood cells as they travel through the image capture site 432*l*, as indicated in FIG. 4L. Hence, for example, a central portion of the white blood cell (WBC) can be positioned within the sample fluid ribbon R, and peripheral portions of the white blood cell can be positioned within the sheath fluid. Hence, as the white blood cell is transported through the flowcell by the ribbon, the sides of the white blood cell can extend into the sheath fluid.

According to some embodiments, viscosity differences between the sheath fluid and the sample fluid can operate to align organelles or other intracellular features which are present within cells such as white blood cells. Without being bound by any particular theory, it is believed that shear forces associated with the viscosity differential between the sheath fluid and the sample fluid may act upon the white blood cells so as to align the intracellular features. In some cases, shear forces associated with velocity differentials between the sheath fluid and sample fluid may contribute to such alignment. These alignment effects may be impacted by a size differential between the particles and the sample fluid ribbon as well. For example, where portions of the particles extend out of the sample fluid ribbon and into the surrounding sheath fluid, shear forces associated with the difference in viscosity may have a pronounced effect on the intracellular feature alignment.

As depicted in FIG. 4L, portions of a cell such as a white blood cell can extend into the sheath fluid. Embodiments of the present invention encompass sheath fluid compositions that do not lyse or shred the cell, or otherwise compromise the integrity of the outer cell membrane, when the cell is exposed to the sheath fluid. A viscosity agent in the sheath fluid can operate to retain viability of cells in the sample fluid stream, so as to leave the structure (e.g. shape) and the content (e.g. nucleus) of the cells intact when the cell membrane or wall traverses an interface between the sample fluid ribbon and the sheath fluid envelope or otherwise extends from the sample fluid stream into the flowing sheath fluid.

Often, there are compressive forces acting upon the cells or particles as they flow within the sample fluid ribbon along the flowcell. Hence, the cells may come into contact with the sheath fluid while the cells are in a compressed state or are otherwise subject to compressive forces as a result of a narrowing transition zone. The viscosity agent of the sheath fluid can operate to protect the compressed cells from being shredded or destroyed when they emerge from the thin sample fluid ribbon and become exposed to the viscous sheath fluid, at least until the cells reach the image capture site. Hence, the viscosity agent composition of the sheath fluid can operate as a cellular protectorant, while also enhancing alignment of the particles or intraparticle content.

With reference to FIGS. 4K and 4L, in some instances portions of the cell or particle may extend out of the thin sample fluid ribbon R and into the surrounding sheath fluid. As discussed in co-pending U.S. patent application Ser. No. 14/215,834, filed Mar. 17, 2014, the sheath fluid may contain cellular protectants that inhibit or prevent the sheath fluid from disrupting or lysing the cells or particles. For example, the sheath fluid may contain cellular protectants that preserve the structural integrity of the cells walls as the cells are exposed to the chemical environment of the sheath fluid. Similarly, the cellular protectants may also operate to preserve the structural integrity of the cells walls as the cells experience any shear forces induced by flowcell geometry, and a difference in velocity and/or viscosity between the sample fluid and the sheath fluid. Relatedly, the protectorants can protect the cells or particles from forces resulting from the difference in velocity between the sample fluid and sheath fluid. In this way, the cells retain their viability as they reach the image capture site.

The shear forces can be significant at the interface between the sample fluid ribbon and the sheath fluid envelope. According to some embodiments, flow within the flowcell flowpath can be characterized by a parabolic flow profile. FIG. 4L-1 depicts exemplary aspects of parabolic flow profiles 400*l*-1*a* and 400*l*-1*b*. The parabolic profile 400*l*-1*a* in the upper panel is a typical velocity profile found in flows within certain flowcell embodiments of the present invention (e.g. where there is little or no viscosity differential between a sample fluid flowstream that is enveloped within a sheath fluid flowstream). As can be seen, a highest linear velocity is observed in the middle of the fluid stream and slower linear velocities are observed near the flowcell wall. Profile 400*l*-1*a* can also be observed in fluid stream with a slight viscosity difference between the sheath and sample fluids. In a case where there is a high viscosity differential between the sheath and fluid streams, a central bump is observed as shown in profile 400*l*-1*b*, where there is a localized central area with amplified linear velocities. According to some embodiments, particles that are sufficiently large in size will be subjected to some amount of shear force, even where such particles are fully contained within a single fluid phase (i.e. either within the sheath fluid envelope, or alternatively within the sample fluid ribbon).

In some instances, the velocity of the sheath fluid may be different from the velocity of the sample fluid. For example, the sheath fluid may be traveling at 80 mm/second and the sample fluid may be traveling at 60 mm/second. Hence, in some instances, the sample fluid exits the distal cannula port at a sample fluid speed that is slower than the sheath fluid speed of the surrounding envelope. Hence, the sheath fluid can operate to drag the sample fluid along the flowpath of the cannula, thus accelerating the sample fluid and reducing the thickness of the sample fluid ribbon. The sample fluid ribbon maintains the overall volume and mass, so as it travels faster it becomes thinner. According to some embodiments, both the sheath fluid and the sample fluid have a velocity of between about 20 and 200 mm/second at the image capture site.

Typically, the velocity of the sample fluid increases as the sample fluid travels from the cannula exit port to the image capture site. In some instances, the velocity of the sample fluid at the image capture site is 40 times the velocity of the sample fluid as it exits the cannula port at the cannula distal portion. According to some embodiments, the decrease in cross sectional area of the sample ribbon is linear to the increase in velocity. According to some embodiments, if the sheath velocity at the cannula exit is higher than the sample ribbon velocity this will also increase the final sample ribbon velocity at the imaging area.

The sheath fluid can operate to apply significant shear forces on the sample fluid ribbon and on particles within the sample fluid ribbon. Some forces are parallel to the direction of flow, and particles may also encounter forces which are perpendicular to the direction of flow. Often, as the sheath fluid and sample fluid approach the image capture site or zone, the sheath and sample fluids are traveling at or near the same velocity. Hence, the boundary or interface between the sheath and sample fluids as they pass the image capture site may present lower shear forces, as compared to the boundary or interface at the distal cannula exit port or at the tapered transition zone. For example, at the tapered transition zone, the boundary or interface between the sheath fluid envelope and sample fluid ribbon can be in transition, such that the sample ribbon which is initially slower and thicker becomes faster and thinner, and particles in the sample fluid become more aligned. Put another way, the shear forces may be prominent at the tapered transition zone, and can dissipate toward the image capture site. The shear forces at the image capture site can be represented by a parabolic profile, and can be much lower than the shear forces at the tapered transition zone. Hence, cells or particles can experience higher shear forces as they pass through the transition zone, and lower shear forces as they pass through the image capture site. According to some embodiments, the viscosity difference between the sheath and sample fluids can bring the red blood cells into alignment and thereby into focus. According to some embodiments, the viscosity difference between the sheath and sample fluids can bring white blood cell organelles into alignment and thereby into focus. Relatedly, enhanced imaging results can be obtained for cellular and organelle components that are aligned and brought into focus, resulting from the geometric narrowing of the stream and the velocity difference between the sheath and sample fluids.

As noted elsewhere herein, and with reference to FIGS. 4K and 4L, as the sheath fluid and the sample fluid R flow through a reduction in flowpath size or transition zone of a flowcell, and toward an imaging site 432k or 432l, a viscosity hydrofocusing effect induced by an interaction between the sheath fluid and the sample fluid associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site 432k or 432l.

In some cases, the target imaging state is a target orientation relative to a focal plane F at the imaging site. For example, as depicted in FIG. 4K-1, the particle (RBC) can be displaced at a distance from the focal plane F. In some cases, the target orientation involves a target particle orientation relative to the focal plane F at the imaging site 432k-1. The particle can be a blood cell, such as a red blood cell, a white blood cell, or a platelet. As shown here, the flowpath at the imaging site 432k-1 can define a P plane that is substantially parallel to or coplanar with the focal plane F. In some cases, a portion of the particle may be positioned along the focal plane F, yet the central portion of the particle may otherwise be offset from the focal plane F. In some cases, the target orientation involves a target position relative to the focal plane F at the imaging site 432k-1. For example, the target position may involve positioning of the particle so that at least a portion of the particle is disposed along the focal plane F. In some cases, the target position may involve positioning of the particle so that a distance between the particle and the focal plane F does not exceed a certain threshold. In some cases, the target position involves a target particle position that is relative to the focal plane F at the imaging site 432k-1. In some cases, the target position is at or less than a distance D from the focal plane F, where distance D corresponds to a positional tolerance. A viscosity differential between the sheath fluid and the sample fluid can be selected so as to achieve a desired positioning of the ribbon sample stream within the flowcell (e.g. relative to flowpath plane P and/or focal plane F). In some cases, the viscosity differential can be selected so as to achieve a target particle position that is at or less than the positional tolerance D.

In some cases, the focal plane F has a thickness or depth of field as indicated in FIG. 4K-2, and the particle (RBC) has a target imaging state relative to the focal plane thickness. For example, the target position for the particle can be within the focal plane F or at least partially within the focal plane F. In some cases a high optical resolution imaging device or camera can have a depth of field or focal plane thickness of about 7 μm. In some cases, the depth of field or focal plane thickness has a value with a range from about 2 μm to about 10 μm. In some cases, the depth of the field of the camera is similar or equal to the sample ribbon thickness at the image capture site.

In some cases, the target orientation can involve a target alignment relative to the focal plane F at the imaging site. For example, the target alignment can indicate that a plane defined by the particle is aligned with the focal plane F, not to exceed a certain angle α relative to the focal plane F at the image capture site 432k-3 as shown in FIG. 4K-3. In some cases, the target imaging state can involve a limitation on the number or percentage of misaligned particles in a sample. For example, a difference in viscosity between the sheath fluid and the sample fluid R can be effective to limit red blood cells imaging orientation misalignment in the urine sample to less than about 10%. That is, 90 or more red blood cells out of 100 red blood cells in a sample can be aligned so that their major surfaces face toward the imaging device (as depicted in FIGS. 4K-1 and 4K-2) or so that the alignment of those 90 or more RBCs is within 20 degrees from a plane substantially parallel to the direction of flow (e.g. RBC alignment angle α is 20 degrees or less). As discussed elsewhere herein, in some cases at least 92% of non-spherical particles such as RBCs can be aligned in a plane substantially parallel to the direction of flow. In some cases, at least between 75% and 95% of non-spherical particles such as RBCs can be substantially aligned, namely within 20 degrees from a plane substantially parallel to the direction of flow (e.g. alignment angle α is 20 degrees or less). According to some embodiments, 90% or more of certain particles (e.g. red blood cells and/or platelets) can be oriented transverse to the imaging axis of the imaging device.

In some cases, embodiments of the present invention include compositions for use with a urinalysis system as described herein, such as a sheath fluid or particle and intracellular organelle alignment liquid (PIOAL). Such sheath fluids or PIOALs are suitable for use in a combined viscosity and geometric hydrofocusing visual analyzer. The PIOAL can operate to direct or facilitate flow of a urine sample fluid of a given viscosity through a narrowing flowcell transition zone of the visual analyzer. The PIOAL can include a fluid having a higher viscosity than the viscosity of the sample. A viscosity hydrofocusing effect induced by an interaction between the PIOAL fluid and the sample fluid associated with the viscosity difference, in combination with a geometric hydrofocusing effect induced by an interaction between the PIOAL fluid and the sample fluid associated with the narrowing flowcell transition zone, can be effective to provide a target imaging state in at least some of the plurality of particles at an imaging site of the visual analyzer while retaining viability of cells in the urine sample fluid.

Figure 4M:
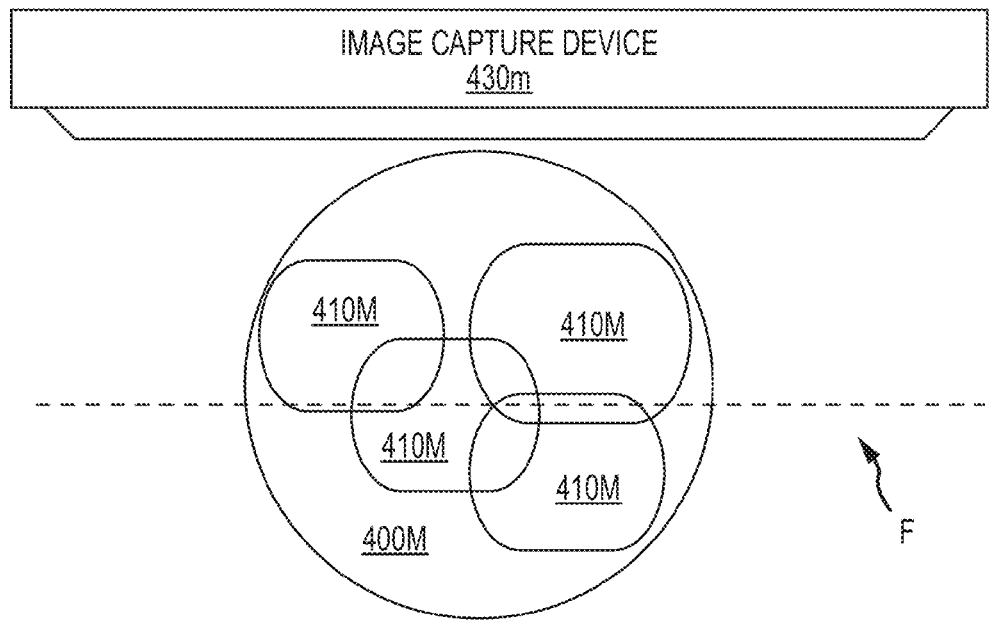
FIGS. 4M and 4N show exemplary intracellular particle alignment features according to embodiments of the present invention.
Figure 4N:
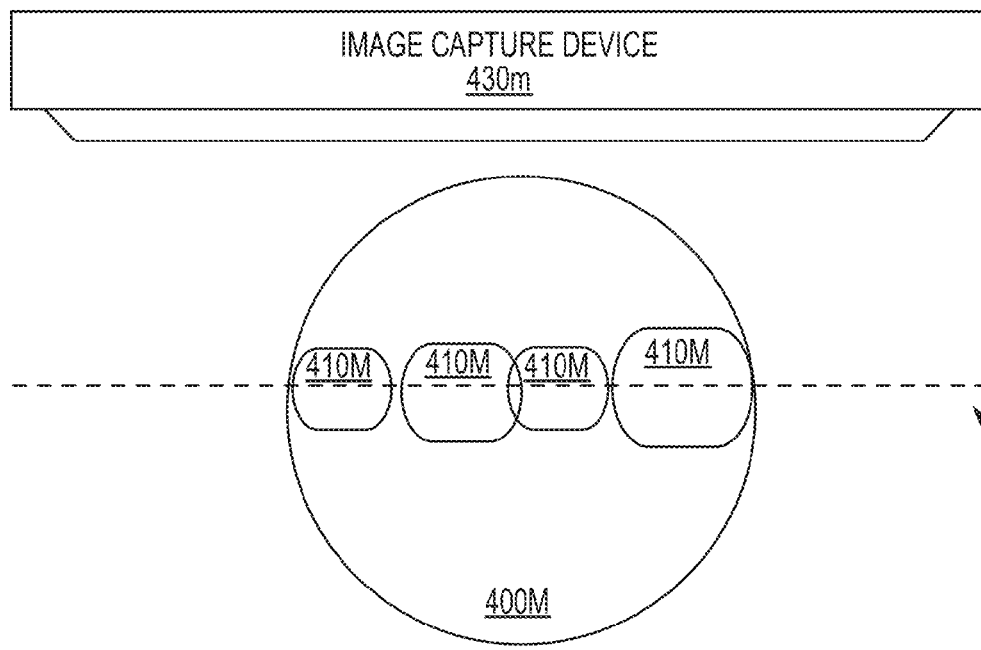

FIG. 4M depicts an exemplary neutrophil 400m (a type of white blood cell) having internal organelles such as lobes 410m. As a result of the viscosity differential between the sample fluid and the sheath fluid, the internal organelles can align within the cell, as indicated by FIG. 4N. Hence, the intracellular organelles can be effectively imaged with an image capture device 430m, without the organelles overlapping one another. That is, instead of the lobes being stacked upon one another as depicted in FIG. 4M, when viewed from the imaging or optical axis of the image capture device the lobes are aligned and sitting side by side as depicted in FIG. 4N. Hence, the lobes can be visualized in the captured imaged more effectively. The internal organelle alignment is a surprising and unexpected result of the viscosity differential between the sample and sheath fluids.

As noted elsewhere herein, and with reference to FIGS. 4M and 4N, as the sheath fluid and the sample fluid R flow through a reduction in flowpath size or transition zone of a flowcell, and toward an imaging site of an image capture device 430m or 430n, a viscosity hydrofocusing effect induced by an interaction between the sheath fluid and the sample fluid R associated with a viscosity difference between the sheath fluid viscosity and the sample fluid viscosity, in combination with a geometric hydrofocusing effect induced by an interaction between the sheath fluid and the sample fluid R associated with the reduction in flowpath size or transition zone, provides a target imaging state in at least some of the plurality of particles at the imaging site. According to some embodiments, the target imaging state may correspond to a distribution of imaging states.

In some cases, the target imaging state can involve a target intraparticle structure orientation (e.g. alignment and/or position) relative to a focal plane at the imaging site. For example, as depicted in FIG. 4N, the internal structures 410m (e.g. intracellular structure, organelle, lobe, or the like) can be oriented relative to the focal plane F. In some cases, the target alignment involves a target intraparticle structure alignment relative to a focal plane F at the imaging site, similar to the particle alignment relationship depicted in FIG. 4K-3. In some cases, the target position involves a target intraparticle structure position relative to a focal plane at the imaging site, similar to the particle position relationship depicted in FIG. 4K-1. In some cases, the target orientation of the intraparticle structure can include both a target alignment relative to the focal plane and also a target position relative to the focal plane. In some cases, the target imaging state can involve a target deformation at the imaging site. For example, as depicted in FIG. 4N, the particle 400m has a compressed shape as compared to the particle shape depicted in FIG. 4M. Hence, it can be seen that operation of the flowcell can produce a lateral compression effect on the particle shapes. Relatedly, the intraparticle features can be positionally or directionally oriented (e.g. aligned with respect to the focal plane F and/or ribbon flow plane) as the particle itself is compressed in shape. According to some embodiments, a velocity difference between the sheath and sample fluids can produce friction within the flowstream, and a viscosity difference between the sheath and sample fluids can amplify that hydrodynamic friction.

EXAMPLES

Any of a variety of urinalysis or urine particle analysis techniques can be performed using images of sample fluid flowing through the flowcell. Often, image analysis can involve determining certain cell or particle parameters, or measuring, detecting, or evaluating certain cell or particle features. For example, image analysis can involve evaluating cell or particle size, cell nucleus features, cell cytoplasm features, intracellular organelle features, and the like. Relatedly, analysis techniques can encompass certain counting or classification methods or diagnostic tests. Relatedly, with reference to FIG. 4, the processor 440 can include or be in operative association with a storage medium having a computer application that, when executed by the processor, is configured to cause the system 400 to differentiate different types of cells or particles based on images obtained from the image capture device. For example, diagnostic or testing techniques can be used to differentiate various particles present in urine (e.g. red blood cells, white blood cells, squamous epithelial cells, casts, crystals, and yeasts.)

The Examples provided herein are for the purpose of illustration only, and the invention is not limited to these Examples, but rather encompasses all variations that are evident as a result of the teaching provided herein.

Prior to the experiments described herein, there was no published protocol that allows for the development and the methods of use comprising PIOAL for aligning particles in urine and repositioning intracellular content as disclosed herein. This is useful for image-based analysis and differential categorization and subcategorization of particles in body fluid (e.g. urine) samples. The methods and compositions disclosed herein can optionally stain and/or lyse particles in a suitable manner to achieve white cell staining, epithelial cells, bacteria staining, that enhance differential visualization on microscope slide. Relatedly, prior to the experiments described herein, there was no published protocol that allows for the development and the methods of use comprising PIOAL for image-based analysis and for performing particle/cellular differential categorization and subcategorization in urine) samples and methods of using such compositions, while maintaining viable or substantially intact cells, with the option of staining and permeabilizing steps occurring while in flow, to achieve white cell, epithelial cells, bacteria staining, that enhance differential visualization on microscope slide.

The exemplary compositions described herein allow staining to occurs at a relatively low blood to reagent dilution and the staining can occurs rapidly (e.g. within 30 sec). If desired, the exemplary method can employ the use of a surfactant in combination with heat to achieve red cell lysis. The exemplary formulations can be modified to retain RBC integrity and still achieve WBC, retic and platelet staining efficacy.

Aspects and embodiments of the present disclosure are based on the surprising and unexpected discovery that certain PIOAL compositions have unexpected properties aligning cells and re-positioning intracellular structures when used to perform image-based particle/cell analysis.

By way of example, several exemplary PIOAL formulations and methods of use thereof were developed. The following are some exemplars of PIOAL formulations with the desired properties.

The exemplary compositions described herein allow staining to occur at a relatively high urine to reagent ratio and the staining can occurs rapidly (e.g., within 30 sec). If desired, the exemplary method can employ the use of a surfactant in combination with heat to achieve membrane permeabilization to retain RBC integrity and still achieve WBC, epithelial cells and bacteria staining efficacy at the desired resolution.

FIGS. 4O and 4P show images demonstrating the comparison between images obtained using a PIOAL (FIG. 4P) versus a conventional sheath fluid (FIG. 4O). The sample containing a concentrated version of the iQ200 positive urine control was analyzed after the instruments were focused using the focusing protocol (on an exemplary autofocus pattern). The sample was injected into the flowcell through a cannula, generating a ribbon-shaped sample stream approximately 2.5 microns thick between two layers of PIOAL or conventional sheath (in controls). The visual analyzer then generates focused images of the particles in the ribbon-shaped sample stream (e.g. at about 60 frames per second) to be used for analysis. As can be seen from FIGS. 4O and 4P, the PIOAL significantly increases the percentage of aligned particles in the concentrated urine sample.

Figure 4Q:
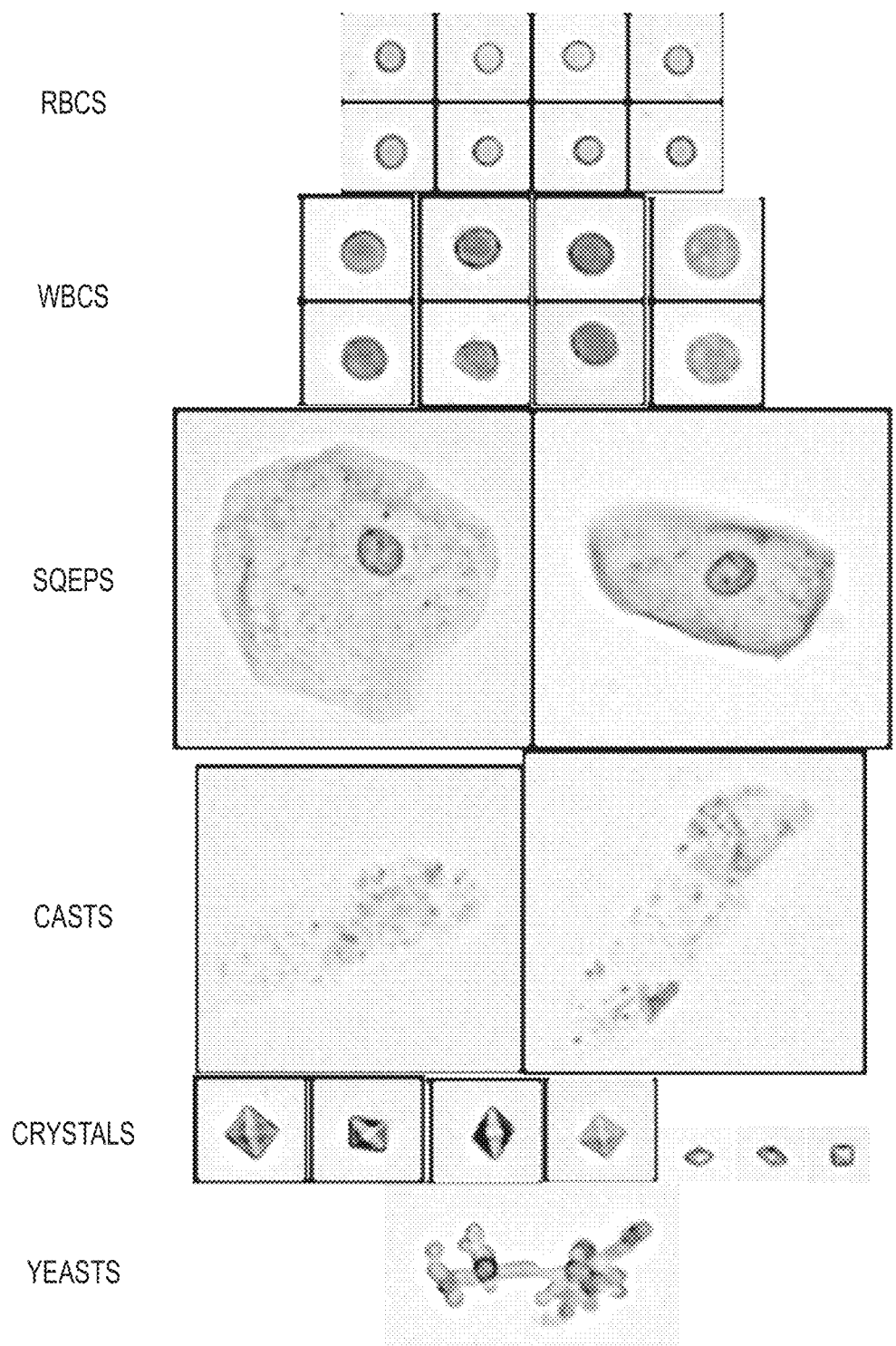
FIG. 4Q shows the resultant images obtained using systems and methods according to embodiments of the present invention.

By way of example, FIG. 4Q shows the resultant images obtained using the exemplary composition and methods of the disclosure, which demonstrated the efficacy in categorizing and/or subcategorizing the following particles: red blood cells, white blood cells, squamous epithelial cells, casts, crystals, and yeasts. The images revealed various cellular components and that nuclear lobes and granular structures are clearly distinguishable for each cell type. The urine sample was collected using the following protocol: The sample was contacted with a particle contrast agent composition as set forth below. The following liquids were mixed together to obtain the exemplary particle contrast agent composition: 0.150 mL of a 1 mg/mL crystal violet dissolved in a lytic solution (CDS 5PD-Lytic), and 0.150 mL of PBS, pH 7.2. The exemplary sample was prepared initially by pipetting 300 uL of the exemplary particle contrast agent composition into a test tube and mixing it with 1.7 mL of urine sample. The mixture was warmed for 30 seconds in a 60° C. water bath. The sample was analyzed on an exemplary analyzer (e.g. as depicted in FIG. 1) using the following conditions: 0.56 uL/s sample flow rate, and 46 uL/s sheath fluid flow rate. The results are shown in FIG. 4Q. Hence, it can be seen that sample processing techniques disclosed herein can provide favorable imaging results, such that the particle structure and content is preserved, and enhanced alignment with regard to an imaging axis is achieved.

It was also observed that the implementation of PIOAL results in improved alignment based on using increasing levels of glycerol (gly) in symmetric and asymmetric flowcells.

These results provide evidence for the surprising and unexpected discovery that certain PIOAL compositions have unexpected properties aligning cells and re-positioning intracellular structures when used to perform image-based particle/cell analysis.

By way of example, several exemplary PIOAL formulations and methods of use thereof were developed. The following are some exemplars of PIOAL formulations with the desired properties. The PIOAL comprises a diluent and at least one viscosity modifying agent.

Exemplary PIOAL formulation A includes a 30% (v/v) glycerol solution having 300 mL glycerol and QS (quantity sufficient or to bring the final volume up to) to 1 L with diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation B includes a 6.5% (v/v) glycerol solution having 65 mL glycerol and QS to 1 L with suitable exemplary diluent containing 9.84 g sodium sulfate, 4.07 g sodium chloride, 0.11 g Procaine HCl, 0.68 g potassium phosphate monobasic, 0.71 g sodium phosphate dibasic, and 1.86 g disodium EDTA. The initial mixture was followed by QS to 1 L with deionized water while adjusting pH to 7.2 with sodium hydroxide.

Exemplary PIOAL formulation C includes a 5% glycerol (v/v) solution with 1% PVP(w/v) in buffer having 50 mL glycerol, 10 g PVP (MW: 360,000), 1 packet of Sigma PBS powder, at pH 7.4 (0.01M phosphate buffered saline; 0.138M sodium chloride; 0.0027M potassium chloride), and QS to 1 L with deionized water.

Exemplary PIOAL formulation D includes a 1.6% PVP (w/v) solution having 16 g PVP (MW: 360,000) and 1 packet of Sigma PBS powder, at pH 7.4 (0.01M phosphate buffered saline; 0.138M sodium chloride; 0.0027M potassium chloride), and QS to 1 L with deionized water.

Throughput

Figure 5:
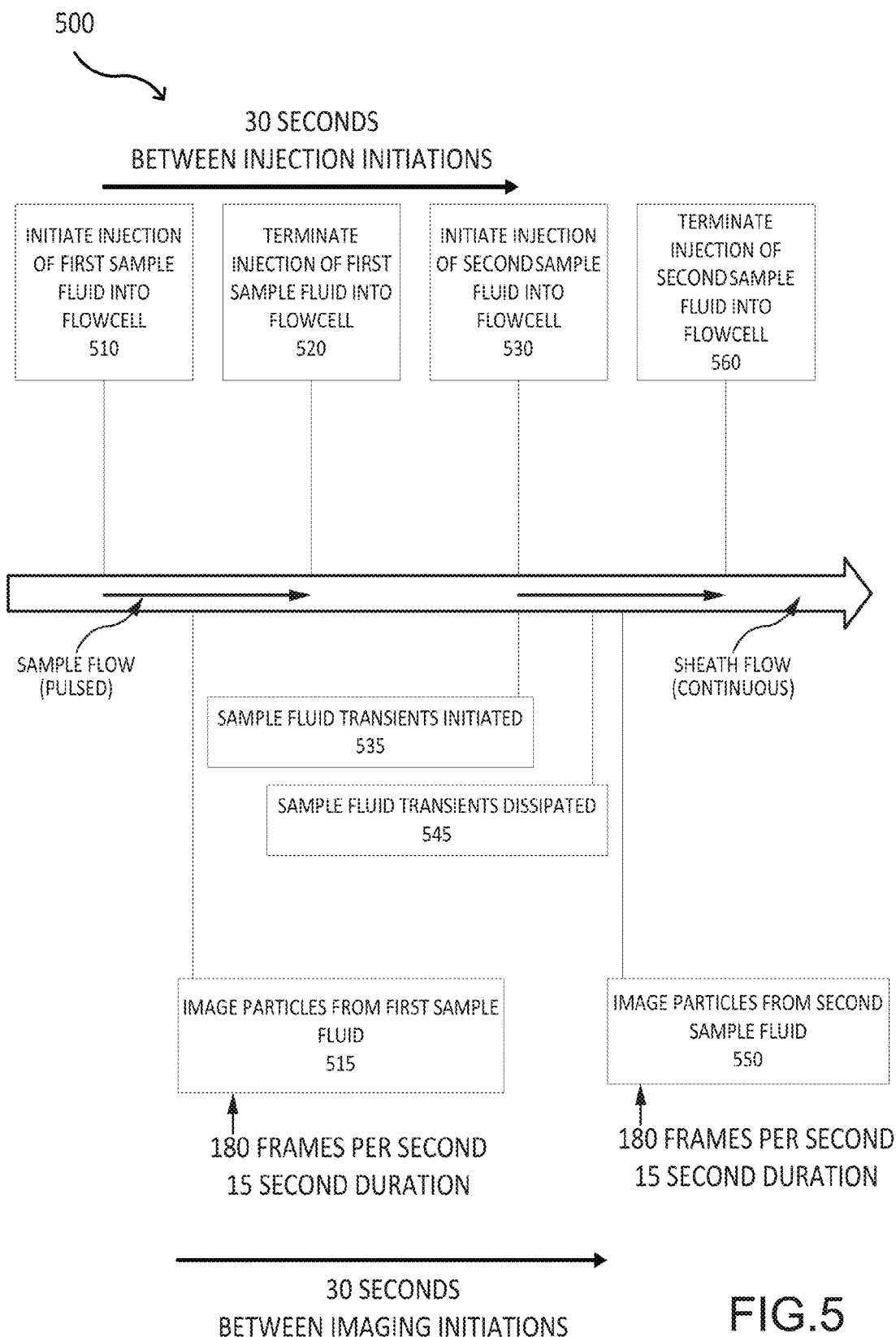
FIG. 5 depicts a timeline corresponding to the injection of one or more sample fluids in a flowcell according to embodiments of the present invention.

FIG. 5 depicts a timeline 500 corresponding to the injection of one or more sample fluids in a flowcell. As shown here, injection of a first sample fluid can be initiated into a flowcell, as indicated by step 510. Thereafter, particles from the first sample fluid can be imaged in the flowcell, as indicated by step 515. The first sample fluid can have a volume of about 900 µl. In some cases, the flow is 0.232 µL/sec (or within a range from 0.2 µL/sec to 0.35 µL/sec) at the imaging area. The injection of the first sample fluid can be terminated, as indicated by step 520, and injection of a second sample fluid can be initiated into the flowcell, as indicated by step 530. Sample fluid transients can be initiated, as indicated by step 535, as a result of termination of the first sample fluid injection and initiation of the second sample fluid injection. Subsequently, sample fluid transients in the flowcell can dissipate, as indicated by step 445. Particles from the second sample fluid can be imaged in the flowcell, as indicated by step 550. The injection of the second sample fluid can be terminated, as indicated by step 560. In some instances, the injection and flow procedures are performed at temperatures within a range from about 18° C. to about 40° C.

Typically, the stream of the sheath fluid remains flowing within the flowcell as the sample is injected, and as the injection is terminated. Hence, according to some embodiments, a continuous flow of sheath fluid is maintained while injections of sample fluid are pulsed into the flowing sheath. The continuous flow of the sheath fluid can contribute to preservation of a ribbon shape in the sample fluid as the sample fluid flows along the flowcell.

According to some embodiments, the image capture associated with step 550 can be performed within four seconds of the image capture associated with step 515. According to some embodiments, the time between first and second sample fluid injections (e.g. between steps 510 and 530) is about 30 seconds. Relatedly, according to some embodiments, the time between initiation of imaging of the first and second sample fluids (e.g. between initiation of step 515 and initiation of step 550) is about 30 seconds. In this way, it is possible to process 120 sample fluids per hour. In some cases, an image capture device operates at a frame rate of 180 frames per second (FPS), thus producing multiple unique consecutive images or frames at a high frequency or rate. As shown here, the duration of an imaging step (e.g. 515 or 550) can be 15 seconds, thus producing 2,700 images per sample fluid.

In some instances, the first sample fluid reaches a stabilized state within about 1 to 3 seconds following injection (e.g. step 510) of the first sample fluid from the sample fluid injection tube into the flowing sheath fluid. In some instances, the first sample fluid reaches a stabilized state within less than 1 second following injection (e.g. step 510) of the first sample fluid from the sample fluid injection tube into the flowing sheath fluid. The injection of the sample into the flowcell can be a two-step process. According to this embodiment, the first step is a high speed push that clears all the diluent out of the cannula, and after the initial push the flow rate of the sample is reduced significantly. The transition time can be defined as the time it takes the sample (e.g. a cell) to travel from the cannula exit to the imaging area under the imaging flow conditions (slower sample flow rate). In some instances, the first sample fluid reaches a stabilized state within about 1.8 seconds from injection (e.g. step 510) of the first sample fluid from the sample fluid injection tube into the flowing sheath fluid. In some instances, the sample fluid has a transit time through the flowcell (e.g. from an cannula exit port to an image capture site) within a range from about 2 to 4 seconds.

According to some embodiments, it takes about 5 seconds for the flow to stabilize, or to travel from a distal exit port of the cannula to the imaging area. In some cases, an image capture duration period can be about 20 seconds.

A urinalysis system according to embodiments of the present invention can process a urine sample having a volume of about 900 µL. According to some embodiments, the cannula or injection tube has an internal volume of less than about 30 uL. According to some embodiments, the cannula or injection tube has an internal volume of greater than about 30 uL. The volume of urine sample is effective to flush the cannula before starting image collection, and thus can avoid extended periods of time where the sample flow is not stable. For example, use of a cannula having an internal volume of about 13 uL can correspond to a sample flow instability period of about 2 to 3 seconds. According to some embodiments, the cannula internal volume may not impact sample flow stability. According to some embodiments, the cannula internal volume may impact the cell concentration stability in the sample ribbon itself if the initial high speed sample push is insufficient to replace all diluent inside the cannula. Relatedly, the cannula can be cleaned in between samples in a short amount of time using a small amount of diluent. In this way, it is possible to achieve a stable sample flow which facilitates the capture of a high quality image, and at the same time achieve a high throughput, with a low carry-over. According to some embodiments, a cannula with a high internal volume may require a high volume initial high speed push of sample to clear out all diluent in the lines and cannula.

According to some embodiments, urinalysis systems can be configured to limit transients and sequential sample cross-contamination so as to speed image acquisition from urine samples.

Methods

Figure 6:
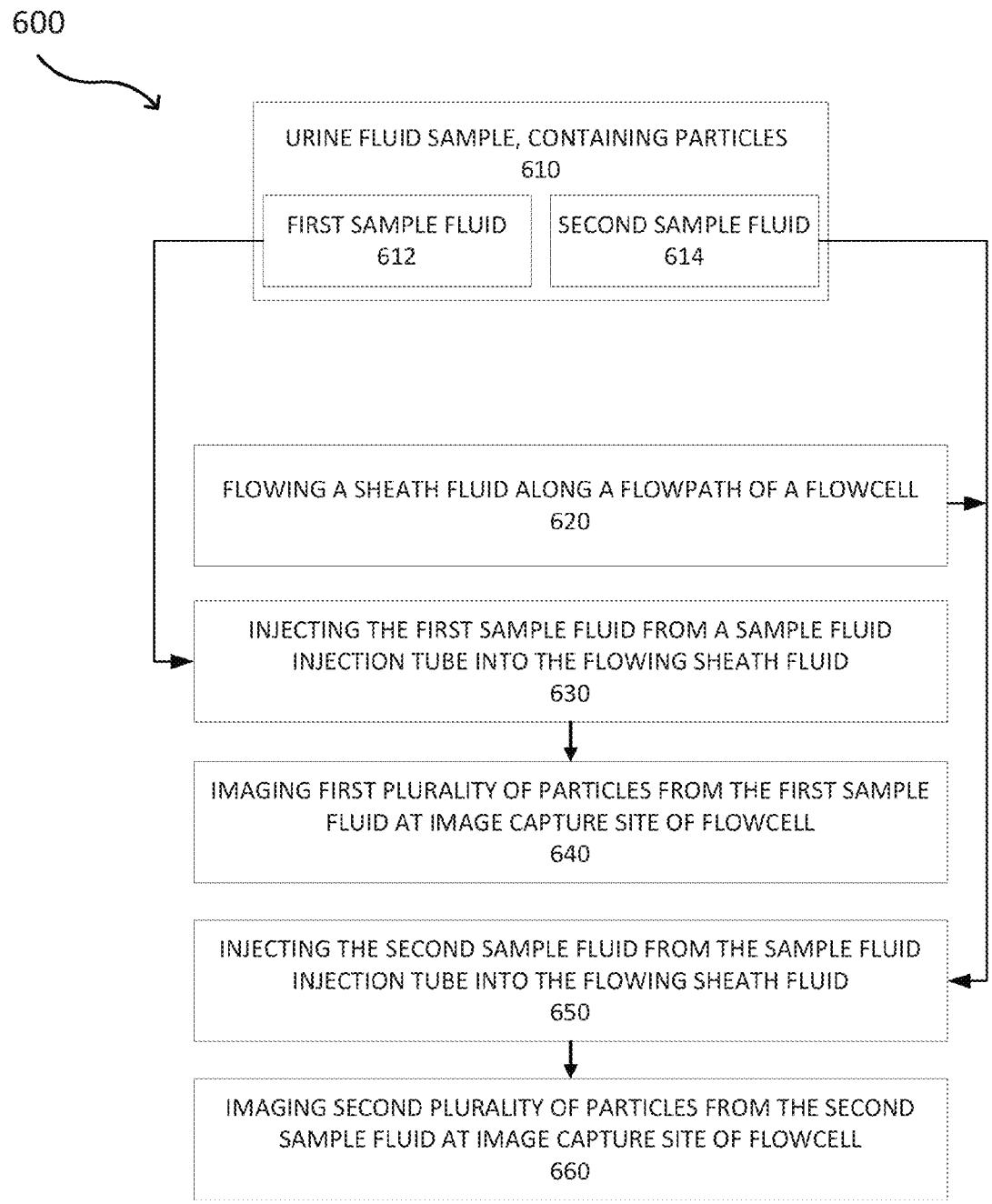
FIG. 6 depicts aspects of an exemplary method for imaging particles in a urine fluid sample, according to embodiments of the present invention.

FIG. 6 depicts aspects of an exemplary method 600 for imaging a plurality of particles using a particle analysis system configured for combined viscosity and geometric hydrofocusing, according to embodiments of the present invention. The particles can be included in a urine fluid sample 610 having a sample fluid viscosity. As shown here, the urine sample 610 includes particles, and can be portioned into one or more sample fluids, such as a first sample fluid 612 containing particles and a second sample fluid 614 containing particles.

The method can include flowing a sheath fluid 620 along a flowpath of a flowcell, as indicated by step 630. The sheath fluid 620 can have a sheath fluid viscosity that differs from the sample fluid viscosity by a viscosity difference in a predetermined viscosity difference range. The method can also include injecting the urine fluid sample 610 (first sample fluid 612) from a sample fluid injection tube into the flowing sheath fluid within the flowcell, as indicated by step 630, so as to provide a sample fluid stream enveloped by the sheath fluid.

The flowpath of the flowcell can have a decrease in flowpath size, such that a thickness of the sample fluid stream and the sheath fluid through a reduction in flowpath size toward an imaging site decreases from the initial thickness to a second thickness adjacent an image capture site. The method 600 may further include imaging a first plurality of the particles from the first sample fluid at the image capture site of the flowcell, as indicated by step 640. As the sample stream and sheath fluids pass through the reduction in flowpath size or narrowing transition zone, a viscosity hydrofocusing effect induced by an interaction between the sheath fluid and the sample fluid stream associated with the viscosity difference (as depicted in step 650), in combination with a geometric hydrofocusing effect induced by an interaction between the sheath fluid and the sample fluid stream associated with the reduction in flowpath size (as depicted in step 660), is effective to provide a target imaging state in at least some of the plurality of particles at the imaging site while a viscosity agent in the sheath fluid retains viability of cells in the sample fluid stream leaving structure and content of the cells intact when the cells extend from the sample fluid stream into the flowing sheath fluid as depicted by step 670. Methods may also include imaging the plurality of particles at the imaging site, as depicted by step 680.

The method 600 can also include initiating sample fluid transients. For example, sample fluid transients can be initiated by terminating injection of the first sample fluid into the flowing sheath fluid, and injecting the second sample fluid into the flowing sheath fluid as indicated by step 650. Further, the method 600 can include imaging a second plurality of the particles from the second sample fluid at the image capture site of the flowcell, as indicated by step 660. According to some embodiments, the imaging of the second plurality of particles can be performed substantially after the sample fluid transients and within 4 seconds of the imaging of the first plurality the particles.

Figure 6A:
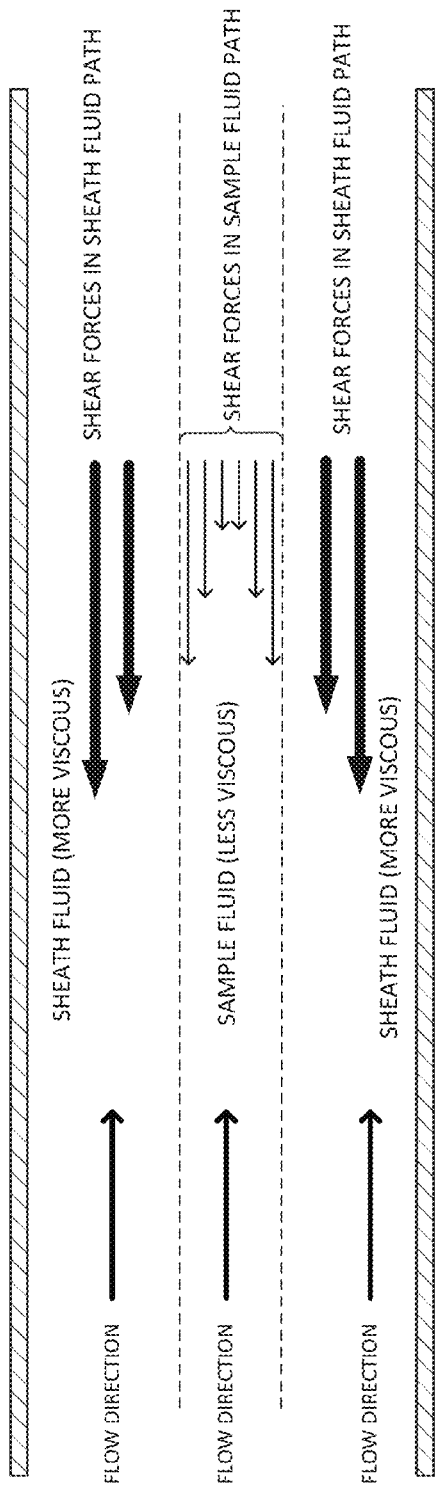
FIGS. 6A and 6B depict exemplary flowstream characteristics according to embodiments of the present invention.
Figure 6B:
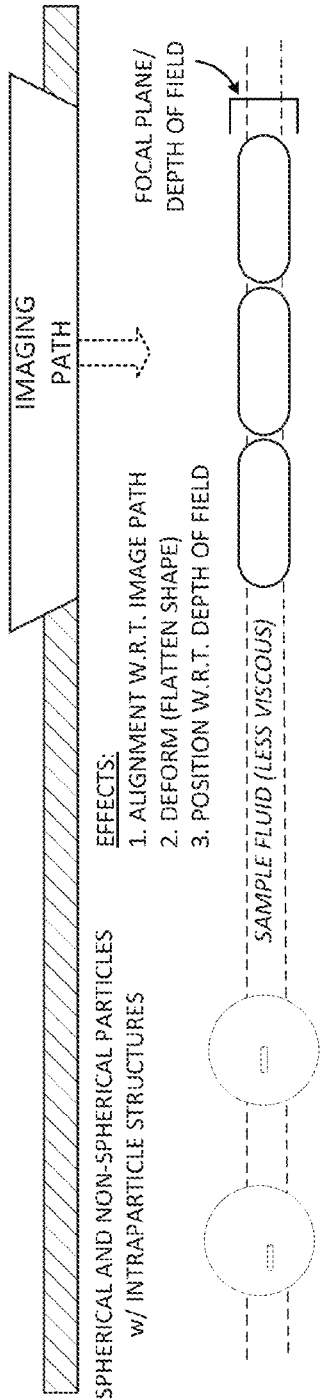
Figure 6B:
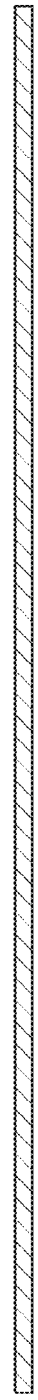

FIGS. 6A and 6B depict exemplary flowstream characteristics related to shear force, lateral compression, orientation, differential viscosity, relative movement between sheath and sample fluids, and the like.

Shear Strain Rate

Figure 7:
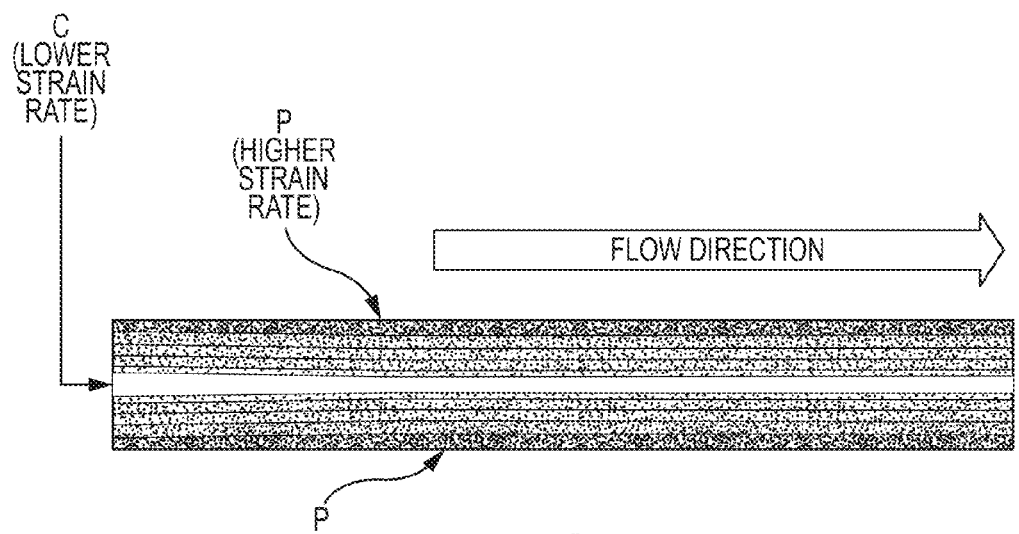
FIGS. 7 and 8 depict aspects of flowstream strain rates present within a flowpath of a flowcell according to embodiments of the present invention.
Figure 8:
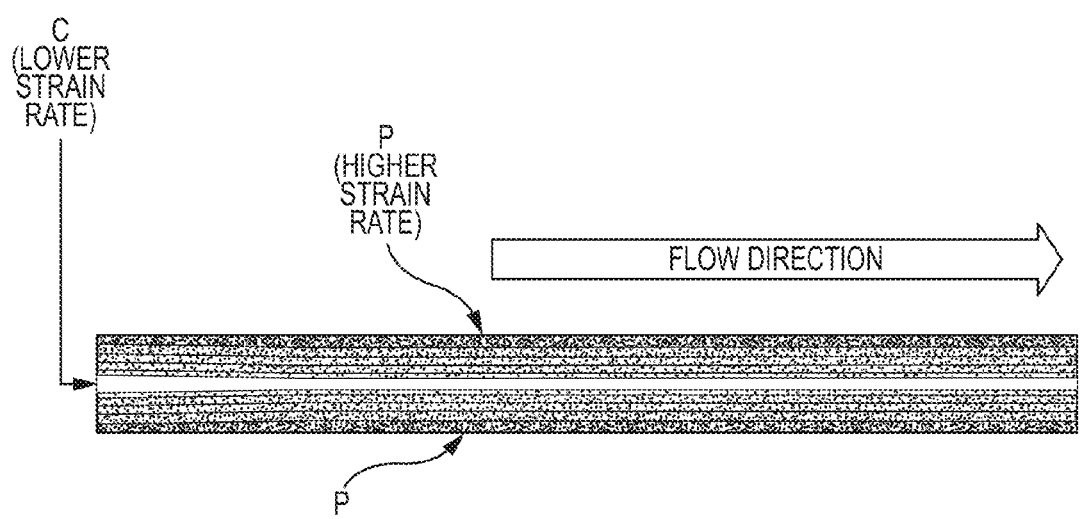

FIGS. 7 and 8 depict aspects of shear strain rate values for certain flow conditions in a flowcell according to embodiments of the present invention. In each of these drawings, a 30% glycerol sheath fluid is used. In some cases, the viscosity can have a value of $2.45 \times 10^{-3}$. A shear stress value can be equal to the product obtained by multiplying a viscosity value with a strain rate value. With regard to FIG. 7, the sample can have a flow rate of 0.3 µL/sec and the sheath fluid can have a flow rate of 21 µL/sec. With regard to FIG. 8, the sample can have a flow rate of 1 µL/sec and the sheath fluid can have a flow rate of 70 μL/sec. In each of these figures, it can be seen that the flow presents a lower strain value toward the center (C) and a higher strain value toward the periphery (P). Such strain values can correspond to an asymmetric flowcell configuration, in some embodiments.

As depicted in FIG. 7, according to some embodiments, the lower strain rate toward the center (C) portion of the flowstream can have a value of about 500 (1/s) or lower and the higher strain rate toward the periphery (P) of the flowstream can have a value of about 3000 (1/s) or higher. As depicted in FIG. 8, according to some embodiments, the lower strain rate toward the center (C) portion of the flowstream can have a value of about 1000 (1/s) or lower and the higher strain rate toward the periphery (P) of the flowstream can have a value of about 9000 (1/s) or higher.

Hence, it can be seen that lower sample and sheath fluid rates (e.g. FIG. 7) correspond to lower strain rates, and higher sample and sheath fluid rates (e.g. FIG. 8) correspond to higher strain rates. It is understood that embodiments of the present invention encompass the use of sample and/or sheath fluids corresponding to various viscosity values, various strain rate values, and/or various shear stress values.

The PIOAL has a suitable viscosity and density, and flow rates at the point of introduction to the flowcell of the sample are such that the sample fluid flattens into a thin ribbon. The ribbon-shaped sample stream is carried along with the PIOAL, to pass in front of a viewing port where an objective lens and a light source are arranged to permit viewing of the ribbon-shaped sample stream. The sample fluid is introduced, for example, injected at a point where the flowpath of the PIOAL narrows symmetrically. As a result, the sample fluid stream is flattened and stretched into a thin ribbon. A PIOAL of this disclosure may be used as the sheath fluid with any visual analyzer of this disclosure. In one embodiment, the PIOAL can be introduced into an end of the flowcell to carry along the sample fluid toward the discharge.

The dimension of the ribbon-shaped sample stream in the viewing zone is affected by geometric thinning of the PIOAL flowpath and differential linear velocity of the sample fluid and PIOAL resulting in thinning and stretching of the ribbon-shaped sample stream. The initial differential linear velocity of the sample to PIOAL may range from 0.5:1 to 5:1. The PIOAL flowpath cross section may be thinned by reducing the depth by a factor of about 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, or 200:1. In one embodiment, the geometric thinning is 40:1. In one embodiment, the geometric thinning is 30:1. Factors taken into account are transit time through the flowcell, desired rate of sample throughput, achieving a ribbon-shaped sample stream thickness comparable to particle size, obtaining alignment of particles and organelles, achieving in focus content of particles, balancing pressure, flow, and viscosity within operational limits, optimizing ribbon-shaped sample stream thickness, obtaining a desired linear velocity, manufacturability considerations, and volumes of sample and PIOAL required.

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flowcell is 1, 2, 3, or 4 seconds, or any range in between any two of those times. In some embodiments the transit time may be less than 4, 3 or 2 seconds.

The viscosities and the flow rates of the sample fluid and the PIOAL and the contour of the flowcell are arranged such that the PIOAL flow flattens and stretches the sample flow into a flat ribbon consistently through the viewing zone at a dependable location corresponding to an image capture site. The sample fluid stream may be compressed to approximately 2 to 3 μm in fluid flow thickness. Several blood cell types have diameters larger than the stream thickness. Shear forces in the direction parallel to the direction of the flow cause an increase of an image projection of the particles under imaging conditions in the focal plane of the high optical resolution imaging device and/or causing the intra-particle structures, for example, intracellular structures, organelles or lobes, to be positioned, repositioned, and/or better-positioned to be substantially parallel to the direction of flow. The high optical resolution imaging device depth of field is up to 7 μm, for example, 1-4 μm.

The flow cross section of the PIOAL, with the ribbon-shaped sample stream carried along, is constant through a viewing zone in front of a viewing port through which the objective lens is directed. The objective lens may be the objective component of a high optical resolution imaging device or the digital image capture device. The ribbon-shaped sample stream follows a path across the viewing zone at a known and repeatable position within the flowcell, for example, at a known and repeatable distance from two walls of the flowcell, being discharged downstream.

In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using a visual analyzer comprising a flowcell, a high optical resolution imaging device or the digital image capture device, optionally with an autofocus feature.

Optical information from the particles in the sample are detected by a detecting section in the analyzer, when the ribbon-shaped sample stream is carried through the viewing zone in front of the viewing port, thereby generating data from the particles/cells contained in the sample. The use of this analyzer allows capture, processing, categorization and subcategorization and counting of cells and/or particles contained in samples. The PIOAL liquid can be prepared by the addition of viscosity modifying agent, buffer agent, pH adjusting agent, antimicrobial agent, ionic strength modifier, surfactant, and/or a chelating agent. Exemplary functional components and/or features of the analyzer in the present disclosure can include, for example, the ability to acquire and/or process data from image analysis, sample staining processing, image processing, and/or particle image identification, counting, and/or categorization and subcategorization.

In one embodiment this disclosure is based on the surprising and unexpected discovery that the addition of a suitable amount of a viscosity agent in the PIOAL significantly improves particle/cell alignment in a flowcell, leading to a higher percentage of in-focus cells, or cellular components, and higher quality images of cells and/or particles in flow. A viscosity differential in combination with a geometric focusing effect of a narrowing transition zone can achieve enhanced alignment and focus results. The addition of the viscosity agent increases the shear forces on cells like RBCs, which improves the alignment of the cells in a plane substantially parallel to the flow direction, which results in image optimization. This also results in positioning, repositioning, and/or better-positioning of intraparticle structures such as intracellular structures, organelles or lobes substantially parallel to the direction of flow, which results in image optimization. The viscosity agent also reduces misalignment of cells, generally, but not limited to cells that are smaller in diameter than the flow stream.

Alignment of cells that are smaller in diameter than the flow stream, for example, red blood cells may be obtained by for example, increasing the viscosity of the PIOAL, or by increasing the flow speed ratio. This results in alignment of the RBCs parallel to the direction of the flow. In some embodiments, a reduction in RBC misalignment and/or increase in RBC alignment is achieved by increasing the viscosity of the PIOAL.

The flow cross section of the PIOAL, with the ribbon-shaped sample stream carried along, is constant through a viewing zone in front of a viewing port through which the high optical resolution imaging device is directed. The ribbon-shaped sample stream follows a path across the viewing zone at a known and repeatable distance from either of the front and rear walls of the flowcell, being discharged downstream of that.

The present disclosure provides a technique for automatically achieving a correct working position of the high optical resolution imaging device for focusing on the ribbon-shaped sample stream. The flowcell structure is configured such that the ribbon-shaped sample stream has a fixed and repeatable location between the walls of the flowcell defining the flow path of sample fluid, in a thin ribbon between layers of PIOAL, passing through a viewing zone in the flowcell. In the flowcell embodiments disclosed, for example in FIG. 1-4G, the cross section of the flowpath for the PIOAL can narrow symmetrically at a transition zone, and a sample can be inserted through a flattened orifice such as a tube with a rectangular lumen at the orifice. The narrowing flowpath (for example geometrically narrowing in cross sectional area by a ratio of 20:1 to 40:1) and also due to an optionally greater linear velocity of the PIOAL compared to the flow of the sample, cooperate to flatten the sample cross section by a ratio of about 20:1 to 70:1. According to some embodiments, the ratio can be within a range from 10:1 to 100:1, within a range from 50:1 to 100:1, within a range from 70:1 to 80:1. According to some embodiments, the ratio is 75:1. Effectively, due to the combination of flow rate, viscosity, and geometry, the sample is formed into a thin ribbon. The narrowing flowpath (for example geometrically narrowing in cross sectional area by a ratio of 40:1, or by a ratio between 20:1 to 70:1) and a difference in linear speed of the PIOAL compared to the flow of the sample, cooperate to compress the sample cross section by a ratio of about 20:1 to 70:1. In some embodiments the cross section thickness ratio may be 40:1. In some embodiments the cross section thickness ratio may be 30:1.

As a result, process variations such as the specific linear velocities of the sample and the PIOAL, do not tend to displace the ribbon-shaped sample stream from its location in the flow. Relative to the structure of the flowcell, the ribbon-shaped sample stream location is stable and repeatable.

In another aspect, this invention relates to a kit comprising the particle contrast agent compositions of this invention. The kit may also contain instructions on the use of particle contrast agent composition according to any of the methods described herein. The kit may also include a particle and/or intracellular organelle alignment liquid (PIOAL). The kit may also contain a programmable storage medium and related software for image based identification of particles such as neutrophil, lymphocytes, monocyte, eosinophils, basophils, platelets, reticulocytes, nucleated RBCs, blasts, promyelocytes, myelocytes, metamyelocytes, bacteria, fungi, protists, protozoa, or parasites. The kit may also comprise one or more buffers, which may include isotonic buffers and/or diluents. The kit and or buffer may further comprise a surfactant, a pH adjusting agent, and/or an antimicrobial agent. In other embodiments, the kit may also comprise a cleaning or flushing solution. The kit may also comprise standards for positive and negative controls. In some embodiments the standard may comprise a standard stained cell reagent. The kit may also comprise disposables such as disposable micropipettes, tips or tubes for transferring the components of the kit. The kit may contain any one, or any combination of two or more of these kit components.

The discrimination of blood cells or other particles in a urine sample is an exemplary application for which embodiments of the instant invention are particularly well suited. The sample is prepared by automated techniques and presented to a high optical resolution imaging device as a thin ribbon-shaped sample stream to be imaged periodically while the ribbon-shaped sample stream flows across a field of view. The images of the particles (such as blood cells) can be distinguished from one another, categorized, subcategorized, and counted, using pixel image data programmed processing techniques, either exclusively automatically or with limited human assistance, to identify and count cells or particles. In addition to the cell images, which can be stored and made available in the case of unusual or critical features of particles, the output data includes a count of the occurrences of each particular category and/or subcategory of cell or particle distinguished in the recorded sample images.

The counts of the different particles found in each image can be processed further, for example used to accumulate accurate and statistically significant ratios of cells of each distinguished category and/or subcategory in the sample as a whole. The sample used for visual discrimination can be diluted, but the proportions of cells in each category and/or subcategory are represented in the diluted sample, particularly after a number of images have been processed.

The apparatus, compositions, and methods disclosed herein are useful in discriminating and quantifying cells in samples based on visual distinctions. The sample can be a biological sample, for example, a body fluid sample comprising white blood cells, including without limitation, blood, serum, bone marrow, lavage fluid, effusions, exudates, cerebrospinal fluid, pleural fluid, peritoneal fluid, and amniotic fluid. In some embodiments, the sample can be a solid tissue sample, e.g., a biopsy sample that has been treated to produce a cell suspension. The sample may also be a suspension obtained from treating a fecal sample. A sample may also be a laboratory or production line sample comprising particles, such as a cell culture sample. The term sample may be used to refer to a sample obtained from a patient or laboratory or any fraction, portion or aliquot thereof. The sample can be diluted, divided into portions, or stained in some processes.

In one aspect, the systems, compositions and methods of this disclosure provide surprisingly high quality images of cells in a flow. In one aspect, the visual analyzer can be used in methods of this disclosure to provide automated image based WBC differential counting. In certain embodiments, the methods of this disclosure relate to automated identification of visual distinctions, including morphological features and/or abnormalities for determining, diagnosing, prognosing, predicting, and/or supporting a diagnosis of whether a subject is healthy or has a disease, condition, abnormality and/or infection and/or is responsive or non-responsive to treatment. The system may further comprise a particle counter in some embodiments. Applications include categorizing and/or subcategorizing, and counting cells in a fluid sample, such as a urine sample. Other similar uses for counting additional types of particles and/or particles in other fluid samples are also contemplated. The system, compositions, and methods of this invention can be used for real-time categorization and subcategorization and viewing of images using any suitable automated particle recognition algorithm. The captured images for each sample can be stored to be viewed at a later date.

In another aspect, the apparatus, compositions, and methods of this invention provide surprisingly more accurate image based cell categorization and subcategorization and flagging which reduces the manual review rate compared to the manual review rate when using current automated analyzers. The systems, compositions, and methods reduce the manual review rate and permit the manual review to be performed on the instrument. In addition, the systems, compositions, and methods of this disclosure also reduce the percentage of samples flagged during automated analysis as requiring manual review.

Accordingly, in some embodiments, the present disclosure provides an apparatus and a method for analyzing a sample containing particles, for example, blood cells. According to this disclosure, a visual analyzer is provided for obtaining images of a sample comprising particles suspended in a liquid. In some embodiments, the visual analyzer comprises a flowcell and an autofocus component, in which a liquid sample containing particles of interest is caused to flow through a flowcell having a viewport through which a camera coupled to an objective lens captures digital images of particles. Exemplary autofocus techniques which can be implemented using embodiments of the present invention are disclosed in co-pending U.S. patent application Ser. No. 14/216,811, filed Mar. 17, 2014, the content of which is incorporated herein by reference. The flowcell is coupled to a source of sample fluid, such as a diluted and/or treated urine sample or other bodily fluid sample as described herein, and to a source of a clear sheath fluid, or particle and/or intracellular organelle alignment liquid (PIOAL).

In one embodiment, the apparatus also comprises a particle counter having at least one detection range, as well as an analyzer, and a processor. The analyzer and the processor are configured to provide additional information to correct counting, categorization, and subcategorization errors associated with the particle counter, and further determine accurate particle count or concentration of different categories and/or subcategories of particles in the sample.

In other embodiments, this disclosure relates to a PIOAL that can be used in image based analysis of particles as described herein. Cell category and/or subcategory count in urine samples is used in this disclosure as nonlimiting examples of the sort of samples that may be analyzed. In some embodiments, cells present in samples may also include bacterial or fungal cells as well as white blood cells and/or red blood cells.

According to some embodiments, the particulars of sample preparation apparatus and methods for sample dilution, permeabilizing and histological staining, generally are accomplished using precision pumps and valves operated by one or more programmable controllers, and are not central to this disclosure. Examples can be found in patents assigned to International Remote Imaging Systems, Inc., such as U.S. Pat. No. 7,319,907, concerning programmable controls. Likewise, techniques for distinguishing among certain cell categories and/or subcategories by their attributes such as relative size and color can be found in U.S. Pat. No. 5,436,978 in connection with white blood cells. The disclosures of these patents are hereby incorporated by reference. According to some embodiments, sample preparation techniques may include staining, lysing, permeabilizing, and other processing modalities such as those described in co-pending U.S. patent application Ser. No. 14/216,562, filed Mar. 17, 2014, the content of which is incorporated herein by reference.

The term high optical resolution imaging device can include devices that are capable of obtaining particles images with sufficient visual distinctions to differentiate morphological features and/or changes. Exemplary high optical resolution imaging devices can include devices with an optical resolution of 1 µm or lower, including for example, 0.4 to 0.5 µm, such as for example, 0.46 µm.

In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using a visual analyzer comprising a flowcell, a high optical resolution imaging device or the digital image capture device, optionally with an autofocus feature.

In one embodiment, the images provide information relating to the cytosolic, cell nucleus and/or nuclear components of the cell. In one embodiment, the images provide information relating to the granular component and/or other morphological features of the cell. In one embodiment, the images provide information relating to cytosolic, nuclear and/or granular components of the cell. The granular and/or nuclear images and/or features are determinative for cell categorization and subcategorization both independently or in combination with each other.

Autofocus Target

With returning reference to FIG. 1, particle imaging systems can include an autofocus pattern or target 44 that is fixed relative to the flowcell 22. The autofocus target 44 can be used to achieve focused images of urine fluid particles that flow through the flowcell.

Figure 9A:
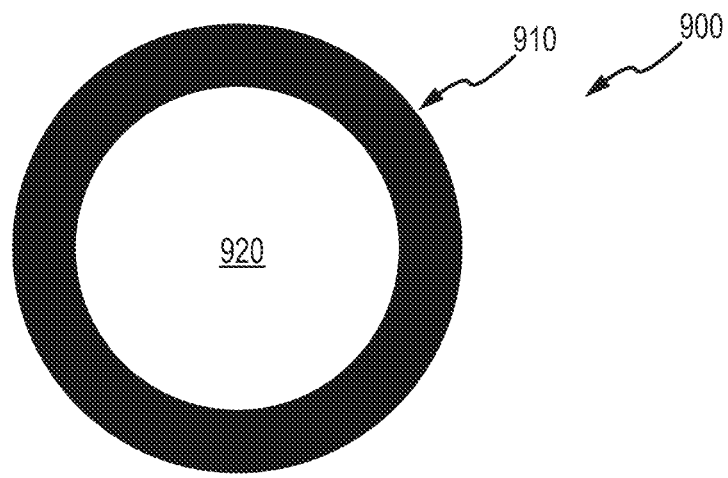
FIG. 9A depicts an exemplary autofocus target according to embodiments of the present invention.
Figure 9B:
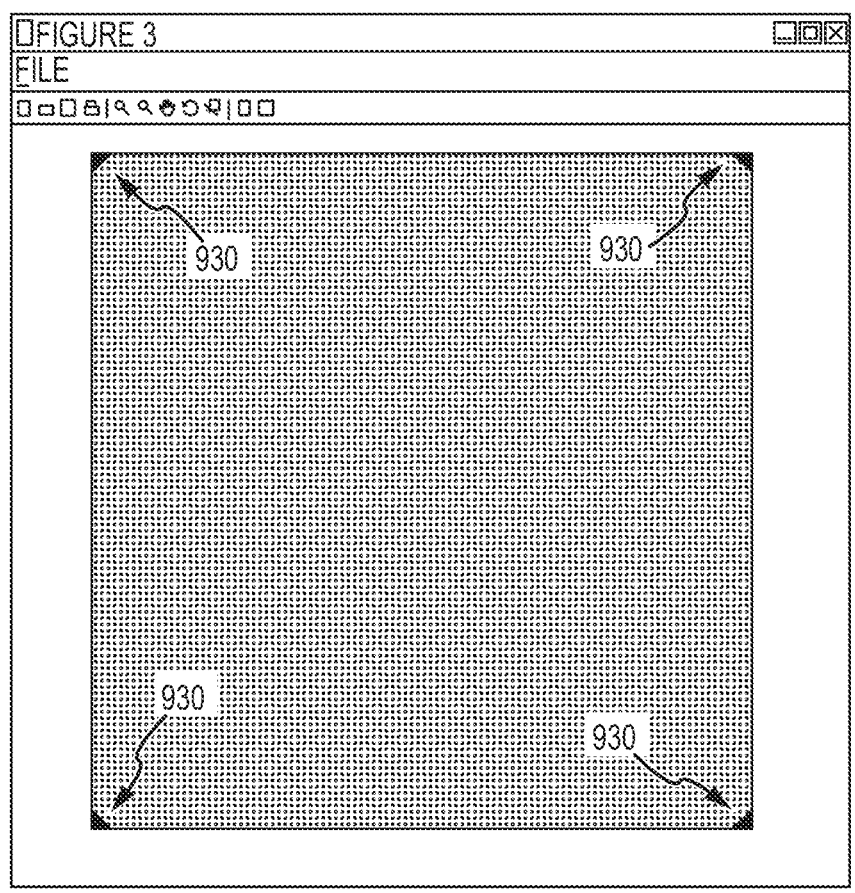
FIG. 9B shows a captured image according to embodiments of the present invention.

FIG. 9A depicts an exemplary autofocus target 900 according to embodiments of the present invention. As shown here, the target 900 includes an opaque annular band 910 and a transparent center or aperture 920. In operation, the imaging device focuses on the band 910, and captures the image through the aperture. As discussed elsewhere herein, and in co-pending U.S. patent application Ser. No. 14/618,811, filed Mar. 17, 2014, an image capture process can involve first focusing (or auto-focusing) on the band 910, and then adjusting a distance between the image capture device and the sample fluid stream prior to obtaining the image through the aperture 920. Accordingly, the band 910 can present a target upon which an auto-focus system of the image capture device can detect and focus upon, and certain portions of the target (e.g. edges or segments) can be included in the image. In some cases, the target can be provided as a chrome disc having a central aperture. An exemplary target can be provided with a central pinhole, having a diameter of about 0.5 mm, that is glued or fixed to the flowcell. The size of the central pinhole or aperture 920 can be selected so that only four edge portions 930 of the opaque annular band 910 are visible in the captured image 940, as illustrated in FIG. 9B. Hence, the annular band 910 does not interfere with the capturing of cell images (e.g. light can pass through the aperture 920 so as to illuminate the sample particles, and the field of view is substantially unimpeded by the annular band). In this way, the band 910 shows up only in the corners of the image.

Figure 11:
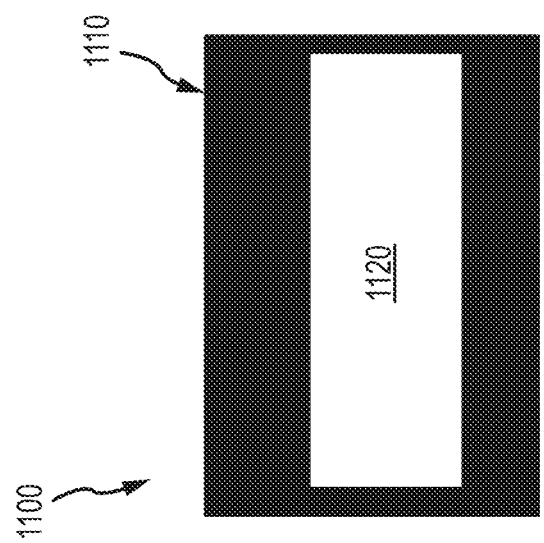
FIGS. 10 and 11 depict exemplary autofocus targets according to embodiments of the present invention.
Figure 10:
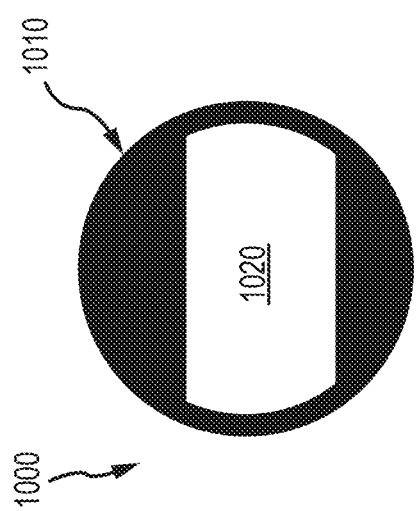

FIG. 10 depicts an exemplary autofocus target 1000 according to embodiments of the present invention. The target 1000 includes a band or border 1010 and a central aperture 1020. FIG. 11 shows another exemplary autofocus target 1100 according to embodiments of the present invention. The target 1100 includes a band or border 1110 and a central aperture 1120. According to some embodiments, the autofocus target 1100 provides an image having 50 pixels of black on the top and the bottom. In some cases, the autofocus target 1100 provides an flowcell focus offset (FCFO) of about 65.3 µm.

Figure 12A:
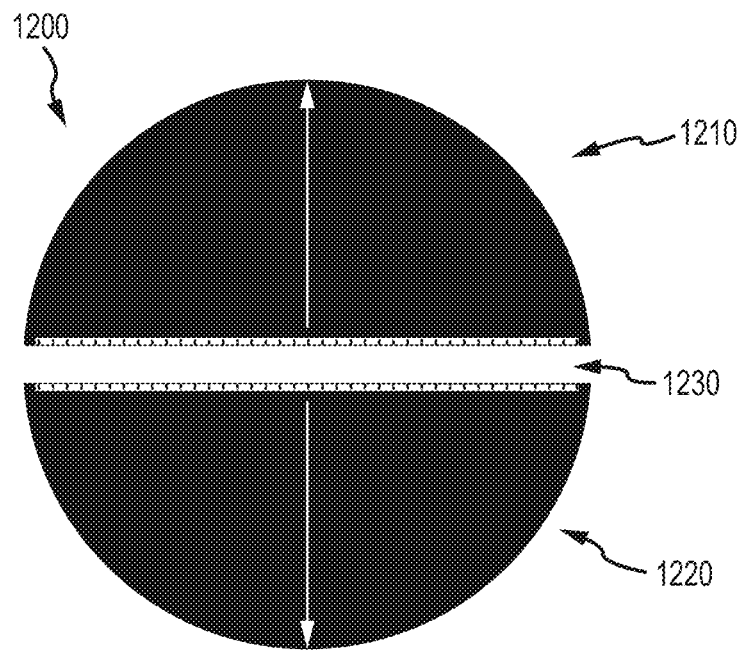
FIG. 12A depicts an exemplary autofocus target according to embodiments of the present invention.

FIG. 12A depicts an exemplary autofocus target 1200 according to embodiments of the present invention. The target 1200 is presented as a letterbox design, and includes a first or upper border 1210 and a second or lower border 1220. The target 1200 also includes an aperture or transparent passage 1230 between the first and second borders. According to some embodiments, the target has a diameter of about 4 mm, and the height of the letterbox is 265 µm. In some cases, the upper and lower borders can be present as half circles, and can be produced with a deposited metal such as chromium oxide or some other opaque material.

In another aspect of the methods of this invention, the cells contacted with particle contrast agent composition and/or imaged are abnormal cells, such as malaria-infected cells, atypical lymphocytes. In some aspects of this invention, the cells are abnormal cells which can be used to identify, predict, diagnose, prognose, or support a diagnosis of a condition, disease, infection and/or syndrome.

Figure 12B:
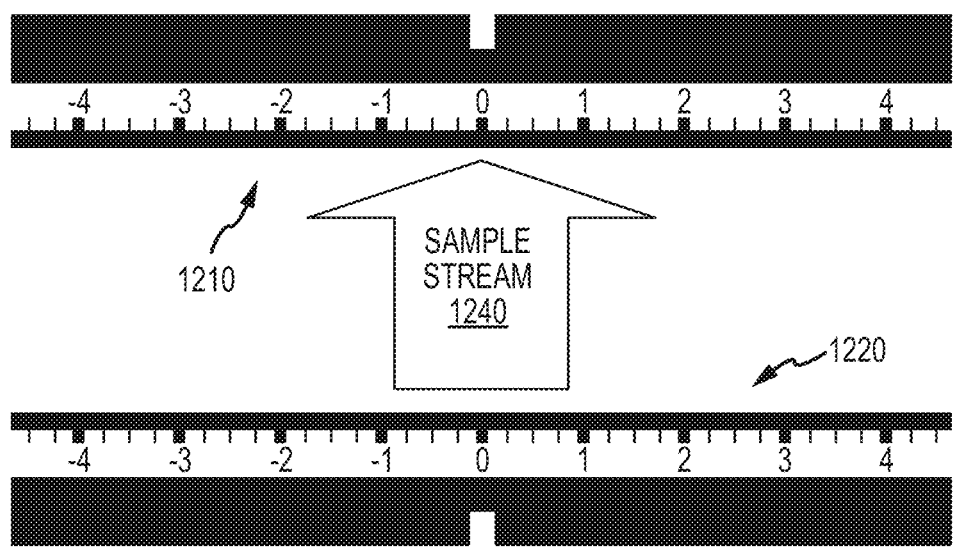
FIG. 12B shows a close-up view of the central portion of the autofocus target according to embodiments of the present invention.

FIG. 12B shows a close-up view of the central portion of the autofocus target 1200. As shown here, the first border 1210 includes a negative/positive numerical scale, with a centered zero value. The second border 1220 includes a similar scale. In some cases, the scale increments are 100 µm. According to some embodiments, the scales can be used to facilitate positioning of the flow cell so that the field of view of the imaging device or camera can be centered on the sample stream. As shown here, the sample stream 1240 flows in a direction perpendicular to the scales of the first and second borders. As part of a focusing protocol, the image capture device can operate to focus on the numbers or other characters or imagable objects present on the borders 1210, 1220.

Figure 13A:
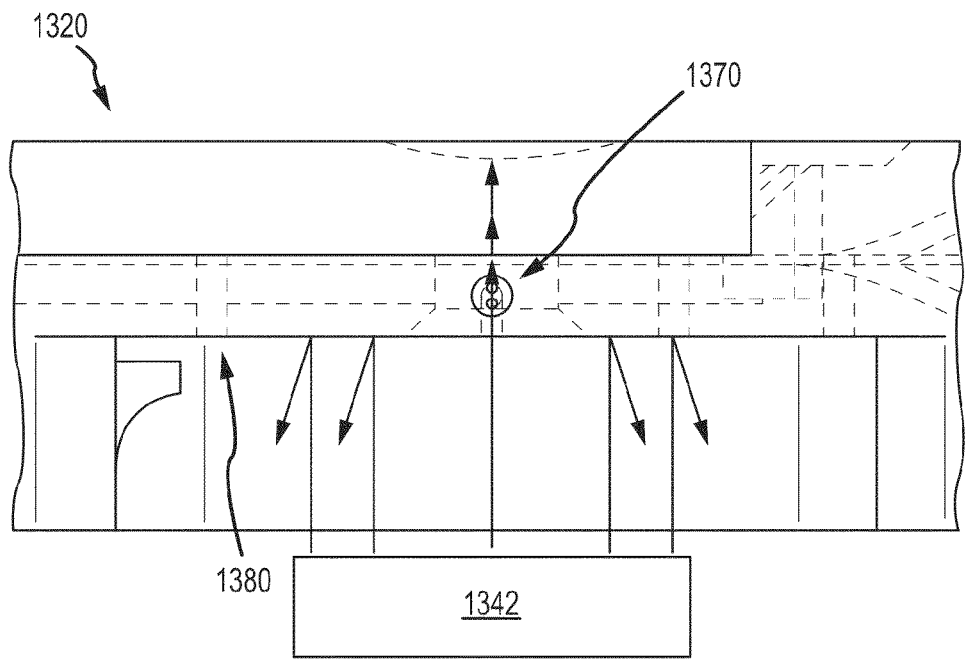
FIGS. 13A, 13B, and 13C depict views of flowcell temperature sensors according to embodiments of the present invention.
Figure 13B:
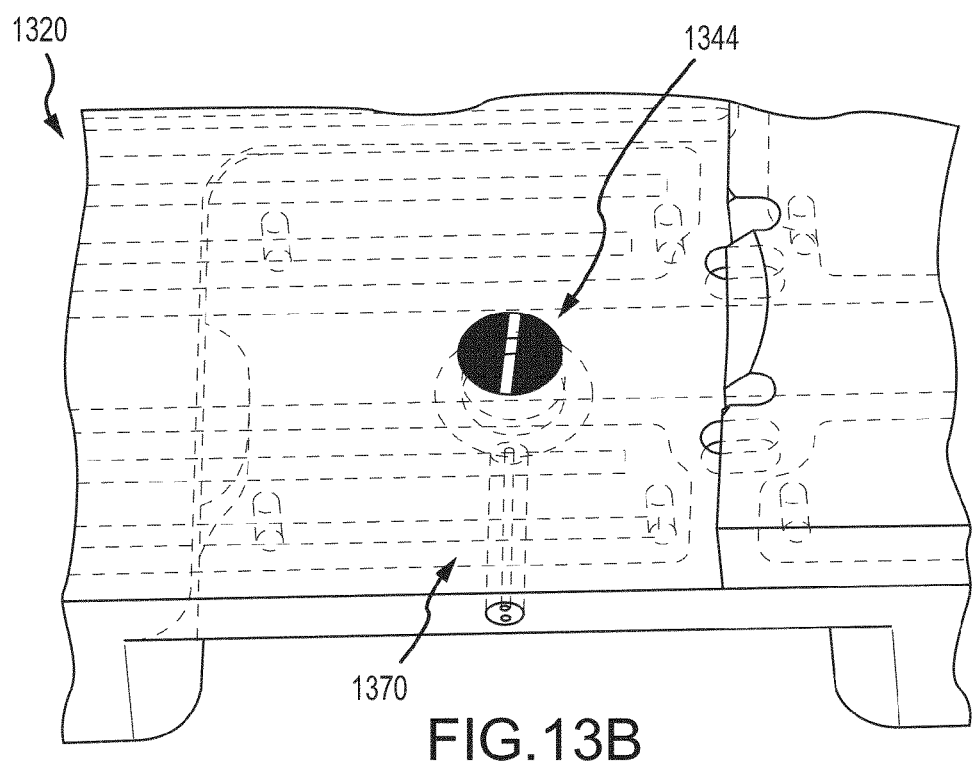

Embodiments of the present invention encompass techniques for addressing thermal drift associated with use of the particle analysis system, whereby such thermal effects may otherwise compromise the quality of images obtained with the imaging device. FIG. 13A depicts a partial side view of a flowcell 1320 having a thermal sensor 1370, a reflector 1380, and an autofocus target 1344. During operation of a particle analysis system, thermal effects may cause the sample stream to slowly drift out of focus of the imaging device. For example, thermal effects can be caused by thermal expansion of the flow cell through radiated heat coming from the lamp. Further, thermal effects can be caused by thermal expansion of the flowcell and optical bench assembly (OBA) assembly through conductive and radiative heating. In some embodiments, certain components of the OBA can expand, which may contribute to focusing errors. For example, such components may include metal plates that hold camera 24 together, a metal plate that holds or is connected to the flow cell, or a metal plate that holds both the flowcell and camera 24 together. FIG. 13B depicts a partial perspective view of flowcell 1320 having thermal sensor 1370 and autofocus target 1344. Further, FIG. 13C depicts another perspective view of flowcell 1320 having a thermal sensor 1370, reflector 1380, and autofocus target 1344.

Figure 13C:
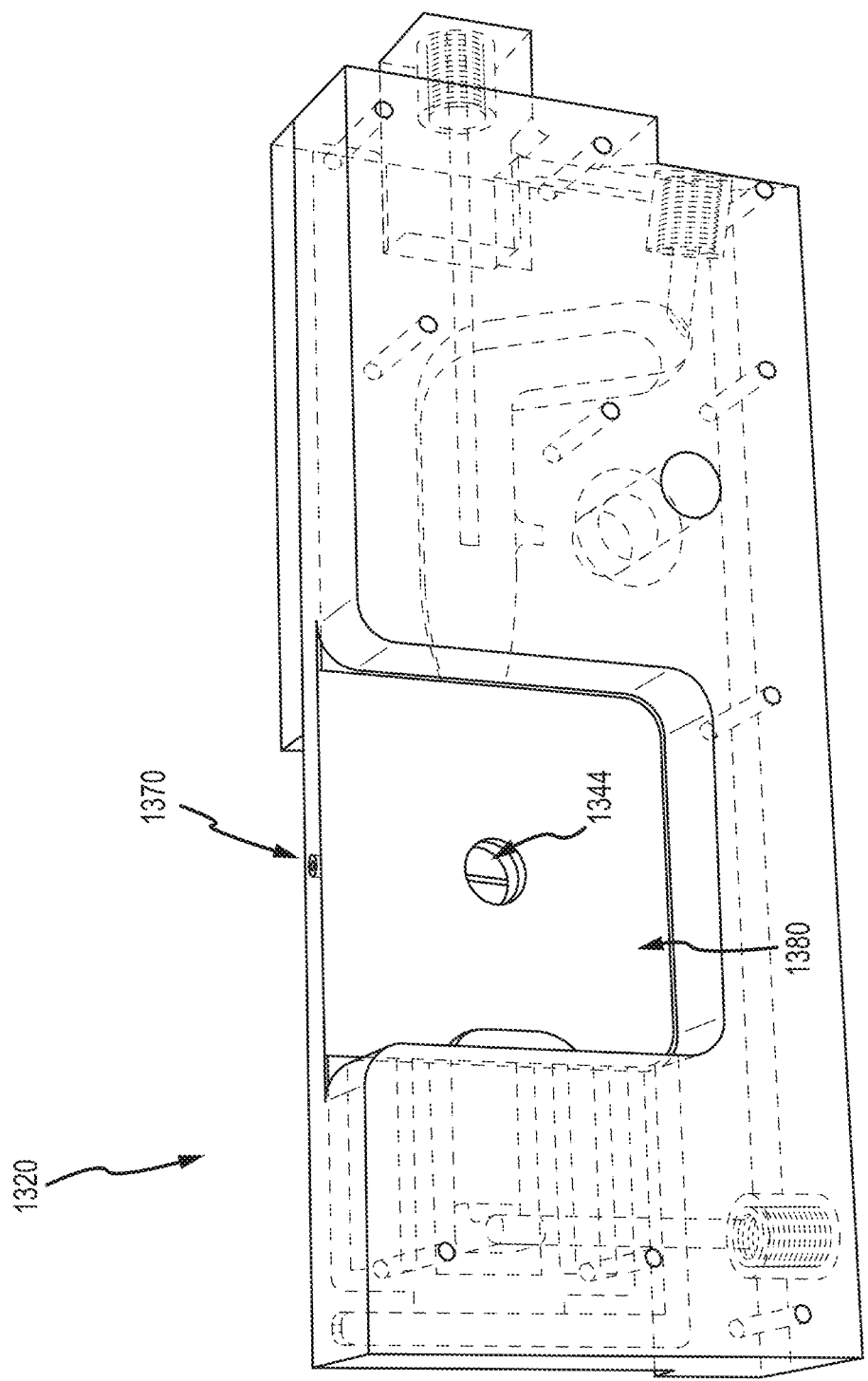

FIG. 13C depicts another perspective view of flowcell 1320 having a thermal sensor 1370, reflector 1380, and autofocus or imaging target 1344. Reflector 1380 can operate to reduce or limit the amount of heat absorbed by flowcell 1320. For example, reflector 1380 can block heat radiated by a flash lamp 1342 as indicated in FIG. 13A. Hence, reflector 1380 can minimize the thermal impact of the lamp. Reflector 1342 can also reduce glare and light scatter generated by the lamp, thus resulting in improved image quality. Thermal sensor 1370 is positioned near the fluid flow channel and adjacent to the image capture site, so that accurate temperature readings can be obtained. Information from the temperature sensor can be used to focus the image capture device on the sample fluid ribbon stream. Exemplary autofocusing techniques disclosed herein can be based on temperature fluctuations occurring within certain elements of the analyzer.

Figure 13D:
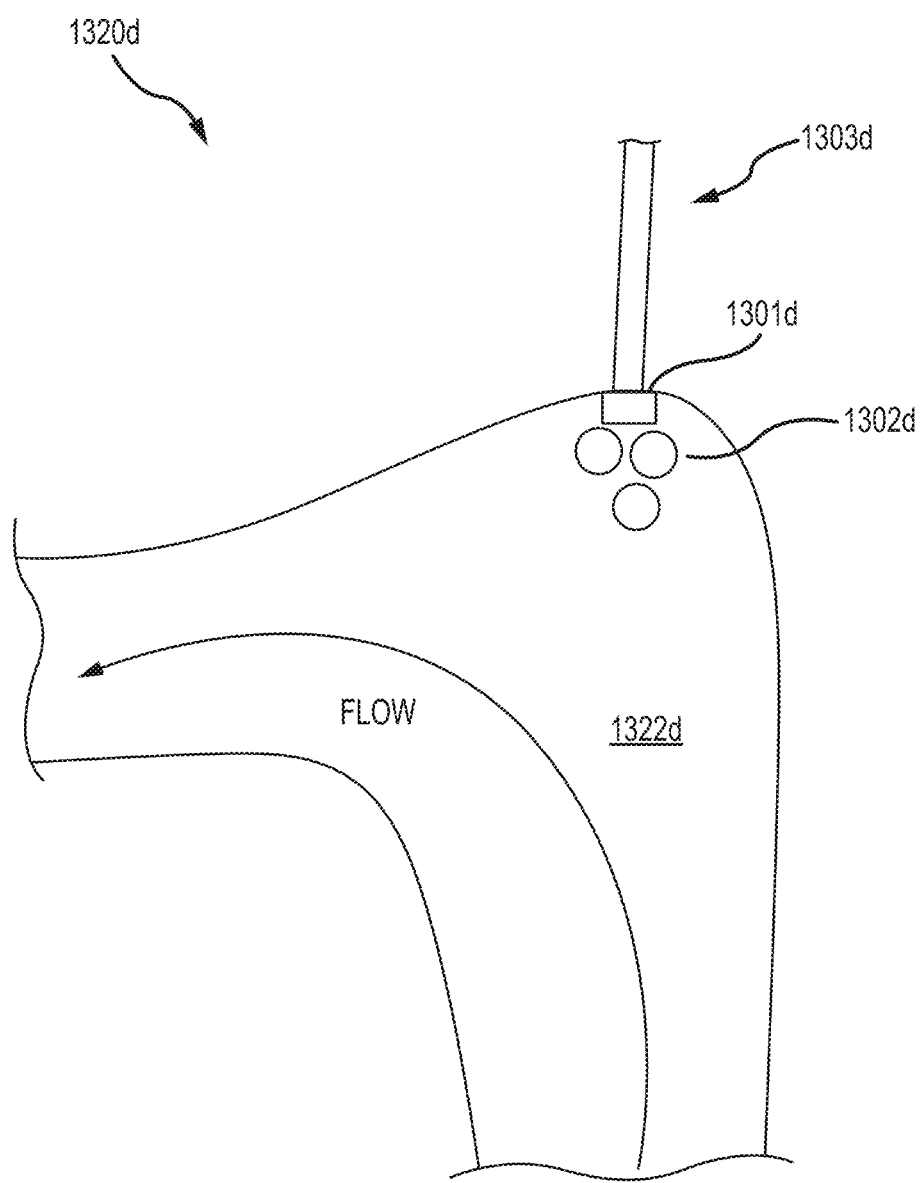
FIG. 13D depicts aspects of flowcell bubble removal techniques according to embodiments of the present invention.

As depicted in FIG. 13D, a flowcell 1300d can include a flowpath 1322d having a port or vent 1301d through which bubbles 1302d may be released or removed. As depicted here, a tube 1303d, through which vacuum can be applied, can be contacted with the port 1301d so as to withdraw bubbles 1302d from the flowstream. Such a bubble removal mechanism is suitable for removing bubbles from the flowing fluid within the flowcell, and can operate to prevent bubbles or microbubbles from becoming lodged or stuck inside of the flowcell. The flowsteam is depicted in an upward direction in FIG. 13D. It is understood that in some embodiments, the flowstream may travel through the flowcell in a downward direction. The bubbles shown here float toward the top of the fluid within the flowcell.

According to some embodiments, a method for imaging particles in a urine sample may include flowing a sheath fluid along a flowpath of a flowcell, and injecting the urine sample into the flowing sheath fluid within the flowcell so that the urine sample flows in a sample flowstream with a flowstream width greater than a flowstream thickness, such that the flowcell has an associated temperature. Further, the method may include focusing an image capture device, along an imaging axis, on the flowstream to a first focal state while the temperature associated with the flowcell is at a first temperature, and acquiring a first focused image of a first subset of the particles within the flowstream with the image capture device at the first focal state. What is more, the method may include determining that the temperature associated with the flowcell has undergone a change from the first temperature to a second temperature, and automatically adjusting focus of the image capture device from the first focal state to a second focal state in response to the change in temperature and a known relationship between flowcell temperature and desired focus. Still further, the method may include acquiring a second focused image of a second subset of the particles within the flowstream with the image capture device at the second focal state.

In some cases, the process of adjusting focus of the image capture device includes adjusting a distance between the image capture device and the flowcell using the change in temperature and the known relationship between flowcell temperature and desired focus. In some cases, the process of adjusting focus of the image capture device includes adjusting a focal distance of the image capture device using the change in temperature and the known relationship between flowcell temperature and desired focus.

Focused Images

Figure 14A:
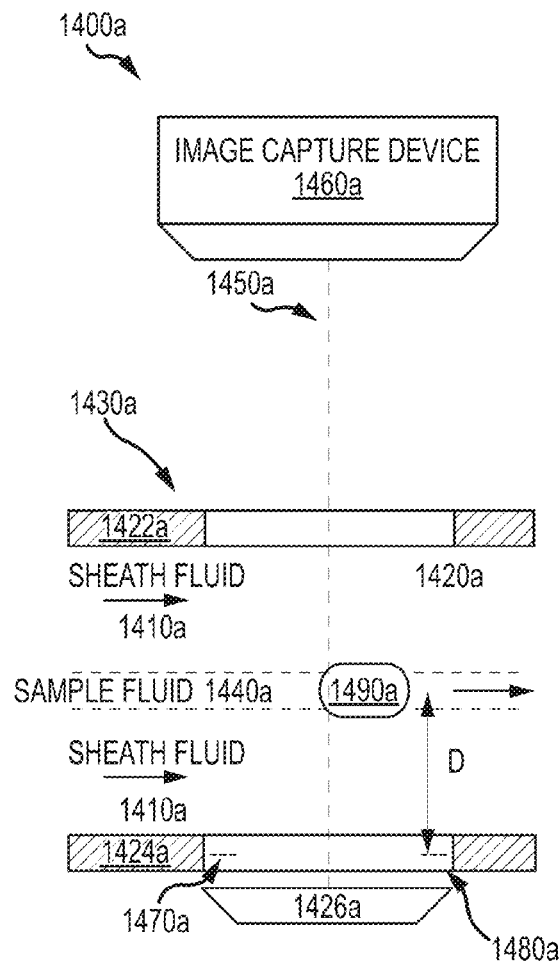
FIGS. 14A and 14B provide cross-section side views that illustrate aspects of focusing systems and methods, according to embodiments of the present invention.
Figure 14B:
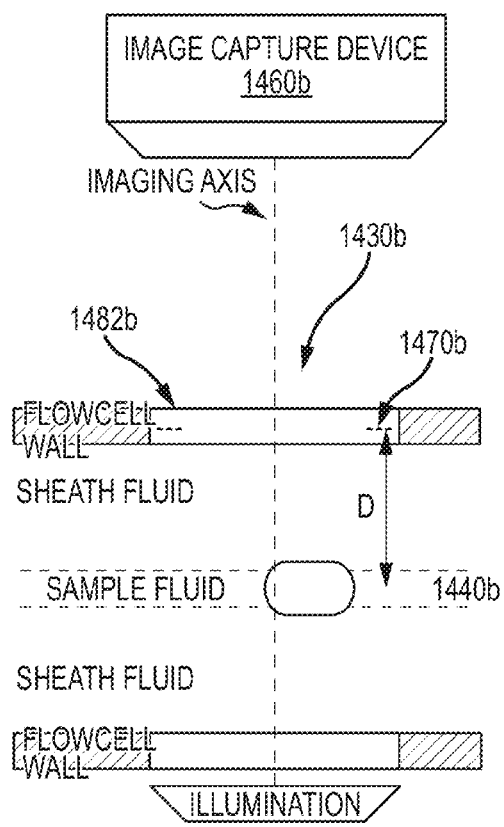

FIGS. 14A and 14B provide cross-section side views that illustrate aspects of imaging systems and methods, according to embodiments of the present invention. With reference to FIG. 14A, a particle analysis system 1400a such as a urine sample analyzer can be configured for viscosity and/or geometric hydrofocusing, for example using flowcell and viscous sheath fluid techniques such as those described herein. An exemplary method for imaging particles in a urine sample using the particle analysis system can include flowing a sheath fluid 1410a along a flowpath 1420a of a flowcell 1430a of the particle analysis system. The flowpath 1420a can be defined at least in part by opposing flowcell walls 1422a, 1424a of the flowcell. The sheath fluid 1410a can have a viscosity that is different from a viscosity of the urine sample. The imaging method can further include injecting the urine sample into the flowing sheath fluid 1410a within the flowcell 1430a so that the urine sample fluid flows in a sample flowstream 1440a. The sample flowstream 1440a can have a flowstream width greater than a flowstream thickness. The sample flowstream 1440a can also flow through a decrease in flowpath size and traverse an imaging axis 1450a. In the FIG. 14A illustration, the direction of flow is from the left to the right.

Additionally, the imaging method can include focusing an image capture device 1460a by imaging an imaging target 1470a having a position fixed relative to the flowcell 1430a. For example, as depicted here, the imaging target 1470a can have a position fixed relative to an illumination window 1480a of the flowcell. In some cases, the imaging target 1470a can be embedded within or fixed upon the window 1480a. Methods can also include acquiring a focused image of the particles of the sample fluid (e.g. particle 1490a, disposed at least partially within the flowstream 1440a) with the image capture device 1460a. The focused image is suitable for particle characterization and counting.

The image capture device 1460a can be focused on the sample flowstream 1440a using a displacement distance. For example, the displacement distance can correspond to a distance D between the sample flowstream 1440a and the imaging target 1470a. The viscosity difference between the sheath fluid 1410a and urine sample, in combination with the decrease in flowpath size, is effective to hydrofocus the sample fluid in the sample flowstream 1440a at the imaging axis 1450a while retaining viability of cells in the urine sample. For example, a viscosity hydrofocusing effect induced by an interaction between the sheath fluid 1410a and the sample fluid stream 1440a associated with the viscosity difference, in combination with a geometric hydrofocusing effect induced by an interaction between the sheath fluid 1410a and the sample fluid stream 1440a associated with the reduction in flowpath size, can be effective to provide a target imaging state in at least some of the fluid sample particles at the imaging axis 1450a while a viscosity agent in the sheath fluid 1410a retains viability of cells in the sample fluid stream 1440a leaving structure and content of the cells intact when the cells extend from the sample fluid stream 1440a into the flowing sheath fluid 1410a.

As the image capture device 1460a is focused on the sample flowstream 1440a using the displacement distance, the image capture device 1460a can obtain images of particles or cells within the sample flowstream 1440a at the imaging axis 1450a, or at an image capture site associated with the imaging axis 1450a. In some cases, the particles can be illuminated with an illumination source or lamp 1426a. Images of the sample flowstream 1440a can be obtained as particles approach the imaging axis 1450a, as the particles traverse the imaging axis 1450a, and/or as the particles flow away from the imaging axis 1450a.

FIG. 14B depicts aspects of an alternative flowcell configuration, where the imaging target 1470b has a position fixed relative to a viewport window 1482b of the flowcell 1430b. For example, the imaging target 1470b can be embedded within or fixed upon the window 1482b. As shown here, the imaging method can include focusing an image capture device 1460b by imaging an imaging target 1470b having a position fixed relative to the flowcell 1430b. Further, the image capture device 1460b can be focused on the sample flowstream 1440b using a displacement distance. For example, the displacement distance can correspond to a distance D between the sample flowstream 1440b and the imaging target 1470b.

Figure 14C:
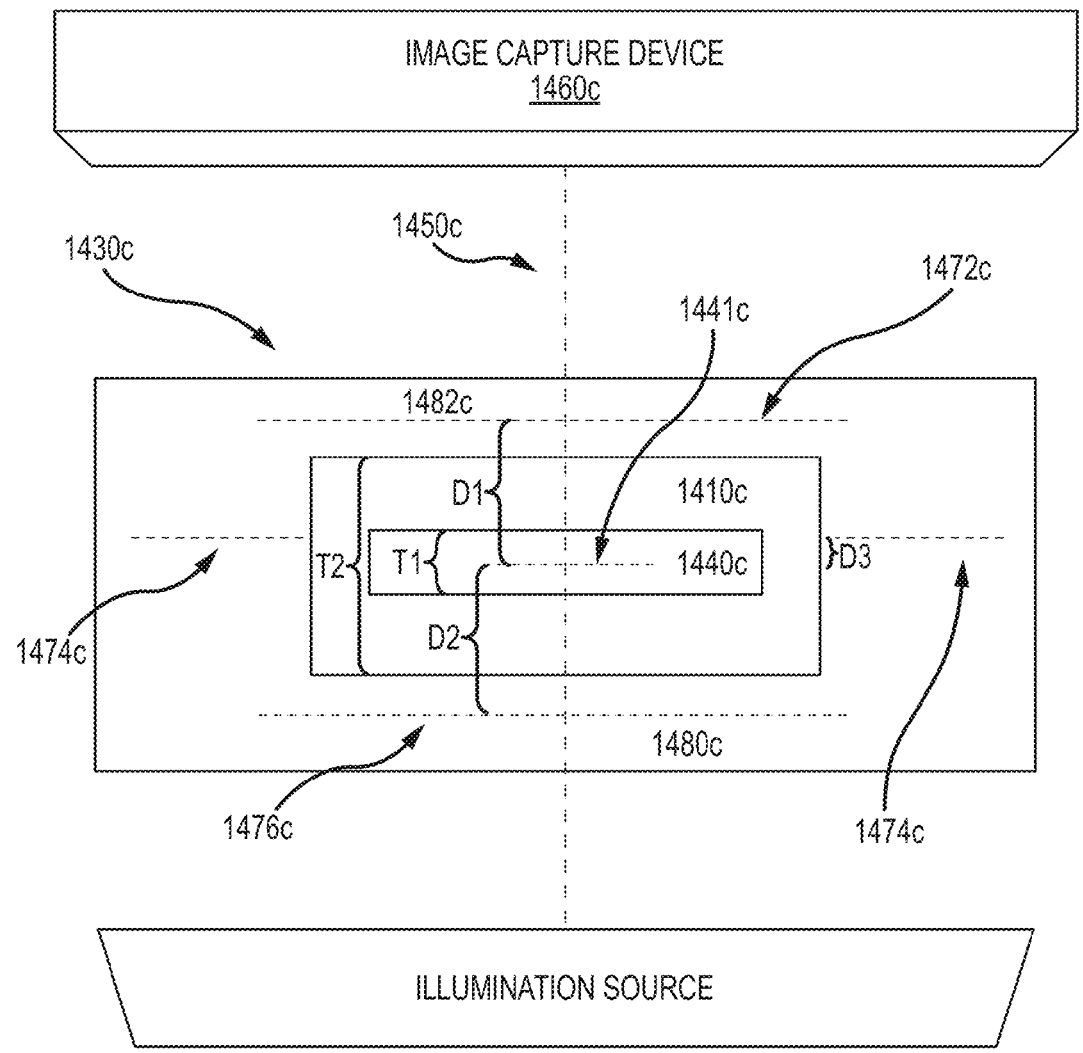
FIG. 14C depicts a cross-section side view of a flowcell illustrating aspects of focusing systems and methods, according to embodiments of the present invention.

FIG. 14C depicts a cross-section end view of a flowcell 1430c, illustrating various alternative placement locations for an autofocus or imaging target. For example, an imaging target 1472c can be located at a viewport window 1482c of the flowcell 1430c. Optionally, an imaging target 1474c can be located at an illumination window 1480c of the flowcell 1430c. Further optionally, an imaging target 1476c can be located in a lateral flowcell wall (e.g. 1432c and/or 1434c). The image capture device 1460c can be focused on a sample flowstream 1440c, which is enveloped within a sheath fluid 1410c, a using the displacement distance. In some embodiments, the displacement distance can correspond to or be defined by a distance D1 along the imaging axis 1450c between the sample flowstream 1440c (or a central plane 1441c defined by the flowstream 1440c) and the viewport window imaging target 1472c. In some embodiments, the displacement distance can correspond to or be defined by a distance D2 along the imaging axis between the sample flowstream 1440a (or the central plane 1441c) and the illumination window imaging target 1476c. In some embodiments, the displacement distance can correspond to or be defined by a distance D3 along the imaging axis between the sample flowstream 1440a (or the central plane 1441c) and the flowcell lateral wall imaging target 1474c. In some cases, distance D3 has a value greater than zero. In some cases, distance D3 has a value of zero; that is, where the sample flowstream 1440a (or the central plane 1441c) is coplanar with the imaging target 1474c. In some cases, it is possible to define a displacement distance that is not calculated based on distance D1, distance D2, or distance D3. For example, a displacement distance may be a predetermined number or value that is provided by a flowcell or hematology analyzer manufacturer.

According to some embodiments, the sample flowstream 1440c can have a thickness T1 at the imaging axis within a range from about 2 μm to about 10 μm. In some cases, the flowpath or the sheath fluid 1410c can have a thickness T2 of about 150 μm at the imaging axis. As shown here, an imaging target 1472c can be located on a viewport window 1482c disposed between the sample flowstream 1440c and the image capture device 1460c. In some cases, an imaging target (e.g. 1474c) can be located between an illumination window 1480c and a viewport window 1482c. As discussed elsewhere herein, the process of acquiring a focused image can include adjusting a distance between the image capture device 1460c and the flowcell 1430c using the displacement distance. In some cases, as discussed elsewhere herein, the process of acquiring a focused image can include adjusting a focal distance of the image capture device 1460c using the displacement distance. In some cases, the process of acquiring a focused image can include adjusting the distance between the image capture device 1460c and the flowcell 1430c, and the process of adjusting the distance includes moving the flowcell 1430c, for example to a position closer to the image capture device 1460c, or to a position more distant from the image capture device 1460c.

Figure 14D:
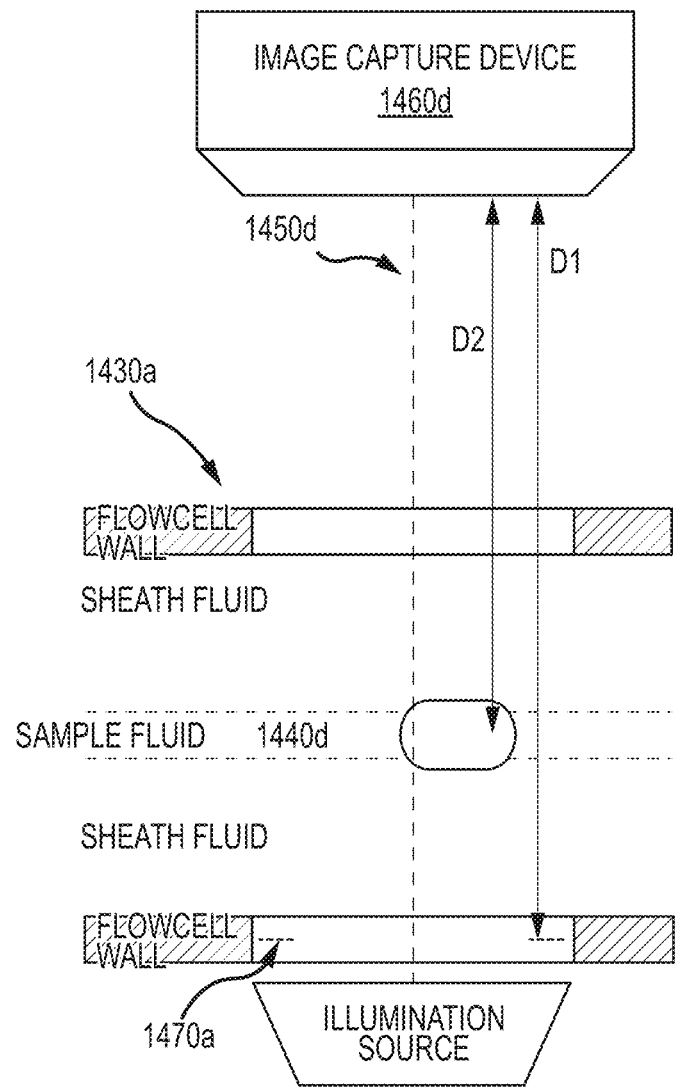
FIG. 14D provides a cross-section side view that illustrates aspects of focusing systems and methods, according to embodiments of the present invention.

As depicted in FIG. 14D, a first focal distance of the image capture device 1460d can correspond to a distance D1 (e.g. along the imaging axis 1450d) between the image capture device 1460d and the imaging target 1470d, and a second focal distance of the image capture device 1460d can correspond to a distance D2 (e.g. along the imaging axis 1450d) between the image capture device 1460d and the sample flow stream 1440d (or a central plane defined by the sample flow stream). In some cases, the imaging target may be located in another location in the flowcell, for example as depicted in FIG. 14C. According to some embodiments, the displacement distance can correspond to a distance difference between the first focal distance (or distance D1) and the second focal distance (or distance D2). The image capture device 1460d can be focused on the sample flowstream 1440d using this displacement distance (e.g. difference between D1 and D2).

FIG. 15 depicts an elevation view showing embodiments of an autofocus pattern (or imaging target), which for example can be located on illuminating orifices or window, on a viewing portal or window, or at another flowcell location. The target can fade as the distance or position of the high optical resolution imaging device is moved relative to the ribbon-shaped sample stream. As depicted in FIGS. 9-12B, an imaging or focus target (autofocus pattern) can reside on the periphery of the area of view in which the sample is to appear. With returning reference to FIG. 15, it can be seen that it is also possible that the focus target can be defined by contrasting shapes that reside in the field of view.

Figure 16A:
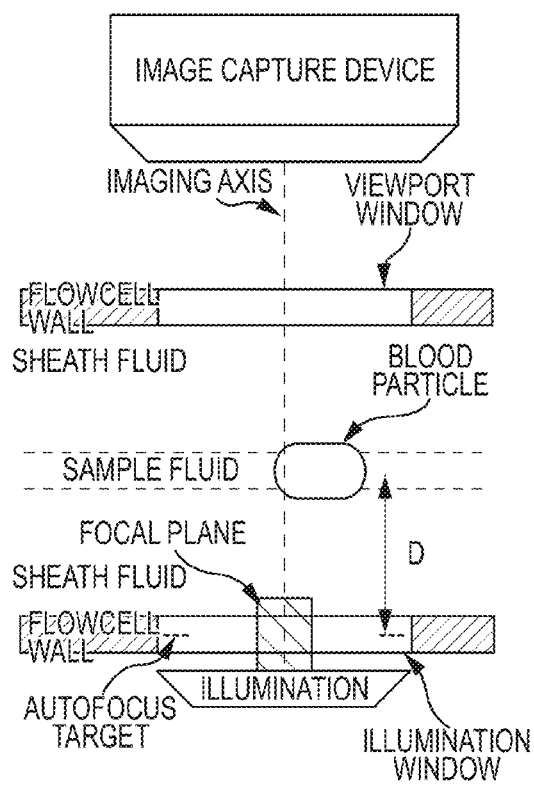
FIGS. 16A and 16B show aspects of focusing systems and methods, according to embodiments of the present invention.

When the imaging device is in focus on the autofocus pattern (target) (panel B in FIG. 15), the shapes as imaged by the device are well defined and can be used for autofocusing as described herein, namely to seek the distance between the target and the imaging device at which the shapes produce the highest contrast in amplitude between adjacent pixels located along lines that cross over the shapes, such as the lines shown as arrow heads. The focus configuration depicted in panel B corresponds to an analogous focus configuration depicted in FIG. 16A. As illustrated in FIG. 16A, the focal plane of the image capture device is aligned with the autofocus target, and hence the image capture device is in a position to obtain sharp images of the autofocus target.

Figure 16B:
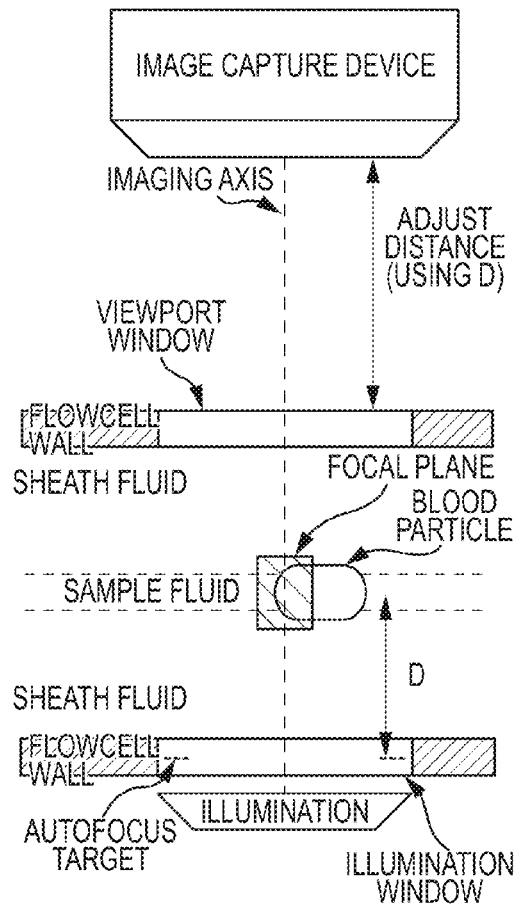

With returning reference to FIG. 15, when the working location (e.g. focal plane of imaging device) is moved away from the autofocus pattern (shown in panels A and C, shown left and right of autofocus pattern in FIG. 15), for example by adjusting the working distance of the objective or the distance between the objective and its focal plane, the focus target shapes now go out of focus, and at the position where the high optical resolution imaging device is focused on the ribbon-shaped sample stream, the focus target shapes are no longer discernible at all (see panel D in FIG. 15). The focus configuration depicted in panel D can corresponds to an analogous focus configuration depicted in FIG. 16B. As illustrated in FIG. 16B, the focal plane of the image capture device is aligned with the sample fluid stream, and hence the image capture device is in a position to obtain sharp images of particles in the sample flowstream. The focal plane of FIG. 16A is separated from the focal plane of FIG. 16B by a distance D. As shown in FIG. 16B, by moving the image capture device a distance D it is possible to also move the focal plane a distance D, and hence move the focal plane from the autofocus target to the sample flowstream. In some cases, the focal plane can be moved from the autofocus target to the sample flowstream by internally adjusting the focal distance of the image capture device while keeping the image capture device in a fixed position relative to the flowcell. In some cases, the focal plane can be moved from the autofocus target to the sample flowstream by internally adjusting the focal distance of the image capture device in combination with adjusting the position of the image capture device relative to the flowcell. The autofocus shapes can be provided at any location that is within view and is fixed relative to the flowcell, such as on the illumination opening or window, or on the front or back of the viewing port or window through which the high optical resolution imaging device is directed, or at a fixture attached to the photocell to hold a target in position to be imaged.

According to some embodiments, when the high optical resolution imaging device is moved over the displacement distance and the autofocus pattern goes out of focus, the features that appear in focus are the blood cells as opposed to the autofocus pattern. In the embodiment of FIG. 15, the autofocus pattern is defined by shapes in the field of view. The shapes are relatively thin discrete forms of a limited size, and therefore after moving by the displacement distance, the forms become substantially invisible in the digitized image when focused on the ribbon-shaped sample stream. A typical displacement distance may be, for example, 50 to 100 µm in a flowcell dimensioned for urinalysis imaging applications. In some embodiments, the autofocus feature maintains the high optical resolution imaging device within 1 µm of the optimal focus distance.

Accordingly, the features described in FIG. 15 provide an exemplary technique for determining a displacement distance. For example, a method of determining a displacement distance may include an autofocusing process that involves injecting a test fluid sample into a sheath fluid to form a test sample flowstream within a flow cell, and obtaining a first focused image of the imaging target using an image capture device. The first focused image can correspond to panel B in FIG. 15, where the focused imaging target and the image capture device define a first focal distance. As depicted here, the focal plane or working distance/location of the image capture device is positioned at the imaging target. The autofocusing process can also include obtaining a second focused image of the test sample flowstream using the image capture device. The second focused image can correspond to panel D in FIG. 15, where the focused test sample flow stream and the image capture device define a second focal distance. As depicted here, the focal plane or working distance/location of the image capture device is positioned at the imaging target. The autofocusing process may further include obtaining the displacement distance by calculating a difference between the first focal distance and the second focal distance. In some cases, the test fluid sample is the same as the urine sample and the test sample flowstream is the same as the sample flowstream. In some cases, the autofocusing process establishes a focal plane associated with the image capture device, and the focal plane remains stationary relative to the image capture device. In some cases, the process of autofocusing the image capture device includes determining an optimal focus position from among a plurality of focus positions.

According to some embodiments, the image capture device can be focused on the sample flowstream without using temperature data. For example, a process of focusing the image capture device on the sample flowstream can be performed independently of a temperature of the image capture device. In some cases, an imaging target can include a scale (e.g. as depicted in FIG. 12B) for use in positioning the imaging axis of the image capture device relative to the sample flowstream. In some cases, the imaging target can include an iris aligned relative to the imaging axis, such that the imaged particles are disposed within an aperture defined by the iris, and one or more edge portions of the iris are imaged during autofocusing.

In exemplary embodiments, autofocusing techniques can position the flowcell to within ±1 μm from an optimal focal position of the sample stream. In some cases, embodiments encompass autofocus techniques that can automatically focus the imaging system without the need for a separate focusing liquid or solution or any user intervention. Exemplary autofocusing techniques can also account for mechanical causes of suboptimal focusing performance, such as drift or thermal expansion which can cause fluctuations in the distance between the imaging device objective and flowcell. In some cases, it was observed that the location of the sample flow within the flowcell can be very stable and temperature independent. Hence, exemplary imaging techniques can involve focusing on an imaging target in the flowcell, and using a fixed offset to achieve optimal focus on the sample stream.

According to some embodiments, the microscope objective that is used on an imaging system has a numerical aperture of 0.75, resulting in a theoretical depth of field (DOF) of ±0.5 μm. In certain experimental trials, it was observed that good image quality could be obtained at ±1.25 μm from an optimal focal point. It was also observed that a practical or experimental depth of field could be different from the theoretical depth of field. For example, in certain experimental trials it was observed that the depth of field was around 2.5 to 3 μm. Based on certain experimental studies, it was determined that autofocus performance for positioning the flowcell within ±1.25 μm could ensure good image quality. In some embodiments, an autofocus system can operate to position the flowcell within ±1 μm from an optimal focus position of the sample stream. In certain experimental trials, it was observed that autofocus techniques as disclosed herein can repeatedly locate a target in a flowcell with a standard deviation of less than 0.3 μm. In some cases, trial autofocus system runs demonstrated excellent repeatability (standard deviation≤0.23 μm) and were able to determine the focus position of the sample stream to within <0.6 μm from an optimized metric position which is within a ±1 μm positional tolerance. Additional autofocus trial runs at a variety of temperature conditions also exhibited excellent positioning performance (e.g. flowcell positioning within a required ±1 μm tolerance of and optimal focus position). This degree of accuracy in an automated analyzer system is well suited for consistently and reliably obtaining high quality images of particles from a urine sample flowing in a thin ribbon flowstream as disclosed elsewhere herein, over an operational temperature range corresponding to standard laboratory conditions.

Unless expressly indicated otherwise, references to "particle" or "particles" made in this disclosure will be understood to encompass any discrete or formed object dispersed in a fluid. As used herein, "particle" can include all measurable and detectable (e.g., by image and/or other measurable parameters) components in biological fluids. The particles are of any material, any shape and any size. In certain embodiments, particles can comprise cells. Examples of particles include but are not limited to cells, including blood cells, fetal cells, epithelials, stem cells, tumor cells, or bacteria, parasites, or fragments of any of the foregoing or other fragments in a biological fluid. Blood cells may be any blood cell, including any normal or abnormal, mature or immature cells which potentially exist in a biological fluid, for example, red blood cells (RBCs), white blood cells (WBCs), platelets (PLTs) and other cells. The members also include immature or abnormal cells. Immature WBCs may include metamyelocytes, myelocytes, pro-myelocytes and blasts. In addition to mature RBCs, members of RBCs may include nucleated RBCs (NRBCs), normal or abnormal RBCs, and reticulocytes. PLTs may include "giant" PLTs and PLT clumps. Blood cells and formed elements are further described elsewhere in this disclosure.

Exemplary particles can include formed elements in biological fluid samples, including for example, spherical and non-spherical particles. In certain embodiments, the particles can comprise non-spherical components. The image projection of non-spherical components can be maximized in the focal plane of the high optical resolution imaging device. In certain embodiments, the non-spherical particles are aligned in the focal plane of the high optical resolution imaging device (aligned in a plane substantially parallel to the direction of the flow). In some embodiments, platelets, reticulocytes, nucleated RBCs, and WBCs are counted and analyzed as particles. As used herein, exemplary white blood cells (WBC) can include, for example, neutrophils, lymphocytes, monocytes, eosinophils, basophils, immature granulocytes including meta-myelocyes, myelocytes, pro-myelocytes and blasts, and abnormal white blood cells.

As used herein, detectable and measurable particle parameters can include, for example, visual and/or non-image based indices of size, shape, symmetry, contour and/or other characteristics.

In another embodiment, this disclosure relates to a method for imaging particles using, for example, the kits of this invention, in methods comprising, for example: 1) illuminating the particles with light in a visual analyzer; 2) obtaining a digitized image of sample particles enveloped in a PIOAL; and 3) analyzing particle containing samples based on the image information. In other embodiments, the method may further comprise contacting the sample containing particles with a particle contrast agent composition prior to illuminating the treated sample.

In one embodiment, the particles analyzed comprise at least one of a spherical particle, a non-spherical particle, or both. In another embodiment, the particles comprise at least one spherical particle. In still another embodiment, the particles comprise at least one non-spherical particle. In another embodiment, an image projection of non-spherical particles or particles having non-spherical components is maximized in a plane substantially parallel to the flow direction. The particles may be, for example, WBCs, RBCs, and/or platelets. In one embodiment, at least 50% of the non-spherical particles are aligned in a plane substantially parallel to the direction of flow. In another aspect, use of the PIOALs of this invention in a flowcell permits at least 90% of the non-spherical particles to be aligned in a plane substantially parallel to the direction of flow.

In one embodiment, the non-spherical particles comprise red blood cells. In another aspect of this invention, the spherical particles comprise white blood cells or nucleated red blood cells.

Flow of the cells smaller than the thickness of the ribbon-shaped sample stream enveloped in PIOAL, results in alignment of those cells parallel to the direction of the flow. In one embodiment of this disclosure, at least 92% of the non-spherical particles are aligned in a plane substantially parallel to the direction of flow. In yet another embodiment, at least 90% of the non-spherical particles are aligned in a plane substantially parallel to the direction of flow. In another embodiment, at least 75%, 80%, 85%, 86%, 87%, 88%, 89%, 90%, 91%, 92%, 93%, 94% or at least 95% of the particles are substantially aligned, namely within 20 degrees from a plane substantially parallel to the direction of flow. In another embodiment, the percentage of non-spherical and/or spherical particles are aligned in a plane substantially parallel to the direction of flow may be any range between any two of the recited percentages, for example, at least 75-85%, 75-80%, and other ranges such as 75-92%.

Shear forces in the direction parallel to the direction of the flow as a result of flow of larger cells in the sample enveloped in the PIOAL, such as WBCs, results in positioning, repositioning, and/or better positioning of nuclear structures, cytosolic structures or granules or other intracellular components or structures closer to a plane parallel to the direction of the flow In one embodiment of this disclosure, the image cross-section comprises at least one of differentially stained nuclear structure, differentially stained cytosolic structure or differentially stained granules in a WBC, including a neutrophil, lymphocyte, monocyte, eosinophil, basophil, or immature WBC including a blast, promyelocyte, myelocyte, or metamyelocyte. In another embodiment, at least 50%, 55%, 60%, 65%, 70%, 75%, 80%, 85%, 86%, 87%, 88%, 89%, 90%, 91%, 92%, 93%, 94% or at least 95% of the spherical and/or non-spherical particles have nuclear structures, cytosolic structures or granules in the focal plane or depth of field of the high optical resolution imaging device.

In some embodiments of the methods of this invention, the image information is the image cross-section of a particle. In some aspects, the image cross-section comprises at least one of a differentially stained nuclear structure, a differentially stained cytosolic structure or differentially stained granules in a WBC, including a neutrophil, lymphocyte, monocyte, eosinophil, basophil, or immature WBC including a blast, promyelocyte, myelocyte, or metamyelocyte.

In one embodiment, the methods of this invention provide surprisingly high quality images of cells with a high percentage of particles and particle content in-focus in flow, which are useful in obtaining automated, image based WBC differentials, as well as automated identification of morphological abnormalities useful in determining, diagnosing, prognosing, predicting, or supporting a diagnosis of whether a subject is healthy or has a disease, condition, abnormality or infection and/or is responsive or non-responsive to treatment.

In another aspect, the compositions and methods of this invention provide more accurate image based cell categorization and subcategorization and flagging which greatly reduces the manual review rate compared to current analyzers.

As used herein, viscosity agent can include viscosity agents or viscosity modifiers. An exemplary viscosity agent/modifier has a characteristic viscosity that is different from the viscosity of the sample such that when the PIOAL and the viscosity agent are mixed, the viscosity of the PIOAL is altered or and/or increased in order to maximize the alignment of particles. In certain embodiments, the viscosity difference and/or a speed difference between the ribbon-shaped sample stream and the PIOAL can introduce shear forces to act on the particles while in flow thereby reducing the misalignment and/or causing the particles to align.

As used herein, the particle contrast agent compositions can be adapted for use in combination with a particle and/or intracellular organelle alignment liquid (PIOAL) in a visual analyzer for analyzing particles in a sample from a subject. The exemplary PIOAL is useful, as an example, in methods for automated recognition of different types of particles in a sample from a subject.

In another aspect, the cells may be enveloped in PIOAL when images are obtained. Suitable exemplary intracellular organelle alignment liquids are described herein.

In one embodiment, this disclosure relates to a PIOAL for use in a visual analyzer. In certain embodiments, the PIOAL may comprise at least one of a buffer; a pH adjusting agent; a buffer; a viscosity agent/modifier; ionic strength modifier, a surfactant, a chelating agent, and/or an antimicrobial agent.

In one aspect, the PIOAL may comprise two or more viscosity agents/modifiers.

In one aspect, the PIOAL of this invention may have a viscosity of between about 1 to about 10 centipoise. In one embodiment, the PIOAL of this invention may comprise a viscosity agent/modifier. In one embodiment, the PIOAL comprises up to 100% of a viscosity agent.

As used herein, the viscosity agent and/or viscosity modifier can include any substance suitable to achieve a viscosity of about 1 to about 10 centipoise, with optical characteristics, including optical clarity, appropriate for use in an imaging system. Generally, the viscosity agent or modifier is non-toxic, biocompatible and leaves the cellular structure and contents substantially intact. The viscosity agent and/or viscosity modifier may comprise at least one of glycerol; glycerol derivative; ethylene glycol; propylene glycol (dihydroxypropane); polyethylene glycol; water soluble polymer and/or dextran. In one aspect, the viscosity agent/modifier in the PIOAL may be glycerol. As an example, in one aspect, the viscosity agent/modifier in the PIOAL may be a glycerol derivative. As an example, in one aspect, the viscosity agent/modifier in the PIOAL may be polyvinylpyrrolidone (PVP). As another example, the viscosity agent/modifier in the PIOAL may be ethylene glycol. As another example, the viscosity agent/modifier in the PIOAL may be propylene glycol (dihydroxypropane). As another example, the viscosity agent/modifier in the PIOAL may be polyethylene glycol. As another example, the viscosity agent/modifier in the PIOAL may be water soluble polymer or dextran. In other aspects, the viscosity agent/modifier in the PIOAL may comprise two or more of glycerol, glycerol derivative; ethylene glycol; propylene glycol (dihydroxypropane); polyvinylpyrrolidone (PVP); polyethylene glycol; water soluble polymer or dextran. Viscosity agent/modifying agents may include any agent suitable to provide a viscosity of about 1 to about 10 centipoise, with optical characteristics, including optical clarity, appropriate for use in an imaging system.

As used herein, other exemplary viscosity agents/modifiers can include, for example, natural hydrocolloids (and derivatives), such as *Acacia*, tragacanth, alginic acid, carrageenan, locust bean gum, guar gum, xanthan gum, gum arabic, guar gum, gelatin, cellulose, alginates, starches, sugars, dextrans; gelatin; sugars (and derivatives), such as dextrose, fructose; polydextrose; dextrans; polydextrans; saccharides; and polysaccharides; semisynthetic hydrocolloids (and derivatives), such as glycerol, methylcellulose, hydroxyethyl starch (hetastarch), sodium carboxymethylcellulose, hydroxyethylcellulose, hydroxypropylmethylcellulose, polyvinylpyrrolidone (PVP); synthetic hydrocolloids (and derivatives), such as Polyvinyl alcohol (PVA) and/or Carbopol®. Other cell compatible viscosity agents/modifiers are also considered useful for this purpose.

In another aspect, the viscosity agent/modifier in the PIOAL may be glycerol present at a concentration of about 1 to about 50% (v/v) of the PIOAL. As an example, in one embodiment, the viscosity agent/modifier may be present in the PIOAL at a concentration of about 5.0% to about 8.0% (v/v). In another aspect, the viscosity agent/modifier may be present at a concentration of about 6.5% (v/v). In one embodiment, the viscosity agent/modifier is glycerol present at a concentration of about 6.5% (v/v).

In yet another embodiment, the PIOAL can comprise a glycerol viscosity agent/modifier present at a concentration of about 30% (v/v).

In another aspect, the viscosity agent/modifier in the PIOAL may be PVP present at a concentration of about 0.5 to about 2.5% (w/v). As an example, in one embodiment, the viscosity agent/modifier PVP may be present in the PIOAL at a concentration of about 1.0 to about 1.6% (w/v). In one embodiment, the PVP is present at a concentration of about 1.0% (w/v).

In another aspect, the viscosity agent/modifier in the PIOAL may be PVP and glycerol. As an example, in one embodiment, the glycerol may be present in the PIOAL at a concentration of about 5% (v/v) in combination with about 1% (w/v) of PVP.

In one embodiment, the PIOAL of this invention may be used in a visual analyzer to image particles. In one aspect, the visual analyzer comprises a flowcell with a symmetrical flow path, and an autofocus component.

A viscosity agent and/or viscosity modifying/adjusting agents, such as glycerol, may be included in the PIOAL. The viscosity agent, or viscosity modifying agent when introduced, can appropriately adjust the viscosity of the PIOAL to the desired range. Any suitable viscosity agent may be used which sufficiently increases the viscosity of the PIOAL, which has suitable optical characteristics to permit high quality imaging of cells in flow. The PIOAL will have a suitable viscosity to align cells and/or cellular structures into a single plane that is substantially parallel to the direction of the flow, thereby, in part, increasing the in-focus contents of the particles.

The PIOAL may be used with any analyzer of this disclosure.

As used herein, the term "glycerols" encompasses glycerol and a derivative of glycerol (hereinafter referred to as glycerol derivative). Examples of a glycerol derivative include thioglycerol, polyglycerol, and the like. Usable examples of polyglycerol may include diglycerol, POLYGLYCERIN #310 (Sakamoto Yakuhin Kogyo Co., Ltd.), POLYGLYCERIN #750 (Sakamoto Yakuhin Kogyo Co., Ltd.), POLYGLYCERIN #500 (Sakamoto Yakuhin Kogyo Co., Ltd.), and the like.

In another embodiment, the PIOAL of this disclosure further comprises a pH adjusting agent. In one aspect, the final pH of the PIOAL and/or the sample is between about 6.0 to about 8.0. In another aspect, the final pH of the PIOAL and/or the sample is between about 6.6 to about 7.4. In one aspect, the final pH of the PIOAL may be the same pH as the prepared sample 12A (referring to FIG. 1C).

Exemplary pH adjusting agents can include, for example, acids (exemplars include organic acids and mineral acids), bases (exemplars include organic bases and hydroxides of alkaline metals and alkaline earth metals). Exemplary organic acids can include acetic, lactic, formic, citric, oxalic, and uric acids. Exemplary mineral acids can include, for example, hydrochloric, nitric, phosphoric, sulphuric, boric, hydrofluoric, hydrobromic and perchloric acids. Exemplary organic bases can include, for example, pyridine, methylamine, imidazole, benzimidazole, histidine, phosphazene, and hydroxides of cations. Exemplary hydroxides of alkali metal and alkaline earth metals can include, for example, Potassium hydroxide (KOH), Barium hydroxide ($Ba(OH)_2$), Caesium hydroxide (CsOH), Sodium hydroxide (NaOH), Strontium hydroxide ($Sr(OH)_2$), Calcium hydroxide ($Ca(OH)_2$), Lithium hydroxide (LiOH), and Rubidium hydroxide (RbOH).

In some embodiments, using a buffer, the pH of PIOAL is preferably maintained from about 6.0 to about 8.5, more preferably from about 7.0 to about 8.0. In some embodiments it is preferable to add a buffer agent to the PIOAL in order to adjust the pH of PIOAL. Any suitable buffer agent or agents may be used as long as the agent or agents adjust the pH of the PIOAL to the proper range. Examples of such a buffer agent include PBS, Good's buffers (specifically, tris buffer, MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, and the like), disodium hydrogenphosphate, sodium dihydrogen phosphate, monobasic potassium phosphate, veronal sodium-HCl, collidine-HCl, tris(hydroxymethyl)aminomethane-maleic acid, tris(hydroxymethyl)aminomethane-HCl, which may be used alone or in combination.

In another embodiment, the PIOAL of this invention comprises an ionic strength modifier to adjust the ionic strength of the resulting formulation. Exemplary ionic strength modifiers may include $Li^+$, $Na^+$, $K^+$, $Mg^{++}$, $Ca^{++}$, $Cl^-$, $Br^-$, $HCO^-_3$, sulphates, pyrosulphates, phosphates, pyrophosphates (e.g., potassium pyrophosphate), citrates, cacodylates, or other suitable salts. In one embodiment, the PIOAL may be isotonic.

Surfactants may be added to the PIOAL. The kinds of surfactants are not particularly limited as long as they are compatible with other components of the PIOAL, and compatible with the ribbon-shaped sample stream and the particles in the sample. Surfactants may include, for example, cationic, anionic, nonionic, and ampholytic surfactants. Exemplary surfactants may include polyoxyethylenealkyl ether-type surfactants, polyoxyethylenealkylphenyl ether-type surfactants, (for example, NISSAN NONION NS-240 (NOF CORPORATION, registered trademark)), polyoxyethylenesorbitan alkyl ester-type surfactants (for example, RHEODOL TW-0120 (Kao Corporation, registered trademark)), polyol copolymers (for example, PLURONIC F-127, F-123, F-109, F-87, F-86, F-68, T-1107, T-1102 (BASF Corporation, registered trademark)), MEGA-8, sucrose monocaprate, deoxy-BIGCHAP, n-octyl-β-D-thioglucoside, n-nonyl-β-D-thiomaltoside, n-heptyl-β-D-thioglucoside, n-octyl-β-D-thioglucoside, CHAPS, CHAPSO, and the like may be used. Other surfactants may include Triton-X-100 and Tween 20 at sample and ribbon-shaped sample stream compatible concentrations.

The concentration of the surfactant in PIOAL is preferably the concentration level at which particles such as cells in the sample are not affected and/or remain substantially intact. Specifically, the concentration is preferably from 5 to 5000 mg/L, more preferably from 100 to 3000 mg/L.

When particles contained in the sample are analyzed with the analyzer, amorphous salts such as ammonium phosphate, magnesium phosphate, calcium carbonate may precipitate in the sample. Chelating agents may be added to the PIOAL in order to dissolve these amorphous salts. The addition of chelating agents enables not only dissolving amorphous salts, but also inhibiting the oxidation of PIOAL. Usable examples of a chelating agent include EDTA salts, CyDTA, DHEG, DPTA-OH, EDDA, EDDP, GEDTA, HDTA, HIDA, Methyl-EDTA, NTA, NTP, NTPO, EDDPO, and the like. The concentration of the chelating agent in the PIOAL is preferable within the range of 0.05 to 5 g/L.

In another embodiment, the PIOAL may further comprise one or more antimicrobial agents. In some aspects, the antimicrobial agent may be, for example, substances which have fungicidal activity (fungicidal agents) and/or substances which have bactericidal activity (bactericidal agents). In certain embodiments, suitable antimicrobial agents can include, for example, parebens, isothiazolinone, phenolics, acidic preservatives, halogenated compounds, quarternia, and alcohol. Exemplary parabens can include Parabens and Paraben salts. Exemplary isothiazolinones can include methylchloroisothiazolinone, methylisothiazolinone, benzisothiazolinone ProClin 150, ProClin 200, ProClin 300, and ProClin 950. Exemplary phenolic types can include phenoxyethanol, benzyl alcohol, and phenethyl alcohol. Exemplary acidic preservatives can include dehydroacetic acid, benzoic acid, sorbic acid, salicylic acid, formic acid, propionic acid. Exemplary halogenated compounds can include 2-bromo-2-nitropropane-1,3-diol, chloroacetamide, chlorobutanol, chloroxylenol, chlorphenesin, dichlorobenzyl alcohol, iodopropynyl butylcarbamate, methyldibromo glutaronitrile. Exemplary quaternia can include benzalkonium chloride, benzethonium chloride, chlorhexidine, hexamidine diisethionate, and polyaminopropyl biguanide. Exemplary alcohols can include ethyl alcohol and isopropyl alcohol. Examples thereof include triazine antimicrobial agents, thiazole bactericidal agents (for example, benzisothiazolone etc.), pyrithione, pyridine bactericidal agents (for example, 1-hydroxy pyridine-2-thiosodium etc.), 2-phenoxyethanol, and the like. Specifically, Proxel GXL (Avecia), TOMICIDE S (API Corporation), and the like may be used. The bactericidal and/or fungicidal agents help improve the stability of the PIOAL.

In one embodiment, the concentration of the antimicrobial agent may be 0.01% to 0.5% (w/v). The concentration may be 0.03 to 0.05% (w/v).

The sample which is subjected to analysis using the analyzer with the PIOAL in the embodiment is not particularly limited. Samples obtained from the living body (biological samples) are normally used. Alternatively, those samples can be diluted, purified, contacted with a contrast agent, or the like for use. Specifically, examples of such a sample may include blood, semen, cerebrospinal fluid, and the like. Samples may also include particle suspensions derived from tissue samples. The PIOAL in the embodiment is suitably used when particles (red blood cell, white blood cell, bacteria, etc.) are analyzed.

The PIOAL of this invention may be used in a visual analyzer that images particles. In one aspect, the visual analyzer comprises a flowcell capable of maintaining the flow of a ribbon-shaped sample stream with predetermined dimensional characteristics, such as an advantageous ribbon-shaped sample stream thickness. In some embodiments, the flowcell may have a symmetrical flow path, and be used in combination with an autofocus component.

This disclosure relates to a method for imaging a particle comprising: 1) contacting the sample with a particle contrast agent composition; 2) illuminating the prepared particle; 3) obtaining a digitized image of the particle in a ribbon-shaped sample stream enveloped in a PIOAL; and; 4) analyzing the image information to categorize or subcategorize the particles. In some embodiments, the particle may be at least one of any particle disclosed herein and may be counted and analyzed based on particle image information.

In some embodiments the visual analyzer comprises a flowcell with a symmetrical or an asymmetrical flowpath, and an autofocus component.

In a general aspect, the exemplary PIOAL and methods of use thereof are useful when employed in combination with an automated analyzer found in research and/or medical laboratories. Exemplary automated analyzers are instrument designed to measure different formed elements and/or other characteristics in a number of biological samples, quickly, including, for example, human body fluid samples, with minimal human assistance. Exemplary automated analyzers can include, for example, urinalysis analyzers. The exemplary analyzers can process samples singly, in batches, or continuously.

In one aspect, the exemplary analyzer/system comprises an automated particle counter configured to detect a plurality of particles that meet one or more selection criteria, and to provide a particle count thereof, wherein the selection criteria encompasses members of at least two categories within said particles. An analyzer, which may comprise a processor, which may include components of the counter, is programmed to distinguish the particles of the at least two categories. A distribution of each of the particles is determined using the analyzer. The processor uses the distribution to correct the particle count for the members of at least one of the at least two categories and/or subcategories. In some embodiments, the particle counter comprises at least one channel configured to provide the particle count of the at least one category and/or subcategory of particles based on a predetermined range based on volume, size, shape, and/or other criterion. For example, the members of the at least one category and/or subcategory comprise at least one type of particle selected from a group consisting of subcategories of white blood cells (WBCs), red blood cells (RBCs), giant platelets (PLTs), and nucleated red blood cells (NRBCs). On a particle counter, due to similar size or other measured characteristic, cells such as giant PLTs and NRBCs may be counted as WBCs. By operating the apparatus as described herein, particle count or concentration of giant PLTs and NRBCs can be measured accurately.

In one aspect, the systems, compositions and methods of this disclosure provide surprisingly high quality images of cells in a flow. In one aspect, the visual analyzer can be used in methods of this disclosure to provide automated image based urine sediment particle counting. In certain embodiments, the methods of this disclosure relate to automated identification of visual distinctions, including morphological abnormalities for determining, determining, diagnosing, prognosing, predicting, and/or supporting a diagnosis of whether a subject is healthy or has a disease, condition, abnormality or infection and/or for monitoring whether a subject is responsive or non-responsive to treatment. Applications include categorizing, subcategorizing, and counting cells in a fluid sample, such as a urine sample, especially according to category, or subcategory. Other similar uses for counting additional types of particles and/or particles in other fluid samples are also contemplated. The system, compositions, and methods of this invention can be used for real-time categorization and subcategorization and viewing of images using any suitable automated particle recognition algorithm. The captured images for each sample can be stored to be viewed at a later date.

In another aspect, the analyzer, compositions, and methods of this invention provide surprisingly more accurate image based cell categorization and subcategorization and flagging which reduces the manual review rate compared to the manual review rate when using current automated image-based analyzers. The systems, compositions, and methods reduce the initial manual review rate and permit the initial manual review to be performed on the instrument. In addition, the systems, compositions, and methods of this disclosure also reduce the percentage of samples flagged during the automated analysis as requiring manual review.

Accordingly, in some embodiments, the present disclosure provides an analyzer and a method for analyzing a sample containing particles, for example, particles in urine. According to this disclosure, a visual analyzer is provided for obtaining images of a sample comprising particles suspended in a liquid. In some embodiments, the visual analyzer comprises a flowcell and an autofocus component, in which a liquid sample containing particles of interest is caused to flow through a flowcell having a viewport through which a camera coupled to an objective lens captures digital images of particles. The flowcell is coupled to a source of sample fluid, such diluted and/or undiluted urine sample or the like, and to a source of a clear sheath fluid, or particle and/or intracellular organelle alignment liquid (PIOAL).

In one embodiment, the analyzer also comprises a particle counter having at least one detection range, as well as an analyzer, and a processor. The analyzer and the processor are configured to provide information to categorize, subcategorize and determine accurate particle count and/or concentration in the sample.

In other embodiments, this disclosure relates to a PIOAL that can be used in image based analysis of particles as described herein. Particle category and/or subcategory count in urine samples is used in this disclosure as nonlimiting examples of the sort of samples that may be analyzed. In some embodiments, cells present in samples may also include bacterial or fungal cells as well as white blood cells, or red blood cells. In some embodiments, particle suspensions obtained from tissues or aspirates may be analyzed.

The discrimination of urine sediment particles in a urine sample is an exemplary application for which the subject matter is particularly well suited. The sample is prepared by automated techniques and presented to a high optical resolution imaging device as a ribbon-shaped sample stream to be imaged periodically while the sample flows across a field of view. The images of the particles (such as urine sediment particles) can be distinguished from one another, categorized, subcategorized, and counted, using pixel image data programmed processing techniques, either exclusively automatically or with limited human assistance, to identify and count cells or particles. In addition to the particle images, which can be stored and made available in the case of unusual or critical features, the output data includes a count of the occurrences of each particular category and/or subcategory of cell or particle distinguished in the recorded sample images. The counts of the different particles found in each image can be processed further, for example used to accumulate accurate and statistically significant proportionate ratios, or functions thereof of particles of each distinguished category and/or subcategory in the sample as a whole. The sample used for visual discrimination can also be highly diluted, but the proportions of cells in each category and/or subcategory are represented in the distribution for the diluted sample, particularly after a number of images have been processed. As used herein, the use of image-based (e.g. visual) information for the identification of particles/cells covers the spectral range for ultraviolet, visible and infrared from 200 nm to 10 mm.

In some aspects, samples are presented, imaged and analyzed in an automated manner. In the case of urine samples, the sample may be substantially diluted with water or saline solution, which reduces the extent to which the view of some cells and/or particles might be hidden by other cells and/or particles in an undiluted or less-diluted sample. The cells can be treated with agents that enhance the contrast of some cell aspects, for example using permeabilizing agents to render cell membranes permeable, and histological stains to adhere in and to reveal features, such as cytoplasm in the cell. In some embodiments it may be desirable to stain an aliquot of the sample for counting and characterizing particles and subpopulation counting, characterization and analysis of particles which include white blood cells, epithelial cells and/or bacteria.

The particulars of sample preparation analyzer and methods for sample dilution, histological staining, generally are accomplished using precision pumps and valves operated by one or more programmable controllers, and are not central to this disclosure. Examples can be found in patents assigned to International Remote Imaging Systems, Inc., such as U.S. Pat. No. 7,319,907, concerning programmable controls. Likewise, techniques for distinguishing among certain cells by their attributes such as color when stained by B021 can be found in U.S. Pat. No. 5,436,978. The disclosures of these patents are hereby incorporated by reference.

To facilitate the capacity, speed and effectiveness by which particles such as cells are categorized and subcategorized, it is advantageous to provide clear high quality images of the urine particles for automated analysis by the data processing system. According to the present disclosure, a prepared sample stream is arranged in a thin ribbon having a stable position between opposite walls of a flowcell. The positioning of the sample stream and its flattening into a ribbon-shaped sample stream may achieved by flow between layers of a PIOAL introduced into the flowcell that that differs in viscosity from the sample fluid and is flowed through a symmetrical flow channel.

The PIOAL and the sample have coordinated viscosities and flow rates at the point of introduction to the flowcell of the sample such that the sample fluid flattens into a thin ribbon shape. The ribbon-shaped sample stream is carried along with the PIOAL, to pass in front of a viewing port where an objective lens and a light source are arranged to permit viewing of the ribbon-shaped sample stream. The sample fluid is introduced, for example, injected at a point where the flowpath of the PIOAL narrows symmetrically. As a result, the sample fluid stream is flattened and stretched into a thin ribbon. A PIOAL of this disclosure may be used as the sheath fluid with any visual analyzer of this disclosure. In one embodiment, the PIOAL can be introduced into an end of the flowcell to carry along the sample fluid toward the discharge.

The dimension of the ribbon-shaped sample stream in the viewing zone is affected by geometric thinning of the PIOAL flowpath and differential linear velocity of the sample fluid and PIOAL resulting in thinning and stretching of the ribbon-shaped sample stream. The initial linear velocity ratios of the sample to PIOAL may range from 0.5 to 5.0. The PIOAL flowpath cross section may be thinned by reducing the depth to achieve a reduction of the cross sectional area of the flowpath by a factor of about 5:1, 10:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 105:1, 110:1, 115:1, 125:1, 130:1, 140:1, 150:1, 160:1, 170:1, 180:1, 190:1, or 200:1. In one embodiment, this geometric thinning is 40:1. Factors taken into account are transit time through the flowcell, desired rate of sample throughput, achieving a ribbon-shaped sample stream thickness comparable to particle size, obtaining alignment of particles and organelles, achieving in focus content of particles, balancing pressure, flow, and viscosity within operational limits, optimizing ribbon-shaped sample stream thickness, obtaining a desired linear velocity, manufacturability considerations, and volumes of sample and PIOAL required.

The length and volume of the cannula and the cross-section flattening may be selected to reduce the period of sample flow instability, thereby increasing throughput. In some embodiments the period of flow instability may be less than about 3, 2.75, 2.5, 2.25, 2, 1.75, 1.5 1.25, or less than about 1 second. A smaller cannula volume may also reduce the time and volume of diluent needed to clean the cannula between sample runs. In some embodiments the transit time through the flowcell is 1, 2, 3, or 4 seconds, or any range in between any two of those times. In some embodiments the transit time may be less than 4, 3, or 2 seconds.

The viscosities and the flow rates of the sample fluid and the PIOAL and the contour of the flowcell are arranged such that the PIOAL flow flattens and stretches the sample flow out into a flat ribbon consistently through the viewing zone at a dependable location. The sample fluid stream may be compressed to approximately 2 to 3 µm in fluid flow thickness. Several urine cell types have diameters larger than the stream thickness. Shear forces in the direction parallel to the direction of the flow cause an increase of an image projection of the particles under imaging conditions in the focal plane of the high optical resolution imaging device and/or to cause the intracellular structures, organelles or lobes to be positioned, repositioned, and/or better-positioned to be substantially parallel to the direction of flow. The high optical resolution imaging device depth of field is up to 7 µm, for example, 1-4 µm.

The flow thickness of the PIOAL, with the ribbon-shaped sample stream carried along, is constant through a viewing zone in front of a viewing port through which the objective lens is directed. The objective lens may be the objective component of a high optical resolution imaging device or the digital image capture device. The ribbon-shaped sample stream follows a path across the viewing zone at a known and repeatable position within the flowcell, for example, at a known and repeatable distance from two walls of the flowcell, being discharged downstream.

Optical information from the particles in the sample are detected by a detecting section in the analyzer, when the ribbon-shaped sample stream is carried through the viewing zone in front of the viewing port, thereby generating data from the particles/cells contained in the sample. The use of this analyzer allows capture, processing, categorization and subcategorization and counting of cells and/or particles contained in samples. The PIOAL liquid can be prepared by the addition of viscosity modifying agent, buffer agent, pH adjusting agent, antimicrobial agent, ionic strength modifier, surfactant, and/or a chelating agent Exemplary functional components and/or features of the analyzer in the present disclosure can include, for example, the ability to acquire and/or process data from image analysis, sample staining processing, image processing, and/or particle image identification, counting, and/or categorization and subcategorization.

In one embodiment this disclosure was based on the surprising and unexpected discovery that the addition of a suitable amount of a viscosity agent in the PIOAL significantly improves particle/cell alignment in a flowcell, leading to a higher percentage of in-focus cells, or cellular components, and higher quality images of cells and/or particles in flow. The addition of the viscosity agent increases the shear forces on cells like RBCs, which improves the alignment of the cells in a plane substantially parallel to the flow direction, which results in image optimization. This also results in positioning, repositioning, and/or better-positioning of intraparticle structures such as intracellular structures, organelles or lobes substantially parallel to the direction of flow, which results in image optimization. The viscosity agent also reduces misalignment of cells, generally, but not limited to cells that are smaller in diameter than the flow stream.

Alignment of cells that are smaller in diameter than the flow stream, for example, red blood cells and/or bacteria rods, may be obtained by for example, increasing the viscosity of the PIOAL, and/or by increasing the flow linear velocity ratio. This results in alignment of the RBCs or bacteria rods parallel to the direction of the flow. In some embodiments, a reduction in RBC or bacteria rods misalignment and/or an increase in RBC or bacteria rods alignment is achieved by increasing the viscosity of the PIOAL.

In one aspect, this disclosure relates to a method for differentially classifying particles and/or counting particles using image-based particle categorization, subcategorization and counting. Exemplary methods may include contacting a sample containing the particles or cells with a particle contrast agent composition in an amount effective to generate visual distinctions for categorizing and/or subcategorizing the particles, applying the sample to at least one flowcell, introducing with the contacted first portion of the sample into the at least one flowcell a particle and intracellular organelle alignment liquid (PIOAL) having a viscosity different from the viscosity of the treated sample, and effective to support flow of the sample, align particles, and increase the in-focus content of particles and organelles of cells flowing in the flowpath, analyzing the cells using an apparatus comprising a visual analyzer, and a processor, performing particle categorization and subcategorization by determining one or more visual distinctions, and counting the particles in the categories and subcategories based on the visual distinctions.

In this and any of the other methods of this disclosure, the particles may be any category and/or subcategory of cells present in the sample, and may include particles selected from erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps and cell fragments.

The present disclosure provides a technique for automatically achieving a correct working position of the high optical resolution imaging device for focusing on the ribbon-shaped sample stream. The flowcell structure is configured such that the ribbon-shaped sample stream has a fixed and repeatable location between the walls of the flowcell defining the flow path of sample fluid, in a thin ribbon between layers of PIOAL, passing through a viewing zone in the flowcell. In the flowcell embodiments disclosed, schematically in FIG. 1 and in practical embodiment in FIGS. 6 and 7, the cross section of the flowpath for the PIOAL narrows symmetrically at the point at which the sample is inserted through a flattened orifice such as a tube with a rectangular lumen at the orifice. The narrowing flowpath (for example geometrically narrowing in cross sectional area by a ratio of 20:1 to 40:1) and also due to a greater linear speed of the PIOAL compared to the flow of the sample, cooperate to flatten and spread the sample cross section by a ratio of about 20:1 to 70:1. Effectively, due to the combination of flow rate, viscosity, and stream thickness, the sample is formed into a thin ribbon. The narrowing flowpath (for example geometrically narrowing in cross sectional area by a ratio of 40:1, or by a ratio between 20:1 to 70:1) and a difference in linear speed of the PIOAL compared to the flow of the sample, cooperate to thin the sample cross section by a ratio of about 20:1 to 70:1. In some embodiments the cross section thickness ratio may be 40:1. In some embodiments the cross section thickness ratio may be 30:1.

As a result, process variations such as the specific linear velocities of the sample and the PIOAL do not tend to displace the ribbon-shaped sample stream from its central location in the flow. Relative to the structure of the flowcell, the ribbon-shaped sample stream location is stable and repeatable.

The high optical resolution and imaging device optics have a given focal distance, and the optics is first positioned accurately relative to the flowcell, namely by focusing the high optical resolution imaging device on an autofocus pattern. The displacement distance between the autofocus pattern and the sample stream is known precisely, preferably as a result of initial calibration steps. After autofocusing on the autofocus pattern, the flowcell and the high optical resolution image capture device or the digital image capture device are displaced relatively to each other over the displacement distance. As a result, the high optical resolution image capture device is focused precisely on the sample stream.

In this way, it is not necessary to autofocus or rely upon an image content aspect that is variable between different images, or is less highly defined as to contrast, or might be located somewhere in a range of positions, as the basis for determining a distance location for reference. Having found the location of optimal focus for the autofocus pattern, the relative positions of the high optical resolution imaging device and the flowcell are displaced to move the optimal focus position from the location of the autofocus pattern to the location of the ribbon-shaped sample stream.

In one embodiment, this disclosure relates to a particle contrast agent composition which can be used to stain cells. The particle contrast agent compositions and methods of this invention may be used in one embodiment, for example, for categorizing, counting and characterizing any of the particles disclosed herein as well as subcategorizing, counting, characterization and analysis. In one embodiment, the particle contrast agent compositions are suitable for use with image-based automated or partially automated analyzers.

In some embodiments, the particle contrast agent composition is used to enhance cellular and/or subcellular features under conditions where one or more cell types remain vital or viable and/or cells and/or cellular and/or subcellular features remain substantially intact. The particle contrast agent compositions can be used to generate visual distinctions for particle categorization and subcategorization. In some embodiments, the particle contrast agent compositions may be used to stain white blood cells. In some embodiments, the particle contrast agent composition may also enhance visualizable features of, for example, epithelial cells, bacteria and/or inclusions in pathological casts in addition to the white blood cells. In other embodiments, the particle contrast agent compositions may stain white blood cells as well as epithelial cells, bacteria and/or inclusions in pathological casts.

Aspects and embodiments of the instant disclosure stem from the discovery that certain dye formulations comprising these components have surprising and unexpected properties and efficacy when used as contrast agents for enhancement of image based analysis such as categorization, subcategorization and counting. In one embodiment, this disclosure relates to a particle contrast agent composition which can be used to treat and/or stain cells. The particle contrast agent compositions and methods of this invention may be used in one embodiment, for example, for counting and characterizing white blood cells and white blood cell differential characterization and analysis, and for particle counting, characterization and analysis of particles in biological fluids. In one embodiment, the particle contrast agent compositions are suitable for use with analyzers which are automated or partially automated. In some aspects of this invention, methods and compositions for conducting image based urine sediment analysis are provided. In one embodiment, the compositions and related methods allow users to view cells and their cellular content that might facilitate identification of abnormal cells based on contrast and/or morphology.

In other embodiments, the particle contrast agent compositions may enhance and/or stain subcellular structures of WBCs as well as epithelial cells, bacteria, inclusions in pathological casts, or cell fragments.

Aspects and embodiments of the present disclosure are based on the surprising and unexpected discovery that certain dye compositions, and/or combinations thereof, have unexpected properties and efficacy when used to perform urine sediment sample analysis. Exemplary dye compositions, and/or combinations thereof, are discussed in copending U.S. patent application Ser. No. 14/216,562, filed Mar. 17, 2014, the content of which is incorporated herein by reference.

In another aspect, this invention relates to a kit comprising the particle contrast agent compositions of this invention. The kit may also contain instructions on the use of particle contrast agent composition according to any of the methods described herein. The kit may also include a particle and/or intracellular organelle alignment liquid (PIOAL). The kit may also contain a programmable storage medium and related software for image based identification of particles such as erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments. The kit may also comprise one or more buffers, which may include isotonic buffers and/or diluents. The kit and or buffer may further comprise a surfactant, a pH adjusting agent, and/or an antimicrobial agent. In other embodiments, the kit may also comprise a cleaning or flushing solution. The kit may also comprise standards for positive and negative controls. In some embodiments the standard may comprise a standard stained cell reagent. The kit may also comprise disposables, such as disposable micropipettes, tips or tubes for transferring the components of the kit. The kit may contain anyone, or any combination of two or more of these kit components.

In another embodiment, this disclosure relates to methods for performing image-based cell categorization and subcategorization comprising: a) contacting samples containing particles with a particle contrast agent composition according to any of the methods described herein; b) obtaining images of the particles including intraparticle structures; c) determining one or more characteristics of the cells; and d) performing image based categorization and subcategorization and/or analysis of the particles.

As used herein, exemplary functional components and/or features of an analyzer in the present disclosure can include, for example, a visual analyzer capable of acquiring and/or processing images, and/or particle image identification, counting, categorization and subcategorization. The analyzer may be used in the methods of this invention to analyze urine samples or other samples to categorize and/or to subcategorize, and/or count cells present in the sample, or to identify cells present in the sample based on analysis of particle features.

In certain embodiments, the image is obtained by an exemplary analyzer. An analyzer may include a flowcell coupled to a source of the sample and to a source of an organelle and alignment liquid, for example, a PIOAL, wherein the flowcell defines an internal flowpath, the flowcell being configured to direct a flow of the sample enveloped with the PIOAL through a viewing zone in the flowcell. An analyzer may also include a digital high optical resolution imaging device with an objective on an optical axis that intersects the ribbon-shaped sample stream, a relative distance between the objective and the flowcell being variable by operation of a motor drive, for resolving and collecting a digitized image on a photosensor array. Further, an analyzer may include an autofocus pattern and/or autofocus patterns having a position fixed relative to the flowcell, the autofocus pattern being located at a predetermined distance from the plane of the ribbon-shaped sample stream. What is more, an analyzer may include a light source configured to illuminate the ribbon-shaped sample stream and the autofocus pattern, and at least one digital processor coupled to operate the motor drive and to analyze the digitized image. The processor can be configured to determine a focus position of the autofocus pattern and to relatively displace the objective and the flowcell over the predetermined distance from the focused position, for focusing the high optical resolution and imaging device on the ribbon-shaped sample stream.

The term high optical resolution imaging device can include devices that are capable of obtaining particles images with sufficient visual distinctions to differentiate morphological features and/or changes. Exemplary high optical resolution imaging devices can include devices with a resolution of 1 um or lower, including for example, 0.6 to 0.8 um, such as for example, 0.7 um. In another example the high optical resolution imaging device can have a resolution of 0.3 to 0.4 um, such as for example 0.35 um. In another example the high optical resolution imaging device can have a resolution of 0.4 to 0.5 um, such as for example, 0.43 um.

In some embodiments, the images obtained in any of the compositions and/or methods of this invention may be digitized images. In some embodiments, the images obtained are microscopy images. In certain embodiments, the images may be obtained manually. In other embodiments, at least part of the procedure for obtaining the images is automated. In some embodiments, the images may be obtained using an analyzer comprising a flowcell, a high optical resolution imaging device or the digital image capture device, optionally with an autofocus feature.

In one embodiment, the images provide information relating to the cytosolic, cell nucleus and/or nuclear components of the cell. In one embodiment, the images provide information relating to the granular component and/or other morphological features of the cell. In one embodiment, the images provide information relating to cytosolic, nuclear and/or granular component of the cell. The granular and/or nuclear images and/or features are determinative of cellular categorization and subcategorization both independently or in combination with each other.

In one aspect of the methods of this invention, the cells which are contacted with particle contrast agent composition can comprise white blood cells, epithelial cells and/or bacteria. In another aspect, the methods of this invention may further comprise white blood cell categorization and subcategorization.

In one aspect of the methods of this invention, the cells contacted with particle contrast agent composition and/or imaged are red blood cells. In yet another aspect, the methods of this invention relate to a method for performing image-based urine particle categorization and subcategorization comprising: a) imaging a portion of the particles cells; and b) determining the morphology of the imaged particles. In one embodiment, the particles in urine may be red blood cells. As used herein, red blood cells (RBC) can include, for example, normal red blood cells and/or dysmorphic red blood cells. In some embodiments, the imaging is performed using the analyzer of this disclosure such as an analyzer comprising a visual analyzer and a processor As used herein, an exemplary complete urinary sediment analysis can include a test panel typically requested by a doctor or other medical professional that provides information about the formed elements (e.g., cells and/or other particles) present in a patient's urine sample. Exemplary formed elements found in urine can generally include but are not limited to any particle disclosed herein.

As used herein, abnormally high counts may indicate the presence of disease, disorder, and/or condition. Thus, a complete urinary sediment analysis is one of the commonly performed urine tests in medicine, as it can provide an overview of a patient's general health status. Accordingly, a urinary sediment analysis is routinely performed during annual physical examinations.

As used herein, typically the subject collects a urine sample, generally in a cup. The sample is then transported to a laboratory. In a traditional method, the urine sample is first subjected to centrifugal separation and enriched, sediments thus obtained are in some cases stained and then loaded on a microscopy slide (e.g., a wet mount or specialized counting slide), and are subjected to manual determination and counting under the microscope. In another embodiment, the sample is processed with an automated analyzer where particles are categorized, subcategorized, and counted while the particles are enveloped in a sheath fluid.

As used herein, in general, urine analyzers can aspirate a very small amount of the specimen through narrow tubing. Sensors can detect the count and/or the number of cells passing through the tubing, and can identify the type of cell. Exemplary sensors may include detectors of light (e.g., visible, UV, or IR) and/or electrical impedance. Exemplary detection parameters may include size, volume, and/or cellular features. In certain embodiments, the sensors can detect visible and non-visible light in a wavelength spectrum ranging from about 200 nm to about 1.0 mm. In certain embodiments, the sensors can detect a wavelength of between about between 380 nm and about 760 nm, In another aspect of the methods of this invention, the particles contacted with particle contrast agent composition and/or imaged particles, such as blood cells, squamous and non-squamous epithelial cells, casts trichosomas, or bacterias. In some aspects of this invention, the abnormal presence of these particles can be used to identify, predict, diagnose, prognose, or support a diagnosis of a condition, disease, infection and/or syndrome, and/or monitor whether a subject is responsive or non-responsive to treatment.

As used herein, detectable and measurable particle parameters can include, for example, visual images and/or non-image based indices of size, shape, symmetry, contour and/or other characteristics.

As used herein, the urine sample can be diluted, divided into portions, or treated with a particle contrast agent in some processes.

The methods disclosed herein are applicable to samples from a wide range of organisms, including mammals, e.g., humans, non-human primates (e.g., monkeys), horses, cows or other livestock, dogs, cats or other mammals kept as pets, rats, mice, or other laboratory animals; birds, e.g., chickens; reptiles, e.g., alligators; fish, e.g., salmon and other farmed species; and amphibians.

The samples can be obtained by any conventional method, e.g., excretion, draw, harvesting, aspirate, or a biopsy. The sample can be from a subject considered to be healthy, for example, a sample collected as part of a routine physical examination. The sample can also be from a subject who has, who is at risk for, or who is suspected of having a disorder. The disorder can be the result of a disease, a genetic abnormality, an infection, an injury or unknown causes. Alternatively or in addition, the methods can be useful for monitoring a subject during the course of treatment for a disorder. Where there are signs of non-responsiveness to treatment and/or therapy, a clinician can choose an alternative or adjunctive agent. Depending upon the condition of the subject and the particular disorder, if any, samples can be collected once (or twice, three times, etc.) daily, weekly, monthly, or yearly.

The particles can vary depending upon the urine sample. The particles can be cells found in urine, for example, blood cells, fetal cells, stem cells, tumor cells or fragments thereof. In some embodiments the particles can be an infectious agent, for example, a virus, bacterium, protist, protozoan, fungus or parasite.

Reference to a "formed element" will be understood to encompass non-fluid elements present in biological fluid samples. Formed elements include, for example, classes of blood cells based on scientific classification or physiological function including erythrocytes (RBCs), leukocytes (WBCs), WBC clumps, subclasses of leukocytes, which include mature leukocytes, such as monocytes, neutrophils, eosinophils, basophils. "Formed elements" for use herein will also include particles such as casts, epithelial cells, yeasts, crystals, bacteria, mucus, microorganisms, bacteria, fungi, protist, protozoa, parasites, cysts, including parasitic cysts, or fragments thereof or other cell fragments.

Unless expressly indicated otherwise, reference to a "category" of particles made in this disclosure will be understood to encompass a group of particles detected using at least one detection criterion measured, detected or derived such as size, shape, texture, or color. In some embodiments the members of at least one category and/or subcategory of particles counted by the analyzer of this disclosure will be the same type of formed element. Reference to a "category" of particles made in this disclosure will be understood to encompass a grouping of particles corresponding to criteria measured, detected or derived such as size, shape, texture, or color. In some embodiments the members of at least one category and/or subcategory of particles counted by the analyzer of this disclosure will be the same type of formed element.

Reference to a "member" or "members" of a category and/or subcategory of particles made in this disclosure will be understood to encompass individual particles within a category or sub-category of particles.

As used herein, the term high optical resolution imaging device can include devices that are capable of obtaining particles images with sufficient visual distinctions to differentiate morphological features and/or changes. Exemplary high optical resolution imaging devices can include devices with a resolution of 1 um or lower, including for example, 0.7 to 0.9 um such as for example 0.8 um. Another exemplary high optical resolution imaging device has a resolution of 0.4 to 0.5 um, such as for example, 0.43 um Exemplary high optical resolution imaging devices can include devices with an optical resolution of 1 μm or lower, including for example, 0.46 μm.

As used herein, the particle contrast agent compositions can be adapted for use in combination with a particle and/or intracellular organelle alignment liquid (PIOAL) in a visual analyzer for analyzing particles in a sample from a subject. The exemplary PIOAL is useful, as an example, in methods for automated recognition of different types of particles in a sample from a subject.

In another aspect, the cells may be enveloped in PIOAL when images are obtained. Suitable exemplary PIOAL are described herein.

As used herein, "alignment" can be characterized in part by the alignment of spherical and/or non-spherical particles. For example, particles such as non-spherical particles may be aligned in a plane substantially parallel to the direction of the flow. In certain embodiments, alignment of the non-spherical particles is characterized by the orientation of the particles increase an image projection of the non-spherical particles under imaging conditions in the focal plane of the high optical resolution imaging device. Particles such as spherical particles may have an increase in the amount of the in focus intraparticle contents of the particles and cells. The intraparticle structures of particles such as spherical particles may be positioned, repositioned and/or better-positioned to be substantially parallel to the direction of flow. For example, intracellular structures, organelles or lobes may also be positioned, repositioned, and/or better-positioned to be substantially parallel to the direction of flow.

Reference to a "class" of particles made in this disclosure will be understood to encompass a group of particles based on scientific classification. For example, major classes of formed elements in a urine sample include but not limited to erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments.

Reference to a "member" or "members" of particles made in this disclosure will be understood to encompass a subcategory of particles in one category of particles. For example, each class of urine sediments can be further divided into subcategories or subcategories. Major subcategories of WBCs include but are not limited to neutrophils, lymphocytes, monocytes, eosinophils, and basophils. In addition to mature RBCs, members of RBCs may include abnormally shaped RBCs Reference to "abnormal" cells or particles will be understood to encompass those associated with a certain disease or condition, or irregularities which may, in some instances, be associated with certain diseases or conditions. Variations in size, shape, color, quantity of particles, and/or intracellular structures may be associated with certain diseases or conditions or lack thereof.

Reference to "count" of particles or "particle count" made in this disclosure will be understood to encompass the numbers of particles obtained accumulating the number of all particles detected and categorized or subcategorized by the visual analyzer. Reference to "concentration" of a class, category or a sub-class or sub-category of particles made in this disclosure will be understood to mean the numbers of the particles per unit volume (e.g., per liter) or per sample of a known volume. For example, an visual analyzer may provide counts, concentrations, ratios or other concentration based parameters for each category or subcategory of particles.

The present disclosure provides a technique for automatically achieving a correct working position of the high optical resolution imaging device for focusing on the ribbon-shaped sample stream. The flowcell structure is configured such that the ribbon-shaped sample stream has a fixed and dependable location within the flowcell defining the flow path of sample fluid, in a thin ribbon between layers of PIOAL, passing through a viewing zone in the flowcell. In the flowcell embodiments disclosed, schematically in FIG. 1 and in practical embodiment in FIGS. 6 and 7, the cross section of the flowpath for the PIOAL narrows symmetrically at the point at which the sample is inserted through a flattened orifice such as a tube with a rectangular lumen at the orifice, or cannula. The narrowing flowpath (for example geometrically narrowing in cross sectional area by a ratio of 20:1, or by a ratio between 20:1 to 70:1 and a difference in linear speed of the PIOAL compared to the flow of the sample, cooperate to compress and spread the sample cross section by a ratio of about 20:1 to 70:1. In some embodiments the cross section thickness ratio may be 40:1.

In one aspect, the symmetrical nature of the flowcell and the manner of injection of the sample fluid and PIOAL provide a repeatable position within the flowcell for the ribbon-shaped sample stream between the two layers of the PIOAL. As a result, process variations such as the specific linear velocities of the sample and the PIOAL do not tend to displace the ribbon-shaped sample stream from its central location in the flow. Relative to the structure of the flowcell, the ribbon-shaped sample stream location is stable and repeatable.

However, the relative positions of the flowcell and the high optical resolution imaging device of the optical system are subject to change and require occasional position adjustments to maintain the optimal distance between the high optical resolution imaging device to the ribbon-shaped sample stream, thus providing a quality focus image of the enveloped particles in the ribbon-shaped sample stream. There is an optimal distance between the high optical resolution imaging device and the ribbon-shaped sample stream for obtaining focused images of the enveloped particles. The optics are first positioned accurately relative to the flowcell, schematically in FIG. 1, namely by autofocus techniques to locate the high optical resolution imaging device at the optimal distance from an autofocus pattern with a fixed position relative to the flowcell. The displacement distance between the autofocus pattern and the ribbon-shaped sample stream is known precisely, preferably as a result of initial calibration steps. After autofocusing on the autofocus pattern, the flowcell and/or high optical resolution imaging device is then displaced to provide the known displacement distance between the flowcell and high optical resolution imaging device or the digital image capture device and the ribbon-shaped sample stream. As a result, the objective lens of the high optical resolution imaging device is focused precisely on the ribbon-shaped sample stream containing the enveloped particles.

In photographic systems with autofocus aspects, it is usually the case that autofocus processes attempt to increase the contrast of the subject appearing in the image. However according to the present technique, autofocusing is simplified by autofocusing on the autofocus pattern, which, in some instances, is a high contrast figure defining a known location along a line parallel to the optical axis of the high optical resolution imaging device or the digital image capture device. The autofocus pattern has a known displacement or distance relative to the location of the ribbon-shaped sample stream. A contrast measurement algorithm can be employed specifically on the features of the autofocus pattern. In one example, the position of the high optical resolution imaging device is varied along a line parallel to the optical axis of the high optical resolution imaging device to find the depth or distance at which one or more maximum differential amplitudes are found among the pixel luminance values occurring along a line of pixels in the image that is known to cross over an edge of the contrast figure. The autofocus pattern advantageously has no variation along the line parallel to the optical axis of the high optical resolution imaging device, which is also the line along which a motorized control operates to adjust the position of the high optical resolution imaging device to provide the recorded displacement distance.

The method further comprises forming the ribbon-shaped sample stream into a ribbon-shape. The ribbon shape is presented such that the optical axis of the high optical resolution imaging device is substantially perpendicular to the ribbon-shaped sample stream, namely normal to the plane of the ribbon-shaped stream.

Visual analyzer 17 can also comprise at least one contacting chamber 26 configured to provide at least one chemical comprising at least one of a diluent, a permeabilizing agent, a contrast agent effective to generate visual distinctions for particle categorization and subcategorization. For example, as shown in FIG. 1 and elsewhere, the contacted sample is introduced into the flowcell through sample injector 29, and a sheath or intracellular organelle alignment reagent is introduced from injector 27.

A diluent can be used for diluting the sample to a suitable concentration. A contrast agent and/or permeabilizing agent is used to generate visual distinctions for categorizing and/or subcategorizing particles. PIOAL is used to align certain type of cells or cellular structures in a direction for better imaging. In some embodiments, the at least one chemical can be applied to contact a sample first and then the treated sample is provided onto visual analyzer 17.

Treatment of the sample with the at least addition of at least one chemical can be performed at room temperature. In some embodiments, such a treatment can be performed at a temperature such as 10, 15, 20, 25, 30, 35, 36, 37, 38, 38, 39, 40, 45, 46, 47, 48, 49, 50 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C. The treatment at a selected temperature can be conducted in an incubator which is separate from visual analyzer 17, or on a visual analyzer 17 which is temperature controlled.

In some embodiments, the visual analyzer may have a contacting chamber for bringing the sample in contact with a contrast agent and/or permeabilizing agent or surfactant. In other embodiments, the sample may be contacted with contrast agent, and/or permeabilizing agent prior to injection into the visual analyzer. In other embodiments, the visual analyzer containing a heating element for heating the sample while in contact with the contrast agent and/or permeabilizing agent, at a controlled temperature for a controlled time. The visual analyzer may also have a cooling element for cooling the sample mixture after the heating step.

In addition to providing accurate results, the visual analyzer 17 offers significant advantages in improving speed of analysis. In FIG. 1C, accurate results of counting different urine sediments can be output through display 63. During an analysis process, an operator may interact with processor 18 through a terminal 65. The operator may need to make slides to identify or verify classes or members of classes of cells or other particles in a sample, and input the information to processor 18. Previously, up to about 25% to 30% of results were reviewed manually by making microscopy slides (e.g. a wet mounts or specialized counting slides) with which were examined under a microscope by an operator. By operating the analyzer as described in this disclosure, images can be reviewed on the visual analyzer and the samples will require less frequent manual review.

The following categories of applications are described for the purpose of illustration of the analyzer in this disclosure. The applications are not limited to those described below.

The present disclosure provides novel compositions and methods of use thereof for conducting particle analysis. In particular, the present disclosure relates to a particle and/or intracellular organelle alignment liquid (PIOAL) used in an analyzer for analyzing particles in a sample. The terms sheath fluid and PIOAL can be used interchangeably throughout this disclosure. The present disclosure further provides methods for producing the PIOAL and methods for using the PIOAL to analyze particles. The PIOAL of this invention is useful, as an example, in methods for automated categorization and subcategorization of particles in a sample.

The PIOAL can comprise one or more viscosity agents or viscosity modifiers. As used herein, the PIOAL is a compound or composition having a characteristic viscosity that is different from the viscosity of the sample. In some embodiments the viscosity of the PIOAL is increased or decreased in order to maximize the alignment of particles while in flow and surprisingly also increase the in-focus contents of the particles and/or intracellular organelles of particles when presented for imaging. For example, the particles and/or the cells may be oriented to increase an image projection of the particles under imaging conditions in the focal plane of the high optical resolution imaging device. Intraparticle structures such as intracellular structures, organelles or lobes may also be positioned, repositioned, and/or better-positioned to be substantially parallel to the direction of flow In some embodiments one or more viscosity agents comprise the entire liquid portion of the PIOAL which may contain additional salts or other components. In other embodiments the viscosity of the sample is increased or decreased to maximize the relative difference in the viscosity of the sample and the viscosity of the PIOAL, in order to maximize the alignment of particles while in flow and increase the in-focus contents of the particles and/or intracellular organelles of particles when presented for imaging.

In certain embodiments, the viscosity difference and/or speed difference between the ribbon-shaped sample stream and the PIOAL and/or the thickness of the ribbon-shaped sample stream can introduce shear forces to act on the particles while in flow thereby causing the particles to align or remain in alignment throughout the imaging process in the visual analyzer. In some embodiments the sample will be contrast enhanced. In some embodiments the PIOAL may comprise up to 100% of a viscosity agent.

In other embodiments, this disclosure relates to a PIOAL that can be used in image-based analysis of particles in urine samples or other biological fluid samples such as cerebrospinal fluid and/or effusions associated with particular conditions. Particle category and/or subcategory counts as described for use in urine samples in this disclosure are nonlimiting examples of the sort of samples that may be analyzed. In some embodiments, cells present in samples may also include bacterial or fungal cells as well as white blood cells, or red blood cells. In some embodiments, particle suspensions obtained from tissues or aspirates may be analyzed.

In some embodiments a stream of sample fluid can be injected through a cannula with a flattened opening to establish a flowpath with a considerable width. The PIOAL can be introduced into the flowcell and carries the sample fluid along through the imaging area, then toward a discharge. PIOAL has a different viscosity, e.g. relatively higher than the sample fluid, and optionally a different flow rate at the point of injection to the ribbon-shaped sample stream results in the sample fluid flattening into a thin ribbon shape. The thin ribbon of sample fluid is carried along with the PIOAL, to pass in front of a viewing port where a high optical resolution imaging device and a light source are arranged to view the ribbon-shaped sample stream.

In one embodiment, the viscosity of the PIOAL can be higher than the viscosity of the sample. The viscosity of the PIOAL, the viscosity of the sample material, the flow rate of the PIOAL and the flow rate of the sample material are coordinated to maintain the flow in a ribbon-shaped sample stream with predetermined dimensional characteristics, such as an advantageous ribbon-shaped sample stream thickness. Maintaining an advantageous ribbon-shaped sample stream thickness provides, as an example, a high percentage of in-focus particles, such as cells and/or in-focus cellular components.

The disclosure is based on the discovery that the addition of a suitable amount of a viscosity agent in the PIOAL significantly improves particle/cell alignment in a flowcell, and increases in-focus intracellular contents of cells, resulting in higher quality images of cells in flow compared to use of a non viscosity-modified conventional sheath fluid. The addition of the viscosity agent increases the shear forces on cells like RBCs which then aligns the cells in a plane substantially parallel to the flow direction, which results in image optimization. For cells like WBCs, this also results in positioning, repositioning, and/or better-positioning of intracellular structures, organelles or lobes substantially parallel to the direction of flow.

Alignment of particles that are smaller in diameter than the flow stream, may be obtained by increasing the viscosity of the PIOAL. This results in improved alignment of those particles in a plane substantially parallel to the direction of the flow.

An exemplary PIOAL embodiment is used in a flowcell for particle analysis. A sample is enveloped in the stream of the PIOAL and passed through the flowcell of the analyzer device. Then information from the sample when passing through the detection area is collected, enabling it to analyze particles/cells contained in the sample. The use of the PIOAL on such an analyzer allows accurate categorization and subcategorization and counting of particles such as cells and other particles contained in samples.

As used herein, PIOAL is useful in obtaining information relating to following cells and/or particles disclosed herein.

As used herein, the viscosity agent and/or viscosity modifier can include any substance suitable to achieve an absolute value of a difference between the viscosity of the PIOAL and the viscosity of the sample between 0.1 to 10 centipoise, with optical characteristics, including optical clarity, appropriate for use in an imaging system. Viscosity agent/modifying agents may include any agent suitable to achieve an absolute value of a difference between the viscosity of the PIOAL and the viscosity of the sample between 0.1 to 10 centipoise (cP), with optical characteristics, including optical clarity, appropriate for use in an imaging system.

Additional suitable buffers may include, for example, pH buffers that work in a physiological range pH 6-8, including 2-Amino-2-methyl-1,3-propanediol BioXtra, pH 10.0-12.0 (20° C., 0.5 M in $H_2O$); ACES; ADA; BES; Bicine; BIS-TRIS; DIPSO; EPPS; Gly-Gly; HEPBS; HEPES; MES; MOBS; MOPS; MOPSO; Phosphates; PIPES; POPSO; Sodium carbonate; Sodium bicarbonate; TAPS; TAPSO; TES; Tricine; Triethanolamine hydrochloride; and Tris; Trizma.

In one aspect, the exemplary analyzer/system comprises an automated visual analyzer component in which a liquid sample containing particles of interest is caused to flow through a flowcell having a viewport through which a high optical resolution imaging device captures a digital image. The flowcell is coupled to a source of sample fluid, and to a source of PIOAL. The sample may be treated with one or more of the exemplary particle contrast agent compositions described herein before imaging analysis. The urine sample can be diluted, divided into portions, stained in some processes, and caused to flow through a flowcell having a transparent port or window through which a pixel data image is captured using a high optical resolution imaging device comprising a digital camera. The pixel data image can be displayed on a monitor, and analyzed automatically and/or interactively to discern visible features of particles of interest. The features allow the particles to be distinguished, categorized, subcategorized, and counted, such as formed elements in urine samples.

The samples can be obtained by any conventional method, e.g., a urine sample collection. The sample can be from a subject considered to be healthy, for example, a sample collected as part of a routine physical examination. The sample can also be from a subject who has, who is at risk for, or who is suspected of having a disorder. The disorder can be the result of a disease, a genetic abnormality, an infection, an injury or unknown causes. Alternatively or in addition, the methods can be useful for monitoring a subject during the course of treatment. Where there are signs of responsiveness, the clinician can adjust the dose or treatment accordingly. Where there are signs of non-responsiveness to treatment, a clinician can adjust the dose or choose an alternative or adjunctive agent. Depending upon the condition of the subject and the particular disorder, if any, samples can be collected once (or twice, three times, etc.) daily, weekly, monthly, or yearly.

The high optical resolution imaging device and light source can be placed on opposite sides of the flowcell, for obtaining backlighted images of the particles. The high optical resolution imaging device captures a pixel data image of the sample through a viewing port in the flowcell. For example, the high optical resolution imaging device captures images at a repetition rate consistent with the flow rate such that sections of the ribbon-shaped sample stream are imaged without substantial gaps or overlap.

There are a number of structural and functional challenges in the design and operation of a system for collecting high-resolution images of an advancing ribbon-shaped sample stream through a flowcell. One need is to obtain a sharply focused image of the particles, sufficiently clear to reveal the different features of the various particle types that allow the particle types to be distinguished from one another.

In order to maintain focus, the distance between the high optical resolution imaging device and the ribbon-shaped sample stream needs to be set such that the ribbon-shaped sample stream is at the correct distance from the high optical resolution imaging device along the optical axis. The objective lens of the high optical resolution imaging device resolves a focused image on a photosensor array, such as a two dimensional charge coupled device array, from which pixel data is digitized. The dimensions of the area of the sample that is imaged, and the depth of field that is in focus in the sample, are determined by the optical configuration. Aperture adjustments and zoom adjustments may be possible, but for purposes of simplicity, the examples in this disclosure are such that focusing the high optical resolution imaging device on the particles in the ribbon-shaped sample stream simply requires positioning the high optical resolution imaging device at a predetermined correct distance from the ribbon-shaped sample stream in the flowcell, namely the distance that results in a focused particle image on the photosensor array.

In one aspect, the visual analyzers, or image analyzers, for use with the compositions of this invention can capture reliably focused images of the sample by very accurately setting the distance between the ribbon-shaped sample stream and the high optical resolution imaging device of the optical system. In some embodiments, the visual analyzers can be used in combination with the compositions of this invention and algorithms to establish said distance.

It is desirable to image a thin layer of prepared sample. The sample is arranged in the flowcell and illuminated to enable viewing through a viewing port. The individual particles appear clearly in the captured pixel data image, with sufficient feature contrast for example, to reveal attributes that are then compared and contrasted with parameters known to distinguish categories and subcategories of particles from one another.

It is an object to employ a flowcell in combination with suitable particle contrast agent compositions, and an exemplary PIOAL to allow the analyzer to collect optimized images for particle recognition. In addition, the PIOAL and flowcell provide a stable and highly repeatable position for a ribbon-shaped sample stream injected into a flow of PIOAL, in combination with an autofocus mechanism that maintains the optimal distance of the high optical resolution imaging device to the ribbon-shaped sample stream, thus providing a quality focused image.

It is known to use automated focus processes in digital photography in general and in digital image microscopy in particular, for focusing on a subject at an uncertain depth position. However, a programmed processor does not have a sense of the image content. Typically, the quality of focus is assessed by finding the distance at which the image of the subject has the highest overall contrast as determined by a numeric algorithm applied to the pixel data in the image. For example, a sum of the differences in luminance amplitude for each pixel in the image versus its adjacent pixels can be calculated as a measure total contrast. Other things being equal, the highest sum found in images at slightly different distances corresponds to the highest contrast. However image content affects the result of such numeric measures, and image content may differ at different distances. Thus, it is desirable as in manual procedures, to image a thin layer of diluted stained sample, e.g., of a thickness comparable to the thickness of the cells or particles, when using a flowcell instead of glass slide mounted samples. The sample needs to be arranged in the flowcell to enable viewing through a viewing port, and illuminated.

Therefore, it is advantageous to have automated focus processes whereby the individual particles are to appear clearly in the captured pixel data image, with sufficient feature contrast to reveal visible attributes that are then compared and contrasted with parameters known to distinguish categories and subcategories of particles from one another.

It is an object to employ a flowcell in combination with exemplary PIOAL disclosed herein that provides a stable and highly repeatable position for a sample stream injected into a flow of PIOAL, in combination with a high optical resolution imaging autofocus apparatus that keeps the focal plane of the high optical resolution imaging device on the ribbon-shaped sample stream, substantially parallel to the direction of the flow thus providing a quality focused image of the particles in the sample, but which does not require constant or even frequent repetition of the autofocus process. The image is focused in a plane substantially parallel to the direction of the flow of the visual analyzer.

As an example, a first step is to determine a precise relative position of the high optical resolution imaging device relative to the flowcell that carries the exemplary PIOAL and the ribbon-shaped sample stream. Advantageously, the flowcell and/or high optical resolution imaging device are moved relative to one another in an autofocusing process using as a subject an autofocus pattern with sharply contrasting edges as the reference point. The ribbon-shaped sample stream is fixed in position relative to that reference point.

The PIOAL flowpath can be arranged symmetrically such that equal PIOAL flows spread and locate the sample stream as a thin ribbon at a fixed distance from the autofocus pattern along the line parallel to the optical axis of the high optical resolution imaging device. In one embodiment the autofocus pattern comprises an opaque border around an opening admitting light from a source of rear illumination and the distance of the autofocus pattern is readily and unambiguously homed in upon by the autofocus controls. Then, the ribbon-shaped sample stream is brought into focus by displacing the high optical resolution imaging device from the autofocus pattern position to the position of the ribbon-shaped sample stream, which is a fixed displacement distance, without the need for autofocusing on the image content of the sample, although further autofocusing is conceivable.

A motor drive is provided and controlled by a processor that assesses a measure of focus quality, for example, a measure of contrast, and operates the motor drive for autofocusing. In normal operation the processor operates the motor drive to autofocus on the autofocus pattern and then adjusts the distance between the high optical resolution imaging device and the flowcell by the recorded displacement distance from the autofocus pattern to the ribbon-shaped sample stream. As long as the device continues to move the ribbon-shaped sample stream in the same way, and thermal expansion or similar confounding factors do not arise, the image of the ribbon-shaped sample stream will remain in focus.

A preliminary set-up or calibration process can be used to determine and record the displacement distance between the autofocus pattern and the location of a ribbon-shaped sample stream in the flowcell. The exact displacement distance, which may differ for different flowcells, is established by preliminary testing, such as by autofocusing alternatively on the autofocus pattern and on a test ribbon-shaped sample stream several times, and recording the mean result as a constant associated with the flowcell.

The particles in the urine sample are imaged by the high optical resolution imaging device that collects digital images that are analyzed by at least partly automated image analysis processes. An autofocus process is accomplished on an autofocus pattern or similar focusing target, preferably a planar target with little or no distance variation in the direction of the optical axis, and not on the subject ribbon-shaped sample stream. The autofocus pattern has a known distance displacement to the distance of the ribbon-shaped sample stream. An automated focusing configuration includes a motor drive that adjusts the relative position of the flowcell and a high optical resolution imaging device along the optical axis, responsive to control signals from a processor that collects one or more measures of focus quality over a range of distances and seeks an optimal distance. The autofocus is applied to fix the high optical resolution imaging device point of focus at the depth of the target pattern located at a displacement distance from the flat ribbon-shaped sample stream parallel to the flow stream.

Having focused on the autofocus pattern, the processor operates the motor drive over the fixed displacement distance, thereby bringing the ribbon-shaped sample stream into focus in the digital image. The autofocus pattern can have a high degree of visual contrast and in some embodiments can assist in a planar alignment, i.e., arranging the flowcell in a plane normal to the optical axis of the high optical resolution imaging device.

In one aspect, the methods of this invention provide surprisingly high quality images of particles in flow which allow for automated image based urine sediment counting, as well as automated identification of morphological abnormalities useful in determining, diagnosing, prognosing, predicting, and/or supporting a diagnosis of whether a subject has a disease, condition, abnormality or infection and/or monitoring whether a subject is responsive or non-responsive to treatment. In another aspect, the compositions and methods of this invention provide more accurate cell categorization, subcategorization, and more accurate flagging which reduces the manual review rate compared to current automated analyzers.

In some embodiments, this invention further relates to a kit comprising the PIOAL of this invention. In another embodiment, this invention relates to a kit comprising the PIOAL of this invention and at least one particle contrast agent. In some aspects, the kit may contain two particle contrast agents in addition to the PIOAL. In some embodiments the particle contrast agent is a composition comprising New Methylene Blue, Crystal Violet, Safranin O, Eosin Y, and/or Methyl Green.

In one embodiment, the non-spherical particles comprise red blood cells, epithelial cells, casts, white blood cells clumps, and/or budding or hyphae yeasts. In another aspect of this invention, the spherical particles comprise white blood cells, fat bodies, trichomonas.

The particles in urine samples to be analyzed include characteristic sediments, or formed elements. The formed elements may include the exemplary particles disclosed herein.

Exemplary casts can include acellular pigment casts, unclassified cast (e.g. granular casts). Exemplary acellular casts can include, for example, waxy casts, broad casts, fatty casts, and crystal casts. Exemplary cellular casts can include, for example, RBC casts, WBC casts, and cellular casts.

Exemplary crystals can include, for example, calcium oxalate, triple phosphate, calcium phosphate, uric acid, calcium carbonate, leucine, cystine, tyrosine, and amorphous crystals.

Exemplary non-squamous epithelial cells can include, for example, renal epithelials and transitional epithelials.

Exemplary yeast can include, for example, budding yeast and yeast with pseudohyphae Exemplary bacterial pathogens can include, for example, *Bacillus anthracis, Yersinia pestis, Yersinia enterocolitica, Clostridium botulinum, Clostridium perfringens Francisella tularensis, Brucella* species, *Salmonella* spp., including *Salmonella enteriditis, Escherichia coli* including *E. coli* O157: H7, *Streptococcus pneumoniae, Staphylococcus aureus, Burkholderia mallei, Burkholderia pseudomallei, Chlamydia* spp., *Coxiella burnetii, Rickettsia prowazekii, Vibrio* spp., *Shigella* spp. *Listeria monocytogenes, Mycobacteria tuberculosis, M. leprae, Borrelia burgdorferi, Actinobacillus pleuropneumoniae, Helicobacter pylori, Neisseria meningitidis, Bordetella pertussis, Porphyromonas gingivalis*, and *Campylobacter jejuni*. Fungal pathogens can include, without limitation, members of the genera *Aspergillus, Penecillium, Stachybotrys, Trichoderma, mycoplasma, Histoplasma capsulatum, Cryptococcus neoformans, Chlamydia trachomatis*, and *Candida albicans*. Pathogenic protozoa can include, for example, members of the genera *Cryptosporidium*, e.g., *Cryptosporidium parvum, Giardia lamblia, Microsporidia* and *Toxoplasma*, e.g., *Toxoplasma brucei, Toxoplasma gondii, Entamoeba histolytica, Plasmodium falciparum, Leishmania major* and *Cyclospora cayatanensis*.

Exemplary urinary sediment particle can also include RBC clumps, fat, oval fat bodies, and trichomonas.

Conditions associated with hemoglobin in urine include, for example, bilirubin crystals or amorphous deposits seen in severe hyperbilirubinaemia; cystine crystals, seen in cystinosis; hemosiderin, seen in iron overload; and erythrocytes, seen in paroxysmal cold hemoglobinuria.

In some embodiments, the results obtained can be compared to a reference.

Standard reference levels typically represent the cell numbers derived from a large reference population. The reference population may include individuals of similar age, body size; ethnic background or general health as the individual in question.

In one aspect, the exemplary stain compositions disclosed herein are useful for categorizing, subcategorizing and counting particles disclosed herein.

As used herein, the particle contrast agent composition can be used in combination with a PIOAL in a visual analyzer to generate images that contain a higher number of in-focus cell contents (e.g. lobes, nucleus, nuclear contents, cytoplasm, and granules).

Use of the PIOAL thins out the sample stream, helping to direct the flow into a thin, flat ribbon. In some embodiments, the use of the exemplary PIOAL results in more in-focus cell contents, which can include lobes, cytoplasm, and granule components of the cell. In addition, in some embodiments the flowcell design has a symmetrical flow path which yields lower cell misalignment than a flowcell with an asymmetric flow path.

As used herein, contrast agents are used to stain a variety of cell types, including, for example, white blood cells, epithelial cells, and/or bacteria.

In some embodiments, features of imaged cells stained by the particle contrast agent compositions of this disclosure are noted in Table 1.

TABLE 1

| | Size (relative to RBC) | Shape | Color | Details |
|---|---|---|---|---|
| RBC | Standard | Round | | Light Center |
| WBC | Large | Round | Nucleus Stained | Nucleus & Granules |
| Epithelials | Small to large | Various | Nucleus Stained | Nucleus & Granules |
| Crystals | Small to large | Various | Natural | Corners |
| Bacteria | Very small and large rods | Dots or rods | Stained | |
| Yeast | Very small to large | Single round or clumps | | |
| Sperm | Small | Filaments | | Head and tail |
| Casts | Large to very large | Cylindroid | | Transparent |
| Mucus | Small to very large | Filaments or cylindroid | | Transparent |
| *Trichomonas* | Large | Round | Stained | Tail |

In certain embodiments, the particle contrast agent composition is formulated for stability, ease of storage, disposal, and/or limited toxicity.

In some embodiments, the methods and analyzer disclosed herein can be used to monitor cell morphology. Alterations in cell morphology are associated with many kinds of disorders. Such alterations can vary depending upon the specific disorder and cell type, but generally include irregularities in size, shape, color, and intracellular structures or any combination of irregularities in size, shape, color, and intracellular structures. For example, alterations in RBC shape may be an indicator of kidney/renal disease.

In some embodiments, the values obtained can be compared to a reference level. Standard reference levels typically represent the particle numbers derived from a large population of individuals. The reference population may include individuals of similar age, body size; ethnic background or general health as the individual in question.

The cells may be decoy cells or tumor cells.

In other embodiments, this disclosure includes kits containing one or more reagents for use in the methods disclosed herein. In one embodiment, the kit may comprise one or more units of PIOAL. In other embodiments, the kit may further comprise one or more particle contrast agent compositions. The kit may also comprise one or more buffers, which may be isotonic, and/or a diluent. The kit and or buffer may further comprise a surfactant, a pH adjusting agent, an ionic strength modifier, chelating agent, sugar, sugar alcohol, protein stabilizer, antimicrobial agent, and/or hemoglobin reagent. In other embodiments, the kit may also comprise a cleaning or flushing solution. The kit may also comprise standards for positive and negative controls. In some embodiments the standard may comprise a standard stained particle reagent (calibrators or controls). The kit may also include concentrates of any of the foregoing. The kit may also comprise disposables, such as disposable micropipettes, tips or tubes for transferring the components of the kit, connectors, cleaners (solution), or instruction manual, operating manual, certificate of analysis, MSDS, etc., and packaging associating such elements as a unit.

Particle contrast agents used for enhancing features in particles, cells or cellular structures, including structures in white blood cells, epithelia cells, pathological casts and/or bacteria are described further in copending U.S. patent application Ser. No. 14/216,562 filed Mar. 17, 2014, the content of which is incorporated herein by reference.

The analyzer and methods disclosed herein can be used to evaluate any sample comprising particles in urine. The methods are applicable to samples from a wide range of subjects, including mammals, e.g., humans, non-human primates (e.g., monkeys), horses, cows or other livestock, dogs, cats or other mammals kept as pets, rats, mice, or other laboratory animals; birds, e.g., chickens; reptiles, e.g., alligators; fish, e.g., salmon and other farmed species; and amphibians.

In some embodiments, the methods and compositions disclosed herein can be used to monitor cell counts, cell features/morphology and/or alterations in cell features/morphology. Such alterations can be associated with disorders and may vary depending upon the specific disorder and cell type, but generally include irregularities in size, shape, color, and intracellular features/structures or any combination of irregularities in size, shape, color, and intracellular features/structures. For example, alterations in RBC shape can be indicative of kidney/renal disease.

The present disclosure also provides exemplary particle contrast agent compositions and methods of use in analyzing particles. The particle contrast agent compositions may be used in any analyzer suitable for detecting and/or analyzing a sample containing particles, including the analyzer described herein. In a general aspect, the exemplary particle contrast compositions and methods of use are useful when employed in combination with an automated analyzer found in research and/or medical laboratories. Exemplary automated analyzers are instruments designed to detect different features and/or other characteristics in a number of biological samples, including, for example, human body fluid samples, with minimal human assistance. Exemplary automated analyzers can include, for example, urine sediment automatic analyzers. The exemplary analyzers can process samples individually, in batches, or continuously. In one embodiment, the exemplary particle contrast compositions described herein can also be used in conventional microscopy applications without requiring the use of an automatic particle counter and/or visual analyzer.

The sample can be diluted, or divided into portions, or concentrated. In some aspects, before image analysis, the sample may be contacted, either on or off the analyzer, with an exemplary particle contrast agent composition described herein. Treatment with the exemplary particle contrast agent composition may also be performed on-line in the analyzer. In certain embodiments, the sample containing the particle is contacted with the particle contrast agent composition and the prepared sample is transported through the flowcell while enveloped in an exemplary PIOAL. In some aspects, the prepared sample can be directed to flow through a flowcell having a transparent port or window through which a pixel data image is captured periodically or continuously using a high optical resolution imaging device. The pixel data image can be displayed on a monitor, and/or analyzed automatically and/or at least partly interactively to discern visible features of interest. Visually distinguishable features of a typical object are used to categorize, subcategorize and/or classify or subclassify and count particles such as formed elements in urine samples.

In one aspect, this disclosure relates to an visual analyzer for imaging a sample comprising particles suspended in a liquid, in which the visual analyzer includes a flowcell coupled to a source of the sample and to a source of a PIOAL, wherein the flowcell defines an internal flowpath, the flowcell being configured to direct a flow of the ribbon-shaped sample stream enveloped with the PIOAL through a viewing zone in the flowcell. An objective lens associated with a high optical resolution imaging device is located such that the objective optical axis intersects the ribbon-shaped sample stream in the flowcell. The relative distance between the objective and the flowcell is variable by operation of a motor drive coupled to a controller, for resolving and collecting a digitized image on a photosensor array. An autofocus pattern (e.g. visible in the digitized images) is situated at a position fixed relative to the flowcell, the autofocus pattern being located at a predetermined distance from the plane of the ribbon-shaped sample stream. A light source illuminates the ribbon-shaped sample stream and the autofocus pattern. At least one digital processor is associated with the controller coupled to operate the motor drive. The processor is also arranged to analyze the digitized image. The processor determines a focus position of the autofocus pattern and relatively displaces the objective and the flowcell over the predetermined distance (e.g. the "displacement distance") from the focused position, to focus the high optical resolution imaging device on the ribbon-shaped sample stream.

In another aspect, a visual analyzer may comprise a processor to facilitate automated analysis of the images. In one aspect, the visual analyzer can be used in methods of this disclosure to provide automated image-based urine formed elements counts. In certain aspects, the methods of this disclosure relate to automated identification of morphological abnormalities for determining, diagnosing, prognosing, predicting, and/or supporting a diagnosis of whether a subject is healthy or has a disease, condition, abnormality and/or infection and/or monitoring whether a subject is responsive or non-responsive to treatment.

In one embodiment the PIOAL is introduced into the flowcell and carries the sample fluid through the imaging area, then along toward the discharge. The stream of sample fluid can be injected through a cannula with a flattened opening to establish a flowpath with a considerable width. In some embodiments, the sample fluid injected has been prepared by treating with a particle contrast agent composition prior to injection. In another aspect of this invention, the sample may be injected into the flow cell by operating a sequence of valves and pumps. In one aspect, flows of sample fluid and PIOAL are introduced into the flow cell at selected flow rates by precision fluid pumps.

The viscosities and the flow rates of the sample fluid and the PIOAL and the contour and dimensions of the flowcell may be selected such that the PIOAL flow flattens and stretches the sample flow out into a flat ribbon consistently through the viewing zone at a dependable location. For example, the PIOAL may flow along a flow path with a symmetrically flattening cross section, which tends to hold an injected sample in position at a constant level in the flow. In some embodiments, the PIOAL has a relatively higher viscosity than the sample fluid, and the relative PIOAL and sample linear flow rates at the point of injection of the sample are such that the sample fluid flattens into a thin ribbon shaped sample stream.

The ribbon shaped sample stream is carried along with the PIOAL, to pass in front of a viewing port where a high optical resolution imaging device and a light source (e.g., UV, visible, IR) are arranged to view the particles in the ribbon-shaped sample stream. The high optical resolution imaging device and light source can be placed on opposite sides of the flowcell, for obtaining back-lit images of the particles. The high optical resolution imaging device captures pixel data images of the sample particles through a viewing port in the flowcell. For example, the high optical resolution imaging device captures images at a repetition rate consistent with the sample flow velocity such that sections of the ribbon-shaped sample stream are imaged without substantial gaps or overlap.

Embodiments of the present invention provide a number of unique structural and functional features implemented in the design and operation of a system for collecting images of a ribbon-shaped sample stream flowing through a flowcell. Exemplary embodiments are configured to obtain sufficiently focused images of the particles, with sufficient clarity and resolution to reveal the different features of the various particles such as blood cells, that allow the particle and/or cell types to be distinguished from one another.

In one aspect, the symmetrical nature of the flowcell and the manner of injection of the sample fluid and PIOAL provide a repeatable position within the flowcell for the ribbon-shaped sample stream in the PIOAL. However, the relative positions of the flowcell and the high optical resolution imaging device are subject to change and require occasional position adjustments to maintain the optimal distance between the high optical resolution imaging device and the ribbon-shaped sample stream, thus providing a quality focus image of the particles.

Embodiments of the present invention encompass automated visual analyzer systems and methods for urine and/or other biological fluids that incorporate an autofocus device/apparatus to provide reliably focused images of the sample by very accurately setting the distance between the ribbon-shaped sample stream and the high optical resolution imaging device. In one aspect, autofocus system embodiments disclosed herein can very accurately set the distance between the ribbon-shaped sample stream and the high optical resolution imaging device and capture reliably focused images of the sample. In some embodiments, algorithms are used to establish the distance that achieves good focus results.

It is an object to employ a flowcell that provides a stable and highly repeatable position for a ribbon-shaped sample stream enveloped in a flow of PIOAL, in combination with a high optical resolution imaging device and autofocus device/analyzer that maintains the optimal focal distance between the high optical resolution imaging device and the ribbon-shaped sample stream, thus providing a quality focused image.

Such apparatus and methods are disclosed and claimed herein. A symmetrical flowcell is provided, which has been found to produce a repeatable ribbon-shaped sample stream distance within the flowcell. Focusing involves setting a precisely correct relative position of the high optical resolution image device relative to the ribbon-shaped sample stream, so as to maintain focus on the ribbon-shaped sample stream.

Advantageously, the flowcell and/or the high optical resolution image device can be moved relative to one another in an autofocusing process using an autofocus pattern such as high contrast pattern or similar focusing target, preferably a planar pattern with sharply contrasting features such as edges, the autofocus pattern being fixed in position relative to the flowcell and used as a focusing subject in lieu of the sample itself. The ribbon-shaped sample stream is a thin ribbon at a fixed distance from the autofocus pattern along a line parallel to the optical axis of the high optical resolution imaging device. The displacement distance between the autofocus pattern and the ribbon-shaped sample stream position is a constant distance, which is determined initially and programmed into the autofocus device/analyzer. The exemplary technique thereafter is to autofocus on the autofocus pattern, then to displace the high optical resolution image device and/or flowcell relative to one another by the predetermined distance, whereupon the distance between the high optical resolution image device and the location of the ribbon-shaped sample stream is the optimal distance to provide a quality focused image of the ribbon-shaped sample stream. For example, at first, an autofocus algorithm focuses the position of the high optical resolution imaging device on the autofocus pattern located at a fixed distance from the ribbon-shaped sample stream. Having focused on the autofocus pattern, the processor operates the motor drive over the predetermined displacement, thereby bringing the ribbon-shaped sample stream into focus of the high optical resolution imaging device.

An exemplary high optical resolution image device comprises an objective lens and associated pixel image sensor, capable of capturing an image that reveals the particles at sufficient magnification and resolution to provide sufficient detail to resolve image (e.g. visual) features of the particles.

The PIOAL flowpath can be arranged symmetrically such that equal amounts of PIOAL flow above and below the sample stream which stretches and locates the sample stream as a thin ribbon at a fixed distance from the autofocus pattern along the line parallel to the optical axis of the high optical resolution imaging device. In one embodiment the autofocus pattern comprises an opaque border around an opening admitting light from a source of rear illumination and the distance of the autofocus pattern is readily and unambiguously homed in upon by the autofocus controls. There is no need for autofocusing directly on the image content of the sample, although further autofocusing is conceivable.

An automated focusing configuration includes a motor drive that adjusts the relative position of the flowcell and a high optical resolution imaging device along the optical axis, responsive to control signals from a processor that assesses one or more measures of focus quality over a range of distances and seeks an optimal distance. For example, the processor may assess a measure of contrast and operate the motor drive for autofocusing. In normal operation the processor operates the motor drive to autofocus on the pattern and then adjusts the distance between the high optical resolution imaging device and the flowcell by the recorded displacement from the autofocus pattern to bring the ribbon-shaped sample stream into focus. So long as the device continues to move the ribbon-shaped sample stream in the same way, and thermal expansion or similar confounding factors do not arise, the image of the ribbon-shaped sample stream will remain in focus.

A preliminary set-up or calibration process can be used to determine and record the displacement distance between the autofocus pattern and the ribbon-shaped sample stream position in the flowcell. The exact displacement distance, which may differ slightly for different flowcells, is established by preliminary testing, such as by autofocusing alternatively on the autofocus pattern and on a test sample stream several times, and recording the mean result as a constant associated with the flowcell.

Accordingly, a sample to be imaged, such as a prepared urine sample, is directed along a defined flowpath through a viewing zone in a flowcell. The PIOAL flowpath preferably is symmetrical and the sample is injected in the center of the PIOAL flow, with which the sample is enveloped. The flow rates and viscosity and density characteristics of the sample and the PIOAL, together with the contour of the flowcell, cooperate so as to form the sample into a flat ribbon flowing consistently through the viewing zone at a repeatable position.

The sample may be imaged by a camera component of the high optical resolution imaging device and digital images collected to be analyzed by at least partly automated image analysis processes, including an autofocus process as described herein.

One object is to distinguish, categorize, subcategorize and/or count particles in a urine sample such as blood cells described herein, which may be associated with particular conditions. In one aspect, the particle contrast agent compositions of this disclosure can be combined with an analyzer such as the analyzer described herein in a method to provide surprisingly high quality images of particles in flow. The high quality images of particles may be automatically captured and processed.

The images allow for automated image-based urine formed elements count, as well as automated identification of morphological abnormalities useful in determining, diagnosing, prognosing, predicting, and/or supporting a diagnosis of whether a subject is healthy or has a disease, condition, abnormality and/or infection, and/or monitoring whether a subject is responsive or non-responsive to treatment. Cell category and/or subcategory count in urine samples is used in this disclosure as nonlimiting examples of the sort of fluids that may be analyzed.

It is an object to employ a flowcell in combination with the exemplary contrast agent compositions described herein, and an exemplary PIOAL, that provides images of optimal quality and detail for particle recognition. In addition, the PIOAL and apparatus provides a stable and highly repeatable position for a ribbon-shaped sample stream enveloped in a flow of PIOAL. This, in combination with a high optical resolution imaging device and the autofocus device/apparatus that maintains the optimal distance of the high optical resolution imaging device to the ribbon-shaped sample stream, provides a quality focused image.

In comparison, other analyzers, for example, image-based discriminators such as visual analyzers are able to discriminate between exemplary cells and/or particles of different categories and subcategories, based on the appearance of the cells or aggregated cells and/or particles or aggregated particles. In one embodiment, the images provide information relating to the cell nucleus or nuclear component of the cell. In one embodiment, the images of the particles treated with the particle contrast agent compositions of this disclosure provide information relating to the granular composition and/or features of the cell. In one embodiment, the images provide information relating to nuclear cytoplasmic, and granular components of the cell. The granular, cytoplasmic and/or nuclear features are image based (e.g. visual) distinctions that may be at least in part determinative of cellular categorization and subcategorization both independently or in combination with each other.

By selecting the particle contrast agent compositions of this disclosure to provide optimal contrast for particle recognition by software on an automated device, the compositions of this disclosure are useful in methods of particle categorization and subcategorization such as urine sediment particles categorization and subcategorization.

In one aspect of the methods of this invention, the cells which are contacted with particle contrast agent composition and imaged may be white blood cells. In another aspect, the methods of this invention may comprise white blood cell categorization and subcategorization.

In another aspect of the methods of this invention, the cells contacted with a particle contrast agent composition and imaged are abnormal particles, such as malaria-infected cells, cancer cells, bacteria, or parasites.

Conventional sheath fluids used in particle imaging systems do not substantially align particles or increase in-focus particle content. There is a need for methods and compositions useful for particle and/or intracellular organelle alignment liquid (PIOAL) to perform accurate automated particle categorization and subcategorization. Also provided in some aspects of this disclosure PIOALs are used in the flowcells of the systems of this disclosure.

The present disclosure provides novel compositions and methods of use thereof for conducting particle analysis. In particular, the present disclosure relates to a PIOAL used in an analyzer for analyzing particles in a sample. The present disclosure further provides methods for producing the PIOAL and methods for using the PIOAL to analyze particles. The PIOAL of this invention is useful, as an example, in methods for automated categorization and subcategorization of particles in a sample.

One aspect of the invention of this disclosure is based on the unexpected observation that the inclusion of at least one viscosity agent and/or viscosity modifying agent in the PIOAL significantly improves the alignment of particles, cells, and the in-focus contents of intraparticle structures such as intracellular structures of cells flowing through a flowcell. The PIOAL improves the alignment of the cells in a plane substantially parallel to the flow direction, maximizing an image projection of non-spherical particles in the focal plane of the high optical resolution imaging device, which results in image optimization and an increase in the number of in-focus particles. This also results in positioning, repositioning, and/or better-positioning of intraparticle structures such as intracellular structures, organelles or lobes, substantially parallel to the direction of flow. Accordingly, in some aspects, the compositions and methods of this invention result in increased in-focus cell content, such as in-focus lobes, cytoplasm and/or granules. The compositions and methods of this invention further provide for more precise categorizing and/or subcategorizing and counting of particles and permit differential particle counts.

This invention relates to a PIOAL suitable for use in an analyzer. In one aspect, the present disclosure provides a PIOAL for use in an analyzer configured to direct flow of a urine sample of a given viscosity in a flow path, wherein the PIOAL comprises: a fluid having a viscosity different from the viscosity of the sample wherein the PIOAL is effective to support the flow of the sample and to align particles and/or to improve alignment in a plane substantially parallel to the flow direction and to increase the in-focus content of particles and cells flowing in the flowpath whereby the aligned particles and intracellular organelles of cells can be imaged. In one embodiment, the PIOAL further comprises at least one of: a buffer; a pH adjusting agent; an antimicrobial agent; an ionic strength modifier; a surfactant, and a chelating agent. In some embodiments, the PIOAL can contain additional compatible components.

In one aspect, the viscosity agent/modifier is present in the PIOAL at a concentration sufficient to effectively achieve an absolute value of a difference between the viscosity of the PIOAL and the viscosity of the sample between about 0.1 to about 10 centipoise (cP), about 1.0 to about 9.0 centipoise, 3.0 to 7.0 centipoise, or about 5.0 centipoise under operating conditions. In one aspect the PIOAL can be used with a sample with a lower viscosity. In another aspect, the PIOAL can be used with a sample having a higher viscosity. In one aspect the PIOAL comprises up to 100% viscosity agent.

In another aspect, the PIOAL of this invention further comprises a pH-adjusting agent. In one embodiment, the pH of the PIOAL is between about 6.0 to about 8.0 under operating conditions prior to its introduction into the sample. In one embodiment, the pH of the PIOAL is between about 6.5 to about 7.5 under operating conditions. In one embodiment, the pH is between about 6.8 to about 7.2 under operating conditions.

In one aspect, the PIOAL of this invention may further comprise one or more antimicrobial agents. In some aspects, the antimicrobial agent may be, for example, a substance which has fungicidal activity (fungicidal agents) and/or substances that have bactericidal activity (bactericidal agents).

In certain embodiments, the PIOAL can contain additional compatible components such as Procaine HCl.

In certain embodiments, the PIOAL may further comprise detectable inert markers suitable for batch or lot-identification. In one aspect, the disclosure provides a PIOAL for use in a visual analyzer/analyzer configured to direct flow of a sample of a given viscosity in a flow path, where the liquid comprises a fluid having a different viscosity than the viscosity of the sample, for example, a PIOAL higher viscosity than the sample, where the PIOAL is effective to align and increase the in-focus content of particles and intracellular organelles of cells flowing in the flowpath and to permit high quality imaging of particles and cells in flow.

In another embodiment, the PIOAL of this disclosure comprises an ionic strength modifier to adjust the ionic strength. Exemplary ionic strength modifiers may include $Li^+$, $Na^+$, $K^+$, $Mg^{++}$, $Ca^{++}$, $Cl^-$, $Br^-$, $HCO_3^-$, sulphates, pyrosulphates, phosphates, pyrophosphates, citrates, cacodylates or other suitable salts. In one embodiment, the PIOAL may be isotonic. In one embodiment, the PIOAL is isotonic and/or comprises an aqueous solution that is isotonic. In one embodiment, the PIOAL comprises sodium chloride. In one embodiment, said sodium chloride is present at a concentration of about 0.9%. In one aspect the PIOAL has the same osmolality as urine. In one embodiment, the sodium chloride in the PIOAL of this invention may be present in a concentration of between about 0.1 and about 10% (w/v). The concentration of sodium chloride in the PIOAL may be, for example, about 0.9 gram of sodium chloride in 100 milliliters.

In one aspect, the PIOAL has a target viscosity of between about 1-10 centipoise under operating temperatures and conditions. In one embodiment, a stock solution of concentrated PIOAL is provided wherein said concentrated stock solution can be diluted to achieve the PIOAL viscosity. In one embodiment, the concentration of the stock solution is present at least about 1.1× to at least about 100× concentration of the PIOAL under operating conditions. As used herein, operating temperature can range from about 10-40° C., including about 20, 21, 22, 23, 24, 25, 26, 27, 28, 29 and 30° C. Typically the viscosity measurements are reported at room temperature, or at about 25° C.

In one aspect, the disclosure provides a stock solution of concentrated particle and intracellular organelle alignment liquid wherein the concentrated stock solution can be diluted to achieve a viscosity of between about 1-10 centipoise under operating conditions.

The viscosity agent is any compound capable of aligning the cells in a plane substantially parallel to the flow direction, and/or for positioning, repositioning, and/or better-positioning of intraparticle structures, such as intracellular structures, organelles or lobes substantially parallel to the direction of flow. In one embodiment, the PIOAL comprises at least one viscosity agent selected from at least one of glycerol, glycerol derivative, ethylene glycol, propylene glycol (dihydroxypropane), polyethylene glycol, polyvinylpyrrolidone (PVP), carboxymethylcellulose (CMC), water soluble polymer and dextran. In one embodiment, the viscosity agent is glycerol. In one embodiment, the viscosity agent comprises glycerol and polyvinylpyrrolidone (PVP). In one embodiment, the viscosity agent comprises PVP. In one embodiment, the viscosity agent comprises propylene glycol (dihydroxypropane). In one embodiment, the viscosity agent comprises polyethylene glycol. In one embodiment, the viscosity agent comprises water soluble dextran. In one embodiment, the viscosity agent comprises glycerol and carboxymethylcellulose (CMC). In one embodiment, the viscosity agent comprises glycerol and dextran, e.g., dextran sulfate. In one embodiment, the viscosity agent comprises a glycerol derivative. In one embodiment, the viscosity agent comprises ethylene glycol. In one embodiment, the viscosity agent comprises propylene glycol (dihydroxypropane). The viscosity agent may also comprise lactose, sucrose, sucralose, maltodextrin, dextrose, mannitol, sorbitol, cellulose, maize starch, wheat starch, rice starch, potato starch, gelatin, gum tragacanth, methyl cellulose, hydroxypropylmethyl-cellulose, a carboxymethyl cellulose (CMC), sodium carboxymethyl-cellulose (NaCMC), ethyl cellulose (EC), hydroxypropylmethyl-cellulose (HPMC), sodium carboxymethylcellulose (CMC), polyvinylpyrrolidone (PVP: povidone), hydroxypropylmethyl cellulose (HPMC) and combinations thereof. Moreover, additional agents to modify viscosity have been described in Remington's Pharmaceutical Sciences; June 1990, Mack Publishing Co. These agents can be selected according to final tonicity and viscosity desired. Viscosity modifying agents may include any agent suitable to provide a viscosity of about 1, 1.5, 2, 2.5, 3, 3.5, 4, 4.5, 5, 5.5, 6, 6.5, 7, 7.5, 8, 8.5, 9, 9.5 to about 10 centipoise in PIOAL, with optical characteristics, including optical clarity, appropriate for use in a visual analyzer.

In another aspect, the viscosity agent/modifier in the PIOAL may be present at a concentration of about 1 to about 50% (v/v) of the PIOAL under operating conditions. For example, the viscosity agent/modifier may also be present in the PIOAL at a concentration of about 3 to about 30% (v/v) under operating conditions. As an example, in one embodiment, the glycerol viscosity agent/modifier may be present in the PIOAL at a final concentration of about 5.0% to about 8.0% (v/v) under operating conditions. In another aspect, the glycerol viscosity agent/modifier may be present at a final concentration of about 6.5% (v/v) under operating conditions. In yet another embodiment, the glycerol viscosity agent/modifier is glycerol present at a concentration of about 5% (v/v) under operating conditions. In yet another embodiment, the glycerol viscosity agent/modifier is glycerol present at a concentration of about 30% (v/v) under operating conditions.

In another aspect, the viscosity agent/modifier in the PIOAL may be PVP present at a concentration of about 1 to about 50% (v/v) of the PIOAL under operating conditions. As an example, the viscosity agent/modifier PVP may be present in the PIOAL at a concentration of about 1.0 to about 1.6% (w/v). In one embodiment, the PVP is present at a concentration in the PIOAL of about 1.0% (w/v).

In another aspect, the viscosity agent/modifier in the PIOAL may be a combination of glycerol and PVP with glycerol present at a concentration of about 1 to about 10% (v/v) of the PIOAL with PVP present at a concentration of about 0.5 to about 2.5% (w/v). As an example, in one embodiment, the glycerol may be present in the PIOAL at a concentration of about 5% (v/v) in combination with about 1% (w/v) of PVP.

In one embodiment, the PIOAL of this disclosure may be used with any of the analyzer of this disclosure, for example, an analyzer comprising a visual analyzer, and a processor. In one embodiment, the visual analyzer comprises a flowcell with a symmetrical flow path, and an autofocus component. In one embodiment the analyzer may comprise a particle counter.

In one aspect, the disclosure provides a method of imaging particles using the exemplary PIOAL by providing an visual analyzer/analyzer for a sample comprising particles in a liquid. The visual analyzer has a flowcell coupled to a source of the sample and to a source of a PIOAL, wherein the flowcell defines an internal flowpath, the flowcell directing a flow of the ribbon-shaped sample stream enveloped with the PIOAL through a viewing zone in the flowcell. The analyzer may comprise a high optical resolution imaging device of this disclosure.

A laminar flow is established including the ribbon-shaped sample stream enveloped by or between at least two PIOAL layers. The ribbon-shaped sample stream and the PIOAL may have different viscosities. In one embodiment, the viscosity of the sample is lower than that of the PIOAL. In another embodiment, the viscosity of the PIOAL is lower than that of the sample.

In one embodiment, the particles analyzed comprise at least one of a spherical particle which can include a spherical particle, a non-spherical particle, or both. In respective embodiments, the particles can comprise erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments. In one embodiment, the particles comprise at least one spherical particle. In one embodiment, the spherical particles are white blood cells or microorganisms. In one embodiment, the particles comprise at least one non-spherical particle. In one embodiment, an image projection of non-spherical particles under imaging conditions is increased in the focal plane of the analyzer. In one embodiment, the non-spherical particles are red blood cells, epithelial cells, casts, white blood cells clumps, and/or budding or hyphae yeasts.

In one aspect, the disclosure provides a method for differentially categorizing and/or subcategorizing a particle comprising: a) contacting the particle in a sample with the particle contrast agent composition; b) illuminating the particle in the prepared sample with light in an visual analyzer; c) obtaining a digitized image of the particle enveloped in the PIOAL; d) analyzing the particle in the sample based on image (e.g. visual) features; and e) categorizing and/or subcategorizing the particle according to the characteristic visual features of each category and/or subcategory of particles.

In one embodiment, the image information includes the in-focus content of a particle/cell, including spherical particles. In one embodiment, said particle, cell or portion thereof can be selected from at least one of erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus. Particulate matter, Cell clumps, or Cellular fragments or components. In one embodiment, said in-focus content of a particle comprises at least one of differentially stained nuclear structure, differentially stained cytosolic structure or differentially stained elements.

In one embodiment, at least 50% of the non-spherical particles are aligned in a plane substantially parallel, e.g., parallel, to the direction of the flow, or have image projections maximized under imaging conditions in the focal plane of the high optical resolution imaging device. In another aspect, use of the PIOAL of this invention in a flowcell permits at least 90% of the non-spherical particles to be aligned in a plane substantially parallel to the direction of the flow, or have image projections maximized under imaging conditions in the focal plane of the high optical resolution imaging device. In one aspect of this invention, at least 92% of the non-spherical particles are aligned in a plane substantially parallel to the direction of the flow, or have image projections maximized under imaging conditions in the focal plane of the high optical resolution imaging device. In another embodiment, at least 75%, 80%, 85%, 86%, 87%, 88%, 89%, 90%, 91%, 92%, 93%, 94% or 95% of the non-spherical particles are aligned in a plane substantially parallel to the direction of the flow, and/or have image projections maximized under imaging conditions in the focal plane of the high optical resolution imaging device. In another embodiment, the percentage of non-spherical particles aligned in a plane substantially parallel to the direction of the flow, or having image projections maximized under imaging conditions in the focal plane of the high optical resolution imaging device may be any range between any two of the recited percentages, for example, at least 75-85%, 75-80%, 75%-92%, 92%-95% or other ranges.

In one embodiment, the spherical particles have organelles, nuclear structures, cytosolic structures or granules better positioned, repositioned, and/or better positioned substantially parallel to the direction of flow, and at least 50% of the nuclear structures, cytosolic structures or granules are substantially parallel to the direction of flow in the focal plane of the high optical resolution imaging device. In one embodiment, the spherical particles have at least about 50%, 55%, 60%, 65%, 70%, 75%, 80%, 85%, 86%, 87%, 88%, 89%, 90%, 91% or at least 92% of nuclear structures, cytosolic structures or granules are substantially parallel to the direction of flow in the focal plane of the high optical resolution imaging device, or aligned in a plane substantially parallel, e.g., parallel, to the direction of the flow. In another embodiment, the percentage of spherical particle structures substantially parallel to the direction of flow in the focal plane of the high optical resolution imaging device may range between any two of the recited percentages. In one embodiment, at least 75% of content of the non-spherical particles are substantially parallel to the direction of flow in the focal plane of the high optical resolution imaging device. In another aspect, use of the PIOAL of this invention in a flowcell permits at least 90% or 92% of the content of non-spherical particles to be substantially parallel to the direction of flow in the focal plane of the high optical resolution imaging device.

In some embodiments of the methods of this invention, the image information is the image of the particle contents. In some aspects, the particle content comprises at least one of a differentially stained nuclear structure, a differentially stained cytosolic structure or differentially stained elements in a particle. Examples of particles sensitive to staining are WBCs and epithelial cells.

In one aspect, the methods of this invention provide surprisingly high quality images of cells in flow useful in obtaining automated image based urine formed elements analysis, as well as automated identification of morphological abnormalities useful in determining, diagnosing, prognosing, predicting, and/or supporting a diagnosis of whether a subject has a disease, condition, abnormality or infection and/or monitoring whether a subject is responsive or non-responsive to treatment.

In one aspect, the present disclosure relates to a particle contrast agent composition which can be used to stain particles in biological fluids such as urine. The compositions and methods of this invention may be used in one aspect, for example, for enhancing particle features for counting and characterizing particles such as erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments, as well as for white blood cell differential counting and white blood cell categorization, subcategorization, characterization and analysis. In some aspects in the methods of this disclosure, a sample may be treated with a particle contrast agent composition in-line on the analyzer. In other aspects a sample may be treated with a particle contrast agent composition before introduction to the visual analyzer.

In one aspect, the particle contrast agent composition is used to enhance features of particle and/or cells under conditions where one or more cell types remain substantially intact. In other aspects the particle contrast agent composition is used to treat cell fragments or other particles. In some aspects, the particle contrast agent compositions may be used to stain and/or enhance cellular features of white blood cells and/or epithelial cells and/or bacteria.

Aspects and embodiments of the present invention are based on the surprising and unexpected discovery that certain particle contrast agent compositions, including for example, stain/dye compositions, and/or combinations thereof, have unexpected properties and efficacy when used to perform imaged-based automated urine sample analysis. In one aspect, this invention relates to a particle contrast agent composition comprising at least one of Crystal Violet, Safranin O, Eosin Y, New Methylene Blue, and/or Methyl Green. The stain/dyes may be present in an amount effective to stain viable and/or substantially intact cells and generate visual distinctions for image-based categorization and subcategorization. In certain embodiments, the particles of interests may comprise cell particles further comprising cell membranes. In certain embodiments, the permeability of the cell membrane may be altered or modulated by the use of permeabilizing agents and/or fixatives to increase accessibility of the contrast agents to the intracellular contents in these cell particles thereby enhancing the features of the cell contents when viewed or imaged. In one embodiment, the permeabilizing agent comprises a quaternary ammonium salt.

In certain aspects, various components of the particle contrast agent composition are present in an amount to effectively permit a rapid, one-step particle staining procedure.

In some aspects, methods for purifying particle contrast agents are provided. Purifying one of more stains/dyes used in the compositions and methods of this invention reduces the level of precipitates formed upon contact with a sample, thereby reducing the background, and improving the results from the image-based urine sample analysis with a decreased need for further review of images or manually prepared microscopy.

In one aspect, a particle contrast agent composition is used to contact particles which may be cells or other particles, to generate visual distinctions for categorizing and subcategorizing particles, e.g., by enhancing cellular features under conditions where cells remain substantially intact. The exemplary particle contrast agent composition can be used in the methods of this disclosure to obtain stained images of vital and/or substantially intact cells using contrast agents in non-alcohol based solvent system. In another aspect, the particle contrast agent composition may also include a particle permeabilizing agent to permeabilize cell membranes and/or cell walls. In some aspects, it has been surprisingly found that the particle contrast agent compositions of this invention which comprise a permeabilizing agent are able to permeabilize the cells membrane allowing the contrast agent to penetrate inside the cells, while the cells remain substantially intact.

In some aspects, the particle contrast agent compositions may be used to treat white blood cells, epithelial cells and/or bacteria. As an example, in some aspects, the particle contrast agent compositions may be used to treat at least one of a white blood cells, epithelial cells, bacteria, and/or to analyze the morphologies of the cells. In another aspect, the methods of this invention may further comprise white blood cell categorization and subcategorization.

In one aspect of the methods of this invention, the cells contacted with particle contrast agent composition and/or imaged are, for example, bacteria, parasites, or trichomonas. In some aspects of this invention, the cells are abnormal cells which can be used to identify, predict, diagnose, prognose, and/or support a diagnosis of a condition, disease, infection and/or syndrome and/or monitoring whether a subject is responsive or non-responsive to treatment. Exemplary contrast agent compositions and methods for their use and manufacture are disclosed in copending U.S. patent application Ser. No. 14/216,562, filed Mar. 17, 2014, the content of which is incorporated herein by reference.

In another aspect, the disclosure provides a kit. In one aspect the kit comprises one or more units of a PIOAL as described herein. In another aspect, this invention relates to a kit comprising the particle contrast agent compositions of this invention or components and/or concentrates thereof that can be combined to form the particle contrast agent compositions of this invention, and any of the compositions described herein can be included in the kit. The kit may also contain instructions on the use of particle contrast agent composition according to any of the methods described herein and/or instructions for use of any other component of the kit. The kit may also comprise one or more buffers and/or diluents. The kit and or buffer may further comprise at least one of a pH adjusting agent; ionic strength modifier, a surfactant, a chelating agent, sugar, sugar alcohol, protein stabilizers, and/or an antimicrobial agent. In other embodiments, the kit may also comprise a cleaning or flushing solution. The kit may also comprise standards for positive and negative controls, calibrators, or controls. In some embodiments the standard may comprise a standard contain calibrators and/or controls. The kit may also comprise disposable micropipettes, tips or tubes for transferring the components of the kit.

In another aspect, this invention relates to a kit comprising PIOAL of this invention and at least one contrast agent. In some aspects, the kit may contain two contrast agents in addition to the PIOAL. In one embodiment, the kit comprises at least one permeabilizing agent and at least one of Crystal Violet, New Methylene Blue, Eosin Y, Safranin O and Methyl Green in an amount effective to stain viable and/or substantially intact cells for categorization and subcategorization.

The kit may be used in the methods disclosed herein and may be useful for identification of urine formed elements such as erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, cell trichomonas, clumps and/or cell fragments. The kit may also contain software for image-based identification of urine formed elements such as erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps and/or cell fragments.

In another aspect, the disclosure provides a method for performing differential particle/cell categorization and subcategorization using the exemplary reagent kits.

In one aspect, this method relates to a method for categorizing, subcategorizing and/or counting particles using, for example, the reagent kits of this invention, where the method comprises: 1) contacting the sample containing the particles with a particle contrast agent composition, 2) introducing the resulting treated sample into a visual analyzer; 3) illuminating the treated sample particles with light in the visual analyzer; 4) obtaining digitized images of the treated sample particles enveloped in a PIOAL; and 5) categorizing, subcategorizing and counting particles based on the images information. In one embodiment, the method comprises automatic inline staining. In another embodiment the sample may be introduced into the visual analyzer before contact with the particle contrast agent composition.

In another aspect, the disclosure provides a method of making the PIOAL liquid composition described herein.

In another aspect, the disclosure provides a method for differentially categorizing and/or subcategorizing particles/cell using image-based particle categorization and subcategorization comprising: a) contacting a sample of particles with a particle contrast agent composition as described herein, in an amount effective to generate visual distinctions for categorizing and subcategorizing particles, for example, by enhancing intracellular content features of particles in a sample when presented for imaging; b) obtaining images of the particles and their internal details; and c) performing image based categorization and subcategorization of the particles based on visual distinctions. In some aspects, the particle contrast agent comprises at least one permeabilizing agent, at least one fixative, and at least one of Crystal Violet, New Methylene Blue, Safranin O, Eosin Y, and Methyl Green in an amount effective to generate visual distinctions for particle categorization and subcategorization. In one embodiment, the contacting of the sample containing particles with the particle contrast agent composition is carried out at an elevated temperature.

In some aspects, categorizing subcategorizing and counting may comprise a) contacting the sample containing the particles with a particle contrast agent composition, b) enveloping the ribbon-shaped sample stream containing the treated particles in a PIOAL; c) illuminating the treated sample particles with light in a visual analyzer; d) obtaining digitized images of the treated sample particles enveloped in a PIOAL or imaging the particles using a visual analyzer; and e) categorizing and/or subcategorizing and counting the particles based on image characteristics, where the particles may be any of the particles disclosed herein. In some aspects, the PIOAL may comprise any of the viscosity agents disclosed herein. The analyzer may be any of the analyzer disclosed herein.

In another aspect, the disclosure provides a fluid composition for PIOAL in an analyzer configured to support a flow of a sample carrying at least one of particles and/or cells. The fluid composition can include a sample fluid containing particles, and the sample fluid can have a given viscosity. Further, the fluid composition can include a PIOAL abutting the sample fluid along an interface surface, a PIOAL being substantially transparent, having a higher or lower viscosity than the viscosity of the sample fluid, such that the particles and the cells are aligned. Particles may be aligned or positioned as disclosed herein.

In one embodiment, the PIOAL and the sample fluid have different average linear velocities at an initial point of contact between the sample fluid and the PIOAL. In one embodiment, the sample fluid is arranged between two layers of the PIOAL, thereby defining two said interface surfaces at which the PIOAL abuts the sample fluid, the interface surfaces being spaced apart by a distance. In one embodiment, the distance spacing the interface layers is less than or equal to the wider dimension of said at least one of the particles and cells. In one embodiment, the distance spacing the interface layers narrows along a direction of flow of at least one of the PIOAL and the sample fluid. In one embodiment, the distance spacing the interface layers narrows in a transition zone in the direction of flow to a distance that is less than or equal to the wider dimension of at least one of the particles. In one embodiment, the alignment of the wider dimension of at least one of the particles and relative positions of intracellular organelles or portions of the organelles of the cells in a direction parallel to the direction of the flow is increased in the transition zone. In one embodiment, a difference in the viscosity of the PIOAL to the viscosity of the sample fluid is about 0.1 centipoise to about 10 centipoise. The differences in viscosities enable the generation of favorable/suitable shear forces to act on the ribbon-shaped sample stream.

The present disclosure provides exemplary particle contrast agent compositions and methods of use thereof in a suitable analyzer for analyzing a sample containing particles. In a general aspect, the exemplary compositions and methods of use thereof are useful when employed in combination with an automated analyzer found in research and/or medical laboratories. Exemplary automated analyzers are instruments designed to measure different parameters of particles and biochemical components in a number of biological samples, including, for example, urine, with minimal human assistance, and a high throughput. Exemplary automated analyzers can include, for example, automated urine microscopy analyzers and/or cell counters, which can perform for example, complete urine formed elements count. In some aspects, the analyzers can process samples singly, in batches, or continuously.

In some aspects, the sample may be treated with the exemplary particle contrast agent compositions described herein before imaging analysis. In some aspects treatment with the exemplary particle contrast agent compositions may also be performed on-line in the analyzer or prior to providing the sample to the analyzer. In some embodiments the sample may be heated during part or all of particle staining process. The sample may also be cooled after heating.

In one aspect, the present disclosure provides a method for analyzing a urine sample, the method comprising: a) introducing the sample into at least one flowcell configured to direct flow of the sample along a flow path; b) introducing into the flowcell along with the sample, a PIOAL having a viscosity different from a viscosity of the sample, wherein the PIOAL is effective to support the flow of the sample in a flat ribbon; c) imaging the particle on an analyzer comprising a visual analyzer; d) detecting and counting particles having one or more visual distinctions, wherein the particles include at least one of erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments.

In another aspect, the present disclosure also provides a method of focusing a visual analyzer for urine analysis comprising: a) a high optical resolution imaging device on an autofocus pattern fixed relative to a flowcell, b) the autofocus pattern being located at a displacement distance from a urine ribbon-shaped sample stream that is predetermined, c) the high optical resolution image device with an objective on an optical axis that intersects the ribbon-shaped sample stream, d) a relative distance between the high optical resolution imaging device and the flowcell being variable by operation of a motor drive, e) the high optical resolution imaging device configured to resolve and collect a digitized image on a photosensor array; and operating the motor drive over the displacement distance to focus the high optical resolution imaging device on the ribbon-shaped sample stream. In one embodiment, the method further comprises forming the ribbon-shaped sample stream into a ribbon-shape. In another embodiment, the optical axis is substantially perpendicular to the ribbon-shaped sample stream. In another embodiment, the autofocus pattern includes forms with limited size and the displacement distance is sufficient that the forms are substantially invisible in the digitized image when focused on the ribbon-shaped sample stream. In yet another embodiment, the method comprises: a) detecting an autofocus re-initiation signal; b) refocusing on the autofocus pattern; c) operating the motor drive over the displacement distance (the predetermined distance between the autofocus pattern and the ribbon-shaped sample stream); whereby the high optical resolution imaging device becomes focused on the ribbon-shaped sample stream. In one embodiment, the autofocus re-initiation signal includes at least one of a change in temperature, a decrease in focus quality, time, or user-input.

In one embodiment, the internal flowpath forms a ribbon-shaped sample stream. In one embodiment, the source of the sample is configured to provide the sample at a controllable sample flow rate. In one embodiment, the source of the PIOAL is configured to provide the PIOAL at a controllable PIOAL flow rate. In one embodiment, the PIOAL has a predetermined viscosity. In one embodiment, the PIOAL has a different viscosity than the sample. In one embodiment, the viscosity of the PIOAL, the viscosity of the sample material, the linear velocity of the PIOAL and the linear velocity of the sample material are coordinated to maintain the ribbon-shaped sample stream at the displacement distance from the autofocus pattern. In one embodiment, the PIOAL has a higher linear velocity than the ribbon-shaped sample stream upon initial contact with the ribbon-shaped sample stream. In one embodiment, the autofocus pattern is located at an edge of a field of view of the high optical resolution imaging device.

In one embodiment, the at least one said digital processor is further configured to perform image based categorization and subcategorization of the erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments. In one embodiment, the at least one said digital processor is further configured to: detect an autofocus re-initiation signal; wherein the autofocus re-initiation signal is triggered by at least one of a change in temperature, a decrease in focus quality, time, or user-input. In one embodiment, the analyzer has an internal flowpath of the analyzer narrows to produce the ribbon-shaped sample stream thickness of 2-4 µm in thickness. In one embodiment, the internal flowpath results in the ribbon-shaped sample stream of 500-3,000 µm in width. In one embodiment, the internal flowpath results in the ribbon-shaped sample stream of 1500-2500 µm in width. In one embodiment, the analyzer is configured wherein a linear velocity of the particles in the sample is such that the particles are not substantially blurred in the image. In one embodiment, the analyzer is configured wherein a light source is further configured to illuminate the ribbon-shaped sample stream and the autofocus pattern.

In one aspect, the present disclosure provides a method of imaging particles in urine using a PIOAL as described herein comprising: providing a visual analyzer for a sample comprising particles suspended in a liquid; establishing a flow having laminar sections that are of higher and lower viscosity in the analyzer wherein the analyzer further comprising: a flowcell coupled to a source of the sample and to a source of a PIOAL wherein the flowcell defines an internal flowpath, the flowcell directing a flow of the sample enveloped with the PIOAL through a viewing zone in the flowcell; a high optical resolution imaging device with an objective on an optical axis that intersects the ribbon-shaped sample stream, a relative distance between the high optical resolution imaging device and the flowcell being variable by operation of a motor drive, for resolving and collecting a digitized image on a photosensor array; an autofocus pattern having a position fixed relative to the flowcell, the autofocus pattern being located at a displacement distance from the plane of the ribbon-shaped sample stream; a light source configured to illuminate the ribbon-shaped sample stream and the autofocus pattern; and at least one digital processor coupled to operate the motor drive and to analyze the digitized image, wherein the processor is configured to determine a focus position of the autofocus pattern and to relatively displace the high optical resolution imaging device and the flowcell over the displacement distance from the focused position, whereby the high optical resolution imaging device becomes focused on the ribbon-shaped sample stream. In one embodiment, the particles comprise at least one spherical particle. In one embodiment, the particles comprise at least one non-spherical particle. In one embodiment, the method comprises wherein a feature wherein an image projection of non-spherical particles under imaging conditions is increased in the focal plane of the high optical resolution imaging device. In one embodiment, the particles comprise at least one of erythrocytes (RBCs), dysmorphic erythrocytes, leukocytes (WBCs), neutrophils, lymphocytes, phagocytic cells, eosinophils, basophils, squamous epithelial cells, transitional epithelial cells, decoy cells, renal tubular epithelial cells, casts, crystals, bacteria, yeast, parasites, oval fat bodies, fat droplets, spermatozoa, mucus, trichomonas, cell clumps, and cell fragments.

In one embodiment, at least 50% of the non-spherical particles are aligned in a plane substantially parallel to the direction of the flow whereby the image projection of non-spherical particles under imaging conditions in the focal plane of the high optical resolution imaging device (HORID) is increased or maximized. In one embodiment, at least 90% of the non-spherical particles are aligned in a plane substantially parallel to the direction of the flow whereby the image projection of non-spherical particles under imaging conditions in the focal plane of the HORID is increased or maximized. In one embodiment, at least 92% of the non-spherical particles are aligned in a plane substantially parallel to the direction of the flow whereby the image projection of non-spherical particles under imaging conditions in the focal plane of the HORID is increased or maximized.

In one embodiment, at least 50% of the spherical particles are aligned, i.e., intraparticle structures of the spherical particles are positioned, repositioned and/or better-positioned substantially parallel to the direction of flow. For example, spherical cells have at least 50% of organelles, nuclear structures, cytosolic structures or granules in the focal plane of the analyzer. In one embodiment, at least 90% of the intraparticle structures of spherical particles such as cells are positioned, repositioned and/or better-positioned substantially parallel to the direction of flow. In one embodiment, at least 92% of the intraparticle structures of spherical particles such as cells are positioned, repositioned and/or better-positioned substantially parallel to the direction of flow.

In one embodiment, the particle categorization, subcategorization and counting is based on visual distinctions selected from at least one of size, shape, symmetry, and contour. In one embodiment, the imaging is digitized imaging. In one embodiment, the imaging is performed by microscopy. In one embodiment, the imaging is performed manually using conventional microscopy. In one embodiment, the imaging is automated. In one embodiment, the particle may include any of the particles disclosed herein. In one embodiment, the imaging is performed using an analyzer in any of the embodiments disclosed herein.

Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described above. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. In certain cases, method steps or operations may be performed or executed in differing order, or operations may be added, deleted or modified. It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention. Accordingly, the present invention is not limited to the embodiments described above or depicted in the drawings, and various embodiments and modifications can be made without departing from the scope of the claims below.

What is claimed is:

1. A particle analysis system that performs geometric hydrofocusing for imaging particles in a body fluid sample, the system comprising:
   a flowcell having a flowpath, the flowpath comprising a first channel and a second channel;
   a sheath fluid injection system, wherein an output of the sheath fluid injection system is fluidly connected to the first channel,
   a sample fluid injection system in fluid communication with the flowpath, the sample fluid injection system comprising an injection tube, wherein:
      an outlet of the injection tube is fluidly connected to the second channel,
      the first channel and the second channel are coaxial about a longitudinal axis, and
      a cross-sectional area of the second channel decreases from the outlet of the injection tube to an image capture site, the cross sectional area orthogonal to the longitudinal axis;
   an image capture device aligned with the image capture site along an imaging axis;
   an imaging target fixed to the flowcell;
   a focusing module comprising a focusing mechanism to move the image capture device; and
   a processor operatively coupled to the image capture device, wherein the processor is programmed to:
      control the image capture device to acquire a first image of the imaging target,
      analyze the first image for a level of contrast,
      determine, using the level of contrast, a first position of the image capture device from the imaging target where an image of the imaging target is focused,
      control the focusing mechanism to move the image capture device to a second position a predetermined distance from the first position along the imaging axis, wherein the predetermined distance is nonzero, and
      control the image capture device at the second position to acquire a second image, wherein the second image is focused at the predetermined distance from the imaging target.

2. The system of claim 1, further comprising the body fluid sample, wherein the body fluid sample is a urine fluid sample.

3. The system of claim 1, wherein the decrease in the cross-sectional area is defined by opposed walls of the flowpath angling radially inwardly along the flowpath generally symmetric about the longitudinal axis.

4. The system of claim 1, wherein the imaging target is fixed on the flowcell.

5. The system of claim 1, further comprising the body fluid sample and a sheath fluid, wherein the body fluid sample has a sample viscosity, and the sheath fluid has a sheath fluid viscosity that is different from the sample viscosity.

6. A particle analysis system that performs geometric hydrofocusing for imaging particles in a body fluid sample, the system comprising:
   a flowcell having a flowpath with an injection tube and an imaging window with an imaging axis therethrough, wherein:
      the flowpath is characterized by a first cross-sectional area parallel to the imaging axis at the injection tube,
      the flowpath is characterized by a second cross-sectional area parallel to the imaging axis at an imaging target,
      the second cross-sectional area is less than the first cross-sectional area,
      the injection tube is characterized by a third cross-sectional area, and
      the third cross-sectional area is less than the first cross-sectional area;
   an image capture device aligned with the imaging window along the imaging axis;
   an imaging target fixed to the flowcell;
   a focusing module comprising a focusing mechanism to move the image capture device; and
   a processor operatively coupled to the image capture device, wherein the processor is programmed to:
      control the image capture device to acquire a first image of the imaging target,
      analyze the first image for a level of contrast,
      determine, using the level of contrast, a first position of the image capture device from the imaging target where an image of the imaging target is focused,
      control the focusing mechanism to move the image capture device to a second position a predetermined distance from the first position along the imaging axis, wherein the predetermined distance is nonzero, and control the image capture device at the second position to acquire a second image, wherein the second image is focused at the predetermined distance from the imaging target.

7. The system of claim 6, further comprising the body fluid sample, wherein the body fluid sample is a urine sample.

8. A system for imaging a plurality of particles in a body fluid sample having a sample fluid viscosity, the system comprising:
- a flowcell having a flowpath and a sample fluid injection tube, the flowpath comprising a first channel and a second channel;
- a sheath fluid input in fluid communication with the flowpath of the flowcell, the sheath fluid input fluidly connected to the first channel;
- a body fluid sample input in fluid communication with the injection tube of the flowcell, wherein:
  - the body fluid sample input fluidly connected to the second channel,
  - the first channel and the second channel are coaxial about a longitudinal axis, and
  - a cross-sectional area of the second channel decreases from an outlet of the injection tube to an imaging site, the cross sectional area orthogonal to the longitudinal axis;
- an imaging device that images the plurality of particles at the imaging site;
- the body fluid sample;
- a sheath fluid, the sheath fluid having a sheath fluid viscosity that differs from the sample fluid viscosity by a viscosity difference in a predetermined viscosity difference range;
- an imaging target fixed to the flowcell,
- a focusing module comprising a focusing mechanism to move the imaging device, and
- a processor operatively coupled to the imaging device, wherein the processor is programmed to:
  - control the imaging device to acquire a first image of the imaging target,
  - analyze the first image for a level of contrast,
  - determine, using the level of contrast, a first position of the imaging device from the imaging target where an image of the imaging target is focused,
  - control the focusing mechanism to move the imaging device to a second position a predetermined distance from the first position, wherein the predetermined distance is nonzero, and
  - control the imaging device at the second position to acquire a second image of the cells, wherein the second image is focused at the predetermined distance from the imaging target, wherein:
    - the body fluid sample is disposed within the sheath fluid in the second channel,
    - the plurality of particles comprise cells that extend from the body fluid sample into the sheath fluid.

9. The system of claim 8, wherein the body fluid sample is a urine sample.

10. The system of claim 1, wherein the processor is further programmed to:
- control the sheath fluid injection system to inject a sheath fluid, and
- control the sample fluid injection system to inject the body fluid sample.

11. The system of claim 1, wherein the predetermined distance depends on temperature.

12. The system of claim 1, wherein the focusing mechanism comprises a stepper motor.

13. The system of claim 1, wherein the imaging axis is perpendicular to the longitudinal axis.

14. The system of claim 1, wherein the image capture device comprises a charge coupled device (CCD).

15. The system of claim 1, wherein the image capture device comprises a photosensor array.

* * * * *